US008962299B2

(12) United States Patent
Holtzapple et al.

(10) Patent No.: US 8,962,299 B2
(45) Date of Patent: Feb. 24, 2015

(54) FOUR-GENE PATHWAY FOR WAX ESTER SYNTHESIS

(75) Inventors: Erik Holtzapple, San Diego, CA (US); John H. Verruto, San Diego, CA (US)

(73) Assignee: ExxonMobil Research and Engineering Company, Annandale, NJ (US)

( * ) Notice: Subject to any disclaimer, the term of this patent is extended or adjusted under 35 U.S.C. 154(b) by 0 days.

(21) Appl. No.: 13/408,270

(22) Filed: Feb. 29, 2012

(65) Prior Publication Data

US 2013/0224811 A1 Aug. 29, 2013

(51) Int. Cl.

| | |
|---|---|
| *C12N 1/12* | (2006.01) |
| *C12N 15/00* | (2006.01) |
| *C12P 7/64* | (2006.01) |

(52) U.S. Cl.

USPC ..................... 435/257.2; 435/134; 435/320.1; 536/23.2

(58) Field of Classification Search

CPC .... C12N 9/1029; C12N 15/52; C12N 9/0006; C12N 1/20; C12N 9/20; C12N 15/74; C12N 1/32; C12N 15/63; C12N 15/79; C12N 15/8243; C12N 9/1025; C12N 15/113; C12P 7/6472; C12P 7/6463; C12P 7/649; Y02E 50/13; Y02E 50/343; Y02E 50/10; C12Y 203/0102; C12Y 602/01003; C12Y 102/0108; C12Y 102/0105; C12Y 203/01075; C12R 1/01; C12R 1/89

See application file for complete search history.

(56) References Cited

U.S. PATENT DOCUMENTS

| | | | | |
|---|---|---|---|---|
| 5,298,421 | A | 3/1994 | Davies et al. | |
| 5,403,918 | A | 4/1995 | Metz | 530/379 |
| 5,455,167 | A | 10/1995 | Voelker et al. | |
| 5,654,495 | A | 8/1997 | Voelker et al. | |
| 5,723,747 | A | 3/1998 | Lassner et al. | 800/205 |
| 5,851,796 | A | 12/1998 | Schatz | |
| 6,143,538 | A | 11/2000 | Somerville et al. | 285/323 |
| 6,492,509 | B1 | 12/2002 | Lardizabal et al. | |
| 7,118,896 | B2 | 10/2006 | Kalscheuer et al. | |
| 7,135,290 | B2 | 11/2006 | Dillon | |
| 7,897,369 | B2 | 3/2011 | Schmidt-Dannert et al. | 435/134 |
| 2009/0117629 | A1 | 5/2009 | Schmidt-Dannert et al. | |
| 2009/0298143 | A1 | 12/2009 | Roessler et al. | |
| 2010/0203614 | A1 | 8/2010 | Wahlen et al. | 435/189 |
| 2010/0251601 | A1 | 10/2010 | Hu et al. | 44/313 |
| 2011/0000125 | A1 | 1/2011 | McDaniel et al. | |
| 2011/0020883 | A1 | 1/2011 | Roessler et al. | |
| 2011/0072714 | A1 | 3/2011 | Gaertner | 44/388 |
| 2011/0111470 | A1 | 5/2011 | Berry et al. | |
| 2011/0195469 | A1 | 8/2011 | Roessler et al. | |
| 2013/0078684 | A1 | 3/2013 | Holtzapple et al. | |

FOREIGN PATENT DOCUMENTS

| | | | |
|---|---|---|---|
| WO | WO 2007/136762 | 11/2007 | C12N 1/00 |
| WO | WO-2007/136762 A2 | 11/2007 | |
| WO | WO-2008-119082 * | 2/2008 | |
| WO | WO 2008/119082 | 10/2008 | C12P 7/64 |
| WO | WO 2009/009391 | 1/2009 | C07C 67/08 |
| WO | WO-2009/009391 A2 | 1/2009 | |
| WO | WO 2009/076559 | 6/2009 | C12P 7/64 |
| WO | WO-2009/076559 A1 | 6/2009 | |
| WO | WO 2009/111513 | 9/2009 | C12M 1/00 |
| WO | WO-2009/111513 A1 | 9/2009 | |
| WO | WO 2009/140701 | 11/2009 | C12N 15/87 |
| WO | WO-2009/140701 A2 | 11/2009 | |
| WO | WO 2010/006312 | 1/2010 | C12N 1/21 |
| WO | WO-2010/006312 A2 | 1/2010 | |
| WO | WO 2010/011754 | 1/2010 | C12P 7/64 |
| WO | WO 2010/042664 | 4/2010 | C07C 47/02 |
| WO | WO 2010/044960 | 4/2010 | C12P 7/06 |
| WO | WO 2010/075483 | 7/2010 | C12N 9/16 |
| WO | WO-2010/075483 A2 | 7/2010 | |
| WO | WO 2010/118410 | 10/2010 | C12N 1/20 |
| WO | WO-2010/118410 A1 | 10/2010 | |
| WO | WO 2010/126891 | 11/2010 | C12P 7/64 |
| WO | WO-2010/126891 A1 | 11/2010 | |
| WO | WO 2010/135624 | 11/2010 | C07C 31/125 |
| WO | WO 2011/008535 | 1/2011 | C12P 7/64 |
| WO | WO-2011/008535 A1 | 1/2011 | |
| WO | WO 2011/019858 | 2/2011 | C12N 1/13 |
| WO | WO-2011/019858 A1 | 2/2011 | |
| WO | WO 2011/157848 | 12/2011 | C12N 1/18 |
| WO | WO-2011/157848 A1 | 12/2011 | |

OTHER PUBLICATIONS

Black, P., et al. (2007), "Yeast acyl-CoA synthetases at the crossroads of fatty acid metabolism and regulation", *Biochim. Biophys. Acta.*, 1771: 286-298.

Black, P., et al. (1997), "Mutational Analysis of a fatty Acyl-Coenzyme a synthetase signature motif identifies seven amino acid residues that modulate fatty acid substrate specificity", *The Journal of Biological Chemistry,* 4896-4903.

Campbell, J., (2002), "The Enigmatic *Escherichia coli fade gene is YafH", Journal of Bacteriology,* 184(13): 3759-3764.

(Continued)

*Primary Examiner* — Iqbal H Chowdhury

(74) *Attorney, Agent, or Firm* — Harness, Dickey & Pierce, P.L.C.

(57) ABSTRACT

The invention relates to methods for producing a wax ester in recombinant host cells engineered to express a thioesterase, an acyl-CoA synthetase, an alcohol-forming fatty acyl reductase, and a wax ester synthase. The methods of the invention may take place in photosynthetic microorganisms, and particularly in cyanobacteria. Isolated nucleotide molecules and vectors expressing the thioesterase, acyl-CoA synthetase, alcohol-forming fatty acyl reductase, and wax ester synthase, recombinant host cells expressing the thioesterase, acyl-CoA synthetase, alcohol-forming fatty acyl reductase, and wax ester synthase, and systems for producing a wax ester via a pathway using these four enzymes, are also provided.

33 Claims, 14 Drawing Sheets

(56) References Cited

OTHER PUBLICATIONS

Cheng, J., et al., (2004), "Mammalian wax biosynthesis", *The Journal of Biological Chemistry,* 279(36): 37789-37797.
Copeland L., et al., (2011), Genbank CP000514.1; http://www.ncbi.nlm.nih.gov/nuccore/CP000514.1.
Doan, T., et al., (2009) "Functional expression of five *Arabidopsis* fatty acyl-CoA reductase genes in *Escherichia coli", Journal of Plant Physiology,* 166: 787-796.
Gupta, R., et al., (2003), "Expression of the *Photorhabdus luminescens lux* genes (*lux*A, B, C, D, and E) in *Saccharomyces cerevisiae*", FEMS Yease Research, 4: 305-313.
Hofvander, P., et al., (2011), "A prokaryotic acyl-CoA reductase performing reduction of fatty acyl-CoA to fatty alcohol" *FEBS Letters,* 3538-3543.
Honsho, M., et al., (2010), Posttranslational Regulation of Fatty Acyl-CoA Reductase 1, Far1, Controls Ether Glycerophospholipid synthesis, *Journal of Biological Chemistry,* 285(12): 8537-8542.
Huu, N., et al., (1999), "*Marinobacter aquaeolei* sp. nov., a halophilic bacterium isolated from a Vietnamese oil-producing well", *International Journal of Systematic Bacteriology,* 1999: 49: 367-375.
International Search Report for PCT/US2012/027899 dated Oct. 2, 2012.
Ishige, T., et al., (2000), "Long-chain aldehyde dehydrogenase that participates in *n*-Alkane utilization and wax ester synthesis in *Acinetobacter* sp. strain M-1", *Applied and Environmental Microbiology,* 66(8): 3481-3486.
Kaczmarzyk, D., et al. (2010), "Fatty acid activation in cyanobacteria mediated by acyl-acyl carrier protein synthetase enables fatty acid recycling", *Plant Physiology,* 152: 1598-1610.
Kalscheuer, R., et al. (2004), "Synthesis of Novel Lipids in *Saccharomyces cerevisiae* by heterologous expression of an unspecific bacterial acyltransferase", *Applied and Environmental Microbiology,* 70(12): 7119-7125.
Kalscheuer, R., et al. (2006), "Microdiesel: *Escherichia coli* engineered for fuel production", *Microbiology,* 152: 2529-2536.
Kalscheuer, R. (2010), "Genetics of wax ester and triacylglycerol biosynthesis in bacteria", *Handbook of Hydrocarbon and Lipid Microbiology,* 528-535.
King, A., et al. (2007), "Cuticular wax biosynthesis in petunia petals: cloning and characterization of an alcohol-acyltransferase that synthesizes wax-esters", *Planta,* 226: 381-394.
Kunst, L., et al. (2003), "Biosynthesis and secretion of plant cuticular wax", *Progress in Lipid Research,* 42: 51-80.
Koksharova, O., et al. (2002), "Genetic tools for cyanobacteria", *Applied Microbiology biotechnology,* 58: 123-137.
Meighen, E, et al. (1993), "Bacterial bioluminescence: organization, regulation, and application of the *lux* genes" *The FASEB Journal,* 7: 1016-1022.
Morgan-Kiss, R., et al. (2004), "The *Escherichia coli fadK* (*ydiD*) Gene encodes an anerobically regulated short chain Acyl-CoA synthetase" *The Journal of Biological Chemistry,* 279: 36: 37324-37333.
Moto, K., et al. (2003), "Pheromone gland-specific fatty-acyl reductase of the silkmoth, *Bombyx mori" PNAS,* 100(16): 9156-9161.
Pighin, J.A., et al. (2004), "Plant cuticular lipid export requires an ABC transporter", *Science,* 306:702-704.
Quintana, N., et al. (2011), "Renewable energy from cyanobacteria: energy production optimization by metabolic pathway engineering", *Appl Microbiol Biotechnol,* 91: 471-490.
Rontani, J., et al. (1999), "Production of wax esters during aerobic growth of marine bacteria on isoprenoid compounds", *Applied and environmental Microbiology,* 65(1): 221-230.
Sandager, et al. (2002), "Storage Lipid synthesis is Non-essential in Yeast", *Journal of Biol. Chem.* 277: 6478-6482.
Schirmer, A., et al. (2010), "Microbial biosynthesis of alkanes", *Science,* 329(5991): 559-562.
Shi, et al. (2012), "Functional expression and characterization of fix wax ester synthases in *Saccharomyces cerevisiae* and their utility for biodiesel production", *Biotechnology for Biofuels,* 5:7.
Shockey, J., et al. (2002), "*Arabidopsis* contains nine long-chain acyl-coenzyme a synthetase genes that participate in fatty acid and glycerolipid metabolism", *Plant Physiology,* 129: 1710-1722.
Soupene, E., et al. (2012), "Mammalian long-chain Acyl-CoA synthetases", *Exp. Biol. Med.,* 233: 507-521.
Steen, E., et al. (2010), "Microbial production of fatty-acid-derived fuels and chemicals from plant biomass", *Nature,* 463: 559-563.
Suzuki, E., et al. (2010), "Carbohydrate Metabolism in Mutants of the Cyanobacterium *Synechococcus elongates* PCC 7942 defective in glycogen synthesis" *Applied and Environmental Microbiology,* 76(10): 3153-3159.
Tan, X., et al. (2011), "Photosynthesis driven conversion of carbon dioxide to fatty alcohols and hydrocarbons in cyanobacteria" *Metabolic Engineering,* 13: 169-176.
Teerawanichipan, P., (2010), "Fatty Acyl-CoA reductase and wax synthase from *Euglena gracilis* in the biosynthesis of Medium-Chain Wax Esters" *Lipids,* 45: 263-273.
Terrawanichipan, P., (2010), "A Fatty acyl-CoA reductase highly expressed in the head of honey bee (*Apis mellifera*) involves biosynthesis of a wide range of aliphatic fatty alcohols", *Insect Biochemistry and Molecular Biology,* 40: 641-649.
Van Dijck, P., et al. (2002), Truncation of *Arabidopsis thaliana* and *Selaginella lepidophylla* trehalose-6-phosphate synthase unlocks high catalytic activity and supports high trehalose levels on expression in yeast, 366: 63-71.
Vioque, J., et al. (1997), Resolution and purification of an aldehyde-generating and an alcohol-generating fatty Acyl-CoA reductase from pea leaves (*Pisum sativum* L.), *Arch. Biochem. Biophys.* 340: 64-72.
Voelker, T., et al. (1994), "Alteration of the specificity and regulation of fatty acid synthesis of *Escherichia coli* by expression of a plant medium-chain Acyl-Acyl carrier protein thioesterase" *Journal of Bacteriology,* 176(23): 7320-7327.
Wagner, M., et al. (2010), "Identification and characterization of an acyl-CoA:diacylglycerol acyltransferase 2 (DGAT2) gene from the microalga *O. tauri", Plant Physiology and Biochemistry,* 48(6): 407-416.
Wahlen, B., et al. (2009), "Purification, characterization, and potential bacterial wax production role of an NADPH-dependent fatty aldehyde reductase from *Marinobacter aquaeolei* VT8", *Applied and Environmental Microbiology,* 75(9): 2758-2764.
Wang, X., et al. (1995), "Solubilization and purification of aldehyde-generating fatty acyl-CoA reductase from green alga *Botryococcus braunii", FEBS Letters,* 370: 15-18.
Wolk, P., et al. (1984), "Construction of shuttle vectors capable of conjugative transfer from *Escherichia coli* to nitrogen-fixing filamentous cyanobacteria", *Proc. Natl. Acad. Sci. USA,* 81: 1561-1565.
Yen, C., et al. (2005), "The triacylglycerol synthesis enzyme DGAT1 also catalyzes the synthesis of diacylglycerols, waxes, and retinyl esters", *Journal of Lipid Research,* 46: 1502-1511.
Honsho, M., et al. (2010), "Posttranslational regulation of Fatty Acyl-CoA reductase 1, FAR1 , Controls Ether glycerophospholipid synthesis", *Journal of Biological Chemistry,* 285(12): 8537-8542.
International Search Report for PCT/US12/27091 dated Jun. 21, 2012.
Lénard, M., et al. (2010), "Evolution of multicomponent pheromone signals in small ermine moths involves a single fatty-acyl reductase gene", *Proc Natl. Acad. Sci.,* 107(24): 10955-10960.
Méndez-Alvarez, S., et al. (1994), "Transformation of chlorobium limicola by a plasmid that confers the ability to utilize thiosulfate" *Journal of Bacteriology,* 176(23): 7395-7397.
Stemmer, W., (1994), "DNA shuffling by random fragmentation and reassembly: in vitro recombination for molecular evolution", *Proc. Natl. Acad. Sci. USA,* 91: 10747-10751.
Office Action dated Jul. 9, 2013 issued in U.S. Appl. No. 13/413,426.
Office Action dated Dec. 11, 2013 issued in U.S. Appl. No. 13/413,426.
Lu, X., A perspective: Photosynthetic production of fatty acid-based biofuels in genetically engineered cyanobacteria, *Biotechnology Advances,* vol. 28, (2010) pp. 742-746.
Office Action dated Dec. 27, 2013 issued in U.S. Appl. No. 13/413,426.
International Preliminary Report on Patentability dated Sep. 12, 2014 issued in PCT/US2012/027091.

(56) References Cited

OTHER PUBLICATIONS

Hibbit, O., et al. (2011), "Physiologically-Regulated Expression Vectors for Gene Therapy", *Targets in Gene Therapy,* 6: 99-118.
Li, X., (1999), "Synthetic muscle promoters: activities exceeding naturally occurring regulatory sequences", *Nature Biotechnology,* 17: 241-245.
Office Action dated Aug. 4, 2014 issued in U.S. Appl. No. 13/413,426.
Altschul, S., et al. (1997), "Gapped BLAST and PSI-BLAST: a new generation of protein database search programs", *Nucleic Acids Research,* 25(17): 3389-3402.
Bateman, A., et al. (2000), "The pfam protein families database", *Nucleic Acids Research,* 28(1):263-266.
Bateman, A., et al. (2004), "The pfam protein families database", *Nucleic Acids Research,* 32: Database Issue: D138-D141.
Benson, D., et al. (2010), "GenBank", *Nucleic Acids Research*: Database Issue: D32-D37.
Cheng, J., et al. (2004), "Mammalian wax biosynthesis", *The Journal of Biosynthesis,* 279(36): 37798-37807.
Domergue, F., et al., (2010), "Three *arabidopsis* fatty acyl-coenzyme a reductases, FAR1, FAR4, and FAR5, generate primary fatty alcohols associated with suberin deposition", *Plant Physiology,* 153: 1539-1554.
Finn, R., et al. (2006), "Pfam: clans, web tools and services", *Nucleic Acids Research,* 34: Database Issue 34:D247-D251.
Finn, R., et al. (2010), "The pham protein families database", *Nucleic Acids Research,* 38: Database Issue 38:D211-D222.
Holtzapple, E., et al. (2007), "biosynthesis of isoprenoid wax ester in *Marinobacter hydrocarbonoclasticus* DSM 8798: identification and characterization of isoprenoid coenzyme a synthetase and wax ester synthases", *Journal of Bacteriology,* 189(10): 3804-3812.
International Preliminary Report on Patentability dated Apr. 10, 2014 issued in PCT Application No. PCT/US2012/027899.
International Search Report and Written Opinion dated Jun. 21, 2012 issued in PCT/US12/27091.
Ishige, T., et al. (2002), "Wax ester production from *n*-Alkanes by *Acinetobacter* sp. strain M-1: ultrastructure of cellular inclusions and role of acyl coenzyme a reductase", *Applied and Environmental Microbiology,* 68(3): 1192-1195.
Kalscheuer, R., et al. (2003), "A novel bifunctional wax ester synthase/Acyl-CoA:Diacylglcerol acyltransferase mediates wax ester and triacylglycerol biosynthesis in *Acinetobacter calcoaceticus* ADP1", *The Journal of Biological Chemistry and Molecular Biology, INC.,* 278(10): 8075-8082.
Kalscheuer, R., et al., (2006), "Neutral lipid biosynthesis in engineered *Escherichia coli*: jojoba oil-like wax esters and fatty acid butyl esters", *Applied and Environmental Microbiology,* 72(2): 1373-1379.
Karlin, S., et al., (1990), "Methods for assessing the statistical significance of molecular sequence features by using general scoring schemes", *Proc. Natl. Acad. Sci. USA,* 87: 2264-2268.
Lardizabal, K., et al. (2000), "Purification of a jojoba embryo wax synthase, cloning of its cDNA, and production of high levels of wax in seeds of transgenic *Arabidopsis", Plant Physiol.,* 122: 645-655.
Li, F., et al. (2008), "Identification of the wax ester synthase/acyl-coenzyme A:Diacylglycerol Acyltransferase WSD1 required for stem wax ester biosynthesis in *Arabidopsis", Plant Physiology,* 148: 97-107.
Liénard, M., et al. (2010), "Evolution of multicomponent pheromone signals in small ermine moths involves a single fatty-acyl reductase gene", *Proc Natl. Acad. Sci.,* 107(24): 10955-10960.
Maes, L., et al. (2011), "Dissection of the phytohormonal regulation of trichome formation and biosynthesis of the antimalarial compound artemisinin in *Artemisia annua plants", New Phytologist Trust* 189: 176-189.
Metz, J., et al. (2000), "Purification of a jojoba embryo fatty acyl-coenzyme a reductase and expression of it's cDNA in high erucic acid rapeseed", *Plant Physiology,* 122: 635-644.
Méndez-Alvarez, S., et al. (1994), "Transformation of chlorobium limicola by a plasmid that confers the ability to utilize thiosulfate" *Journal of Bacteriology,*176(23):7395-7397.
Office Action dated May 9, 2013 issued in U.S. Appl. No. 13/332,101.
Office Action dated Nov. 14, 2012 issued in U.S. Appl. No. 13/324,623.
Office Action dated Apr. 15, 2013 issued in U.S. Appl. No. 13/413,426.
Office Action dated Apr. 18, 2013 issued in U.S. Appl. No. 13/404,717.
Office Action dated Jul. 20, 2012 issued in U.S. Appl. No. 13/324,623.
Office Action dated Feb. 25, 2013 issued in U.S. Appl. No. 13/324,623.
Ohnuma M., et al. (2008), "Polyethylene glycol (PEG)-mediated transient gene expression in a red alga, cyanidioschyzon merolae 10D", *Plant Cell Physiol.* 49(1):117-120.
Perrone, C., et al. (1998), "the chlamydomonas IDA7 locus encodes a 140 kDa dynein intermediate chain required to assemble the I1 inner arm complex", *Molecular biology of the Cell,* 9:3351-3365.
Reiser, S., et al. (1997), "Isolation of mutants of *Acinetobacter calcoaceticus* deficient in wax ester synthesis and complementation of one mutation with a gene encoding a fatty acyl coenzyme a reductase", *Journal of Bacteriology,* 179(9), 2969-2975.
Rowland, O., et al. (2006), "CER4 encodes an alcohol-forming fatty acyl-coenzyme a reductase involved in cuticular wax production in *arabidopis", Plant Physiology,* 142: 866-877.
Sonnhammer, E., et al. (1998), "Pfam: multiple sequence alignments and HMM-profiles of protein domains" *Nucleic Acids Research* 26(1):320-322.
Stemmer, W. (1994), "DNA shuffling by random fragmentation and reassembly: in vitro recombination for molecular evolution", *Proc. Natl. Acad. Sci. USA,* 91: 10747-10751.
Yen, C., et al. (2005), "A human skin multifunctional O-acyltransferase that catalyzes the synthesis of acylglycerols, waxes, and retinyl esters", *Journal of Lipid Research* 46: 2388-2397.

* cited by examiner

| Thioesterases | |
|---|---|
| Cc1FatB1: construct sequence | SEQ ID NO: 1 |
| MANGSAVSLKSGSLNTQEDTSSSPPPRAFINQLPDWSMLLTAITTVFVAAEKQWTMLDRKSKRSDMLVDS<br>FGMERIVQDGLVFRQSFSIRSYEIGADRRASIETLMNHLQETSLNHCKSIRLLNEGFGRTPEMCKRDLIW<br>VVTRMHIMVNRYPTWGDTVEINTWVSQSGKNGMGRDWLISDCNTGEILIRATSAWAMMNQKTRRLSKLPY<br>EVSQEIAPHFVDSPPVIEDGDRKLHKFDVKTGDSIRKGLTPRWNDLDVNQHVNNVKYIGWILESMPTEVL<br>ETHELCFLTLEYRRECGRDSVLESVTAMDPSNEGGRSHYQHLLRLEDGTDIVKGRTEWRPKNARNIGAIS<br>TGKTSNGNPAS | |
| Cc1FatB1: coding sequence from genomic DNA | SEQ ID NO: 2 |
| AASSAFFPVTTPGTSRKPGKFGNWLSSLSPPFRPKSIPSGGFQVKANASAHPKANGSAVSLKSGSLNTQE<br>DTSSSPPPRAFINQLPDWSMLLTAITTVFVAAEKQWTMLDRKSKRSDMLVDSFGMERIVQDGLVFRQSFS<br>IRSYEIGADRRASIETLMNHLQETSLNHCKSIRLLNEGFGRTPEMCKRDLIWVVTRMHIMVNRYPTWGDT<br>VEINTWVSQSGKNGMGRDWLISDCNTGEILIRATSAWAMMNQKTRRLSKLPYEVSQEIAPHFVDSPPVIE<br>DGDRKLHKFDVKTGDSIRKGLTPRWNDLDVNQHVNNVKYIGWILESMPTEVLETHELCFLTLEYRRECGR<br>DSVLESVTAMDPSNEGGRSHYQHLLRLEDGTDIVKGRTEWRPKNARNIGAISTGKTSNGNPAS | |
| Cd1FatB1: construct sequence | SEQ ID NO: 3 |
| MGINGSSVGLKSGSLKTQEDTPSSPPPRTFINQLPDWSMLLAAITTVFLAAEKQWMMLDWKPKRPDMLVD<br>PFGLGRIVQDGLVFRQNFSIRSYEIGADRTASIETLMNHLQETALNHVKSAGLLNDGFGRTPEMYKRDLI<br>WVVAKMQVMVNRYPTWGDTVEVNTWVAKSGKNGMRRDWLISDCNTGEILTRASSVWVMMNQKTRRLSKIP<br>DEVRHEIEPHFVDSPPVIEDDDRKLPKLDEKTADSIRKGLTPRWNDLDVNQHVNNVKYIGWILESTPQEV<br>LETQELCSLTLEYRRECGRDSVLESLTAVDHSGKGSGSNFQHLLRLEDGGEIVKGRTEWRPKNAVINGAV<br>APGETSPGNSVS | |
| Cd1FatB1: coding sequence from genomic DNA | SEQ ID NO: 4 |
| AASSACFPVPSPDASRKPGKHGNGASSLSPFKPKSIPSGGLQVQANASAPPKINGSSVGLKSGSLKTQED<br>TPSSPPPRTFINQLPDWSMLLAAITTVFLAAEKQWMMLDWKPKRPDMLVDPFGLGRIVQDGLVFRQNFSI<br>RSYEIGADRTASIETLMNHLQETALNHVKSAGLLNDGFGRTPEMYKRDLIWVVAKMQVMVNRYPTWGDTV<br>EVNTWVAKSGKNGMRRDWLISDCNTGEILTRASSVWVMMNQKTRRLSKIPDEVRHEIEPHFVDSPPVIED<br>DDRKLPKLDEKTADSIRKGLTPRWNDLDVNQHVNNVKYIGWILESTPQEVLETQELCSLTLEYRRECGRD<br>SVLESLTAVDHSGKGSGSNFQHLLRLEDGGEIVKGRTEWRPKNAVINGAVAPGETSPGNSVS | |
| Cp1FatB1: construct sequence | SEQ ID NO: 5 |
| MANGSAVSLKDGSLETQEGTSSSHPPRTFINQLPDWSMLLSAITTVFVAAEKQWTMLDRKSKRPDMLVE<br>PFVQDGVSFRQSFSIRSYEIGADRTASIETLMNIFQETSLNHCKSLGLLNDGFGRTPEMCKRDLIWVVTK<br>MQIEVNRYPTWGDTIEVTTWVSESGKNGMSRDWLISDCHTGEILIRATSVWAMMNQKTRRLSKIPDEVRQ<br>EIVPYFVDSAPVIEDDRKLHKLDVKTGDSIRNGLTPRWNDLDVNQHVNNVKYIGWILKSVPTEVFVTQEL<br>CGLTLEYRRECRRDSVLESVTAMDPSKEGDRSLYQHLLRLENGADIALGRTEWRPKNAGTNGAISTTKTS<br>PGNSVS | |
| Cp1FatB1: coding sequence from genomic DNA | SEQ ID NO: 6 |
| AASSAFFSFPAPGTSLKPGKFGNWPSNLSVPFNPKANHNGGFHVKANTSAHPKANGSAVSLKDGSLETQE<br>GTSSSSHPPRTFINQLPDWSMLLSAITTVFVAAEKQWTMLDRKSKRPDMLVEPFVQDGVSFRQSFSIRSY<br>EIGADRTASIETLMNIFQETSLNHCKSLGLLNDGFGRTPEMCKRDLIWVVTKMQIEVNRYPTWGDTIEVT<br>TWVSESGKNGMSRDWLISDCHTGEILIRATSVWAMMNQKTRRLSKIPDEVRQEIVPYFVDSAPVIEDDRK<br>LHKLDVKTGDSIRNGLTPRWNDLDVNQHVNNVKYIGWILKSVPTEVFVTQELCGLTLEYRRECRRDSVLE<br>SVTAMDPSKEGDRSLYQHLLRLENGADIALGRTEWRPKT | |

Figure 1

| Thioesterases (cont.) | |
|---|---|
| oil palm thioesterase | SEQ ID NO: 7 |
| MVASIVAWAFFPTPSFSPTASAKASKTIGEGSENLNVRGIIAKPTSSSAAKQGKVMAQAVPKINGAKVGL<br>KAESQKAEEDAAPSSAPRTFYNQLPDWSVLLAAVTTIFLAAEKQWTLLDWKPRRPDMLTGAFSLGKIVQD<br>GLVFRQNFSIRSYEIGADRTASIETLMNHLQETALNHVRNAGLLGDGFGATPEMSKRNLIWVVTKMQVLI<br>EHYPSWGDVVEVDTWVGASGKNGMRRDWHVRDYRTGQTILRATSIWVMMDKHTRKLSKMPEEVRAEIGPY<br>FMEHAAIVDEDSRKLPKLDDDTADYIKWGLTPRWSDLDVNQHVNNVKYIGWILESAPISILENHELASMT<br>LEYRRECGRDSVLQSLTAVANDCTGGLPEASIECQHLLQLECGAEIVRGRTQWRPRRASGPTSAGSA | |
| oil palm thioesterase without transit peptide | SEQ ID NO: 8 |
| LPDWSVLLAAVTTIFLAAEKQWTLLDWKPRRPDMLTGAFSLGKIVQDGLVFRQNFSIRSYEIGADRTASI<br>ETLMNHLQETALNHVRNAGLLGDGFGATPEMSKRNLIWVVTKMQVLIEHYPSWGDVVEVDTWVGASGKNG<br>MRRDWHVRDYRTGQTILRATSIWVMMDKHTRKLSKMPEEVRAEIGPYFMEHAAIVDEDSRKLPKLDDDTA<br>DYIKWGLTPRWSDLDVNQHVNNVKYIGWILESAPISILENHELASMTLEYRRECGRDSVLQSLTAVANDC<br>TGGLPEASIECQHLLQLECGAEIVRGRTQWRPRRASGPTSAGSA | |
| oil palm thioesterase without residues 1-118 | SEQ ID NO: 9 |
| DWKPRRPDMLTGAFSLGKIVQDGLVFRQNFSIRSYEIGADRTASIETLMNHLQETALNHVRNAGLLGDGF<br>GATPEMSKRNLIWVVTKMQVLIEHYPSWGDVVEVDTWVGASGKNGMRRDWHVRDYRTGQTILRATSIWVM<br>MDKHTRKLSKMPEEVRAEIGPYFMEHAAIVDEDSRKLPKLDDDTADYIKWGLTPRWSDLDVNQHVNNVKY<br>IGWILESAPISILENHELASMTLEYRRECGRDSVLQSLTAVANDCTGGLPEASIECQHLLQLECGAEIVR<br>GRTQWRPRRASGPTSAGSA | |

Figure 1 (cont.)

| Acyl-CoA Synthetases | |
|---|---|
| Faa2p | SEQ ID NO: 10 |
| MAAPDYALTDLIESDPRFESLKTRLAGYTKGSDEYIEELYSQLPLTSYPRYKTFLKKQAVAISNPDNEAG<br>FSSIYRSSLSSENLVSCVDKNLRTAYDHFMFSARRWPQRDCLGSRPIDKATGTWEETFRFESYSTVSKRC<br>HNIGSGILSLVNTKRKRPLEANDFVVAILSHNNPEWILTDLACQAYSLTNTALYETLGPNTSEYILNLTE<br>APILIFAKSNMYHVLKMVPDMKFVNTLVCMDELTHDELRMLNESLLPVKCNSLNEKITFFSLEQVEQVGC<br>FNKIPAIPPTPDSLYTISFTSGTTGLPKGVEMSHRNIASGIAFAFSTFRIPPDKRNQQLYDMCFLPLAHI<br>FERMVIAYDLAIGFGIGFLHKPDPTVLVEDLKILKPYAVALVPRILTRFEAGIKNALDKSTVQRNVANTI<br>LDSKSARFTARGGPDKSIMNFLVYHRVLIDKIRDSLGLSNNSFIITGSAPISKDTLLFLRSALDIGIRQG<br>YGLTETFAGVCLSEPFEKDVGSCGAIGISAECRLKSVPEMGYHADKDLKGELQIRGPQVFERYFKNPNET<br>SKAVDQDGWFSTGDVAFIDGKGRISVIDRVKNFFKLAHGEYIAPEKIENIYLSSCPYITQIFVFGDPLKT<br>FLVGIVGVDVDAAQPILAAKHPEVKTWTKEVLVENLNRNKKLRKEFLNKINKCTDGLQGFEKLHNIKVGL<br>EPLTLEDDVVTPTFKIKRAKASKFFKDTLDQLYAEGSLVKTEKL | |
| SCRG_04483 | SEQ ID NO: 11 |
| MAAPDYALTDLIESDPRFESLKTRLAGYTKGSDEYIEELYSQLPLTSYPRYKTFLKKQAVAISNPDNEAG<br>FSSIYRSSLSSENLVSCVDKNLRTAYDHFMFSARRWPQRDCLGSRPIDKATGTWEETFRFESYSTVSKRC<br>HNIGSGILSLVNTKRKRPLEANDFVVAILSHNNPEWILTDLACQAYSLTNTALYETLGPNTSEYILNLTE<br>APILIFAKSNMYHVLKMVPDMKFVNTLVCMDELTHDELRMLNESLLPVKCNSLNEKITFFSLEQVEQVGC<br>FNKIPAIPPTPDSLYTISFTSGTTGLPKGVEMSHRNIASGIAFAFSTFRIPPDKRNQQLYDMCFLPLAHI<br>FERMVIAYDLAIGFGIGFLHKPDPTVLVEDLKILKPYAVALVPRILTRFEAGIKNALDKSTVQRNVANTI<br>LDSKSARFTARGGPDKSIMNFLVYHRVLIDKIRDSLGLSNNSFIITGSAPISKDTLLFLRSALDIGIRQG<br>YGLTETFAGVCLSEPFEKDVGSCGAIGISAECRLKSVPEMGYHADKYLKGELQIRGPQVFERYFKNPNET<br>SKAVDQDGWFSTGDVAFIDGKGRISVIDRVKNFFKLAHGEYIAPEKIENIYLSSCPYITQIFVFGDPLKT<br>FLVGIVGVDVDAAQPILAAKHPEVKTWTKEVLVENLNRNKKLRKEFLNKINKCTDGLQGFEKLHNIKVGL<br>EPLTLEDDVVTPTFKIKRAKASKFFKDTLDQLYAEGSLVKTEKL | |
| FadD | SEQ ID NO: 12 |
| MKKVWLNRYPADVPTEINPDRYQSLVDMFEQSVARYADQPAFVNMGEVMTFRKLEERSRAFAAYLQQGLG<br>LKKGDRVALMMPNLLQYPVALFGILRAGMIVVNVNPLYTPRELEHQLNDSGASAIVIVSNFAHTLEKVVD<br>KTAVQHVILTRMGDQLSTAKGTVVNFVVKYIKRLVPKYHLPDAISFRSALHNGYRMQYVKPELVPEDLAF<br>LQYTGGTTGVAKGAMLTHRNMLANLEQVNATYGPLLHPGKELVVTALPLYHIFALTINCLLFIELGGQNL<br>LITNPRDIPGLVKELAKYPFTAITGVNTLFNALLNNKEFQQLDFSSLHLSAGGGMPVQQVVAERWVKLTG<br>QYLLEGYGLTECAPLVSVNPYDIDYHSGSIGLPVPSTEAKLVDDDDNEVPPGQPGELCVKGPQVMLGYWQ<br>RPDATDEIIKNGWLHTGDIAVMDEEGFLRIVDRKKDMILVSGFNVYPNEIEDVVMQHPGVQEVAAVGVPS<br>GSSGEAVKIFVVKKDPSLTEESLVTFCRRQLTGYKVPKLVEFRDELPKSNVGKILRRELRDEARGKVDNK<br>A | |

Figure 2

Acyl-CoA Synthetases (cont.)

| FadK | SEQ ID NO: 13 |
|---|---|

MKVTLTFNEQRRAAYRQQGLWGDASLADYWQQTARAMPDKIAVVDNHGASYTYSALDHAASCLANWMLAK
GIESGDRIAFQLPGWCEFTVIYLACLKIGAVSVPLLPSWREAELVWVLNKCQAKMFFAPTLFKQTRPVDL
ILPLQNQLPQLQQIVGVDKLAPATSSLSLSQIIADNTSLTTAITTHGDELAAVLFTSGTEGLPKGVMLTH
NNILASERAYCARLNLTWQDVFMMPAPLGHATGFLHGVTAPFLIGARSVLLDIFTPDACLALLEQQRCTC
MLGATPFVYDLLNVLEKQPADLSALRFFLCGGTTIPKKVARECQQRGIKLLSVYGSTESSPHAVVNLDDP
LSRFMHTDGYAAAGVEIKVVDDARKTLPPGCEGEEASRGPNVFMGYFDEPELTARALDEEGWYYSGDLCR
MDEAGYIKITGRKKDIIVRGGENISSREVEDILLQHPKIHDACVVAMSDERLGERSCAYVVLKAPHHSLS
LEEVVAFFSRKRVAKYKYPEHIVVIEKLPRTTSGKIQKFLLRKDIMRRLTQDVCEEIE

| MACS | SEQ ID NO: 14 |
|---|---|

MQWLKSFQICKVLQGFSLSPTQLHRRLFSRVGAPRWNDHDSPEEFNFASDVLDYWAQMEEEGKRGPSPAF
WWVNGQGDEIKWSFRKLRDLTCRTANVFEQICGLQQGDHLALILPRVPEWWLVTVGCMRTGIIFMPGTTQ
LKAKDILYRIQISRAKAIVTTASLVPEVESVASECPDLKTKLVVSDHSHEGWLDFCSLIKSASPDHTCIK
SKMKDPMAIFFTSGTTGYPKMAKHNQGLAFRSYIPSCRKLLKLKTSDILWCMSDPGWILATVGCLIEPWT
SGCTVFIHHLPQFDPKVIVEVLFKYPITQCLAAPGVYRMVLQQKTSNLRFPTLEHCTTGGESLLPEEYEQ
WKQRTGLSIHEVYGQSETGISSATLREMKIKRGSIGKAILPFDLQIIDEKGNILPPNTEGYIGIRIKPTR
PLGLFMEYENSPESTSEVECGDFYNSGDRATIDEEGYIWFLGRGDDVINASGYRIGPAEVENALAEHPAV
AESAVVSSPDKDRGEVVKAFIVLNPEFLSHDQEQLIKELQHHVKSVTAPYKYPRKVEFVSELPKTVTGKI
KRKELRNKEFGQL

Figure 2 (cont.)

Alcohol-Forming Fatty Acyl Reductases

| Maqu_2220 | SEQ ID NO: 15 |
| --- | --- |
| MAIQQVHHADTSSSKVLGQLRGKRVLITGTTGFLGKVVLERLIRAVPDIGAIYLLIRGNKRHPDARSRFL EEIATSSVFDRLREADSEGFDAFLEERIHCVTGEVTEAGFGIGQEDYRKLATELDAVINSAASVNFREEL DKALAINTLCLRNIAGMVDLNPKLAVLQVSTCYVNGMNSGQVTESVIKPAGEAVPRSPDGFYEIEELVRL LQDKIEDVQARYSGKVLERKLVDLGIREANRYGWSDTYTFTKWLGEQLLMKALNGRTLTILRPSIIESAL EEPAPGWIEGVKVADAIILAYAREKVTLFPGKRSGIIDVIPVDLVANSIILSLAEALGEPGRRRIYQCCS GGGNPISLGEFIDHLMAESKANYAAYDHLFYRQPSKPFLAVNRALFDLVISGVRLPLSLTDRVLKLLGNS RDLKMLRNLDTTQSLATIFGFYTAPDYIFRNDELMALANRMGEVDKGLFPVDARLIDWELYLRKIHLAGL NRYALKERKVYSLKTARQRKKAA | |
| **FAR6** | **SEQ ID NO: 16** |
| MATTNVLATSHAFKLNGVSYFSSFPRKPNHYMPRRRLSHTTRRVQTSCFYGETSFEAVTSLVTPKTETSR NSDGIGIVRFLEGKSYLVTGATGFLAKVLIEKLLRESLEIGKIFLLMRSKDQESANKRLYDEIISSDLFK LLKQMHGSSYEAFMKRKLIPVIGDIEEDNLGIKSEIANMISEEIDVIISCGGRTTFDDRYDSALSVNALG PAYVTGKREGTVLETPLCIGENITSDLNIKSELKLASEAVRKFRGREEIKKLKELGFERAQHYGWENSYT FTKAIGEAVIHSKRGNLPVVIIRPSIIESSYNEPFPGWIQGTRMADPIILAYAKGQISDFWADPQSLMDI IPVDMVANAAIAAMAKHGCGVPEFKVYNLTSSSHVNPMRAGKLIDLSHQHLCDFPLEETVIDLEHMKIHS SLEGFTSALSNTIIKQERVIDNEGGGLSTKGKRKLNYFVSLAKTYEPYTFFQARFDNTNTTSLIQEMSME EKKTFGFDIKGIDWEHYIVNVHLPGLKKEFLSKKKTE | |
| **FAR6 without transit peptide** | **SEQ ID NO: 17** |
| CFYGETSFEAVTSLVTPKTETSRNSDGIGIVRFLEGKSYLVTGATGFLAKVLIEKLLRESLEIGKIFLLM RSKDQESANKRLYDEIISSDLFKLLKQMHGSSYEAFMKRKLIPVIGDIEEDNLGIKSEIANMISEEIDVI ISCGGRTTFDDRYDSALSVNALGPAYVTGKREGTVLETPLCIGENITSDLNIKSELKLASEAVRKFRGRE EIKKLKELGFERAQHYGWENSYTFTKAIGEAVIHSKRGNLPVVIIRPSIIESSYNEPFPGWIQGTRMADP IILAYAKGQISDFWADPQSLMDIIPVDMVANAAIAAMAKHGCGVPEFKVYNLTSSSHVNPMRAGKLIDLS HQHLCDFPLEETVIDLEHMKIHSSLEGFTSALSNTIIKQERVIDNEGGGLSTKGKRKLNYFVSLAKTYEP YTFFQARFDNTNTTSLIQEMSMEEKKTFGFDIKGIDWEHYIVNVHLPGLKKEFLSKKKTE | |
| **FARXIII** | **SEQ ID NO: 18** |
| MSANTMETDEQFTDNSPIVNFYSGKSVFVTGATGFLGTVLVEKLLFSCKGINNIYILIKQTEDLTIEARI LNYLNSKAFHRVKNTNPELMKKIIPICGNLEDKNLGISDSDMKTLLEEVSIVFHVAAKLLFKMSLTAAVN INTKPTEQLIAICKKMRRNPIFIYVSSAYSNVNEQIIDEKVYNTGVPLETIYDTLDTENTRITDIFLDKR PNTYTYSKALAEVVVEKEFDESAAIVRPSIIVSSIREPIPGWLSGSHGFPRVVGAACKGLLLRWHGDGTV VCDLIPVDHVANLIIAAAWESNERRLMGNKGVKVYNCCSSLRNPIDVITVVKTCIKYRKYFGTRTMSIFT PRFIMKKNYFIYKLLYFTCHTIPAAIIDGFFWLTGRIPIMLKTLDKLSKISSVLEYFTHHQFIFLDSNVR GLLRRMEGTDRQIFNFDVTEIEWEPYLQNFVRGIANNYDYSM | |

Figure 3

| Alcohol-Forming Fatty Acyl Reductases (cont.) | |
|---|---|
| Maqu_2507 | SEQ ID NO: 19 |
| MNYFLTGGTGFIGRFLVEKLLARGGTVYVLVREQSQDKLERLRERWGADDKQVKAVIGDLTSKNLGIDAK<br>TLKSLKGNIDHVFHLAAVYDMGADEEAQAATNIEGTRAAVQAAEAMGAKHFHHVSSIAAAGLFKGIFRED<br>MFEEAEKLDHPYLRTKHESEKVVREECKVPFRIYRPGMVIGHSETGEMDKVDGPYYFFKMIQKIRHALPQ<br>WVPTIGIEGGRLNIVPVDFVVDALDHIAHLEGEDGNCFHLVDSDPYKVGEILNIFCEAGHAPRMGMRIDS<br>RMFGFIPPFIRQSIKNLPPVKRITGALLDDMGIPPSVMSFINYPTRFDTRELERVLKGTDIEVPRLPSYA<br>PVIWDYWERNLDPDLFKDRTLKGTVEGKVCVVTGATSGIGLATAEKLAEAGAILVIGARTKETLDEVAAS<br>LEAKGGNVHAYQCDFSDMDDCDRFVKTVLDNHGHVDVLVNNAGRSIRRSLALSFDRFHDFERTMQLNYFG<br>SVRLIMGFAPAMLERRRGHVVNISSIGVLTNAPRFSAYVSSKSALDAFSRCAAAEWSDRNVIFTTINMPL<br>VKTPMIAPTKIYDSVPTLTPDEAAQMVADAIVYRPKRIATRLGVFAQVLHALAPKMGEIIMNTGYRMFPD<br>SPAAAGSKSGEKPKVSTEQVAFAAIMRGIYW | |
| Hch_05075 | SEQ ID NO: 20 |
| MKQSLTLTAFANKNVLITGTTGFVGKVVLEKLLRSVPTIGKIYLLIRGNSKNPTARKRFQNEIATSSIFD<br>TLKASQGSRFEELCEIRIHCVTGEVTEPLFGLSEKDFTDLAADIDVIINSAASVNFREALDQALTINTLC<br>LKNIIELSRRAADCPVVQVSTCYVNGFNQGVMEEEIVSPAGERIERSERGYYEVEPLIARLLQDVEQVSA<br>AAADDHSREKDLIDLGIKEANKYGWNDTYTFTKWMGEQLLMKELYGKTLTILRPSIVESTLLGPAPGWIE<br>GVKVADAIILAYAREKVSLFPGKKNAVIDIIPADLVANSIILSATEALLDSGAHRIYQCCSSEVNPIRIR<br>EVIGHVQQEAEHNYQTHDKLFYRKPKKPFVMIPGAVFHALMAISFHMLKWSSRLQSLFGRKASGRKLSNM<br>ETTMKLSKVFSFYTSPSYTFSNRRLQELSTRLGEYDQSEFPVNAGMYDWAHYLREVHVAGLNKYALRPKV<br>VKMNFPAAKPRSRAA | |
| jjfar | SEQ ID NO: 21 |
| MEEMGSILEFLDNKAILVTGATGSLAKIFVEKVLRSQPNVKKLYLLLRATDDETAALRLQNEVFGKELFK<br>VLKQNLGANFYSFVSEKVTVVPGDITGEDLCLKDVNLKEEMWREIDVVVNLAATINFIERYDVSLLINTY<br>GAKYVLDFAKKCNKLKIFVHVSTAYVSGEKNGLILEKPYYMGESLNGRLGLDINVEKKLVEAKINELQAA<br>GATEKSIKSTMKDMGIERARHWGWPNVYVFTKALGEMLLMQYKGDIPLTIIRPTIITSTFKEPFPGWVEG<br>VRTIDNVPVYYGKGRLRCMLCGPSTIIDLIPADMVVNATIVAMVAHANQRYVEPVTYHVGSSAANPMKLS<br>ALPEMAHRYFTKNPWINPDRNPVHVGRAMVFSSFSTFHLYLTLNFLLPLKVLEIANTIFCQWFKGKYMDL<br>KRKTRLLLRLVDIYKPYLFFQGIFDDMNTEKLRIAAKESIVEADMFYFDPRAINWEDYFLKTHFPGVVEH<br>VLN | |

Figure 3 (cont.)

Wax Ester Synthases

| M.ELB17 WS | SEQ ID NO: 22 |
|---|---|

MKRLATLDASWLAVESDDTPMHVGNLQIFSLPDNAPSTFAGDLVKSMKQAGNVELPWGCKLVWPGFLGRV
LAPTWKHDKHIDLDYHVRHSALPKPGGERELGELVSRLHSNPLDLSRPLWECHMIEGLEHNRFALYTKMH
HCMIDGISGVRLMQRVLSKSPDERDMLPPWSVRPESTRGKKTDSEASVPGAISQAMEALKLQLGLAPRLW
QASNRLIHSVRHPEDGLTAPFTGPVSKINHRVTGQRRFATQQYQLEDMKAMARASGSSMNDIVLYLCGTA
LRRFLLEQDDLPEISLTAGIPVNIRPADDEGTGTQISFMIAALATNQPDPLTRLKCIKESSCKAKEHLQK
LPKKALTQYTMMLMSPYILQLMSGLGGRMRPVFNVTISNVPGPTEDLYYEGAKLEAMYPVSLITHGGALN
ITCLSYAGSLNFGFTGCRDTLPSMQKLAVYTGEALEELRTLLLPPKKKPSPRKPRTAAKKKPAVNSNAS

| DSM8798 WS1 | SEQ ID NO: 23 |
|---|---|

MTPLNPTDQLFLWLEKRQQPMHVGGLQLFSFPEGAPDDYVAQLADQLRQKTEVTAPFNQRLSYRLGQPVW
VEDEHLDLEHHFRFEALPTPGRIRELLSFVSAEHSHLMDRERPMWEVHLIEGLKDRQFALYTKVHHSLVD
GVSAMRMATRMLSENPDEHGMPPIWDLPCLSRDRGESDGHSLWRSVTHLLGLSGRQLGTIPTVAKELLKT
INQARKDPAYDSIFHAPRCMLNQKITGSRRFAAQSWCLKRIRAVCEAYGTTVNDVVTAMCAAALRTYLMN
QDALPEKPLVAFVPVSLRRDDSSGGNQVGVILASLHTDVQEAGERLLKIHHGMEEAKQRYRHMSPEEIVN
YTALTLAPAAFHLLTGLAPKWQTFNVVISNVPGPSRPLYWNGAKLEGMYPVSIDMDRLALNMTLTSYNDQ
VEFGLIGCRRTLPSLQRMLDYLEQGLAELELNAGL

| DSM8798 WS2 | SEQ ID NO: 24 |
|---|---|

MKRLGTLDASWLAVESEDTPMHVGTLQIFSLPEGAPETFLRDMVTRMKEAGDVAPPWGYKLAWSGFLGRVIA
PAWKVDKDIDLDYHVRHSALPRPGGERELGILVSRLHSNPLDFSRPLWECHVIEGLENNRFALYTKMHHSMI
DGISGVRLMQRVLTTDPERCNMPPPWTVRPHQRRGAKTDKEASVPAAVSQAMDALKLQADMAPRLWQAGNRL
VHSVRHPEDGLTAPFTGPVSVLNHRVTAQRRFATQHYQLDRLKNLAHASGGSLNDIVLYLCGTALRRFLAEQ
NNLPDTPLTAGIPVNIRPADDEGTGTQISFMIASLATDEADPLNRLQQIKTSTRRAKEHLQKLPKSALTQYT
MLLMSPYILQLMSGLGGRMRPVFNVTISNVPGPEGTLYYEGARLEAMYPVSLIAHGGALNITCLSYAGSLNF
GFTGCRDTLPSMQKLAVYTGEALDELESLILPPKKRARTRK

| petunia WS | SEQ ID NO: 25 |
|---|---|

MKSLATELRNRSSEPCLKPIETKRKTIEEYETVAVEEEPLSPTARLFHDANFNVHVVVIIALDTRISPQP
IKDKLVHTLLKHPRFTSLMVVDEENLADMKWVQTKIDLDQHIIVPEVDETQLESPDKFVEDYIYNLTKTS
LDRTKPLWDLHLVNVKTRDAEAVALLRVHHSLGDGTSLISLLLACTRQTADELKLPTIPTKKRRPTPSGY
STKEESFKLWHYLAVIWLFIRMIGNTLVDVLMFIITVIFLKDTKTPINTVPDSESRVRRIVHRIIDLDDL
KLVKNAMNMTINDVALGITQAGLSKYLNRRYAVDEEDKGDTERNNNLPKNIRLRSCLVINLRPSAGIEDL
ADMMEKGPKEKRGWGNWFGYVLLPFKIALRDDPLDYVKEAKATVDRKKRSFEALYTLIMAEVLIKIFGIK
VATAVTVRVFSNATVCFSNVVGPQEEIGFCGHPISYLAPSIYGQPSALMINFQSYIDKMIIVVAVDEGAI
PDPQQLLDDFENSLHLIKEAVLERGLVKNLK

| *Mus musculus* WS | SEQ ID NO: 26 |
|---|---|

MFWPTKKDLKTAMEVFALFQWALSALVIVTTVIIVNLYLVVFTSYWPVTVLMLTWLAFDWKTPERGGRRFTC
VRKWRLWKHYSDYFPLKMVKTKDISPDRNYILVCHPHGLMAHSCFGHFATDTTGFSKTFPGITPYMLTLGAF
FWVPFLRDYVMSTGSCSVSRSSMDFLLTQKGTGNMLVVVVGGLAECRYSTPGSTTLFLKKRQGFVRTALKHC
VSLIPAYAFGETDLYDQHIFTPGGFVNRFQKWFQKMVHIYPCAFYGRGLTKNSWGLLPYSQPVTTVVGEPLP
LPKIENPSEEIVAKYHTLYIDALRKLFDQHKTKFGISETQELVIV

Figure 4

| Wax Ester Synthases (cont.) | |
|---|---|
| jojoba WS | SEQ ID NO: 27 |
| MEVEKELKTFSEVWISAIAAACYCRFVPAVAPHGGALRLLLLLPVVLLFIFLPLRLSSFHLGGPTALYLV WLANFKLLLFAFHLGPLSNPSLSLLHFISTTLLPIKFRDDPSNDHEKNKRTLSFEWRKVVLFVAKLVFFA GILKIYEFRKDLPHFVISVLYCFHFYLGTEITLAASAVIARATLGLDLYPQFNEPYLATSLQDFWGRRWN LMVSDILGLTTYQPVRRVLSRWVRLRWEVAGAMLVAFTVSGLMHEVFFFYLTRARPSWEVTGFFVLHGVC TAVEMVVKKAVSGKVRLRREVSGALTVGFVMVTGGWLFLPQLVRHGVDLKTIDEYPVMFNYTQKKLMGLL GW | |
| ADP1 WS | SEQ ID NO: 28 |
| MRPLHPIDFIFLSLEKRQQPMHVGGLFLFQIPDNAPDTFIQDLVNDIRISKSIPVPPFNNKLNGLFWDED EEFDLDHHFRHIALPHPGRIRELLIYISQEHSTLLDRAKPLWTCNIIEGIEGNRFAMYFKIHHAMVDGVA GMRLIEKSLSHDVTEKSIVPPWCVEGKRAKRLREPKTGKIKKIMSGIKSQLQATPTVIQELSQTVFKDIG RNPDHVSSFQAPCSILNQRVSSSRRFAAQSFDLDRFRNIAKSLNVTINDVVLAVCSGALRAYLMSHNSLP SKPLIAMVPASIRNDDSDVSNRITMILANLATHKDDPLQRLEIIRRSVQNSKQRFKRMTSDQILNYSAVV YGPAGLNIISGMMPKRQAFNLVISNVPGPREPLYWNGAKLDALYPASIVLDGQALNITMTSYLDKLEVGL IACRNALPRMQNLLTHLEEEIQLFEGVIAKQEDIKTAN | |

Figure 4 (cont.)

FOUR-GENE PATHWAY FOR WAX ESTER SYNTHESIS

REFERENCE TO A SEQUENCE LISTING

This application contains references to amino acid sequences and/or nucleic acid sequences which have been submitted concurrently herewith as the sequence listing text file "60930821.1.txt", file size 251 KiloBytes (KB), created on 23 Feb. 2012. The aforementioned sequence listing is hereby incorporated by reference in its entirety pursuant to 37 C.F.R. §1.52(e)(5).

FIELD OF THE INVENTION

The present invention relates to the fields of bioengineering, metabolic biochemistry, and molecular biology. In particular, the invention relates to the production in recombinant microorganisms of lipids such as wax esters that can be used for producing fuels and chemicals.

BACKGROUND

The ever-increasing global demand for energy has led to depletion of fossil fuels, which are buried combustible geologic deposits of organic materials that have been converted to crude oil, coal, natural gas, or heavy oils. Because fossil fuels are formed by exposure to heat and pressure in the earth's crust over hundreds of millions of years, they are a finite, non-renewable resource. Further, the burning of fossil fuels is thought to play a key role in global warming. Accordingly, there is a need for non-fossil fuel energy sources.

Hydrocarbons from biological sources represent a cleaner, sustainable alternative energy source. Further, many industries, including plastics and chemical manufacturers, rely heavily on the availability of hydrocarbons for manufacturing processes. Currently, energy-rich lipids and fatty acids ("nature's petroleum") are isolated from plant and animal oils to produce diverse products such as fuels and oleochemicals. Recent efforts have focused on the microbial production of fatty acids and fatty acid derivatives by cost-effective bioprocesses. Methods of producing fatty acids and/or fatty acid derivatives in microbial hosts are described in, e.g., PCT Publication Nos. WO 2007/136762, WO 2008/119082, WO 2009/009391, WO 2009/076559, WO 2009/111513, WO 2010/006312, WO 2010/044960, WO 2010/118410, WO 2010/126891, WO 2011/008535 and WO 2011/019858 and in Schirmer et al., *Science* 329(5991):559-562 (2010).

Free fatty acids are known to cause damage to cellular membranes and are thus difficult to produce in amounts sufficient for large scale production. The reduction of fatty acids to more neutral lipids such as wax esters may help to circumvent free fatty acid toxicity. Wax esters possess high energy density relative to shorter-chain biofuel products such as ethanol, and can be produced in cultured cells via a series of enzymatic processes. Wax esters have numerous commercial applications in, e.g., the medical, cosmetic and dietetic industries. For example, wax esters may be used to produce candles, cosmetics, lubricants, printing inks, solvents and fuels.

SUMMARY OF THE INVENTION

The present invention provides improved nucleic acid molecules, recombinant microorganisms, and methods for producing fatty acid esters, such as but not limited to wax esters, using a four-enzyme pathway engineered into a recombinant microorganism. The enzymes of the pathway can be encoded by genes that are co-regulated, for example, two, three, or all four genes of the pathway can be configured as a single transcriptional unit, in which the genes of the transcriptional unit can be regulated by the same promoter that can optionally be a promoter endogenous to the recombinant host microorganism. The first enzyme in the pathway is a thioesterase capable of converting acyl thioesters (e.g., acyl-ACPs) into free fatty acids. The second enzyme is an acyl-CoA synthetase that is capable of using the free fatty acids as a substrate to produce acyl-CoA. The third enzyme is an alcohol-forming fatty acyl reductase that is capable of using acyl-CoA as a substrate to produce fatty alcohols. The fourth enzyme is a wax ester synthase capable of using acyl-CoA and fatty alcohols as substrates to produce wax esters. Introduction of genes encoding these four enzymes into a recombinant host cell (e.g., a prokaryotic and/or photosynthetic host cell) thus allows for production of wax esters from an acyl thioester produced by the fatty acid biosynthesis pathway, such as acyl-ACP. Additionally, using a photosynthetic host cell, which is able to use carbon dioxide as a carbon source, can allow for more efficient and cost-effective wax ester synthesis methods than using a host cell that depends on reduced and/or longer chain carbon sources. For example, demonstrated herein is expression of a non-native gene encoding an acyl-ACP thioesterase, a non-native gene encoding an acyl-CoA ligase/synthase, a non-native gene encoding an acyl-CoA reductase, and a non-native gene encoding a wax ester synthase together in a *cyanobacterium* (which is unable to naturally synthesize acyl-CoA, fatty alcohols, or wax esters), resulting in wax ester production.

In one aspect, the invention provides a nucleic acid molecule comprising nucleic acid sequences encoding at least one of: a) a thioesterase that releases fatty acids from an acyl thioester substrate (e.g., an acyl-ACP thioesterase), b) an acyl-CoA synthetase, c) an alcohol-forming fatty acyl reductase (e.g., an alcohol-forming acyl-CoA reductase), and d) a wax ester synthase. The nucleic acid sequence encoding d) a wax ester synthase and at least one of the nucleic acid sequences encoding a) a thioesterase, b) an acyl-CoA synthetase, and c) an alcohol-forming fatty acyl reductase may be configured as a single transcriptional unit. The nucleic acid molecule may comprise, for example, nucleic acid sequences encoding a) a thioesterase (e.g., an acyl-ACP thioesterase), b) an acyl-CoA synthetase, c) an alcohol-forming fatty acyl reductase (e.g., an alcohol-forming acyl-CoA reductase), and d) a wax ester synthase, in which all of the nucleic acid sequences are configured as a single transcriptional unit. The transcriptional unit of the isolated or recombinant nucleic acid molecule can in some examples be promoterless. Alternatively, a transcriptional unit of the nucleic acid molecule can be configured as an operon that includes a promoter, in which the promoter can be any promoter that can direct expression of the genes of the transcriptional unit/operon, and can be, for example, a promoter that is heterologous with respect to the genes of the transcriptional unit, a promoter heterologous or homologous with respect to the host recombinant microorganism, and/or a synthetic promoter, and can additionally be a constitutive promoter or a regulatable promoter, for example, an inducible promoter.

The nucleic acid molecule may further comprise at least one additional nucleic acid sequence of at least 50 nucleotides, at least 100 nucleotides, at least 200 nucleotides, at least 300 nucleotides, at least 400 nucleotides, at least 500 nucleotides, at least 600 nucleotides, at least 700 nucleotides, at least 800 nucleotides, at least 900 nucleotides, or at least 1,000 nucleotides derived from a prokaryotic and/or photosynthetic microorganism. Additionally, the nucleotide sequence derived from a prokaryotic and/or photosynthetic microorganism may mediate recombination of the transcriptional unit into a host genome. Additionally but optionally, an additional nucleic acid sequence derived from a prokaryotic and/or photosynthetic microorganism may comprise a nucleic acid sequence derived from the 5' region of a gene, and can, for example, optionally include at least a portion of a promoter. Additionally or alternatively, the nucleic acid molecule may comprise two or more nucleic acid sequences of at least 50 nucleotides, at least 100 nucleotides, at least 200 nucleotides, at least 300 nucleotides, at least 400 nucleotides, at least 500 nucleotides, at least 600 nucleotides, at least 700 nucleotides, at least 800 nucleotides, at least 900 nucleotides, or at least 1,000 nucleotides derived from a prokaryotic and/or photosynthetic microorganism. In some examples the transcriptional unit that comprises the genes of the wax ester synthesis pathway can be flanked by nucleic acid sequences derived from a prokaryotic and/or photosynthetic microorganism, for example a first nucleotide sequence derived from a prokaryotic and/or photosynthetic microorganism can be 5' of the transcriptional unit and a second nucleotide sequence derived from a prokaryotic and/or photosynthetic microorganism can be 3' of the transcriptional unit or operon. Additionally the nucleic acid sequences flanking the transcriptional unit or operon may mediate recombination of the transcriptional unit into the host genome. A nucleic acid sequence derived from a prokaryotic and/or photosynthetic microorganism positioned 5' of the transcriptional unit that includes two or more enzymes of the wax synthesis pathway may optionally comprise a promoter. Alternatively, the nucleic acid molecule can include a sequence of at least 50 nucleotides of a sequence derived from the genome of a prokaryotic and/or photosynthetic microorganism, but the genomic sequence may not comprise a promoter operably linked to any of the nucleic acid sequences of the transcriptional unit that includes two or more genes of the wax ester synthesis pathway.

The nucleic acid sequences encoding enzymes of the wax ester synthesis pathway provided as a transcriptional unit may each comprise an initiation codon, wherein one or more, and optionally all, of the nucleic acid sequences may additionally comprise a heterologous translational regulatory sequence upstream of the initiation codon. For example, the nucleic acid sequence encoding the acyl-CoA synthetase, the nucleic acid sequence encoding the alcohol-forming fatty acyl reductase, and the nucleic acid sequence encoding the wax ester may each comprise a heterologous translational regulatory sequence upstream of the initiation codon.

Nonlimiting examples of the genes that can be included in the transcriptional unit include genes encoding polypeptides having wax ester synthase activity such as for example, prokaryotic wax ester synthase derived from prokaryotic species including, without limitation, *Acinetobacter* and *Marinobacter* species, as well as wax synthases from algal, plant, and animal species.

In particular examples, the nucleic acid sequence encoding the thioesterase (e.g., an acyl-ACP thioesterase) can encode a thioesterase having sequence identity of, e.g., at least 30%, 40%, 50%, 55%, 60%, 65%, 70%, 75%, 80%, 85%, 90%, 95%, 96%, 97%, 98%, or 99% to the amino acid sequence of any one of SEQ ID NOS: 1-9, or to a functional fragment thereof. The nucleic acid sequence encoding the acyl-CoA synthetase can encode an acyl-CoA synthetase having sequence identity of, e.g., at least 30%, 40%, 50%, 55%, 60%, 65%, 70%, 75%, 80%, 85%, 90%, 95%, 96%, 97%, 98%, or 99% to the amino acid sequence of any one of SEQ ID NOS: 10-14, or to a functional fragment thereof. The nucleic acid sequence encoding the alcohol-forming fatty acyl reductase (e.g., an alcohol-forming acyl-CoA reductase) can encode an alcohol-forming acyl-CoA reductase having sequence identity of, e.g., at least 30%, 40%, 50%, 55%, 60%, 65%, 70%, 75%, 80%, 85%, 90%, 95%, 96%, 97%, 98%, or 99% to the amino acid sequence of any one of SEQ ID NOS: 15-21, or to a functional fragment thereof. The nucleic acid sequence encoding the wax ester synthase may encode a wax ester synthase having sequence identity of, e.g., at least 30%, 40%, 50%, 55%, 60%, 65%, 70%, 75%, 80%, 85%, 90%, 95%, 96%, 97%, 98%, or 99% to the amino acid sequence of any one of SEQ ID NOS: 22-30, or to a functional fragment thereof.

Additionally or alternatively to any of the aforementioned aspects, the nucleic acid sequence(s) encoding a thioesterase, acyl-CoA synthetase, alcohol-forming fatty acyl reductase, and/or wax ester synthase can be integrated into a chromosome of the recombinant host cell, can be present on an autonomously replicating episome in the recombinant host cell, and/or can be present in a vector in the recombinant host cell. The nucleic acid sequence(s) encoding the thioesterase, acyl-CoA synthetase, alcohol-forming fatty acyl reductase, and/or wax ester synthase can be operably linked to a promoter and/or enhancer. The promoter in various aspects can be heterologous with respect to the host organism or homologous to the host organism, can be regulatable, and/or can be inducible.

The invention also provides vectors and recombinant host cells comprising the nucleic acid molecules described herein. The vectors may be, e.g., cloning vectors, and may comprise an origin of replication for propagation in a cloning strain (e.g., yeast or *E. coli*). The vectors may additionally or alternatively comprise at least one selectable marker, for example, a gene encoding a protein that confers resistance to an antibiotic or herbicide. Additionally, a vector may comprise sequences for integration into the genome of a prokaryotic and/or photosynthetic microorganism.

In some aspects, the vectors do not comprise a promoter operably linked to the transcriptional unit comprising genes of the wax ester synthase pathway. The nucleic acid molecules and vectors can be designed for integration of the transcriptional unit that encodes two or more enzymes of the wax ester synthesis pathway into a host genome, such as the genome of a prokaryotic and/or a photosynthetic microorganism. For example, in some aspects, the vectors comprise two nucleic acid sequences derived from the genome of a prokaryotic and/or a photosynthetic microorganism, where the nucleic acid sequences flank the transcriptional unit and can mediate recombination of the transcriptional unit into the genome of a prokaryotic and/or a photosynthetic microorganism. Additionally, the nucleic acid sequence derived from the genome of a prokaryotic and/or a photosynthetic microorganism that is positioned upstream of the transcriptional unit can optionally include sequences from the 5' region of a gene of a prokaryotic and/or a photosynthetic microorganism, where the genomic sequences may or may not comprise a promoter. For example, a transcriptional unit can be positioned between two nucleic acid sequences that can mediate homologous recombination with a host genome, such that the transcriptional unit can become integrated into the host genome. In some examples, the transcriptional unit can be configured as an operon that comprises a promoter, which can be, in various examples, a heterologous promoter (with respect to the genes of the transcriptional unit), an inducible promoter, a constitutive promoter, a synthetic promoter, a promoter heterologous with respect to the intended host microorganism (i.e., from a different species), and/or a promoter a promoter from the same species as the intended host microorganism. A transcriptional unit operably linked to a promoter can be configured as a two, three, or four gene operon. Alternatively, the transcriptional unit can be promoterless, where the nucleic acid molecule and/or vector is designed such that integration into the genomic site of the recombinant host microorganism positions the transcriptional unit 3' of a promoter endogenous to the recombinant host microorganism, where the endogenous promoter of the host genome becomes operably linked to the transcriptional unit. In particular examples, the promoter endogenous to the intended host microorganism can be provided in the sequences derived from the genome of a prokaryotic and/or a photosynthetic microorganism that are positioned 5' of the transcriptional unit in the nucleic acid molecule or vector.

The invention provides a recombinant microorganism, which may be, e.g., a prokaryotic and/or a photosynthetic microorganism, genetically engineered for the production of wax esters, wherein the recombinant host cell contains non-native nucleic acid sequences encoding a thioesterase, an acyl-CoA synthetase, an alcohol-forming fatty acyl reductase, and a wax ester synthase. One or more of the nucleic acid sequences (e.g., all of the nucleic acid sequences) may be non-native with respect to the recombinant host cell. The nucleic acid sequence(s) encoding the thioesterase, acyl-CoA synthetase, alcohol-forming fatty acyl reductase, and/or wax ester synthase can be heterologous with respect to the recombinant host cell, and optionally the nucleic acid sequence(s) encoding the thioesterase, acyl-CoA synthetase, alcohol-forming fatty acyl reductase, and/or wax ester synthase can be codon optimized for expression in the host cell, which can be, for example, a prokaryotic host cell or photosynthetic host cell, e.g., a photosynthetic microorganism such as a *cyanobacterium* or microalga.

For example, the recombinant host cell can be of an *Agmenellum, Anabaena, Anabaenopsis, Anacystis, Aphanizomenon, Arthrospira, Asterocapsa, Borzia, Calothrix, Chamaesiphon, Chlorogloeopsis, Chroococcidiopsis, Chroococcus, Crinalium, Cyanobacterium, Cyanobium, Cyanocystis, Cyanospira, Cyanothece, Cylindrospermopsis, Cylindrospermum, Dactylococcopsis, Dermocarpella, Fischerella, Fremyella, Geitleria, Geitlerinema, Gloeobacter, Gloeocapsa, Gloeothece, Halospirulina, Iyengariella, Leptolyngbya, Limnothrix, Lyngbya, Microcoleus, Microcystis, Myxosarcina, Nodularia, Nostoc, Nostochopsis, Oscillatoria, Phormidium, Planktothrix, Pleurocapsa, Prochlorococcus, Prochloron, Prochlorothrix, Pseudanabaena, Rivularia, Schizothrix, Scytonema, Spirulina, Stanieria, Starria, Stigonema, Symploca, Synechococcus, Synechocystis, Thermosynechococcus, Tolypothrix, Trichodesmium, Tychonema*, or *Xenococcus* species.

The recombinant host cell can comprise, for example, a non-native nucleic acid molecule comprising a non-native nucleic acid sequence encoding a thioesterase, a non-native nucleic acid sequence encoding an acyl-CoA synthetase, a non-native nucleic acid sequence encoding an alcohol-forming fatty acyl reductase, and a non-native nucleic acid sequence encoding a wax ester synthase, wherein two or more of the nucleic acid sequences may optionally be present in the same transcriptional unit, for example, as a single operon. Additionally, the non-native genes encoding a thioesterase, an acyl-CoA synthetase, an alcohol-forming fatty acyl reductase, and a wax ester synthase may be configured as a single operon in the host microorganism. The operon may comprise a promoter heterologous with respect to the nucleic acid sequences, and may be heterologous or homologous with respect to the host cell and may be constitutive, or alternatively may be regulatable (e.g., inducible). Additionally or alternatively, the nucleic acid molecule may be integrated into a genomic site of the recombinant host cell, which may be, e.g., a *cyanobacterium*, such that the transcriptional unit comprising two to four genes of the wax ester synthesis pathway becomes operably linked to a promoter endogenous to the host cell. The genomic insertion site may be, for example, within or adjacent to the 5' region of a gene endogenous to the host cell. The genomic insertion site may in some examples include at least a portion of the protein coding region of a gene regulated to the promoter operably linked to the transcriptional unit, and in particular examples, the gene at the insertion site may be attenuated or disrupted, e.g., integration of the nucleic acid molecule that comprises the wax synthesis transcription unit into the genomic site may inactivate or reduce expression of one or more endogenous genes. Non-limiting examples of genes that may be at or near the locus of insertion include oxidoreductase or dehydrogenase genes (e.g., the slr0338 gene of *Synechocystis* (e.g., *Synechocystis* sp. PCC 6803) or an ortholog thereof in another cyanobacterial species), or genes encoding enzymes that participate in glycogen biosynthesis e.g., a glycogen synthase gene (e.g., glgA), a glycogen branching enzyme gene (e.g., glgB) gene, or a glucose-1-phosphate adenyltransferase gene (e.g., glgC). In a particular aspect, the recombinant host cell may be *Synechocystis* sp. 6803, and the nucleic acid sequences may be integrated at the RS1 site and be operably linked to an endogenous promoter of the RS1 site, such as, for example, the promoter.

In some aspects, the recombinant host cell is a microorganism that does not endogenously produce acyl-CoA, and/or does not include an endogenous gene encoding an acyl-CoA synthetase, e.g., the recombinant host microorganism is a *cyanobacterium*. Alternatively, the recombinant host microorganism may endogenously produce acyl-CoA, and expression of a non-native gene encoding an acyl-CoA synthetase (and, in many cases, an acyl-ACP thioesterase to provide the fatty acid substrate for the acyl-CoA synthetase) causes acyl-CoA to be produced in higher amounts than occur in the absence of acyl-CoA synthetase (and acyl-ACP thioesterase, if present) overexpression.

The invention also provides methods for producing a wax ester, comprising the steps of culturing a recombinant host cell that includes non-native nucleic acid sequences encoding a thioesterase, an acyl-CoA synthetase, an alcohol-forming fatty acyl reductase, and a wax ester synthase in a suitable culture medium (which optionally does not comprise an alcohol or a fatty acid, and additionally or alternatively does not comprise a substantial amount of a reduced carbon source) and allowing expression of the non-native nucleic acid sequences to produce one or more wax esters. The methods can be used to produce wax esters in microorganisms that lack acyl-CoA (such as cyanobacteria). The recombinant host cell may comprise a nucleic acid molecule comprising the nucleic acid sequences encoding a thioesterase, an acyl-CoA synthetase, an alcohol-forming fatty acyl reductase, and a wax ester synthase. The recombinant host cell may produce an increased level of the wax ester relative to a control host cell identical to the recombinant host cell in all respects except that it lacks one or more (e.g., all) of the non-native nucleic acid sequences encoding the thioesterase, the acyl-CoA synthetase, the alcohol-forming fatty acyl reductase, and the wax ester synthase. For example, the recombinant host cell may produce at least 50% more of the wax ester relative to a control host cell lacking the non-native nucleic acid sequences encoding the thioesterase, the acyl-CoA synthetase, the alcohol-forming fatty acyl reductase, and the wax ester synthase. The recombinant host cell may produce, e.g., at least 100%, 200%, 300%, 400%, 500%, 600%, 700%, 800%, 900%, or 1000% more of the wax ester relative to a control host cell lacking the non-native nucleic acid sequences encoding the thioesterase, the acyl-CoA synthetase, the alcohol-forming fatty acyl reductase, and the wax ester synthase. Additionally or alternatively, the recombinant host cell may produce at least 1, 2, 3, 4, 5, 6, 7, 8, 9, 10, 15, 20, 25, 30, 35, 40, 45, 50, 55, 60, 65, 70, 75, 80, 85, 90, 95, or 100 mg/L of wax ester in a culture period of from about one to about thirty days, such as from about one to about fifteen days, from about one to about ten days, from about one to about five days, or per day. Additionally or alternatively, the recombinant host cell may produce less than about 100 g/L, 50 g/L, 20 g/L, 10 g/L, 5 g/L, 2 g/L, 1 g/L, 500 mg/L, 200 mg/L, 100 mg/L, or 50 mg/L of the wax ester in a culture period of from about one to about thirty days, such as from about one to about fifteen days, from about one to about ten days, from about one to about five days, or per day, and/or can produce more than about 1 g/L, 500 mg/L, 200 mg/L, 100 mg/L, 50 mg/L, 25 mg/L, 20 mg/L, 15 mg/L, 10 mg/L, 9 mg/L, 8 mg/L, 7 mg/L, 6 mg/L, 5 mg/L, 4 mg/L, 3 mg/L, 2 mg/L, or 1 mg/L of the wax ester in a culture period of from about one to about thirty days, such as from about one to about fifteen days, from about one to about ten days, from about one to about five days, or per day. As one example, the recombinant microorganism may produce at least 1-5 mg/L of wax ester over a period of seven days.

The methods provided herein include producing at least one wax ester molecule wherein both the A chain derived from a fatty alcohol and the B chain derived from an acyl substrate (e.g., acyl-ACP) can have chain lengths of C8-C24. For example, at least one wax ester molecule produced by a method disclosed herein can have both an A chain and a B chain of C12-C18. Additionally, at least a portion of the wax ester produced by any of the methods described herein may be secreted by the host cell. The methods may optionally further include the step of isolating a wax ester or wax ester derivative.

The invention also provides methods for producing a wax ester using a photosynthetic host cell, e.g., a photosynthetic microorganism. Photosynthetic host cells are able to use carbon dioxide as a carbon source, and may thus provide a more efficient and cost-effective method of wax ester production than host cells that wholly depend on reduced and/or longer chain carbon sources. For example, the methods of the invention are carried out in a photosynthetic microorganism, e.g., a *cyanobacterium*. In certain aspects, the photosynthetic microorganism does not endogenously produce acyl-CoA. The methods of the invention may be advantageously carried out in cyanobacterial host cells, for example. Cyanobacteria synthesize acyl-ACP, but do not naturally make acyl-CoA, fatty alcohols or wax esters. Therefore, cyanobacterial host cells can be engineered to produce wax esters by introducing nucleic acid sequences encoding a) a thioesterase, b) an acyl-CoA synthetase, c) an alcohol-forming fatty acyl reductase, and d) a wax ester synthase. Because cyanobacteria are photosynthetic microorganisms that can utilize inorganic (non-reduced) carbon sources, such as $CO_2$, compared to, e.g., heterotrophic cells that depend on organic carbon sources such as sugars that must be added to the media, cyanobacteria transformed with nucleic acid sequences encoding a thioesterase, an acyl-CoA synthetase, an alcohol-forming fatty acyl reductase, and a wax ester synthase may provide a more streamlined and energy-efficient biological system for producing wax esters.

Additionally, wax ester production may be enhanced by upregulating acyl-ACP production in the recombinant host cell, for example, by expression or overexpression of one or more exogenous or endogenous polypeptides such as, for example, a beta-ketoacyl synthetase, an acetyl-CoA carboxylase, a malonyl CoA:ACP transacylase, an acyl-ACP synthetase, or an acyl carrier protein. Additionally or alternatively, the recombinant host cell can express or overexpress one or more exogenous or endogenous polypeptides that increase carbon fixation or photosynthetic light harvesting efficiency, or promote secretion of the wax ester product, such as, for example, ribulose 1,5-bisphosphate carboxylase, a phycobiliprotein, or a transmembrane transporter. Additionally or alternatively, the recombinant host cell can have attenuated expression of one or more of glycerol-3-phosphate dehydrogenase, acetaldehyde CoA dehydrogenase, pyruvate dehydrogenase, or acetate kinase. Any enzymes that function in the wax ester biosynthesis pathway may optionally be introduced and/or overexpressed.

The invention also provides a system for producing a wax ester that includes a recombinant photosynthetic microorganism (e.g., a recombinant microorganism such as a *cyanobacterium*) having non-native nucleic acid sequences encoding a thioesterase, an acyl-CoA synthetase, an alcohol-forming fatty acyl reductase, and a wax ester synthase cultured in a medium that does not include a substantial amount of an organic (e.g., reduced) carbon source, wherein the photosynthetic microorganism is exposed to light for at least a portion of the production period. Optionally, the system can further include an inorganic (e.g., non-reduced) carbon source, such as, for example, $CO_2$. The inorganic carbon source may provide the carbon for the synthesis of a wax ester product. The system for producing a wax ester may comprise any of the nucleic acid molecules, vectors, or recombinant host cells described herein, and may perform any of the methods described herein.

The invention also provides a composition that includes a wax ester. The wax ester is produced by the methods provided herein, and can include one or more wax esters having both an A chain and a B chain with chain lengths of C8-C24. The composition may comprise, for example, at least one wax ester molecule produced by a method disclosed herein that has both an A chain and a B chain of C12-C18, or of C12-C16, or of C14-C16, of C14, or of C16. Additionally or alternatively, a wax ester composition of the invention may, according to certain aspects, be identifiable as having been produced according to a method of the invention by detection of one or more nucleic acid molecules as a minor component which my be detected for example, by polymerase chain reaction (PCR) or by an alternative sequence-specific nucleic acid amplification detection method, where the nucleic acid molecules may comprise one or more sequences derived from a recombinant nucleic acid molecule as disclosed herein, for example, a recombinant nucleic acid molecule comprising a non-native gene encoding a wax ester synthase, and, preferably, one or more of a non-native gene encoding a thioesterase, a non-native gene encoding an alcohol forming acyl CoA reductase, and a non-native gene encoding an acyl-CoA synthetase.

BRIEF DESCRIPTION OF THE DRAWINGS

FIG. 1 shows the amino acid sequences of exemplary thioesterases for use in the wax ester synthesis pathways of the invention (SEQ ID NOS: 1-9).

FIG. 2 shows the amino acid sequences of exemplary acyl-CoA synthetases for use in the wax ester synthesis pathways of the invention (SEQ ID NOS: 10-14).

FIG. 3 shows the amino acid sequences of exemplary fatty acyl reductases for use in the wax ester synthesis pathways of the invention (SEQ ID NOS: 15-21).

FIG. 4 shows the amino acid sequences of exemplary wax ester synthases for use in the wax ester synthesis pathways of the invention (SEQ ID NOS: 22-30).

DETAILED DESCRIPTION OF THE INVENTION

Figure 5:
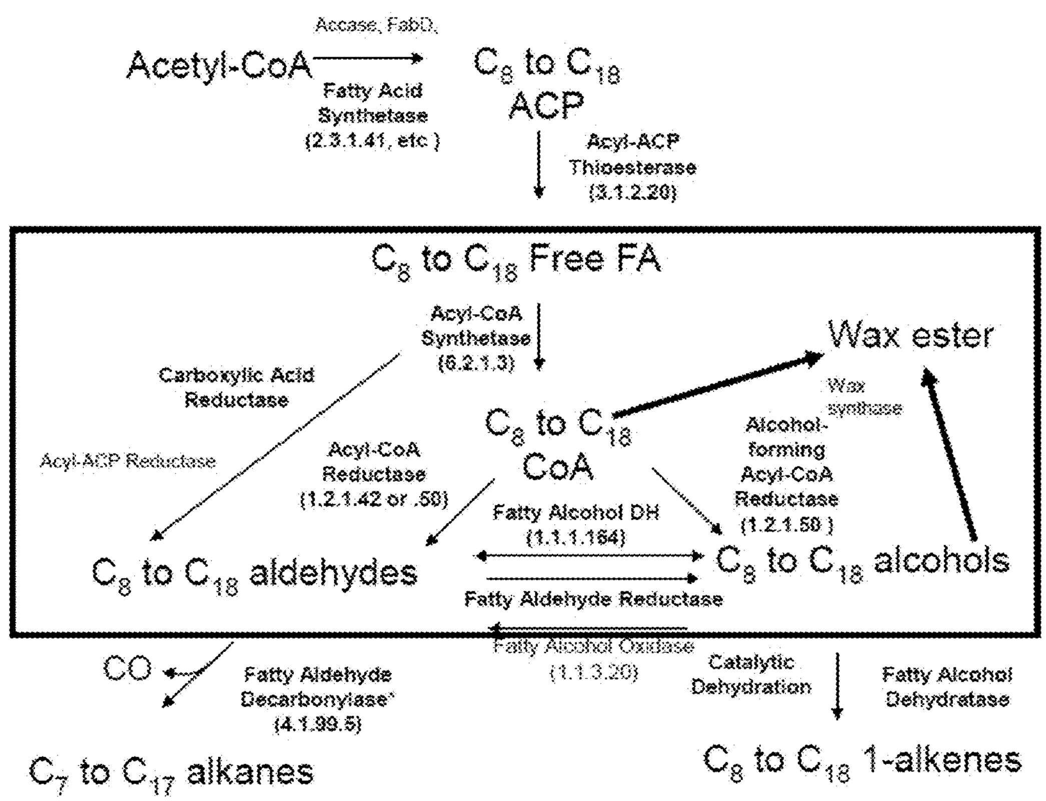
FIG. 5 is a schematic representation of fatty acid derivative metabolic pathways.

The invention provides methods of producing a wax ester in recombinant host cells via a four-gene pathway, as well as isolated nucleotide molecules, vectors, and recombinant host cells and systems for producing a wax ester via a four-gene pathway.

Elements of the aspects described herein can be combined to form additional aspects not specifically described that are also within the scope of the invention. Headings within the application are solely for the convenience of the reader, and do not limit in any way the scope of the invention or its aspects.

All publications and patent applications cited in this specification are incorporated herein by reference as if each individual publication or patent application were specifically and individually indicated to be incorporated by reference.

Definitions

Unless defined otherwise, all technical and scientific terms used herein have the same meaning as commonly understood by one of ordinary skill in the art to which this invention is related.

Throughout this specification and embodiments, the word "comprise," or variations such as "comprises" or "comprising," will be understood to imply the inclusion of a stated entity, item, or group of items but not the exclusion of any other entity, item, or group of items.

Singular articles "a," "an" and "the" include plural references unless the context clearly dictates otherwise. A reference to a cell, for example, includes a plurality of cells.

The term "and/or" as used in a phrase such as "A and/or B" herein is intended to include "A and B", "A or B", "A", and "B".

A "fatty alcohol" is a primary alcohol having the formula ROH, in which R is an aliphatic group, preferably an alkyl group. R can comprise between about 6 and about 24 carbon atoms. The aliphatic chain can be saturated, monounsaturated, or polyunsaturated. "One or more fatty alcohols" refers to one or more fatty alcohols of different chain length and/or saturation pattern, for example, a C16:1 fatty alcohol, a C18:2 fatty alcohol, and a C14 fatty alcohol are particular fatty alcohols.

A "short chain alcohol" is an alcohol having from 1 to 5 carbon atoms. A short chain alcohol can be linear or branched. Nonlimiting examples of short chain alcohols include methanol, ethanol, propanol, butanol, isobutanol, 2-methylbutanol, and 3-methylbutanol.

A "wax ester" is an ester of a fatty acid and a long chain aliphatic alcohol. Wax esters have an A chain, derived from a fatty alcohol, of at least 8 carbons, and a B chain, derived from an acyl-thioester, of at least 8 carbons. The number of carbons in the A and B chains of a wax ester can vary independently.

A "fatty acid ester" is an ester of a fatty acid and an alcohol. The carbon chain originating from an alcohol is referred to as the A chain and the carbon chain originating from a fatty acid (the fatty acid moiety can be provided by an acyl thioester) is referred to as the B chain. A fatty acid ester can have an A side of any length, for example, 1, 2, 3, 4, 5, 6, 7, 8, 9, 10, 12, 14, 16, 18, 20, 22, 24, or more than 24 carbons in length. A fatty acid ester can have a B side of any length, for example, 4, 6, 7, 8, 9, 10, 12, 14, 16, 18, 20, 22, 24, or more than 24 carbons in length. The lengths of the A and B chains of a fatty acid ester can vary independently. For example, condensation of methanol (C1) and an acyl chain (fatty acid or acyl-thioester) of C4 or greater can result in a fatty acid methyl ester ("FAME") and condensation of ethanol and an acyl chain can result in a fatty acid ethyl ester ("FAEE"). Condensation of a fatty alcohol (C8 or above) with an acyl thioester (C8 or greater) produces a wax ester.

The term "acyl-ACP thioesterase" refers to a protein that is able to convert acyl-ACP into free fatty acids. The term "acyl-CoA thioesterase" refers to a protein that is able to convert acyl-CoA into free fatty acids. Acyl-ACP thioesterases include thioesterases that use only acyl-ACP as the acyl-thioester substrate and acyl-ACP thioesterases able to use other acyl-thioester substrates (e.g., acyl-CoA) in addition to acyl-ACP.

The term "alcohol-forming acyl-CoA reductase" refers to a protein that is able to convert acyl-CoA (and optionally other acyl-thioester substrates) to fatty alcohol. The term "alcohol-forming acyl-ACP reductase" refers to a protein that is able to convert acyl-ACP (and optionally other acyl-thioester substrates) to fatty alcohol. "Alcohol-forming fatty acyl reductase" refers to enzymes that can convert either acyl-ACP or acyl-CoA to fatty alcohols, and includes "promiscuous alcohol-forming fatty acyl reductases" that are able to use both acyl-ACP and acyl-CoA as substrates for the production of fatty alcohols.

As used herein, the term "wax ester synthase" or "wax synthase" refers to a protein that is able to transfer an acyl chain from an acyl substrate such as acyl-CoA to a fatty alcohol to form a wax ester. The wax ester synthases used in the methods of the invention can condense a fatty alcohol (e.g., a C6, C7, C8, C10, C12, C14, C16, C18, C20, C22, C24, or longer chain alcohol) with an acyl-thioester substrate to produce a wax ester. A wax ester synthase can also condense a short chain alcohol (e.g., a C1, C2, C3, C4, or C5 alcohol)

with an acyl-thioester substrate such as acyl-CoA to form a fatty acid ester such as a fatty acid methyl ester or fatty acid ethyl ester. The alcohol condensed with the acyl-thioester substrate can be produced by the transgenic host cell or supplied to the transgenic host cell, for example, in the culture medium. Various polypeptides identified or characterized as acyltransferases, including fatty acyl transferases, alcohol acyltransferases (AATs, EC 2.3.1.84) and alcohol synthase/acyl-CoA:diacylglycerol acyltransferases, O-acyltransferases (e.g., long-chain-alcohol O-fatty-acyltransacylases (EC 2.3.1.75) or acyl-CoA:alchol acyltransferases, diacylglycerol O-acyltransferases, membrane bound O-acyltranferases (MBOATs)), diacylglycerol acyltransferases (DGATs), acyl-coA wax alcohol acyltransferases, and bifunctional wax ester synthase/acyl 1-CoA acyltransferases, have been found to have wax ester synthase activity. The term "wax synthase" or "wax ester synthase" without limitation includes enzymes that have wax ester synthase activity regardless of the name formally or informally given to the enzyme or its class. Thus "wax ester synthase" and "polypeptide having wax ester synthase activity" are used interchangeably herein.

As used herein, a "wax ester synthesis pathway" refers to the pathway of four enzymes (or their encoding genes) that convert acyl-ACP to a wax ester: a thioesterase that can use acyl-ACP as a substrate, an acyl-CoA synthetase, an alcohol-forming fatty acyl reductase, and a wax ester synthase.

The terms "peptide," "polypeptide" and "protein" are used interchangeably herein, although "peptide," in some instances, may be used to refer to a polypeptide having no more than about 100 amino acids, or no more than about 60 amino acids.

The term "functional fragment" refers to a polypeptide that has an amino-terminal and/or carboxy-terminal deletion, where the remaining amino acid sequence has at least 30%, 40%, 45%, 50%, 55%, 60%, 65%, 70%, 75%, 80%, 85%, 86%, 87%, 88%, 89%, 90%, 91%, 92%, 93%, 94%, 95%, 96%, 97%, 98%, 99%, or 100% sequence identity to the corresponding positions in the reference sequence, and that retains about 75%, 80%, 85%, 90%, 91%, 92%, 93%, 94%, 95%, 96%, 97%, 98%, 99%, or 100% of the activity of the full-length polypeptide. Functional fragments may comprise, e.g., 90% or less, 80% or less, 70% or less, 60% or less, 50% or less, 40% or less, 30% or less, or 20% or less of the full-length polypeptide, and can include, for example, up to about 20%, 30%, 40%, 50%, 55%, 60%, 65%, 70%, 75%, 80%, 85%, 90%, 92%, 93%, 94%, 95%, 96%, 97%, 98%, or 99% of the full-length polypeptide.

This application discloses and refers to nucleic acids and polypeptides by identifiers used in long-established and extensively referenced databases maintained by the National Center for Biotechnology Information (NCBI). Accession numbers are unique identifiers for a sequence record publicly available at the National Center for Biotechnology Information website (ncbi.nlm.nih.gov) maintained by the United States National Institutes of Health. The "GenInfo Identifier" (GI) sequence identification number is specific to a nucleotide or amino acid sequence. If a sequence changes in any way, a new GI number is assigned. A Sequence Revision History tool is available to track the various GI numbers, version numbers, and update dates for sequences that appear in a specific GenBank record. Searching and obtaining nucleic acid or gene sequences or protein sequences based on Accession numbers and GI numbers is well known in the arts of, e.g., cell biology, biochemistry, molecular biology, and molecular genetics.

Percent identity or homology with respect to amino acid or nucleotide sequences is defined herein as the percentage of amino acid or nucleotide residues in the candidate sequence that are identical with the known polypeptides, after aligning the sequences for maximum percent identity and introducing gaps, if necessary, to achieve the maximum percent homology. Homology or identity at the nucleotide or amino acid sequence level may be determined using methods known in the art, including but not limited to BLAST (Basic Local Alignment Search Tool) analysis using the algorithms employed by the programs blastp, blastn, blastx, tblastn and tblastx (Altschul (1997), Nucleic Acids Res. 25, 3389-3402, and Karlin (1990), Proc. Natl. Acad. Sci. USA 87, 2264-2268), which are tailored for sequence similarity searching.

"Pfam" is a large collection of protein domains and protein families maintained by the Pfam Consortium and is available at several sponsored world wide web sites, including: pfam-.sanger.ac.uk/(Welcome Trust, Sanger Institute); pfam.sbc-.su.se/(Stockholm Bioinformatics Center); pfam.janelia.org/(Janelia Farm, Howard Hughes Medical Institute); pfam.jouy.inra.fr/(Institut national de la Recherche Agronomique); and pfam.ccbb.re.kr/. The latest release of Pfam is Pfam 26.0 (November 2011, 13,672 families) based on the UniProt protein database release 2020_05. Pfam domains and families are identified using multiple sequence alignments and hidden Markov models (HMMs). Pfam-A families, which are based on high quality assignments, are generated by a curated seed alignment using representative members of a protein family and profile hidden Markov models based on the seed alignment. (Unless otherwise specified, matches of a queried protein to a Pfam are Pfam-A matches.) All identified sequences belonging to the family are then used to automatically generate a full alignment for the family (Sonnhammer et al. (1998) Nucleic Acids Research 26: 320-322; Bateman et al. (2000) Nucleic Acids Research 26: 263-266; Bateman et al. (2004) Nucleic Acids Research 32, Database Issue: D138-D141; Finn et al. (2006) Nucleic Acids Research Database Issue 34: D247-251; Finn et al. (2010) Nucleic Acids Research Database Issue 38: D211-222). By accessing the pfam database (for example, using any of the above-reference websites), protein sequences can be queried against the HMMs using HMMER homology search software (e.g., HMMER3, hmmer.janelia.org/). Significant matches that identify a queried protein as being in a pfam family (or as having a particular pfam domain) are those in which the bit score is greater than or equal to the gathering threshold for the Pfam domain. Expectation values (e values) can also be used as a criterion for inclusion of a queried protein in a pfam or for determining whether a queried protein has a particular pfam domain, where low e values (much less than 1.0, for example less than 0.1, or less than or equal to 0.01) represent low probabilities that a match is due to chance.

A "conservative variant" of a polypeptide is a polypeptide having one or more conservative amino acid substitutions with respect to the reference polypeptide, in which the activity (e.g. effect on transcription), affinity for co-regulators or ligands, or DNA-binding affinity of the polypeptide does not substantially differ from that of the reference polypeptide.

The term "conservative amino acid substitution" or "conservative mutation" refers to the replacement of one amino acid by another amino acid with a common property. A functional way to define common properties between individual amino acids is to analyze the normalized frequencies of amino acid changes between corresponding proteins of homologous organisms (Schulz (1979) Principles of Protein Structure, Springer-Verlag). According to such analyses, groups of amino acids can be defined where amino acids within a group exchange preferentially with each other, and therefore resemble each other most in their impact on the overall protein structure (Schulz (1979) Principles of Protein Structure, Springer-Verlag). Examples of amino acid groups defined in this manner can include: a "charged/polar group" including Glu, Asp, Asn, Gln, Lys, Arg and His; an "aromatic or cyclic group" including Pro, Phe, Tyr and Trp; and an "aliphatic group" including Gly, Ala, Val, Leu, Ile, Met, Ser, Thr and Cys. Within each group, subgroups can also be identified. For example, the group of charged/polar amino acids can be sub-divided into sub-groups including: the "positively-charged sub-group" comprising Lys, Arg and His; the "negatively-charged sub-group" comprising Glu and Asp; and the "polar sub-group" comprising Asn and Gln. In another example, the aromatic or cyclic group can be sub-divided into sub-groups including: the "nitrogen ring sub-group" comprising Pro, His, and Trp; and the "phenyl sub-group" comprising Phe and Tyr. In another further example, the aliphatic group can be sub-divided into sub-groups including: the "large aliphatic non-polar sub-group" comprising Val, Leu and Ile; the "aliphatic slightly-polar sub-group" comprising Met, Ser, Thr and Cys; and the "small-residue sub-group" comprising Gly and Ala. Examples of conservative mutations include amino acid substitutions of amino acids within the sub-groups above, such as, but not limited to: Lys for Arg or vice versa, such that a positive charge can be maintained; Glu for Asp or vice versa, such that a negative charge can be maintained; Ser for Thr or vice versa, such that a free —OH can be maintained; and Gln for Asn or vice versa, such that a free —$NH_2$ can be maintained.

The term "gene" is used broadly to refer to any segment of nucleic acid molecule (typically DNA, but optionally RNA) encoding a protein or expressed RNA. Thus, genes include sequences encoding expressed RNA (which can include polypeptide coding sequences). Genes may further comprise the regulatory sequences required for their expression. Genes can be obtained from a variety of sources, including cloning from a source of interest or synthesizing from known or predicted sequence information, and may include sequences designed to have desired parameters.

The "5' region of a gene" as used herein, is a term that refers to nucleic acid sequence of any length, but preferably from 10 to 2,000 nucleotides, or more preferably from 15 to 1,000 nucleotides, or from 20 to 1,000 nucleotides, that includes sequences of the genome of an organism that are upstream, or 5' to, the translational start site of open reading frame of the gene (or, if the gene encodes a functional RNA, are upstream of the transcriptional start site of the functional RNA). The 5' region of a gene includes one or more of the following: a promoter, the 5' untranslated region of the gene or a portion thereof, or at least one codon encoding the N-terminal amino acid(s) of the gene.

The term "nucleic acid" or "nucleic acid molecule" refers to, e.g., DNA or RNA (e.g., mRNA). The nucleic acid molecules can be double-stranded or single-stranded; single stranded RNA or DNA can be the coding (sense) strand or the non-coding (antisense) strand.

The nucleic acid molecules of the present invention may be isolated or purified. As used herein, an "isolated" nucleic acid molecule or nucleotide sequence refers to a nucleic acid molecule or nucleotide sequence that is not flanked by nucleotide sequences normally flanking the gene or nucleotide sequence (as in genomic sequences), and therefore can be a recombinant nucleic acid molecule or sequence, and/or has been completely or partially removed from its native environment (e.g. a cell, tissue). For example, nucleic acid molecules that have been removed or purified from cells are considered isolated. In some instances, the isolated material will form part of a composition (for example, a crude extract containing other substances), buffer system or reagent mix. In some circumstances, the nucleic acid molecules may be purified to near homogeneity, for example as determined by PAGE or column chromatography such as HPLC. An isolated nucleic acid molecule or nucleotide sequence can includes a nucleic acid molecule or nucleotide sequence that is chemically synthesized, using recombinant DNA technology or using any other suitable method. A nucleic acid contained in a vector would also be included in the definition of "isolated" as used herein. Both in vivo and in vitro RNA transcripts of an isolated DNA molecule of the present invention are also encompassed by "isolated" nucleotide sequences.

The term "codon optimized" refers to changes in the codons of a nucleotide sequence encoding a protein to those preferentially used in a particular organism such that the encoded protein is efficiently expressed in the organism of interest. In some aspects, a nucleotide sequence encoding a protein may be codon optimized for optimal production of the protein from a host organism. As used in the context of the invention, a "codon-optimized" gene or nucleic acid molecule of the invention need not have every codon altered to conform to the codon preference of the intended host organism, nor is it required that altered codons of a "codon-optimized" gene or nucleic acid molecule be changed to the most prevalent codon used by the organism of interest. For example, a codon-optimized gene may have one or more codons changed to codons that are used more frequently than the original codon(s), whether or not they are used most frequently in the organism to encode a particular amino acid.

The terms "expression vector" and "expression construct" refer to a nucleic acid molecule that has been generated via human intervention, including by recombinant means and/or direct chemical synthesis, with a series of specified nucleic acid "expression control elements" that permit transcription and/or translation of a particular nucleic acid in a host cell. The expression vector can be a plasmid, a part of a plasmid, a viral construct, a nucleic acid fragment, or the like, or a combination thereof.

An "expression cassette" or "nucleic acid cassette," as used herein, refers to a nucleotide sequence encoding a protein or functional RNA (e.g. a tRNA, a short hairpin RNA, one or more microRNAs, a ribosomal RNA, etc.) operably linked to expression control elements, such as a promoter, and optionally, any or a combination of other nucleic acid sequences that affect the transcription or translation of the gene, such as, but not limited to, a transcriptional terminator, a ribosome binding site (rbs), a splice site or splicing recognition sequence, an intron, an enhancer, a polyadenylation signal, an internal ribosome entry site, etc. "Operable linkage" or "operably linked" refers to a functional linkage between two nucleic acid sequences, such as a control sequence (such as a promoter) and the linked sequence (such as a sequence that encodes a protein and/or functional RNA). A promoter is in operable linkage with a nucleic acid sequence if it can mediate transcription of the gene. A nucleic acid sequence derived from the genome of a host microorganism can be operably linked to a nucleic acid sequence exogenous to the host microorganism, wherein the genome-derived sequence can promote homologous recombination resulting in the insertion of the exogenous nucleic acid sequence into the genome of the host microorganism. For example, a nucleic acid molecule of the invention can include a nucleic acid sequence exogenous to the host microorganism that encodes a protein of interest, wherein the exogenous nucleic acid sequence is operably linked to sequences (for example, flanked by sequences) derived from the host microorganism that allow recombination of the exogenous nucleic acid sequence into the host genome.

The term "transcriptional unit", as used herein, refers to a unit of one or more genes configured such that when placed under the control of a single promoter (e.g., a single promoter 5' of the 5' most gene of the transcriptional unit), the genes transcribed together to produce a single transcript (RNA molecule). Thus, a transcriptional unit does not comprise promoters or transcriptional terminators between genes of the transcriptional unit. A transcriptional unit may or may not be an operon that comprises a promoter at the 5' end of the transcriptional unit.

The term "operon", as used herein, refers to a unit of more than one gene under the control of a single regulatory signal or promoter. The genes may be transcribed, e.g., into a single RNA molecule. The genes may then be translated together as a single RNA strand, or the transcribed RNA molecule may undergo trans-splicing to produce monocistronic RNAs that may be translated separately, etc.

"Stringency conditions" for hybridization of nucleotide sequences refer to the incubation and wash conditions, e.g. conditions of temperature and buffer concentration, which permit hybridization of a particular nucleic acid to a second nucleic acid; the first nucleic acid may be perfectly (i.e., 100%) complementary to the second, or the first and second may share some degree of complementarity, which is less than perfect, e.g., 60%, 75%, 85%, 95% or more. For example, certain high stringency conditions can be used which distinguish perfectly complementary nucleic acids from those of less complementarity.

"High stringency conditions," "moderate stringency conditions" and "low stringency conditions" for nucleic acid hybridizations are explained in Current Protocols in Molecular Biology (2011) John Wiley & Sons). The exact conditions which determine the stringency of hybridization depend not only on ionic strength (e.g. 0.2×SSC, 0.1×SSC, etc.) of the wash buffers, temperature (e.g., 23° C., 42° C., 68° C., etc.) and the concentration of destabilizing agents such as formamide or denaturing agents such as SDS, but also on factors such as the length of the nucleic acid sequence, base composition, percent mismatch between hybridizing sequences and the frequency of occurrence of subsets of that sequence within other non-identical sequences. Thus, high, moderate or low stringency conditions may be determined empirically.

By varying hybridization conditions from a level of stringency at which no hybridization occurs to a level at which hybridization is first observed, conditions which will allow a given sequence to hybridize with the most similar sequences in the sample can be determined.

Exemplary hybridization conditions are described in Krause (1991) *Methods in Enzymology,* 200, 546-556. Washing is the step in which conditions are usually set so as to determine a minimum level of complementarity of the hybrids. Generally, starting from the lowest temperature at which only homologous hybridization occurs, each degree (° C.) by which the final wash temperature is reduced, while holding SSC concentration constant, allows an increase by 1% in the maximum extent of mismatching among the sequences that hybridize. Generally, doubling the concentration of SSC results in an increase in Tm. Using these guidelines, the washing temperature can be determined empirically for high, moderate or low stringency, depending on the level of mismatch sought. Exemplary high stringency conditions include, but are not limited to, hybridization in 50% formamide, 1 M NaCl, 1% SDS at 37° C., and a wash in 0.1×SSC at 60° C. Example of progressively higher stringency conditions include, after hybridization, washing with 0.2×SSC and 0.1% SDS at about room temperature (low stringency conditions); washing with 0.2×SSC and 0.1% SDS at about 42° C. (moderate stringency conditions); and washing with 0.1×SSC at about 68° C. (high stringency conditions). Washing can be carried out using only one of these conditions, e.g. high stringency conditions, washing may encompass two or more of the stringency conditions in order of increasing stringency. Optimal conditions will vary, depending on the particular hybridization reaction involved, and can be determined empirically.

Equivalent conditions can be determined by varying one or more of the parameters given as an example, as known in the art, while maintaining a similar degree of identity or similarity between the target nucleic acid molecule and the primer or probe used. Hybridizable nucleotide sequences are useful as probes and primers for identification of organisms comprising a nucleic acid of the invention and/or to isolate a nucleic acid of the invention, for example.

A "purified" nucleic acid molecule or nucleotide sequence, or protein or polypeptide sequence, is substantially free of cellular material and cellular components. The purified nucleic acid molecule or protein may be free of chemicals beyond buffer or solvent, for example. "Substantially free" is not intended to mean that other components beyond the novel nucleic acid molecules are undetectable.

A "recombinant" or "engineered" nucleic acid molecule is a nucleic acid molecule that has been altered through human manipulation. As non-limiting examples, a recombinant nucleic acid molecule: (1) has been synthesized or modified in vitro, for example, using chemical or enzymatic techniques (for example, by use of chemical nucleic acid synthesis, or by use of enzymes for the replication, polymerization, digestion (exonucleolytic or endonucleolytic), ligation, reverse transcription, transcription, base modification (including, e.g., methylation), or recombination (including homologous and site-specific recombination)) of nucleic acid molecules; (2) includes conjoined nucleotide sequences that are not conjoined in nature, (d) has been engineered using molecular cloning techniques such that it possesses and/or lacks one or more nucleotides with respect to the naturally occurring nucleic acid molecule sequence, or (4) has been manipulated using molecular cloning techniques such that it has one or more sequence changes or rearrangements with respect to the naturally occurring nucleic acid sequence. As non-limiting examples, a cDNA is a recombinant DNA molecule, as is any nucleic acid molecule that has been generated by in vitro polymerase reaction(s), or to which linkers have been attached, or that has been integrated into a vector, such as a cloning vector or expression vector.

When applied to organisms, the term "recombinant," "engineered," or "genetically engineered" refers to organisms that have been manipulated by introduction of a heterologous or recombinant nucleic acid sequence into the organism, and includes gene knockouts, targeted mutations and gene replacement, promoter replacement, deletion, or insertion, as well as introduction of transgenes into the organism. The heterologous or recombinant nucleic acid molecule can be integrated into the recombinant/genetically engineered organism's genome or in other instances are not integrated into the recombinant/genetically engineered organism's genome.

Similarly, the term "recombinant protein" as used herein may refer to a protein altered through human manipulation, e.g., produced by genetic engineering.

The terms "naturally-occurring" and "wild-type" refer to a form found in nature. For example, a naturally occurring or wild-type nucleic acid molecule, nucleotide sequence or protein may be present in and isolated from a natural source, and is not intentionally modified by human manipulation.

As used herein "attenuated" means reduced in amount, degree, intensity, or strength. Attenuated gene expression may refer to a significantly reduced amount and/or rate of transcription of the gene in question, or of translation, folding, or assembly of the encoded protein. For example, an attenuated gene can be a disrupted or deleted gene that results in no detectable production of the encoded protein.

"Exogenous nucleic acid molecule" or "exogenous gene" refers to a nucleic acid molecule or gene that has been introduced ("transformed") into a cell. A transformed cell may be referred to as a recombinant cell, into which additional exogenous gene(s) may be introduced. A descendent of a cell transformed with a nucleic acid molecule is also referred to as "transformed" if it has inherited the exogenous nucleic acid molecule. The exogenous gene may be from a different species (and so "heterologous"), or from the same species (and so "homologous"), relative to the cell being transformed. An "endogenous" nucleic acid molecule, gene or protein is a native nucleic acid molecule, gene or protein as it occurs in, or is naturally produced by, the host.

The term "heterologous" is used broadly in this aspect to refer to nucleic acid molecules or proteins introduced into a host cell, wherein the nucleic acid molecules or proteins are derived from a different strain/organism. A heterologous gene may have an equivalent in the transformed host, i.e., a gene which normally performs the same or a similar function, or the exogenous heterologous gene may encode a protein that does not have an endogenous homolog in the host strain/organism. When referring to a gene regulatory sequence or to an auxiliary nucleic acid sequence used for maintaining or manipulating a gene sequence (e.g. a 5' untranslated region, 3' untranslated region, poly A addition sequence, intron sequence, splice site, ribosome binding site, internal ribosome entry sequence, genome homology region, recombination site, etc.), "heterologous" means that the regulatory sequence or auxiliary sequence is from a different source than the gene with which the regulatory or auxiliary nucleic acid sequence is juxtaposed in a construct, genome, chromosome or episome. Thus, a promoter operably linked to a gene to which it is not operably linked to in its natural state (i.e. in the genome of a non-genetically engineered organism) is referred to herein as a "heterologous promoter," even though the promoter may be derived from the same species (or, in some cases, the same organism) as the gene to which it is linked.

The term "native" is used herein to refer to nucleic acid sequences or amino acid sequences as they naturally occur in the host. The term "non-native" is used herein to refer to nucleic acid sequences or amino acid sequences that do not occur naturally in the host. A nucleic acid sequence or amino acid sequence that has been removed from a host cell, subjected to laboratory manipulation, and introduced or reintroduced into a host cell is considered "non-native." Synthetic or partially synthetic genes introduced into a host cell are "non-native." Non-native genes further include genes endogenous to the host microorganism operably linked to one or more heterologous regulatory sequences that have been recombined into the host genome.

The term "wax ester composition" refers to a composition that comprises at least one wax ester molecule. Wax esters include, e.g., compositions comprising only wax ester molecules (i.e., a composition which does not contain a fatty acid derivative other than wax ester molecules) and compositions comprising wax esters and at least one other type of fatty acid derivative selected from, e.g., alcohols, aldehydes, alkenes, alkynes and alkanes. Wax esters may comprise only one type of wax ester molecule or more than one type of wax ester molecule.

The terms "releasing" and "secreting," as used herein, are used interchangeably to refer to active and/or passive mechanisms to transport substances across the cell membrane. Examples of such transport mechanisms include, but are not limited to, passive diffusion, gradient diffusion, facilitated diffusion, active transport, and combinations thereof.

The terms "recombinant," "engineered" or "genetically engineered," when applied to host cells, refer to cells that have been manipulated by introduction of a non-native (e.g., heterologous or recombinant) nucleic acid sequence into the host cell, or deletion of a native nucleic acid sequence from the host cell, and include, e.g., gene knockouts; targeted mutations and gene replacement; promoter replacement, deletion or insertion; as well as introduction of transgenes into the host cell. In some aspects, an introduced non-native nucleic acid molecule is integrated into the genome of the recombinant/genetically engineered host. In other aspects, an introduced non-native nucleic acid molecule is not integrated into the genome of the recombinant/genetically engineered host.

The terms "transformation," "transfection," "conjugation" and "transduction," as used in the present context, are intended to comprise a multiplicity of methods known to those skilled in the art for the introduction of foreign nucleic acids (for example, exogenous DNA) into a host cell, including calcium phosphate and/or calcium chloride coprecipitation, DEAE-dextran-mediated transfection, lipofection, natural competence, chemically mediated transfer, electroporation, particle bombardment, or the like, or combinations thereof. Transfection may be transient or stable (e.g., genomic integration). Examples of suitable methods for the transformation and/or transfection of host cells, e.g. can be found in Molecular Cloning—A Laboratory Manual (2010), Cold Spring Harbor Laboratory Press.

The term "culturing" refers to the intentional fostering of growth (e.g. increases in cell size, cellular contents and/or cellular activity such as production of biomolecules) and/or propagation (e.g. increases in cell numbers via mitosis) of one or more cells by use of selected and/or controlled conditions. The combination of both growth and propagation may be termed proliferation. Nonlimiting examples of selected and/or controlled conditions can include the use of a defined medium (with known characteristics such as pH, ionic strength and/or carbon source), specified temperature, oxygen tension, carbon dioxide levels, growth in a bioreactor, or the like, or combinations thereof.

The term "bioreactor" refers to an enclosure or partial enclosure in which cells (e.g., microalgal cells) are cultured, optionally in suspension and, when suspended, preferably in an aqueous liquid. The bioreactor can be used to culture cells through the various phases of their physiological cycle.

Metabolic Pathways

The fatty acid biosynthesis pathway is highly conserved in prokaryotes and in the chloroplasts of eukaryotic algae and higher plants. Fatty acid biosynthesis is initiated by the conversion of acetyl-CoA to malonyl-CoA, catalyzed by acetyl-CoA carboxylase (ACCase). Malonyl-CoA is then converted to malonyl-ACP, catalyzed by malonyl-CoA-ACP transacylase (FabD). Finally, malonyl-ACP is converted to acyl-ACP, catalyzed by the enzyme complex fatty acid synthase (FAS). The fatty acid synthase complex initiates the elongation cycle by first condensing malonyl-ACP with acetyl-ACP, catalyzed by a beta-ketoacyl-ACP synthase III (e.g., FabH). The β-ketoacyl-ACP (3-ketoacyl-ACP) formed by the FabH reaction is reduced to a β-hydroxyacyl-ACP (3-hydroxyacyl-ACP) by 3-ketoacyl-ACP reductase (e.g. FabG). The β-hydroxyacyl-ACP is then acted on by a β-hydroxyacyl-ACP dehydratase (e.g. FabA, FabZ) to form trans-2-enoyl-ACP, which in turn is reduced by enoyl-ACP reductase (e.g. Fab I, Fab K, FabL) to form the 2 carbon-elongated acyl-ACP product. Subsequent cycles are initiated by a beta-ketoacyl-ACP synthase I or II (e.g., FabB or FabF) catalyzed condensation of malonyl-ACP with acyl-ACP. The cycles of condensation, reduction, dehydration, and reduction are repeated, with each cycle adding two carbons from malonyl-ACP, until the acyl chain is cleaved from ACP by a thioesterase, such as FatA or FatB in chloroplasts, to form free fatty acid or transferred to another molecule (e.g. glycerol 3-phosphate) by a transacylase. In certain bacteria, the free fatty acids are then converted to acyl-CoA, a precursor for fatty acid derivative biosynthesis.

Unlike plant chloroplasts, cyanobacteria do not produce free fatty acids, and unlike *E. coli* and other heterotrophic bacteria, cyanobacteria do not produce acyl-CoA. After fatty acid elongation with the acyl chain covalently bound to acyl carrier protein, acyl transferases can transfer the acyl chain to a glycerol backbone to produce membrane lipids, or the acyl-ACP can be converted into fatty alkanes. Accordingly, to produce fatty acid derivatives in cyanobacteria, it is typically considered necessary to introduce several exogenous genes encoding enzymes for producing acyl-CoA and converting the acyl-CoA to the desired end product (e.g., an alcohol, aldehyde, alkane, alkene, fatty acid ester or wax ester). As illustrated in FIG. 5, a thioesterase or a gene encoding a thioesterase (e.g., acyl-ACP thioesterase, 3.1.2.20) can be introduced to hydrolyze the acyl-ACP thioester, thus liberating free fatty acid. An acyl-CoA synthetase (e.g., 6.2.1.3) or a gene encoding one can be introduced to convert free fatty acids to acyl-CoA.

If fatty alcohols and/or wax esters are the desired end product, an alcohol-forming fatty acyl reductase or a gene encoding an alcohol-forming fatty acyl reductase (e.g., alcohol-forming acyl-CoA reductase, 1.2.1.50) may be introduced. Further, a fatty aldehyde reductase or a gene encoding one may be introduced to reduce fatty aldehydes to fatty alcohols.

Wax esters may be formed by introducing a wax ester synthase or a gene encoding a wax ester synthase to catalyze condensation of a fatty alcohol with a fatty acyl thioester. As demonstrated herein, a combination of four enzymes is able to produce wax esters in prokaryotic and/or photosynthetic microorganisms such as cyanobacteria, where two, three, or four of the genes of the wax ester synthase pathway may be correlated by the same promoter. The promoter can be a promoter endogenous to the host microorganism, and the transcriptional unit comprising genes of the pathway can optionally be integrated into the host microorganism genome at a locus adjacent to the endogenous promoter for co-regulation of the genes of the transcriptional unit.

Thioesterases

As used herein, the term "thioesterase" is intended to include hydrolases capable of acting on a thioester bond. Such enzymes can correspond to, e.g., Enzyme Commission Number 3.1.2.2, 3.1.2.14, 3.1.2.18, 3.1.2.19, 3.2.1.20, 3.1.2.22, 3.1.2.23, or 3.1.2.27. A thioesterase encoded by nucleic acid sequences of a nucleic acid molecule as disclosed herein, or expressed in a recombinant microorganism or host cell of the invention can be, for example, an acyl-ACP thioesterase, an acyl-CoA thioesterase, or a hydroxylbenzoyl thioesterase. In some aspects, a protein known or suspected of having thioesterase activity against a particular substrate, e.g., a acyl-CoA substrate or hydroxybenzoyl substrate, can also exhibit acyl-ACP thioesterase activity.

A recombinant microorganism or host cell can in some examples be transformed with a gene encoding an exogenous acyl-ACP thioesterase, such as a gene encoding a polypeptide that when queried against the Pfam database, provides a match with Pfam PF01643 having a bit score of less than or equal to 20.3 (the gathering cut-off for PF01643). The acyl-ACP thioesterase gene can encode an acyl-ACP thioesterase from a higher plant species. Genes encoding acyl-ACP thioesterases derived from higher plants can include, without limitation, genes encoding acyl-ACP thioesterases from *Cuphea* species (e.g. *Cuphea carthagenensis, Cuphea wrightii* (e.g., GenBank Accession AAC49784), *Cuphea lanceolata* (e.g., GenBank Accession CAA54060), *Cuphea palustris*, (e.g., GenBank Accessions AAC49783; AAC49179); *Cuphea hookeriana* (e.g., GenBank Accessions AAC72882; AAC49269; AAC72881; AAC72883), *Cuphea calophylla* (e.g., GenBank Accession ABB71580) or genes of various *Cuphea* species disclosed in United States patent application publication US 2011/0020883, incorporated by reference herein) or genes from other higher plant species. In further examples, a microorganism used in the methods and cultures disclosed herein can include a gene encoding an acyl-ACP thioesterase from species such as but not limited to, *Arabidopsis* (GenBank Accessions XP_002885681; NP_172327); *Arachis hypogaea* (e.g., GenBank Accession ABO38556); *Brassica* species (e.g., GenBank Accession CAA52069.1), *Camellia oleifera* (e.g., GenBank Accession ACQ57189); *Cinnamonum camphorum* (e.g., GenBank Accession AAC49151); *Cocos nucifera* (e.g., GenBank Accessions AEM72519; AEM72520; AEM72521); *Glycine max* (e.g., GenBank Accession ABD91726); *Garcinia mangostana* (e.g., GenBank Accession AAB51525); *Gossypium hirsutum* (e.g., GenBank Accession AAD01982); *Helianthus annuus* (e.g., GenBank Accession AAQ08226); *Jatropha curcas* (e.g., GenBank Accession ABU96744); *Macadamia tetraphylla* (e.g., GenBank Accession ADA79524); *Elaeis oleifera* (e.g., GenBank Accession AAM09524); *Elaeis guineensis* (e.g., GenBank Accession AAD42220); *Oryza sativa* (e.g., GenBank Accession BAA83582); *Populus tomentosa* (e.g., GenBank Accession ABC47311); *Umbellularia californica* (e.g., GenBank Accession AAC49001); *Ulmus Americana* (e.g., GenBank Accession AAB71731); and *Zea mays* (GenBank Accession ACG41291), or any of those disclosed in U.S. Pat. No. 5,455,167; U.S. Pat. No. 5,654,495; and U.S. Pat. No. 5,455,167; and in U.S. Patent Appl. Pub. Nos. 2009/0298143 and 2011/0020883; all incorporated by reference herein in their entireties. Further included are acyl-ACP thioesterases from mosses (Bryophyta), such as, for example, *Physcomitrella patens*, (e.g., GenBank Accession XP 001770108). These examples are not limiting with regard to the types or specific examples of acyl-ACP thioesterase genes that can be used.

Further included are acyl-ACP thioesterase genes from prokaryotic organisms. Illustrative examples of prokaryotic acyl-ACP thioesterases that may be expressed by a microorganism useful in the methods and cultures provided herein include, but are not limited to acyl-ACP thioesterases from *Desulfovibrio desulfuricans* (e.g., GenBank Accession Q312L1); *Elusimicrobium minutum* (e.g., GenBank Accession ACC98705); *Carboxydothermus hydrogenoformans* (e.g., GenBank Accession YP_359670); *Clostridium thermocellum* (e.g., GenBank Accession YP_001039461); *Moorella thermoacetica* (e.g., GenBank Accession YP_431036); *Geobacter metallireducens* (e.g., GenBank Accession YP_384688); *Salinibacter ruber* (e.g., GenBank Accession YP_444210); *Microscilla marina* (e.g., GenBank Accession EAY28464); *Parabacteroides distasonis* (e.g., GenBank Accession YP_001303423); *Enterococcus faecalis* (e.g., GenBank Accession ZP_03949391); *Lactobacillus plantarum* (e.g., GenBank Accession YP_003062170); *Leuconostoc mesenteroides* (e.g., GenBank Accession YP_817783); *Oenococcus oeni* (e.g., GenBank Accession ZP_01544069); *Mycobacterium smegmatis* (e.g., GenBank Accession ABK74560); *Mycobacterium vanbaalenii* (e.g., GenBank Accession ABM11638); *Rhodococcus erythropolis* (e.g., GenBank Accession ZP_04385507; *Rhodococcus opacus* (e.g., GenBank Accession YP_002778825), or any of those disclosed in the co-pending, commonly-assigned U.S. patent application Ser. No. 13/324,623 entitled "Prokaryotic Acyl-ACP Thioesterases for Producing Fatty Acids in Genetically Engineered Microorganisms", filed on Dec. 13, 2011, and which is incorporated herein by reference in its entirety.

In additional examples, a gene encoding an acyl-CoA thioesterase can be introduced into a microorganism or host cell and can be from a plant, animal, or microbial source. For example, a gene encoding the TesA or TesB thioesterase of *E. coli*, an ortholog thereof in another species, or a variant thereof, for example, an acyl-CoA thioesterase such as, but not limited to, a variant as disclosed in WO 2010/075483, incorporated by reference herein in its entirety, can be introduced into a microorganism or host cell. Also included are genes encoding proteins that when queried against the Pfam database of protein families are identified as members of Pfam PF02551 (acyl-CoA thioesterase), where the bit score is equal to or greater than the gathering cut off (20.7).

Alternately or in addition, the microorganism or host cell of the invention can include one or more genes encoding a hydroxybenzoyl thioesterase, for example an exogenous 4-hydroxybenzoate thioesterase or 4-chlorobenzoate thioesterase. Genes encoding hydroxybenzoyl thioesterases that may be useful in a recombinant microorganism for producing free fatty acids can include, for example, those disclosed in the commonly-assigned U.S. patent application Ser. No. 13/324,607 entitled "Genetically Engineered Microorganisms Comprising 4-Hydroxybenzoyl-CoA Thioesterases and Methods of Using Same for Producing Free Fatty Acids and Fatty Acid Derivatives", filed on Dec. 13, 2011, and which is incorporated herein by reference in its entirety; 4-hydroxybenzoyl thioesterases from *Bacillus* species and *Geobacillus* species; as well as 4-hydroxybenzoyl thioesterases of *Acidiphilium, Bartonella, Rhodopseudomonas, Magnetospirillum, Burkholderia, Granulibacter, Rhizobium*, and *Labrenzia* species, or the like, or combinations thereof.

Acyl-ACP thioesterases typically can be active to some degree on acyl-ACP substrates having a plurality of different acyl chain lengths, but can have higher activity on (e.g., have a substrate preference for) one or more acyl-ACP substrates having particular acyl chain lengths than on other chain length substrates. In some examples, an enzyme referred to as having a substrate preference for particular acyl chain length substrates produces at least twice as much product of the preferred substrate or substrates as it does from a non-preferred substrate, and for example can produce at least three times, at least four times, or at least five times as much product from a preferred substrate as from a non-preferred substrate. For example, an acyl-ACP thioesterase may have a substrate preference for one or more of acyl-ACP substrates having acyl chain lengths of 8, 10, 12, 14, 16, 18, 20, 22, and/or 24 carbons. Additionally or alternately, the acyl-ACP thioesterase can hydrolyze one or more acyl-ACP substrates having an acyl chain length from 8 to 18 carbons, for example from 12 to 18 carbons. For example, the acyl-ACP thioesterase can hydrolyze one or more acyl-ACP substrates having an acyl chain length from 12 to 16 carbons. Further additionally or alternately, an acyl-ACP thioesterases of the present invention can, in some embodiments, have its highest level of activity on an acyl-ACP substrate having an acyl chain length of 12, 14, and/or 16 carbons.

In some aspects, a nucleic acid sequence encoding a thioesterase useful in the wax ester synthesis constructs disclosed herein can encode an acyl-ACP thioesterase that has at least 30%, 40%, 45%, 50%, 55%, 60%, 65%, 70%, 75%, 80%, 85%, 86%, 87%, 88%, 89%, 90%, 91%, 92%, 93%, 94%, 95%, 96%, 97%, 98%, or 99%, or has 100% amino acid sequence identity to a corresponding thioesterase from a plant species such as a *Cuphea* or *Elaeis* species, e.g., *Cuphea carthagenensis, Cuphea decandra, Cuphea paucipetala, Cuphea lanceolata, Elaeis oleifera*, or *Elaeis guineensis*. In some aspects, a thioesterase useful in the wax synthesis constructs disclosed herein has amino acid sequence identity of at least, e.g., 30%, 40%, 45%, 50%, 55%, 60%, 65%, 70%, 75%, 80%, 85%, 86%, 87%, 88%, 89%, 90%, 91%, 92%, 93%, 94%, 95%, 96%, 97%, 98%, or 99%, or 100% sequence identity to the amino acid sequence of a thioesterase selected from *Cuphea carthagenensis* cc1FatB1 ("Cc1FatB1"; SEQ ID NO:1 or SEQ ID NO:2), *Cuphea decandra* Cd1FatB1 ("Cd1FatB1"; SEQ ID NO:3 or SEQ ID NO:4), *Cuphea paucipetala* Cp1FatB1 ("Cp1FatB1"; SEQ ID NO:5 or SEQ ID NO:6), and *Elaeis guineensis* thioesterase ("oil palm thioesterase"; SEQ ID NO:7, SEQ ID NO:8, or SEQ ID NO:9). See, e.g., FIG. 1. For example, a nucleic acid molecule as disclosed herein can comprise a sequence encoding a thioesterase having at least 85% identity to the amino acid sequence of any one of SEQ ID NOS: 1-9 or a functional fragment thereof, or having at least 90% identity to the amino acid sequence of any one of SEQ ID NOS: 1-9 or a functional fragment thereof, for example, at least 95% identity to the amino acid sequence of any one of SEQ ID NOS: 1-9. Biochemical assays for demonstrating and measuring the activity of a thioesterase are well known (see, for example, U.S. Pat. No. 5,298,421, incorporated herein by reference in its entirety), as are biological assays that measure levels of free fatty acid production such as demonstrated in the examples herein, using, e.g., gas chromatography, gas chromatography-mass spectrometry, liquid chromatography-mass spectrometry, ion chromatography-mass spectrometry, etc.).

In some cases, certain eukaryotic acyl-ACP thioesterase genes (e.g., from *Cuphea, Elaeis*, or other plant species) encode N-terminal transit peptides for transport of the thioesterase into plastids. As the transit peptides are not be necessary for the activity of these thioesterases, in certain aspects, the wax ester synthesis reagents and methods of the invention utilize mature forms of the thioesterases described herein, wherein all or a portion of the transit peptide has been deleted. Further, in some cases, certain thioesterase genes encode N-terminal segments that are not necessary for thioesterase activity, and, in certain aspects, the wax ester synthesis reagents and methods of the invention utilize forms of the thioesterases described herein that lack N-terminal segments that are not necessary for thioesterase activity.

Accordingly, the amino acid sequence of a thioesterase used in the wax ester synthesis reagents and methods of the invention can in some examples be a deletion mutant of any of the thioesterases described herein, wherein 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 residues are deleted from the N-terminus of the reference thioesterase. Preferably, the deletion mutant retains at least 75%, 80%, 85%, 90%, 95%, 96%, 97%, 98%, or 99%, or retains 100% of the thioesterase activity of the reference thioesterase. For example, any eukaryotic thioesterase (e.g., any eukaryotic acyl-ACP thioesterase) used in the wax ester synthesis reagents and methods of the invention may be truncated to remove a transit peptide and/or an N-terminal segment unnecessary for thioesterase activity.

For example, a gene encoding a thioesterase having at least 70%, 75%, 80%, 85%, 90%, 95%, 96%, 97%, 98%, or 99%, or 100% amino acid sequence identity to an oil palm thioesterase can be used in the wax ester synthesis constructs of the invention, for example, a gene encoding a thioesterase having at least 70% identity, for example, at least 85% or at least 95% identity to the amino acid sequence of SEQ ID NO: 7, which may be truncated at the N-terminus to remove transit peptide residues 1-93 of the amino acid sequence of SEQ ID NO: 7 (SEQ ID NO: 8). Alternatively, the oil palm thioesterase having at least 70%, at least 85% or at least 95% identity to the amino acid sequence of SEQ ID NO:7 may be truncated at the N-terminus to remove residues 1-118 of the amino acid sequence of SEQ ID NO: 7 (SEQ ID NO: 9). Alternatively, the polypeptide of SEQ ID NO: 8 or 9 may replace the polypeptide of SEQ ID NO: 7 in any of the methods or systems for producing a wax ester as described herein. In some aspects, a nucleotide sequence encoding the polypeptide of SEQ ID NO: 8 or a nucleotide sequence encoding the polypeptide of SEQ ID NO: 9 may replace a nucleotide sequence encoding the polypeptide of SEQ ID NO: 7 in any of the nucleic acid molecules, constructs, cassettes, vectors, or recombinant host cells described herein.

Any of the thioesterases described herein may be used in any of the wax ester synthesis constructs, host microorganisms, and methods of the invention.

Acyl-CoA Synthetases

A recombinant or isolated nucleic acid molecule used in the microorganisms and methods of the invention can comprise a nucleic acid sequence encoding an acyl-CoA synthetase. The acyl-CoA synthetase can be, for example, a prokaryotic acyl-CoA synthetase, for example, such as FadD (GenBank Accession NP_416319) or FadK of *E. coli* (GenBank Accession NP_416216), or their homologs in other bacterial species, including, as nonlimiting examples, the acyl-CoA synthetase of *Vibrio splendidus* (GenBank Accession EGU44230) or *Marinobacter adhaerens* HP15 (GenBank Accession ADP96803). Additional nonlimiting examples of prokaryotic proteins known to have or suspected of having acyl-CoA synthetase activity include, but are not limited to, *Acinetobacter* sp. ADP1 fadD (GenBank Accession YP_045024), *Haemophilus influenza* RdKW20 fadD (GenBank Accession NP_438551), *Bacillus halodurans* C-125 BH3103 (GenBank Accession NP_243969), *Bacillus subtilis* yhF1 (GenBank Accession NP_388908), *Pseudomonas fluorescens* Pfo-1 Pfl-4354 (GenBank Accession YP_350082), *Comamonas testosteroni* KF-1 EAV15023 (GenBank Accession ZP_01520072), *Pseudomonas aeruginosa* fadD1 (GenBank Accession NP_251989), *Pseudomonas aeurginosa* PAO1 fadD2 (GenBank Accession NP_251990), *Rhizobium etli* CFN42 fadD (GenBank Accession YP_468026), *Rhodopseudomo nas palustris* Bis B18 RPC_4074 (GenBank Accession YP_533919), *Rasltonia Solanacearum* GM1 1000 fadD1 (GenBank Accession NP_520978), *Mycobacterium tuberculosis* H37Rv fadDD35 (GenBank Accession NP_217021), *Mycobacterium tuberculosis* H37Rv fadDD22 (GenBank Accession NP_217464), and *Stenotrophomon* as *Maltophilia* R551-3 PRK0059 (GenBank Accession ZP_01644857).

Alternatively, the nucleic acid sequence encoding an acyl-CoA synthetase can encode an acyl-CoA synthetase derived from a fungal species, such as, for example, a *Saccharomyces cerevisiae* acyl-CoA synthetase (e.g., the medium chain fatty acyl-CoA synthetase Faa2p (GenBank Accession NP_010931) or the SCRG_04483 acyl-CoA synthetase (GenBank Accession EDV08843) or a *Yarrowia lipolytica* acyl-CoA synthetase (e.g., GenBank Accession CAG77892). Additional acyl-CoA synthetase genes that may be used in the constructs and microorganisms disclosed herein include acyl-CoA synthetases of plants, such as, for example, the long chain acyl-CoA synthetase of *Brassica napus* (GenBank Accession CAC19877) or the long chain acyl-CoA synthetase of *Arabidopsis thaliana* (GenBank Accession AEE74324), or the Yng-I-like acyl-CoA synthetase of *Glycine max* (GenBank Accession XP_003524920), and acyl-CoA synthetases of algal species, such as, for example, the long chain acyl-CoA synthetase of *Chlamydomonas reinhardtii* (GenBank Accession XP_001693692), or acyl-CoA synthetases of *Nannochloropsis oculata* (e.g., GenBank Accession ADP09391), or *Chlorella variabilis* (e.g., GenBank Accession EFN56588). Further considered are acyl-CoA synthetases of animal species, including insects (e.g., *Apis mellifera*, for example, the acyl-CoA synthetase family member 2, mitochondrial precursor, GenBank Accession NP_001193902) and mammals such as *Mus musculus* (e.g., the "MACS" acyl-CoA synthetase, GenBank Accession EDL17174).

Specifically included for use in the constructs and microorganisms disclosed herein for making wax esters are nucleic acid sequences that encode polypeptides having at least 30%, 40%, 45%, 50%, 55%, 60%, 65%, 70%, 75%, 80%, 85%, 86%, 87%, 88%, 89%, 90%, 91%, 92%, 93%, 94%, 95%, 96%, 97%, 98%, or 99%, amino acid sequence identity to known or suspected acyl-CoA synthetases, including but not limited to the examples above, where the encoded polypeptides have acyl-CoA synthetase activity. For example, a nucleic acid sequence that encodes an acyl-CoA synthetase can have at least 85%, at least 90%, or at least 95% to an identified acyl-CoA synthetase, including but not limited to those disclosed herein.

For example, an acyl-CoA synthetase useful in the wax ester synthesis pathways and methods of the invention can have sequence identity of at least 30%, 40%, 45%, 50%, 55%, 60%, 65%, 70%, 75%, 80%, 85%, 86%, 87%, 88%, 89%, 90%, 91%, 92%, 93%, 94%, 95%, 96%, 97%, 98%, or 99%, or can have sequence identity of 100%, to the amino acid sequence of an acyl-CoA synthetase selected from *Saccharomyces cerevisiae* "Faa2p" (SEQ ID NO: 10), *Saccharomyces cerevisiae* SCRG_04483 (SEQ ID NO: 11), *E. coli* FadD (SEQ ID NO: 12), *E. coli* FadK (SEQ ID NO: 13), and *Mus musculus* MACS (SEQ ID NO: 14). See, e.g., FIG. 2. For example, the acyl-CoA synthetase encoded by a nucleic acid sequence of a construct of the invention may be or comprise a polypeptide having at least 85% identity to the amino acid sequence of any one of SEQ ID NOS: 10-14 or a functional fragment thereof, or may be or comprise a polypeptide having at least 90% identity to the amino acid sequence of any one of SEQ ID NOS: 10-14 or a functional fragment thereof. For example, the acyl-CoA synthetase can be or comprise a polypeptide having at least 95% identity to the amino acid sequence of any of SEQ ID NOS: 10-14.

Any of the acyl-CoA synthetases described herein may be used in any of the wax ester synthesis reagents and methods of the invention.

Alcohol-Forming Fatty Acyl Reductases

For production of a fatty alcohol that can be used as a substrate by a wax ester synthase, a nucleic acid molecule as provided herein that includes a sequence encoding a wax ester synthase can further include a sequence encoding a fatty alcohol-forming acyl reductase or "FAR" that can reduce acyl-CoA to a fatty alcohol. FARs have been identified in, e.g., *Euglena* (see, e.g., Teerawanichpan et al., *Lipids* 45:263-273 (2010)), *Arabidopsis* (see, e.g., Rowland et al., *Plant Physiol.* 142:866-877 (2006), Doan et al., *J. Plant Physiol.* 166:787-796 (2009) and Domergue et al., *Plant Physiol.* 153: 1539-1554 (2010)), *Artemisia* (see, e.g., Maes et al., *New Phytol.* 189:176-189 (2011)), jojoba (see, e.g., Metz et al., *Plant Physiol.* 122:635-644 (2000)), moth (see, e.g., Lienard et al., *Proc. Natl. Acad. Sci.* 107:10955-10960 (2010)), bee (see, e.g., Teerawanichpan et al., *Insect Biochemistry and Molecular Biology* 40:641-649 (2010)) and mammals (see, e.g., Honsho et al., *J. Biol. Chem.* 285:8537-8542 (2010)). An alcohol-forming fatty acyl reductase useful in the wax ester synthesis reagents and methods of the invention can be any alcohol-forming reductase that has activity in the host microorganism.

For example, an alcohol-forming fatty acyl reductase useful in the wax ester synthesis pathways and methods of the invention can be a prokaryotic alcohol-forming acyl-CoA reductase and can have at least 30%, 40%, 45%, 50%, 55%, 60%, 65%, 70%, 75%, 80%, 85%, 86%, 87%, 88%, 89%, 90%, 91%, 92%, 93%, 94%, 95%, 96%, 97%, 98%, or 99% identity, or can be 100% identical, to the amino acid sequence of a prokaryotic alcohol-forming reductase such as *Marinobacter aquaeolei* VT8 Maqu_2220 (SEQ ID NO: 15, GenBank Accession YP_959486), *Marinobacter algicola* DG893 (GenBank Accession ZP_01892457); *Hahella chejuensis* KCTC 2396 HCH_05075; SEQ ID NO: 20, GenBank Accession YP_436183); *Oceanobacter* sp. RED65 (GenBank Accession ZP_01305629), or *Marinobacter aquaeoli* VT8 2220 Maqu_2507 gene (SEQ ID NO:19, GenBank Accession ABM19582).

Nonlimiting examples of other alcohol-forming fatty acyl reductases that can be used in the wax ester synthesis constructs, microorganisms, and methods of the invention may include, but are not limited to, alcohol-forming fatty acyl reductases that have at least 30%, 40%, 45%, 50%, 55%, 60%, 65%, 70%, 75%, 80%, 85%, 86%, 87%, 88%, 89%, 90%, 91%, 92%, 93%, 94%, 95%, 96%, 97%, 98%, or 99% identity, or have 100% identity to the amino acid sequence of an identified alcohol-forming reductase such as but not limited to bfar from *Bombyx mmori* (GenBank Accession BAC79426), jjfar from *Simmondsia chinensis* (SEQ ID NO: 21, GenBank Accession AAD38039), an acyl-CoA reductase from *Triticum aestivum* (GenBank Accession CAD30694 or CAD30692), mfar1 from *Mus musculus* (GenBank Accession NP_081655), mfar2 from *Mus musculus* (GenBank Accession NP_848912), hfar from *H. sapiens* (GenBank Accession NP_115604), FARXIII from *Ostrinia scapulalis* (SEQ ID NO: 18, GenBank Accession ACJ06520), MS2 from *Z. mays* (GenBank Accession NP_001151388 or EU970865), or MS2 (GenBank Accession NP_187805), FAR4 (GenBank Accession NP_001030809 or NP_190040), FAR6 (SEQ ID NO: 16, SEQ ID NO: 17, GenBank Accession 67633703), CER4 (GenBank Accession NP_567936) or Ath (GenBank Accession NP567936) from *Arabidopsis thaliana*, Yev-pgFAR from *Yponomeuta evonymellus* (GenBank Accession GQ907231-GQ907233), Yro-pgFAR from *Yponomeuta rorellus* (GenBank Accession GQ907234), Ypa-pgFAR from *Yponomeuta padellus* (GenBank Accession GQ907235), OnuE from *Ostrinia nubilalis* (GenBank Accession FJ807735), Has from *Homo sapiens* (GenBank Accession AAT42129), etc.

Specifically included for use in the constructs and microorganisms disclosed herein for making wax esters are nucleic acid sequences that encode polypeptides having at least 30%, 40%, 45%, 50%, 55%, 60%, 65%, 70%, 75%, 80%, 85%, 86%, 87%, 88%, 89%, 90%, 91%, 92%, 93%, 94%, 95%, 96%, 97%, 98%, or 99%, amino acid sequence identity to known or suspected alcohol-forming fatty acyl reductases, including but not limited to the examples above, where the encoded polypeptides have alcohol-forming fatty acyl reductases activity. For example, a nucleic acid sequence that encodes an alcohol-forming fatty acyl reductases can have at least 85%, at least 90%, or at least 95% to an identified alcohol-forming fatty acyl reductases, including but not limited to those disclosed herein.

For example, an alcohol-forming reductase useful in the wax ester synthesis pathways and methods of the invention can have sequence identity of at least 30%, 40%, 45%, 50%, 55%, 60%, 65%, 70%, 75%, 80%, 85%, 86%, 87%, 88%, 89%, 90%, 91%, 92%, 93%, 94%, 95%, 96%, 97%, 98%, or 99%, or can have sequence identity of 100%, to the amino acid sequence of an alcohol-forming reductase selected from *Arabidopsis thaliana* FAR6 (GenBank Accession AEE79553) with or without a transit peptide (SEQ ID NO: 16 or 17, respectively), *Ostrinia scapulalis* FARXIII (GenBank Accession ACJ06520; SEQ ID NO: 18), *M. aquaeolei* VT8 Maqu_2507 (GenBank Accession ABM19582, SEQ ID NO: 19), *Hahella chejuensis* Hch_05075 (GenBank Accession YP_436183; SEQ ID NO: 20), and *Simmondsia chinensis* jjfar (GenBank Accession AAD38039; SEQ ID NO: 21). See, e.g., FIG. 3. For example, the alcohol-forming fatty acyl reductase may be or comprise a polypeptide having at least 85% identity to the amino acid sequence of any one of SEQ ID NOS: 15-21 or a functional fragment thereof, or may be or comprise a polypeptide having at least 90% identity to the amino acid sequence of any one of SEQ ID NOS: 15-21 or a functional fragment thereof. For example, the alcohol-forming fatty acyl reductase can be or comprise a polypeptide having at least 95% identity to the amino acid sequence of any of SEQ ID NOS: 15-21. Methods of demonstrating and measuring the activity of an alcohol-forming fatty acyl reductase are well known (e.g., biochemical assays (Reiser and Somerville (1997) *J. Biol. Chem.* 79: 2969-2975) as well as measuring rates/levels of fatty alcohol production using, e.g., gas chromatography-mass spectrometry, liquid chromatography-mass spectrometry, thin layer chromatography, etc.).

In some aspects, an alcohol-forming fatty acyl reductase useful in the wax ester synthesis reagents and methods of the invention is encoded by a nucleic acid sequence that has at least 30%, 40%, 45%, 50%, 55%, 60%, 65%, 70%, 75%, 80%, 85%, 86%, 87%, 88%, 89%, 90%, 91%, 92%, 93%, 94%, 95%, 96%, 97%, 98%, 99%, or 100% sequence identity to a corresponding alcohol-forming fatty acyl reductase-encoding nucleic acid sequence from a plant species such as an *Arabidopsis* or *Simmondsia* species, e.g., *Arabidopsis thaliana* (e.g., GenBank Accession 67633703) or *Simmondsia chinensis* (e.g., GenBank Accession AAD38039).

In some aspects, an alcohol-forming fatty acyl reductase useful in the wax ester synthesis reagents and methods of the invention is encoded by a nucleic acid sequence that has at least 30%, 40%, 45%, 50%, 55%, 60%, 65%, 70%, 75%, 80%, 85%, 86%, 87%, 88%, 89%, 90%, 91%, 92%, 93%, 94%, 95%, 96%, 97%, 98%, 99%, or 100% sequence identity to a corresponding alcohol-forming fatty acyl reductase-encoding nucleic acid sequence from a moth species such as an *Ostrinia* species (for example, *Ostrinia scapulalis*, e.g., Accession No. ACJ06520).

In some cases, certain eukaryotic fatty acyl reductase genes (e.g., from plants) encode N-terminal transit peptides. As the transit peptides may not be necessary for the activity of these fatty acyl reductases, in certain aspects, the wax ester synthesis reagents and methods of the invention may utilize mature forms of the fatty acyl reductases described herein, wherein all or a portion of the transit peptide not necessary for fatty acyl reductase activity has been deleted.

Accordingly, in some aspects, the amino acid sequence of an alcohol-forming fatty acyl reductase used in the wax ester synthesis reagents and methods of the invention is a deletion mutant of any of the alcohol-forming fatty acyl reductases described herein, wherein 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 residues are deleted from the N-terminus of the reference alcohol-forming fatty acyl reductase. In some aspects, the deletion mutant retains at least 95%, 96%, 97%, 98%, 99%, or 100% of the thioesterase activity of the reference alcohol-forming fatty acyl reductase. In some aspects, any eukaryotic fatty acyl reductase (e.g., any eukaryotic alcohol-forming fatty acyl-CoA reductase) used in the wax ester synthesis reagents and methods of the invention may be truncated to remove a transit peptide unnecessary for fatty acyl reductase activity.

For example, in some aspects, a FAR6 reductase used in the wax ester synthesis reagents and methods of the invention, having the amino acid sequence of SEQ ID NO: 16, is truncated at the N-terminus to remove transit peptide residues 1-47 of the amino acid sequence of SEQ ID NO: 16 (SEQ ID NO: 17). In some aspects, the polypeptide of SEQ ID NO: 17 may replace the polypeptide of SEQ ID NO: 16 in any of the reagents and methods for producing a wax ester as described herein. In some aspects, a nucleotide sequence encoding the polypeptide of SEQ ID NO: 16 lacking the nucleotide residues encoding the transit peptide (e.g., SEQ ID NO: 48) may replace a nucleotide sequence encoding the polypeptide of SEQ ID NO: 16 (e.g., SEQ ID NO: 47) in any of the nucleic acid molecules, constructs, cassettes, vectors, or recombinant host cells described herein.

In some aspects, the conversion of acyl-CoA to fatty alcohol may occur via synthesis of a fatty aldehyde, wherein a fatty aldehyde reductase (e.g., an aldehyde-forming acyl-CoA reductase) expressed in the host cell first reduces acyl-CoA to a fatty aldehyde. In certain aspects, the host cell can be engineered to overexpress an endogenous fatty aldehyde reductase (e.g., by inserting promoter and/or enhancer transcriptional control elements near the fatty aldehyde reductase gene). In other aspects, the host cell may be engineered to express an exogenous fatty aldehyde reductase.

Any of the fatty acyl reductases described herein may be used in any of the wax ester synthesis reagents and methods of the invention.

Wax Ester Synthases

Wax esters are the product of a condensation reaction between a fatty acyl-thioester substrate and a fatty alcohol, catalyzed by a wax ester synthase. Polypeptides having wax ester synthase activity may be polypeptides identified as wax synthases, O-acyltransferases, including membrane-bound O-acyltransferases (MBOATs), diacylglycerol O-acyltransferases, alcohol acyltransferases (AATs, EC 2.3.1.84), or alcohol synthase/acyl-CoA:diacylglycerol acyltransferases. Some polypeptides identified as diacylglycerol acyltransferases (DGATs) may also be found to have wax ester synthase activity. Wax ester synthases have been identified in, e.g., *Acinetobacter* (Ishige et al., *Appl. Environ. Microbiol.* 68:1192-1195 (2002); Kalscheuer and Steinbuchel, *J. Biol. Chem.* 278:8075-8082 (2003); Kalscheuer et al., *Appl. Environ. Microbiol.* 72:1373-1379 (2006)), *Marinobacter* (Holtzapple and Schmidt-Dannert, *J. Bacteriol.* 189:3804-3812 (2007)), *Arabidopsis* (Li et al., *Plant Physiol.* 148:97-107 (2008)), petunia (King et al., *Planta* 226:381-394 (2007)), jojoba (Lardizabal et al., *Plant Physiol.* 122:645-655 (2000), and mammalian species (Cheng and Russell, *J. Biol. Chem.* 279:37798-37807 (2004); Yen et al., *J. Lipid Res.* 46:2388-2397 (2005)).

Wax ester synthases may be identified using methods known in the art, (e.g., Hidden Markov Models ("HMMs") based on pattern similarity to a set of known wax ester synthase/DGAT sequences, respectively. As nonlimiting examples, a gene that encodes a polypeptide that recruits to Pfam PF03007 (wax ester synthase like acyl-CoA acyltransferase domain) with a bit score greater than the gathering cutoff of 20.6 and an E value of 0.01 or less or recruits to Pfam PF13813 ("MBOAT_2") with a bit score greater than the gathering cutoff of 25.0 and an E value of 0.01 or less can be selected for use in the nucleic acid molecules and microorganisms provided herein.

Wax ester synthesis proteins encoded by nucleic acid molecules provided herein can include, but are not limited to: acyltransferases or wax synthases, fatty acyl transferases, diacylglycerol acyltransferases, acyl-coA wax alcohol acyltransferases, and bifunctional wax ester synthase/acyl 1-CoA: diacylglycerol acyl transferase selected from a multienzyme complex from *Simmondsia chinensis, Acinetobacter* sp. strain ADP1 (formerly *Acinetobacter calcoaceticus* ADP1), *Pseudomonas aeruginosa, Fundibacter (Alcanivorax) jadensis, Arabidopsis thaliana*, or *Alkaligenes eutrophus*. Wax synthases can also be from a multienzyme complex from *Alkaligenes eutrophus* and other organisms known in the literature to produce wax and fatty acid esters.

Proteins known or suspected of having wax ester synthase activity that are considered for use in the nucleic acid molecules and transgenic microorganisms provided herein include wax synthases from prokaryotic species, such as but not limited to, *Marinobacter hydrocarbonoclasticus* WS1 (GenBank Accession ABO21020), *M. hydrocarbonoclasticus* DSM 8798 WS2 (GenBank Accession ABO21021), M. sp. ELB 17 (GenBank Accession EBA00388), *M. aquaeolei* Maqu_0168 WS (GenBank Accession YP_957462), *M. adhaerens* HP15 WS (ADP99639), *Hahella chejuensis* KCTC 2396 (GenBank Accession YP_432512), *Acinetobacter baumannii* wax ester synthase (GenBank Accession EGJ63408), *A. calcoaceticus* WS/DGAT (GenBank Accession ZP_06058985) *Acinetobacter baylyi* ADP1 wax ester synthase (GenBank Accession AAO17391 or Q8GGG1), *Bradyrhizobium japonicum* USDA 110 (GenBank Accession NP_769520), *Erythrobacter litoralis* HTCC 2594 (GenBank Accession YP_457389), *Rhodococcus opacus* wax ester synthase (GenBank Accession BAH53702), *Mycobacterium tuberculosis* wax ester synthase (GenBank Accession NP_334638), *M. smegmatis* wax ester synthase (GenBank Accession ABK74273), the "WS/DGAT/MGAT" subfamily proteins of *Alcanivorax* species (GenBank Accessions CAL17252; EDX90960; EDX89052; ZP_05043539; ZP_05041631), wsadpl from *Nocardia farcinica* IFM 10152 (GenBank Accession YP_117375), *Photobacterium profundum* SS9 (GenBank Accession YP_130413), *Rhodoferax*

*ferrireducens* DSM 15236 (GenBank Accession ZP_00691704), and *Salinibacter ruber* DSM 13855 (GenBank Accession YP_446603).

Examples of eukaryotic polypeptides that may be useful as wax synthases include, without limitation, jojoba wax ester synthase JjWS (GenBank Accession AF149919), *Euglena gracilis* wax ester synthase (GenBank Accession ADI60058), *Arabidiopsis thaliana* WSD1 O-acyltransferase (GenBank Accession NP_568547), *Arabidiopsis thaliana* GPAT acyltransferase (GenBank Accession NP_174499), the putative long-chain-alcohol O-fatty-acyltransferase 4 of *Arabidiopsis thaliana* (GenBank Accession NP_200346) *Murraya koenigii* wax ester synthase, acyl-CoA wax alcohol acyltransferase 2 from *H. sapiens* (GenBank Accession NP_001002254), mWS from *Mus musculus* (GenBank Accession Q6E1M8), SAAT from *Fragaria xananas* (GenBank Accession AAG13130), the membrane bound O-acyltransferase (MBOAT) of *Zea mays* (GenBank Accession NP_001131179), mdAAT2 from *Malus x domestica* (GenBank Accession AAS79797), as well as insect wax ester synthases, etc.

In some illustrative examples, a wax ester synthase useful in the wax ester synthesis nucleic acid molecules, production hosts, and methods of the invention can have a sequence identity of at least, e.g., 30%, 40%, 45%, 50%, 55%, 60%, 65%, 70%, 75%, 80%, 85%, 86%, 87%, 88%, 89%, 90%, 91%, 92%, 93%, 94%, 95%, 96%, 97%, 98%, or 99%, or 100% sequence identity to the amino acid sequence of a wax ester synthase selected from *Marinobacter* sp. strain ELB17 MELB17 WS ("MELB17 WS"; SEQ ID NO: 22), *Marinobacter aquaeolei* 0168 WS ("Maqu_0168 WS"; SEQ ID NO: 23), *Marinobacter adhaerens* HP15 wax ester synthase ("HP15 WS"; SEQ ID NO: 24), *Marinobacter hydrocarbonoclasticus* DSM 8798 WS1 ("DSM 8798 WS1"; SEQ ID NO: 25), *Marinobacter hydrocarbonoclasticus* DSM 8798 WS2 ("DSM 8798 WS2"; SEQ ID NO: 26), *Petunia hybrida* wax ester synthase ("petunia WS"; SEQ ID NO: 27), *Mus musculus* WS ("*Mus musculus* WS"; SEQ ID NO: 28), *Simmondsia chinensis* wax ester synthase ("jojoba WS"; SEQ ID NO: 29), and *Acinetobacter* sp. ADP1 wax ester synthase ("ADP1 WS"; SEQ ID NO: 30). See, e.g., FIG. 4. For example, the wax ester synthase encoded by a nucleic acid sequence used in a nucleic acid molecule of the invention may be or comprise a polypeptide having at least 85% identity to the amino acid sequence of any one of SEQ ID NOS: 22-30 or a functional fragment thereof, or may be or comprise a polypeptide having at least 85% identity, at least 90%, or at least 95% identity to the amino acid sequence of any one of SEQ ID NOS: 22-30 or a functional fragment thereof. For example, the wax ester synthase can be or comprise the amino acid sequence of any of SEQ ID NOS: 22-30.

Methods of demonstrating and measuring the activity of a wax ester synthase are well known (e.g., measuring rates/levels of wax ester production using, e.g., gas chromatography-mass spectrometry, liquid chromatography-mass spectrometry, thin layer chromatography, etc.). Methods to identify wax synthase activity are also provided in, e.g., U.S. Pat. No. 7,118,896, which is incorporated herein by reference in its entirety.

For example, a gene useful in the nucleic acid molecules, recombinant microorganisms, and methods of the invention can be encoded by a nucleic acid sequence that has at least 30%, 40%, 45%, 50%, 55%, 60%, 65%, 70%, 75%, 80%, 85%, 86%, 87%, 88%, 89%, 90%, 91%, 92%, 93%, 94%, 95%, 96%, 97%, 98%, or 99% identity, or 100% sequence identity, to a corresponding wax ester synthase-encoding nucleic acid sequence from a bacterium such as *Acinetobacter calcoaceticus* (e.g., GenBank Accession YP_045555.1).

For example, a wax ester synthase useful in the wax ester synthesis reagents and methods of the invention is encoded by a nucleic acid sequence that has at least 30%, 40%, 45%, 50%, 55%, 60%, 65%, 70%, 75%, 80%, 85%, 86%, 87%, 88%, 89%, 90%, 91%, 92%, 93%, 94%, 95%, 96%, 97%, 98%, or 99% identity, or 100% sequence identity, to a corresponding wax ester synthase-encoding nucleic acid sequence from a plant, e.g., a petunia or jojoba species. In some examples, the wax ester synthase is from *Petunia hybrida* (e.g., GenBank Accession AAZ08051) or *Simmondsia chinensis* (e.g., GenBank Accession AF149919).

For example, a wax ester synthase useful in the nucleic acid molecules and methods provided herein can be encoded by a nucleic acid sequence that has at least 30%, 40%, 45%, 50%, 55%, 60%, 65%, 70%, 75%, 80%, 85%, 86%, 87%, 88%, 89%, 90%, 91%, 92%, 93%, 94%, 95%, 96%, 97%, 98%, 99%, or 100% sequence identity to a corresponding wax ester synthase-encoding nucleic acid sequence from a mammal, e.g., *Mus musculus* (e.g., GenBank Accession 49854217).

Any of the wax ester synthases described herein may be used in any of the wax ester synthesis reagents and methods of the invention.

Nucleic Acid Molecules

The present invention provides recombinant nucleic acid molecules comprising nucleic acid sequences that encode a) thioesterases, b) acyl-CoA synthetases, c) alcohol-forming fatty acyl reductases, and/or d) wax ester synthases (e.g., any of the thioesterases, acyl-CoA synthetases, alcohol-forming fatty acyl reductases, and/or wax ester synthases disclosed herein) or functional fragments thereof. A nucleic acid molecule of the invention can be isolated and/or purified. The nucleic acid molecules described herein can be used in any of the methods of the invention, and may be included in any of the vectors or host cells of the invention.

A recombinant nucleic acid molecule as provided herein can encode a polypeptide having wax ester synthase activity and one or more of a) a thioesterase, b) an acyl-CoA synthetase, and c) an alcohol-forming fatty acyl reductase. For example, a recombinant nucleic acid molecule as provided herein can include a sequence that encodes a wax ester synthase and a sequence that encodes a thioesterase; or can include a sequence that encodes a wax ester synthase and a sequence that encodes an acyl-CoA synthetase; or can include a sequence that encodes a wax ester synthase and a sequence that encodes an alcohol-forming fatty acyl reductase. In further examples, a recombinant nucleic acid molecule as provided herein can include a sequence that encodes a wax ester synthase, a sequence that encodes a thioesterase, and a sequence that encodes an acyl-CoA synthetase; or can include a sequence that encodes a wax ester synthase, a sequence that encodes a thioesterase, and a sequence that encodes an alcohol-forming fatty acyl reductase; or can include a sequence that encodes a wax ester synthase, a sequence that encodes an acyl-CoA synthetase, and a sequence that encodes an alcohol-forming fatty acyl reductase. In another example, the nucleic acid molecule encodes a) an acyl-ACP thioesterase, b) an acyl-CoA synthetase, c) an alcohol-forming acyl-CoA reductase, and d) a polypeptide having wax ester synthase activity.

A host cell, e.g., a prokaryotic microorganism such as a *cyanobacterium*, transformed with a nucleic acid molecule that includes a sequence encoding a wax ester synthase and one or more additional genes of the wax ester synthesis pathway (e.g., all four genes of the wax ester synthesis pathway as provided herein) can produce a greater amount of a wax ester than does a control host cell, where the control host cell is cultured under the same conditions and is substantially identical to the host cell expressing the isolated nucleic acid molecule(s) in all respects, with the exception that the host cell does not include or does not express the isolated nucleic acid molecule.

The nucleic acid sequence encoding a thioesterase can encode any thioesterase that is capable of releasing a free fatty acid from any acyl-ACP substrate and can be, for example, of the thioesterases disclosed herein, including an acyl-CoA thioesterase, a hydroxylbenzoyl thioesterase, or an acyl-ACP thioesterase, which can be an acyl-ACP thioesterase from a prokaryotic or eukaryotic species. In some examples the thioesterase encoded by a nucleic acid molecule provided herein has a substrate preference of C8-C24, for example, C12-C18. As nonlimiting examples, a thioesterase encoded by a nucleic acid sequence of a nucleic acid molecule as provided herein can be derived from acyl-ACP thioesterases from a plant species, e.g., a *Cuphea* or *Elaeis* species, and in illustrative and nonlimiting examples can comprise an amino acid sequence having at least 30%, 40%, 45%, 50%, 55%, 60%, 65%, 70%, 75%, 80%, 85%, 86%, 87%, 88%, 89%, 90%, 91%, 92%, 93%, 94%, 95%, 96%, 97%, 98%, or 99% sequence identity to the amino acid sequence of any of SEQ ID NOS: 1-9; or to a functional fragment of the polypeptide having thioesterase activity.

The nucleic acid sequence encoding an acyl-CoA synthetase can encode any acyl-CoA synthetase, such as but not limited to any disclosed herein, and in illustrative and nonlimiting examples can comprise an amino acid sequence having at least 30%, 40%, 45%, 50%, 55%, 60%, 65%, 70%, 75%, 80%, 85%, 86%, 87%, 88%, 89%, 90%, 91%, 92%, 93%, 94%, 95%, 96%, 97%, 98%, or 99% sequence identity to the amino acid sequence of any of SEQ ID NOS: 10-14, or to a functional fragment of the polypeptide having acyl-CoA synthetase activity.

The nucleic acid sequence encoding an alcohol-forming fatty acyl reductase can encode any alcohol-forming fatty acyl reductase, such as but not limited to any disclosed herein, and in illustrative and nonlimiting examples can comprise an amino acid sequence having at least 30%, 40%, 45%, 50%, 55%, 60%, 65%, 70%, 75%, 80%, 85%, 86%, 87%, 88%, 89%, 90%, 91%, 92%, 93%, 94%, 95%, 96%, 97%, 98%, or 99% sequence identity to the amino acid sequence of any of SEQ ID NOS: 15-21; or to a functional fragment of the polypeptide having alcohol-forming fatty acyl reductase activity.

The nucleic acid sequence encoding a wax ester synthase can encode any polypeptide having wax ester synthase activity, such as but not limited to any disclosed herein, and in illustrative and nonlimiting examples can comprise an amino acid sequence having at least 30%, 40%, 45%, 50%, 55%, 60%, 65%, 70%, 75%, 80%, 85%, 86%, 87%, 88%, 89%, 90%, 91%, 92%, 93%, 94%, 95%, 96%, 97%, 98%, or 99% sequence identity to the amino acid sequence of any of SEQ ID NOS: 22-30; or to a functional fragment of the polypeptide having wax ester synthase activity.

Additionally, the invention encompasses isolated nucleic acid molecules comprising nucleic acid sequences encoding one or more of a thioesterase, an acyl-CoA synthetase, an alcohol-forming fatty acyl reductase, or a wax ester synthase, wherein one or more of the polypeptides is a deletion mutant in which one or more amino acids have been deleted from the original polypeptide (e.g., the reference thioesterase, acyl-CoA synthetase, alcohol-forming acyl reductase, or polypeptide having wax ester synthase activity). In some aspects, the deletion mutant lacks at least 1, 2, 3, 4, 5, 6, 7, 8, 9 or 10 amino acids from the N- and/or C-terminus and has an amino acid sequence at least 30%, 40%, 45%, 50%, 55%, 60%, 65%, 70%, 75%, 80%, 85%, 86%, 87%, 88%, 89%, 90%, 91%, 92%, 93%, 94%, 95%, 96%, 97%, 98%, or 99% identical, or 100% identical, to the corresponding amino acid sequence of the original polypeptide. In certain aspects, the deletion mutant retains at least 10%, 20%, 30%, 40%, 50%, 60%, 70%, 80%, 90% or 100% of the activity of the original polypeptide when expressed in a recombinant host cell.

Further, the invention provides variants of thioesterases, acyl-CoA synthetases, alcohol-forming fatty acyl reductases, and wax ester synthases for use in the wax ester synthesis pathways described herein. Variants may be naturally occurring, or non-naturally-occurring, such as those induced by various mutagens and mutagenic processes. In some aspects, at least one amino acid residue has been inserted N- and/or C-terminal to, and/or within, the reference sequence. In some aspects, at least one amino acid residue has been deleted N- and/or C-terminal to, and/or within, the reference sequence. In some aspects, variants may be sequences containing predetermined mutations by, e.g., homologous recombination or site-directed or PCR mutagenesis; corresponding proteins of other species; alleles or other naturally occurring variants; and/or derivatives wherein the protein has been covalently modified by chemical, enzymatic or other appropriate means with a moiety other than a naturally occurring amino acid.

A substitution, insertion or deletion may adversely affect the protein when the altered sequence substantially inhibits a biological function associated with the protein. For example, a variant of a thioesterase used in the methods of the invention may have activity that is reduced by not more than 1%, 2%, 3%, 4%, 5%, 6%, 7%, 8%, 9%, 10%, 15%, 20%, 30%, 40%, 50%, 60%, or 70% in comparison to the activity of the thioesterase from which the variant is derived. For example, a variant of an acyl-CoA synthetase used in the methods of the invention may have activity that is reduced by not more than about 1%, 2%, 3%, 4%, 5%, 6%, 7%, 8%, 9%, 10%, 15%, 20%, 30%, 40%, 50%, 60%, or 70% in comparison to the activity of the acyl-CoA synthetase from which the variant is derived. For example, a variant of an alcohol-forming fatty acyl reductase used in the methods of the invention may have activity that is reduced by not more than 1%, 2%, 3%, 4%, 5%, 6%, 7%, 8%, 9%, 10%, 15%, 20%, 30%, 40%, 50%, 60%, or 70% in comparison to the activity of the alcohol-forming fatty acyl reductase from which the variant is derived. For example, a variant of a wax ester synthase used in the methods of the invention may have activity that is reduced by not more than 1%, 2%, 3%, 4%, 5%, 6%, 7%, 8%, 9%, 10%, 15%, 20%, 30%, 40%, 50%, 60%, or 70% in comparison to the activity of the wax ester synthase from which the variant is derived. For example, the amount of wax ester produced by a host cell expressing a thioesterase, an acyl-CoA synthetase, an alcohol-forming fatty acyl reductase, and/or a wax ester synthase, where at least one of the enzymes is a variant of a thioesterase, an acyl-CoA synthetase, an alcohol-forming fatty acyl reductase, and/or a wax ester synthase disclosed herein, can be not less than about 99%, 98%, 97%, 96%, 95%, 94%, 93%, 92%, 91%, 90%, 85%, 80% or 75% of the amount of wax ester produced by a control host cell expressing the enzyme(s) from which the variant(s) are derived.

The invention also encompasses fragments and variants of any of a thioesterase, an acyl-CoA synthetase, an alcohol-forming fatty acyl reductase, and/or a polypeptide having wax ester synthase activity that has increased activity in comparison to the reference polypeptide. For example, a thioesterase, acyl-CoA synthetase, alcohol-forming fatty acyl reductase, or wax ester synthase fragment or variant may have activity that is increased by at least 5%, 10%, 20%, 30%, 40%, 50%, 60%, 70%, 80%, 90%, 100%, 200%, 300%, 400%, 500%, 600%, 700%, 800%, 900%, or 1000% in comparison to the activity of the enzyme from which the variant is derived. For example, the amount of wax ester produced by a host cell expressing a thioesterase, an acyl-CoA synthetase, an alcohol-forming fatty acyl reductase, and/or a wax ester synthase, where at least one of the enzymes is a fragment or variant of a thioesterase, an acyl-CoA synthetase, an alcohol-forming fatty acyl reductase, and/or a wax ester synthase disclosed herein, can be at least 70%, 80%, 90%, 100%, 200%, 300%, 400%, 500%, 600%, 700%, 800%, 900% or 1000% of the amount of wax ester produced by a host cell expressing the protein(s) from which the fragment(s) or variant(s) are derived.

The invention also encompasses deletion mutants of a thioesterase in which one or more amino acids have been deleted from a thioesterase but where the thioesterase activity of the deletion mutant can be reduced by not more than 1%, 2%, 3%, 4%, 5%, 6%, 7%, 8%, 9%, 10%, 15%, 20%, 30%, 40%, 50%, 60%, or 70% in comparison with the reference thioesterase. For example, a thioesterase deletion mutant can lack at least 1, 2, 3, 4, 5, 6, 7, 8, 9 or 10 amino acids from the N- and/or C-terminus and can have an amino acid sequence at least 30%, 40%, 45%, 50%, 55%, 60%, 65%, 70%, 75%, 80%, 85%, 86%, 87%, 88%, 89%, 90%, 91%, 92%, 93%, 94%, 95%, 96%, 97%, 98%, 99%, or 100% identical to the amino acid sequence of the reference thioesterase (e.g., any of SEQ ID NOS: 1-9). For example, the invention encompasses deletion mutants of an acyl-CoA synthetase in which one or more amino acids have been deleted from an acyl-CoA synthetase as disclosed herein but where the acyl-CoA synthetase activity of the deletion mutant is reduced by not more than 1%, 2%, 3%, 4%, 5%, 6%, 7%, 8%, 9%, 10%, 15%, 20%, 30%, 40%, 50%, 60%, or 70% in comparison with the reference acyl-CoA synthetase. For example, the acyl-CoA synthetase deletion mutant lacks at least 1, 2, 3, 4, 5, 6, 7, 8, 9 or 10 amino acids from the N- and/or C-terminus and has an amino acid sequence at least 30%, 40%, 45%, 50%, 55%, 60%, 65%, 70%, 75%, 80%, 85%, 86%, 87%, 88%, 89%, 90%, 91%, 92%, 93%, 94%, 95%, 96%, 97%, 98%, 99%, or 100% identical to the corresponding amino acid sequence of the reference acyl-CoA synthetase (e.g., any of SEQ ID NOS: 10-14). For example, the invention encompasses deletion mutants of an alcohol-forming fatty acyl reductase in which one or more amino acids have been deleted from an alcohol-forming fatty acyl reductase described herein but where the alcohol-forming fatty acyl reductase activity of the deletion mutant is reduced by not more than 1%, 2%, 3%, 4%, 5%, 6%, 7%, 8%, 9%, 10%, 15%, 20%, 30%, 40%, 50%, 60%, or 70% in comparison with the reference alcohol-forming fatty acyl reductase. For example, the alcohol-forming fatty acyl reductase deletion mutant can lack at least 1, 2, 3, 4, 5, 6, 7, 8, 9 or 10 amino acids from the N- and/or C-terminus and has an amino acid sequence at least 30%, 40%, 45%, 50%, 55%, 60%, 65%, 70%, 75%, 80%, 85%, 86%, 87%, 88%, 89%, 90%, 91%, 92%, 93%, 94%, 95%, 96%, 97%, 98%, 99%, or 100% identical to the corresponding amino acid sequence of the reference alcohol-forming fatty acyl reductase (e.g., any of SEQ ID NOS: 15-21). For example, the invention encompasses deletion mutants of a wax ester synthase in which one or more amino acids have been deleted from a wax ester synthase described herein but where the wax ester synthase activity of the deletion mutant is reduced by not more than 1%, 2%, 3%, 4%, 5%, 6%, 7%, 8%, 9%, 10%, 15%, 20%, 30%, 40%, 50%, 60%, or 70% in comparison with the reference wax ester synthase. For example, the wax ester synthase deletion mutant lacks at least 1, 2, 3, 4, 5, 6, 7, 8, 9 or 10 amino acids from the N- and/or C-terminus and has an amino acid sequence at least 30%, 40%, 45%, 50%, 55%, 60%, 65%, 70%, 75%, 80%, 85%, 86%, 87%, 88%, 89%, 90%, 91%, 92%, 93%, 94%, 95%, 96%, 97%, 98%, 99%, or 100% identical to the corresponding amino acid sequence of the reference wax ester synthase (e.g., any of SEQ ID NOS: 22-30).

The invention also provides nucleic acid molecules that hybridize under high stringency hybridization conditions, such as selective hybridization conditions, to the nucleotide sequences described herein. Hybridization probes include synthetic oligonucleotides or oligonucleotide analogs (including peptide nucleic acids, as described in Nielsen (1991) *Science,* 254, 1497-1500) which bind in a base-specific manner to a complementary strand of nucleic acid or nucleic acid molecules comprising sequences that encode at least a portion of a thioesterase, an acyl-CoA synthetase, an alcohol-forming acyl reductase, or a polypeptide having wax ester synthase activity. For example, further nucleic acid sequences for use in the nucleic acid constructs, transgenic microorganism, and methods of the invention can be detected and/or isolated by specific hybridization, e.g., under high stringency conditions, with nucleic acid sequences encoding the enzymatic activities as disclosed herein or obtained from sequence databases (e.g., NCBI "GenBank", Benson et al. (2011) *Nucleic Acids Res.* 39 (Database Issue): D32-7).

Any of the nucleic acid molecules described herein can further comprise one or more additional nucleic acid sequences of at least 50, 60, 70, 80, 90, 100, 150, 200, 250, 300, 350, 400, 450, 500, 550, 600, 700, 800, 900, 1000, or 1500 nucleotides from a prokaryotic and/or photosynthetic organism, e.g., a *cyanobacterium*. For example a nucleic acid molecule can have two sequences of at least 50, 60, 70, 80, 90, 100, 150, 200, 250, 300, 350, 400, 450, 500, 550, 600, 700, 800, 900, 1000, or 1500 nucleotides from a prokaryotic and/or photosynthetic organism that can mediate recombination of at least a portion of the nucleic acid molecule into the genome of the prokaryotic and/or photosynthetic organism.

Any of the nucleic acid molecules described herein can further comprise one or more regulatory sequences including, for example, a promoter, an enhancer, a transcriptional terminator, one or more ribosome binding sites, etc.

Other Modifications

The nucleic acid molecules provided herein can include further variants of the nucleotide sequences that may encode fragments or variants of the polypeptides described herein. The nucleotide sequence variants can be naturally-occurring, non-naturally-occurring, including, e.g., variants induced by various mutagens and mutagenic processes, or a combination of naturally- and non-naturally-occurring. A given nucleic acid sequence may be modified, for example, according to standard mutagenesis or artificial evolution or domain swapping methods to produce modified sequences. Accelerated evolution methods are described, e.g. by Stemmer (1994) *Nature* 370, 389-391, and Stemmer (1994) *Proc. Natl. Acad. Sci. USA* 91, 10747-10751. Additionally, chemical or enzymatic alteration of expressed nucleic acids and polypeptides can be performed by standard methods. For example, a sequence can be modified by addition of phosphate groups, methyl groups, lipids, sugars, peptides or organic or inorganic compounds, by the inclusion of modified nucleotides or amino acids, or the like.

For optimal expression of a recombinant protein, in certain instances it may be beneficial to employ coding sequences that produce mRNA with codons preferentially used by the host cell to be transformed ("codon optimization"). Thus, additional to any of the above features, for enhanced expression of transgenes, the codon usage of a transgene (e.g., a sequence encoding an enzyme of the wax ester synthesis pathway) can be altered to increase the number of codons most frequently used by the organism in which the transgene is desired to be expressed. Methods of recoding genes for expression in microalgae are described in, e.g., U.S. Pat. No. 7,135,290. The precise mechanisms underlying this effect are believed to be many, but can include the proper balancing of available aminoacylated tRNA pools with proteins being synthesized in the cell, coupled with more efficient translation of the transgenic messenger RNA (mRNA) when this need is met. The coding sequences may be codon optimized for optimal production of a desired product in the host organism selected for expression. For example, the nucleic acid sequences encoding any of a thioesterase, an acyl-CoA synthetase, an alcohol-forming fatty acyl reductase, and/or a polypeptide having wax ester synthase activity can be codon optimized for expression in a photosynthetic microorganism, e.g., a *cyanobacterium*. All or any portion of the codons of a gene may be changed to reflect a preferred codon usage of a host microorganism. One or more codons may be additionally but optionally changed to codons that are not necessarily the most preferred codon of the host microorganism encoding a particular amino acid. Additional information for codon optimization is available, e.g. at the codon usage database of GenBank.

Additionally but optionally, the nucleic acid molecules of the invention may encode fusion proteins that comprise a thioesterase, an acyl-CoA synthetase, an alcohol-forming fatty acyl reductase, and/or a wax ester synthase. For example, the nucleic acids of the invention may comprise polynucleotide sequences that encode glutathione-S-transferase (GST) or a portion thereof, thioredoxin or a portion thereof, maltose binding protein or a portion thereof, polyhistidine (e.g. $His_6$), poly-HN, poly-lysine, a hemagglutinin tag sequence, HSV-Tag and/or at least a portion of HIV-Tat fused to the thioesterase, acyl-CoA synthetase, alcohol-forming fatty acyl reductase, and/or wax ester synthase sequence.

Transcription Units and Operons

A recombinant or isolated nucleic acid molecule of the invention can comprise a transcriptional unit comprising a nucleic acid sequence encoding a polypeptide having wax ester synthase activity and one or more of a) a nucleic acid sequence encoding a thioesterase, b) a nucleic acid sequence encoding an acyl-CoA synthetase, and c) a nucleic acid encoding an alcohol-forming fatty acyl reductase. The nucleic acid sequences of the transcriptional unit are organized such that the two or more sequences encoding separate polypeptides, when operably linked to a promoter, can be transcribed together, as a single RNA transcript. For example, the transcriptional unit does not include a transcriptional termination sequence upstream of any of the genes of the transcriptional unit (e.g., between any of the distinct polypeptide-encoding sequences) and typically does not include any functional promoters between the genes of the transcriptional unit (i.e., downstream of a first protein coding region and upstream of a second, third, or fourth protein coding region).

The nucleic acid sequences encoding the wax ester synthase and one or more of a thioesterase, acyl-CoA synthetase, and alcohol-forming fatty acyl reductase may be any of the nucleic acid sequences described herein. In some examples, the transcriptional unit comprises a) a nucleic acid sequence encoding an acyl-ACP thioesterase, b) a nucleic acid sequence encoding an acyl-CoA synthetase, c) a nucleic acid sequence encoding an alcohol-forming acyl-CoA reductase, and d) a nucleic acid sequence encoding a polypeptide having wax ester synthase activity. In some illustrative examples, the transcriptional unit comprises nucleic acid sequences encoding (a) a polypeptide selected from polypeptides comprising amino acid sequences having at least 85% identity to SEQ ID NOS: 1-9, (b) a polypeptide selected from polypeptides comprising amino acid sequences having at least 85% identity to SEQ ID NOS: 10-14, (c) a polypeptide selected from polypeptides comprising amino acid sequences having at least 85% identity to SEQ ID NOS: 15-21, and a polypeptide selected from polypeptides comprising amino acid sequences having at least 85% identity to SEQ ID NOS: 22-30.

Optionally, a nucleic acid molecule as provided herein can be configured as an operon, i.e., a transcriptional unit (two or more tandemly arranged genes that can be transcribed as a single transcript) operably linked to a promoter. The promoter of the operon is typically positioned upstream of the 5'-most gene of the transcriptional unit. The operon comprises a nucleic acid sequence encoding a polypeptide having wax ester synthase activity and any combination of one or more of a nucleic acid sequence encoding a thioesterase (e.g., an acyl-ACP thioesterase), a nucleic acid sequence encoding an acyl-CoA synthetase, and a nucleic acid sequence encoding an alcohol-forming fatty acyl reductase (e.g., an alcohol-forming acyl-CoA reductase). For example, a nucleic acid sequence encoding a polypeptide having wax ester synthase activity, a nucleic acid sequence encoding a thioesterase, a nucleic acid sequence encoding an acyl-CoA synthetase, and a nucleic acid sequence encoding an alcohol-forming fatty acyl reductase can all be operably linked to the same promoter in an operon.

A promoter operably linked to a nucleic acid sequence encoding a polypeptide having wax ester synthase activity and a nucleic acid sequence encoding a thioesterase, a nucleic acid sequence encoding an acyl-CoA synthetase, and/or a nucleic acid sequence encoding an alcohol-forming fatty acyl reductase may be a promoter that is heterologous with respect to the nucleic acid sequence encoding the wax ester synthase, thioesterase, acyl-CoA synthetase, and/or alcohol-forming fatty acyl reductase, and may be heterologous (from a different species) or homologous (from the same species) with respect to a recombinant host cell. The promoter sequence can be from any organism, provided that it is functional in the host organism. The promoter can be a constitutive promoter or alternatively, the promoter may be a conditional and/or regulatable, for example, the promoter may be inducible, i.e., a promoter that mediates transcription of an operably linked gene in response to a particular stimulus. Regulatable promoters may be advantageous, e.g., to minimize any deleterious effects on the growth of the host cell and/or to maximize production of the wax ester. An inducible promoter can be responsive to, e.g., light or dark or high or low temperature, and/or can be responsive to specific compounds. Nonlimiting examples of inducible promoters include an ara promoter, a lac promoter, a tet promoter (e.g. U.S. Pat. No. 5,851,796), a trp promoter or a hybrid promoter that includes one or more portions of an ara, tet, trp and/or lac promoter. An inducible promoters may be formed by fusing one or more portions or domains from a known inducible promoter to at least a portion of a different promoter that can operate in the host cell, e.g. to confer inducibility on a promoter that operates in the host species.

A nucleic acid molecule that includes genes of a wax ester synthesis pathway can include, for example, a promoter that functions in prokaryotes, such as cyanobacteria, including, but not limited to, the lac, tac and trc promoters, as well as derivatives such as but not limited to the trcE and trcY promoters that are inducible by the addition of isopropyl β-D-1-thiogalactopyranoside (IPTG), promoters that are naturally associated with transposon- or bacterial chromosome-borne antibiotic resistance genes (e.g. neomycin phosphotransferase, chloramphenicol acetyltransferase, spectinomycin adenyltransferase, etc., or combinations thereof), promoters associated with various heterologous bacterial and native cyanobacterial genes, promoters from viruses and phages, synthetic promoters or combinations thereof. Promoters useful in the constructs that include a wax ester synthase gene and one or more additional genes for producing wax esters may be isolated or derived from cyanobacteria, e.g., secA (secretion; controlled by the redox state of the cell), Prbc (Rubisco promoter), psaAB (PS I reaction center proteins; light regulated), NtcA or glnA promoter and psbA (D1 protein of PSII; light-inducible). The cyanobacterial promoter can be a promoter from upstream of the *Synechocystis* sp. PCC 6803 genomic RS1 insertion site, e.g., a promoter of the slr0338 gene of *Synechocystis* or an ortholog of the *Synechocystis* slr0338 gene of another cyanobacterial species.

Promoters may be regulated by nitrogen compounds, such as, for example, nar, ntc, nir or nrt promoters, or may be regulated by phosphate levels (e.g., pho or pst promoters) or nickel (e.g., nrs promoter). Promoters for use in cyanobacteria can also be or be modified from naturally-occurring promoters, and include combinations of naturally-occurring promoters, including, but not limited to, the promoters disclosed herein. Promoter(s) can be selected from prokaryotic promoters from a range of species, including eubacterial and cyanobacterial species, such as, for example, an araC or pBAD promoter, a rha promoter, a Pm promoter, a xylS promoter, a nir promoter, a nar promoter, a pho promoter, a tet promoter, a cys promoter, a metallothionien promoter, an ftf promoter, a gln promoter, a heat shock promoter, a cold-inducible promoter or a viral promoter. The foregoing promoters are exemplary and are not limiting.

The nucleic acid sequences of a four gene transcriptional unit or operon may be can be arranged in the 5' to 3' direction in any of the following orders:

thioesterase-acyl-CoA synthetase-alcohol-forming fatty acyl reductase-wax ester synthase;

thioesterase-acyl-CoA synthetase-wax ester synthase-alcohol-forming fatty acyl reductase;

thioesterase-alcohol-forming fatty acyl reductase-acyl-CoA synthetase-wax ester synthase;

thioesterase-wax ester synthase-acyl-CoA synthetase-alcohol-forming fatty acyl reductase;

thioesterase-alcohol-forming fatty acyl reductase-wax ester synthase-acyl-CoA synthetase;

thioesterase-wax ester synthase-alcohol-forming fatty acyl reductase-acyl-CoA synthetase;

wax ester synthase-thioesterase-acyl-CoA synthetase-alcohol-forming fatty acyl reductase;

wax ester synthase-thioesterase-alcohol-forming fatty acyl reductase-acyl-CoA synthetase;

wax ester synthase-acyl-CoA synthetase-thioesterase-alcohol-forming fatty acyl reductase;

wax ester synthase-alcohol-forming fatty acyl reductase-thioesterase-acyl-CoA synthetase;

wax ester synthase-acyl-CoA synthetase-alcohol-forming fatty acyl reductase-thioesterase;

wax ester synthase-alcohol-forming fatty acyl reductase-acyl-CoA synthetase-thioesterase;

alcohol-forming fatty acyl reductase-wax ester synthase-thioesterase-acyl-CoA synthetase;

alcohol-forming fatty acyl reductase-wax ester synthase-acyl-CoA synthetase-thioesterase;

alcohol-forming fatty acyl reductase-thioesterase-wax ester synthase-acyl-CoA synthetase;

alcohol-forming fatty acyl reductase-acyl-CoA synthetase-wax ester synthase-thioesterase;

alcohol-forming fatty acyl reductase-thioesterase-acyl-CoA synthetase-wax ester synthase;

alcohol-forming fatty acyl reductase-acyl-CoA synthetase-thioesterase-wax ester synthase;

acyl-CoA synthetase-alcohol-forming fatty acyl reductase-wax ester synthase-thioesterase;

acyl-CoA synthetase-alcohol-forming fatty acyl reductase-thioesterase-wax ester synthase;

acyl-CoA synthetase-wax ester synthase-alcohol-forming fatty acyl reductase-thioesterase;

acyl-CoA synthetase-thioesterase-alcohol-forming fatty acyl reductase-wax ester synthase;

acyl-CoA synthetase-wax ester synthase-thioesterase-alcohol-forming fatty acyl reductase; or acyl-CoA synthetase-thioesterase-wax ester synthase-alcohol-forming fatty acyl reductase.

For example, the transcriptional unit or operon can comprise the four nucleic acid sequences arranged in the 5' to 3' direction in the order of thioesterase, acyl-CoA synthetase, alcohol-forming fatty acyl reductase, and wax ester synthase. In another example, the transcriptional unit or operon comprises the four nucleic acid sequences arranged in the 5' to 3' direction in the order of acyl-CoA synthetase, wax ester synthase, thioesterase, and alcohol-forming fatty acyl reductase. The four nucleic acid sequences in the transcriptional unit or operon can be arranged in the order that results in optimal wax ester production, as determined empirically.

A nucleic acid molecule of the invention can comprise a transcriptional unit comprising a nucleic acid sequence encoding a polypeptide having wax ester synthase activity (e.g., a wax ester synthase) and any combination of a nucleic acid sequence encoding a thioesterase (e.g., an acyl-ACP thioesterase), a nucleic acid sequence encoding an acyl-CoA synthetase, and/or a nucleic acid sequence encoding an alcohol-forming fatty acyl reductase (e.g., an alcohol-forming acyl-CoA reductase) arranged in tandem, where the nucleic acid molecule optionally does not include a promoter sequence that operates in the intended host cell upstream of the genes of the transcriptional unit. For example, a promoterless transcriptional unit can preferably be designed for integration (e.g., homologous recombination) into a site of the host genome that includes a promoter sequence, such that the nucleic acid sequences in the operon or cassette can be transcriptionally regulated by a promoter in the genome of the host cell (which may be, e.g., a prokaryotic and/or photosynthetic microorganism, for example, a *cyanobacterium*). In some examples, a promoter endogenous to the intended host cell can be included in a genomic sequence of a prokaryotic and/or photosynthetic microorganism that is positioned upstream of a transcriptional unit in a nucleic acid molecule.

Additionally to any of the above features, a nucleic acid molecule comprising an operon or transcriptional unit that includes a gene encoding a polypeptide having wax ester synthase activity and one or more of a thioesterase gene, an acyl-CoA synthetase gene, and an alcohol-forming fatty acyl reductase gene, can optionally include one or more additional regulatory sequences can be included in the operon or transcriptional unit, for example, a sequence for enhancing translation (e.g., a ribosome binding site; rbs) can be included upstream of any of the polypeptide-encoding sequences, and/or, an intergenic region (e.g., the *S. elongatus* KaiBC intergenic region) may be included between any two genes in the transcriptional unit or operon, or between all of the genes of the transcriptional unit or operon, and/or, a transcription terminator sequence can be positioned 3' of the 3'-most gene of the transcriptional unit or operon. A wide variety of transcriptional terminators can be used in any of the vectors of the invention. Examples of possible terminators can include, but are not limited to, psbA, psaAB, rbc, secA, T7 coat protein, rrnB, and the like, and combinations thereof.

In addition to the nucleic acid sequence encoding the wax ester synthase and a nucleic acid sequence encoding a thioesterase, a nucleic acid sequence encoding an acyl-CoA synthetase, and/or a nucleic acid sequence encoding an alcohol-forming fatty acyl reductase, and, one or more additional nucleic acid sequences can optionally be included in an operon or transcriptional unit as provided herein, where the one or more additional genes may include, for example, one or more nucleic acid sequences encoding enzymes or proteins that may enhance wax ester synthesis, one or more nucleic acid sequences that may enhance photosynthesis or carbon-fixation, one or more nucleic acid sequences that may enhance wax ester transport, and/or one or more reporter genes or selectable markers. For example, any of the nucleic acid molecules, operons, nucleic acid cassettes, and constructs referred to herein may optionally comprise a nucleic acid sequence encoding a wax transporter (e.g., any of the wax transporters described herein). A transcriptional unit or operon for wax synthesis can optionally include five genes, for example, comprising nucleic acid sequences that encode a thioesterase, an acyl-CoA synthetase, an alcohol-forming fatty acyl reductase, a wax ester synthase, and a wax transporter.

Nucleic Acid Constructs

The invention also provides nucleic acid constructs comprising a nucleic acid sequence encoding a polypeptide having wax ester synthase activity in a transcriptional unit with one or more of: a nucleic acid sequence encoding a thioesterase (e.g., an acyl-ACP thioesterase), a nucleic acid sequence encoding an acyl-CoA synthetase, and a nucleic acid sequence encoding an alcohol-forming fatty acyl reductase (e.g., an alcohol-forming acyl-CoA reductase). For example, the nucleic acid construct can comprise a transcriptional unit that includes all four nucleic acid sequences encoding polypeptides of the wax ester synthesis pathway.

The nucleic acid construct can comprise any transcriptional unit or operon as described herein. A nucleic acid construct of the invention may comprise a nucleic acid sequence encoding a polypeptide having wax ester synthase activity and a nucleic acid sequence encoding a thioesterase, an acyl-CoA synthetase, and/or an alcohol-forming fatty acyl reductase, as described herein, and can optionally further include sequences that regulate or mediate transcription, translation, or integration of nucleotide sequences into a host genome. For example, as described herein, a nucleic acid molecule can comprise an operon in which a promoter can be operably linked to the nucleic acid sequences encoding two or more genes of the wax ester pathway. The promoter can be any promoter active in a host cell, and can be, for example, any disclosed herein. For example, a construct can comprise an operon as disclosed hereinabove comprising a nucleic acid sequence encoding a thioesterase, a nucleic acid sequence encoding an acyl-CoA synthetase, a nucleic acid sequence encoding an alcohol-forming fatty acyl reductase, and a nucleic acid sequence encoding a wax ester synthase operably linked to a promoter. In additional examples, a nucleic acid construct does not contain a promoter in operable linkage with the transcriptional unit that includes a nucleic acid sequence encoding a polypeptide having wax ester synthase activity and one or more of a nucleic acid sequence encoding a thioesterase, a nucleic acid sequence encoding an acyl-CoA synthetase, and a nucleic acid sequence encoding an alcohol-forming fatty acyl reductase. For example, the nucleic acid construct can be designed to be transformed into the host cell such that the transcriptional unit becomes operably linked to an endogenous promoter by, e.g., homologous recombination, site specific integration, and/or vector integration.

A nucleic acid construct that comprises a wax synthesis transcriptional unit or operon may additionally comprise at least one nucleic acid sequence of at least 50 nucleotides, at least 100 nucleotides, at least 200 nucleotides, at least 300 nucleotides, at least 400 nucleotides, at least 500 nucleotides, at least 600 nucleotides, at least 700 nucleotides, at least 800 nucleotides, at least 900 nucleotides, at least 1000 nucleotides, or at least 1500 nucleotides derived from a prokaryotic and/or photosynthetic microorganism, where the nucleotide sequence derived from a prokaryotic and/or photosynthetic microorganism can mediate recombination of the transcriptional unit or operon into a host genome. The nucleic acid construct may, for example, comprise two or more nucleic acid sequences of at least 50 nucleotides, at least 100 nucleotides, at least 200 nucleotides, at least 300 nucleotides, at least 400 nucleotides, at least 500 nucleotides, at least 600 nucleotides, at least 700 nucleotides, at least 800 nucleotides, at least 900 nucleotides, at least 1000, or at least 1500 nucleotides derived from a prokaryotic and/or photosynthetic microorganism. For example, the transcriptional unit or operon that includes a gene encoding a polypeptide having wax ester synthase activity and at least one additional gene of a wax ester synthesis pathway can be flanked by the sequences derived from the genome of a prokaryotic and/or photosynthetic microorganism. For example, a first nucleotide sequence derived from a prokaryotic and/or photosynthetic microorganism can be 5' of the transcriptional unit and a second nucleotide sequence derived from a prokaryotic and/or photosynthetic microorganism can be 3' of the transcriptional unit.

A nucleic acid sequence derived from the genome of a prokaryotic and/or photosynthetic microorganism may optionally comprise a nucleic acid sequence derived from the 5' region of a gene. For example, a nucleic acid construct can be designed such that the genomic nucleic acid sequences mediate recombination into a site proximal to and downstream of a promoter in the genome of the host organism, such that the transcriptional unit can be regulated by a promoter of the host microorganism. Further additionally, a genomic nucleic acid sequence of the construct can include at least a portion of a promoter which is endogenous to the intended host microorganism. For example, the transgene(s) of the construct can be operably linked to a promoter that is endogenous to the production host, and the promoter endogenous to the production host can be within or part of a sequence that mediates homologous recombination into the host genome. Optionally, the genomic nucleic acid sequence can include a promoter that may be active in the production microorganism, but may be inactive or have very low activity in a cloning organism, such as *E. coli* or yeast, such that the cloning microorganism does not produce wax esters or wax ester intermediates or is not impaired by production of wax esters or wax ester intermediates such as fatty acids or fatty alcohols. Alternatively, the nucleic acid molecule can include a sequence of at least 50 nucleotides of a sequence derived from the genome of a prokaryotic and/or photosynthetic microorganism, but the genomic sequence may not comprise a promoter operably linked to any of the nucleic acid sequences of the transcriptional unit that includes two or more genes of the wax ester synthesis pathway.

The nucleic acid construct comprising a nucleic acid sequence encoding a thioesterase, a nucleic acid sequence encoding an acyl-CoA synthetase, a nucleic acid sequence encoding an alcohol-forming fatty acyl reductase, and/or a nucleic acid sequence encoding a wax ester synthase can be designed for transformation into cyanobacteria, e.g., *Synechocystis* sp. PCC 6803. For example, the vector can be designed to permit homologous recombination of nucleic acid sequences of the vector with the cyanobacterial genome, such that the enzyme-encoding sequences become integrated into a locus of the genome. For example, sequences of the RS1 site or RS2 site, or genomic sequence that can include or are proximal to sequence of glgA, glgB, or glgC genes can be operably linked to a transcriptional unit or operon that includes genes of the wax ester synthesis pathway.

The nucleic acid sequences encoding enzymes of the wax ester synthesis pathway may each comprise an initiation codon, wherein one or more, and optionally all, of the nucleic acid sequences may additionally comprise a heterologous translational regulatory sequence upstream of the initiation codon. For example, the nucleic acid sequence encoding the acyl-CoA synthetase, the nucleic acid sequence encoding the alcohol-forming fatty acyl reductase, and the nucleic acid sequence encoding the wax ester may each comprise a heterologous translational regulatory sequence upstream of the initiation codon.

A nucleic acid construct of the present invention can include any of the sequences disclosed herein that encode one or more of a thioesterase, an acyl-CoA synthetase, an alcohol-forming fatty acyl reductase, and a wax ester synthase in a vector, such as, but not limited to, an expression vector. A vector can include, for example, one or more of: 1) an origin of replication for propagation of the nucleic acid sequences in one or more hosts (which may or may not include the production host); 2) one or more selectable markers; 3) one or more reporter genes; 4) one or more expression control sequences, such as, but not limited to, promoter sequences, enhancer sequences, terminator sequences, sequence for enhancing translation, etc.; and/or 5) one or more sequences for promoting integration of the nucleic acid sequences into a host genome, for example, one or more sequences having homology with one or more nucleotide sequences of the host microorganism.

The transformation vectors can include a selectable marker, such as but not limited to a drug resistance gene, an herbicide resistance gene, a metabolic enzyme and/or factor required for survival of the host (for example, an auxotrophic marker), or the like, or a combination thereof. Transformed cells can optionally be selected based upon the ability to grow in the presence of the antibiotic and/or other selectable marker under conditions in which cells lacking the resistance cassette or auxotrophic marker could not grow. Additionally or alternatively, a non-selectable marker (e.g., a reporter gene) may be present on a vector, such as a gene encoding a fluorescent protein or an enzyme that generates a detectable reaction product.

The transformation vector may be an integration vector that includes one or more sequences that promote integration of a nucleic acid sequence or nucleic acid cassette into the genome of the host cell. For example, an integration vector used to transform a host cell can include at least one sequence of at least 50, at least 100, at least 200, at least 300, at least 400, at least 500, at least 600, at least 700, at least 800, at least 900, at least 1000, at least 1200, or at least 1500 nucleotides with homology to a sequence in the genome of the host cell to allow integration of the nucleic acid sequence or nucleic acid cassette into the genome of the host cell via homologous recombination. In some examples, the nucleic acid sequence or nucleic acid cassette is flanked by sequences homologous to a region of the host chromosome to promote integration of the gene of interest into the host chromosome. Additionally or alternatively, an integration vector can include one or more sequences that promote site-specific recombination or random integration such as, but not limited to, sequences recognized by recombinases, integrases or transposases. The integration vector can optionally further include a gene encoding a recombinase, integrase or transposase. The integration vector can be designed to promote integration of a nucleic acid sequence encoding a thioesterase, a nucleic acid sequence encoding an acyl-CoA synthetase, a nucleic acid sequence encoding an alcohol-forming fatty acyl reductase, and/or a nucleic acid sequence encoding a wax ester synthase (e.g., all four nucleic acid sequences) into cyanobacteria. In particular examples, the vector promotes integration at the RS1 site or RS2 site of, e.g., *Synechocystis* sp. PCC 6803, where the vector can include RS1 or RS2 sequences.

Vectors can be introduced into host cells (e.g., any of the host cells described herein) via conventional transformation and/or transfection techniques. Cyanobacteria, for example, can be transformed by any suitable methods, including, e.g., natural DNA uptake (Zang (2007) *J. Microbiol.* 45, 241-245), conjugation, transduction, glass bead transformation (Feng (2009) *Mol. Biol. Rep.* 36, 1433-9), silicon carbide whisker transformation (Dunahay (1997) *Methods Mol. Biol.* 62, 503-9), biolistics (Kroth (2007) *Methods Mol. Biol.* 390, 257-267), electroporation (Ludwig (2008) *Appl. Microbiol. Biotechnol.* 78, 729-35), laser-mediated transformation (WO2009/140701), incubation with DNA in the presence of or after pre-treatment with any of poly(amidoamine) dendrimers (Pasupathy (2008) *Biotechnol. J.* 3, 1078-82), polyethylene glycol (Ohnuma (2008) *Plant Cell Physiol.* 49, 117-120), cationic lipids (Muradawa (2008) *J. Biosci. Bioeng.* 105, 77-80), dextran, calcium phosphate and/or calcium chloride (Mendez-Alvarez (1994) *J. Bacteriol.* 176, 7395-7397), optionally after treatment of the cells with cell wall-degrading enzymes (Perrone (1998) *Mol. Biol. Cell* 9, 3351-3365), or the like, or combinations thereof. *Agrobacterium*-mediated transformation can additionally or alternatively be performed on algal cells, for example after removing or wounding the algal cell wall (Kumar (2004) *Plant Sci.* 166, 731-738).

The above-described vectors may be used in any of the recombinant host cells or methods for producing a wax ester as described herein.

Recombinant Host Cells

The invention also provides a recombinant host cell comprising a non-native nucleic acid sequence encoding a wax ester synthase, and one or more of (a) a non-native nucleic acid sequence encoding a thioesterase; (b) a non-native nucleic acid sequence encoding an acyl-CoA synthetase; and (c) a non-native nucleic acid sequence encoding an alcohol-forming fatty acyl reductase; in which the non-native nucleic acid sequence encoding a wax ester synthase and at least one of (a) a non-native nucleic acid sequence encoding a thioesterase; (b) a non-native nucleic acid sequence encoding an acyl-CoA synthetase; and (c) a non-native nucleic acid sequence encoding an alcohol-forming fatty acyl reductase are in an operon. The operon comprising two or more genes of the wax synthesis pathway (for example, comprising any transcriptional unit as described herein) comprises a promoter that can be heterologous or homologous with respect to the host microorganism, and can be endogenous to the host microorganism. For example, the recombinant host cell can include a non-native nucleic acid molecule that comprises an operon that includes a promoter operably linked to a transcriptional unit that includes each of (a) a non-native nucleic acid sequence encoding an acyl-ACP thioesterase; (b) a non-native nucleic acid sequence encoding an acyl-CoA synthetase; (c) a non-native nucleic acid sequence encoding an alcohol-forming fatty acyl reductase; and (d) a non-native nucleic acid sequence encoding a wax ester synthase. The recombinant host cell can be genetically engineered for the production of wax esters, in which expression of the non-native nucleic acid sequences encoding a wax ester synthase and a thioesterase, an acyl-CoA synthetase, and an alcohol-forming fatty acyl reductase results in production of a wax ester. The recombinant host cell may comprise, e.g., non-native nucleic acid sequences encoding any of the thioesterases, acyl-CoA synthetases, alcohol-forming fatty acyl reductases, and/or wax ester synthases described herein, and/or can comprises any of the constructs, operons, and/or transcriptional units as described herein.

The recombinant host cell can be a prokaryotic and/or photosynthetic microorganism. The recombinant host cell can be without limitation, a eubacterium, archaebacterium, green nonsulfur bacterium, purple nonsulfur bacterium, or *cyanobacterium*. The recombinant host cell can be, in particular examples, a host cell that does not endogenously produce acyl-CoA, for example a *cyanobacterium*. For example, the recombinant photosynthetic microorganism can be a *cyanobacterium* of a genus selected from, e.g., *Agmenellum, Anabaena, Anabaenopsis, Anacystis, Aphanizomenon, Arthrospira, Asterocapsa, Borzia, Calothrix, Chamaesiphon, Chlorogloeopsis, Chroococcidiopsis, Chroococcus, Crinalium, Cyanobacterium, Cyanobium, Cyanocystis, Cyanospira, Cyanothece, Cylindrospermopsis, Cylindrospermum, Dactylococcopsis, Dermocarpella, Fischerella, Fremyella, Geitleria, Geitlerinema, Gloeobacter, Gloeocapsa, Gloeothece, Halospirulina, Iyengariella, Leptolyngbya, Limnothrix, Lyngbya, Microcoleus, Microcystis, Myxosarcina, Nodularia, Nostoc, Nostochopsis, Oscillatoria, Phormidium, Planktothrix, Pleurocapsa, Prochlorococcus, Prochloron, Prochlorothrix, Pseudanabaena, Rivularia, Schizothrix, Scytonema, Spirulina, Stanieria, Starria, Stigonema, Symploca, Synechococcus, Synechocystis, Thermosynechococcus, Tolypothrix, Trichodesmium, Tychonema* or *Xenococcus*. A number of cyanobacterial species have genomes that have been completely sequenced. Cyanobacterial strains such as but not limited to *Synechocystis* sp. PCC 6803 and *Synechococcus elongates* PCC 7942 have been manipulated using molecular biological techniques. In some aspects, the cyanobacterial host organism is a *Synechococcus, Synechocystis*, or *Thermosynechococcus* species, and in an illustrative example is *Synechocystis* sp. PCC 6803. Alternatively, the recombinant photosynthetic microorganism can be a *Cyanobium, Cyanothece*, or *Cyanobacterium* species, or further alternatively, the recombinant photosynthetic microorganism can be a *Gloeobacter, Lyngbya*, or *Leptolyngba* species.

A nucleic acid sequence provided in the host recombinant microorganism that encodes a thioesterase can encode any thioesterase, including any disclosed herein. A nucleic acid sequence provided in the host recombinant microorganism that encodes an acyl-CoA synthetase can encode any acyl-CoA synthetase, including any disclosed herein. A nucleic acid sequence provided in the host recombinant microorganism that encodes an acyl-CoA fatty acyl reductase can encode any an acyl-CoA fatty acyl reductase, including any disclosed herein. A nucleic acid sequence provided in the host recombinant microorganism that encodes a wax ester synthase can encode any wax ester synthase, including any disclosed herein. A recombinant host cell expressing a thioesterase (e.g., an acyl-ACP thioesterase), an acyl-CoA synthetase, an alcohol-forming fatty acyl reductase (e.g., an alcohol-forming acyl-CoA reductase), and a polypeptide having wax ester synthase activity can produce a greater amount of a wax ester than a control host cell that does not express these four enzymes. For example, the amount of wax ester produced by a culture of the recombinant host cell expressing the thioesterase, the acyl-CoA synthetase, the alcohol-forming fatty acyl reductase, and/or the wax ester synthase can be at least 10%, 15%, 20%, 25%, 30%, 40%, 50%, 60%, 65%, 70%, 75%, 80%, 90%, 95%, 100%, 125%, 150%, 175%, 200%, 225%, 250%, 275%, 300%, 325%, 350%, 375%, 400%, 425%, 450%, 475%, 500%, 525%, 550%, 575%, 600%, 625%, 650%, 675%, 700%, 725%, 750%, 775%, 800%, 825%, 850%, 875%, 900%, 925%, 950%, 975%, or 1000% greater than the amount of wax ester produced by a control host cell that does not express the thioesterase, the acyl-CoA synthetase, the alcohol-forming fatty acyl reductase, and the wax ester synthase.

In illustrative examples, the recombinant host cell can comprise: (1) a nucleic acid sequence encoding a polypeptide having at least 30%, 40%, 45%, 50%, 55%, 60%, 65%, 70%, 75%, 80%, 85%, 86%, 87%, 88%, 89%, 90%, 91%, 92%, 93%, 94%, 95%, 96%, 97%, 98%, or 99% sequence identity to the polypeptide of any of SEQ ID NOS: 1-9; or to a functional fragment of the polypeptide having thioesterase activity, (2) a nucleic acid sequence encoding a polypeptide having at least 30%, 40%, 45%, 50%, 55%, 60%, 65%, 70%, 75%, 80%, 85%, 86%, 87%, 88%, 89%, 90%, 91%, 92%, 93%, 94%, 95%, 96%, 97%, 98%, or 99% sequence identity to the polypeptide of any of SEQ ID NOS: 10-14, or to a functional fragment of the polypeptide having acyl-CoA synthetase activity, (3) a nucleic acid sequence encoding a polypeptide having at least 30%, 40%, 45%, 50%, 55%, 60%, 65%, 70%, 75%, 80%, 85%, 86%, 87%, 88%, 89%, 90%, 91%, 92%, 93%, 94%, 95%, 96%, 97%, 98%, or 99% sequence identity to the polypeptide of any of SEQ ID NOS: 15-21; or to a functional fragment of the polypeptide having alcohol-forming fatty acyl reductase activity, and (4) a nucleic acid sequence encoding a polypeptide having at least 30%, 40%, 45%, 50%, 55%, 60%, 65%, 70%, 75%, 80%, 85%, 86%, 87%, 88%, 89%, 90%, 91%, 92%, 93%, 94%, 95%, 96%, 97%, 98%, or 99% sequence identity to the polypeptide of any of SEQ ID NOS: 22-30; or to a functional fragment of the polypeptide having wax ester synthase activity.

The nucleic acid sequence encoding a wax ester synthase and one or more of a nucleic acid sequence encoding a thioesterase, a nucleic acid sequence encoding an acyl-CoA synthetase, and a nucleic acid sequence encoding an alcohol-forming fatty acyl reductase, can be organized in an operon in the recombinant host cell. The operon further includes a promoter that can be heterologous or homologous with respect to the recombinant host cell, and can be, for example, an endogenous promoter of the host cell. For example, the recombinant host cell can comprise a nucleic acid sequence encoding a thioesterase, a nucleic acid sequence encoding an acyl-CoA synthetase, a nucleic acid sequence encoding an alcohol-forming fatty acyl reductase, and a nucleic acid sequence encoding a wax ester synthase, where all of the nucleic acid sequences are operably linked to a promoter. A promoter operably linked to a wax ester synthesis operon can be any promoter operable in the host microorganism, including but not limited to any disclosed herein, and can be constitutive or conditional, and can be for example, regulatable, for example inducible by one or more conditions or compounds. In particular examples, the promoter is endogenous to the recombinant host cell.

The nucleic acid sequences encoding the thioesterase, the acyl-CoA synthetase, the alcohol-forming fatty acyl reductase, and the wax ester synthase can be operably linked to a promoter that is endogenous to a photosynthetic host cell, e.g., a photosynthetic microorganism. The photosynthetic microorganism in some examples can be a *cyanobacterium*, e.g., a species of *Synechocystis*, and the nucleic acid sequences encoding the thioesterase, the acyl-CoA synthetase, the alcohol-forming fatty acyl reductase, and the wax ester synthase can be integrated at the RS1 or RS2 site, or within or proximal to a glgA, glgB, or glgC gene, and may be operably linked to an endogenous promoter upstream of the integration site.

For example, a transcriptional unit that comprises a non-native nucleic acid sequence encoding a wax ester synthase and one or more of a non-native nucleic acid sequence encoding a thioesterase, non-native nucleic acid sequence encoding an acyl-CoA synthetase, and a non-native nucleic acid sequence encoding an alcohol-forming acyl-CoA reductase can be inserted into the genome of the host microorganism such that the transcriptional unit becomes juxtaposed with, and operably linked to, an endogenous promoter of the host microorganism. The endogenous promoter can be any endogenous promoter of the host microorganism, and in some examples is a promoter of a gene encoding an oxidoreductase or dehydrogenase, e.g., the slr0338 gene of *Synechocystis* (e.g., *Synechocystis* sp. PCC6803) or an ortholog thereof in another cyanobacterial species. In further nonlimiting examples the endogenous promoter can be a promoter of a glgA (glycogen synthase) gene (e.g., sll0945, protein coding region at nucleotides 2265213-2266646 of the *Synechocystis* sp. PCC6803 genome (GenBank Accession NC_000911) or sll1393, protein coding region at nucleotides 57340-58815 of the *Synechocystis* sp. PCC6803 genome (GenBank Accession NC_000911)), a promoter of a glgB (glycogen branching enzyme) gene (e.g., sll0158, protein coding region at nucleotides 2331505-2333817 of the *Synechocystis* sp. PCC6803 genome (GenBank Accession NC_000911)), or a glg C (glucose-1-phosphate adenyltransferase) gene (e.g., sll1176, protein coding region at nucleotides 3516539-3517858 of the *Synechocystis* sp. PCC6803 genome (GenBank Accession NC_000911)). Insertion of the wax ester synthesis transcriptional unit can in some instances attenuate or disrupt the gene that is naturally regulated by the endogenous promoter. For example, insertion of a wax synthesis transcriptional unit into the RS1 site of *Synechocystis* can disrupt the slr0338 gene. In other examples, the sll0945, sll1393, sll0158, or sll1176 gene of *Synechocystis* or an ortholog of any of these genes in another cyanobacterial host can be disrupted by integration of the wax ester synthesis transcriptional unit.

Alternatively, a transcriptional unit encoding two or more genes of a wax synthesis pathway can be operably linked to a promoter that is homologous with respect to the host microorganism, but the operon that includes the host-homologous promoter and wax synthesis transcriptional unit can be present in a vector in the host microorganism or integrated at a site in the genome of the host microorganism that is not the natural site of the host-homologous promoter. For example, where the host microorganism is a *cyanobacterium*, a cyanobacterial promoter as provided hereinabove (e.g., Prbc, nrs, nir, nar, pho, secA, etc.) can regulate transcription of the operon. Further alternatively, a transcriptional unit encoding two or more genes of a wax synthesis pathway can be operably linked to a promoter that is heterologous with respect to the host microorganism, but the operon that includes the heterologous promoter and wax synthesis transcriptional unit can be present in a vector in the host microorganism or integrated at a site in the genome of the host microorganism. For example, where the host microorganism is a *cyanobacterium*, a promoter of another cyanobacterial or prokaryotic species, or a synthetic promoter, as provided hereinabove (e.g., Trc, TrcE, TrcY, lac, ara, etc.) can regulate transcription of the operon.

Additionally to any of the above features, a recombinant host cell expressing a non-native gene encoding a thioesterase, a non-native gene encoding an acyl-CoA synthetase, a non-native gene encoding an alcohol-forming fatty acyl reductase, and/or a non-native gene encoding a wax ester synthase can optionally expresses at least one additional recombinant or exogenous gene, or can overexpresses an endogenous gene, that functions in the wax ester biosynthesis pathway. The additional gene may be encoded by a nucleic acid molecule that is the same as the nucleic acid molecule that encodes any of the thioesterase, the acyl-CoA synthetase, the alcohol-forming fatty acyl reductase, and the wax ester synthase, or the additional gene may be encoded by a separate nucleic acid molecule. Where two or more genes are encoded by the same nucleic acid molecule (e.g., on the same expression vector), the expression of each gene may optionally be independently regulated by a same or a different promoter and/or enhancer. An additional gene may increase the rate and/or level of wax ester production. Additionally and/or alternatively, an additional gene may, e.g., increase the concentration of wax ester precursors such as acyl-ACP, free fatty acids, acyl-CoA, and fatty alcohol; decrease the amount of acyl-ACP, fatty alcohol or wax ester conversion to other products (such as, for example, other fatty acid derivatives, or fatty alcohol or wax ester breakdown products); or lower fatty acid, fatty alcohol, and/or wax ester toxicity to the cell. For example, the polypeptide encoded by the additional gene can be selected from, e.g., one or more enzymes of the fatty acid synthase complex (e.g., a beta-ketoacyl-ACP synthase, a 3-ketoacyl-ACP reductase, a β-hydroxyacyl-ACP dehydratase, an enoyl-ACP reductase, etc.), an acetyl-CoA carboxylase, a malonyl-CoA:ACP transacylase, an acyl carrier protein, or an acyl-ACP synthetase. Additionally or alternatively, the recombinant host cell can express a ribulose 1,5-bisphosphate carboxylase, a phycobiliprotein (e.g., phycocyanin), an acyl carrier protein, and/or a transmembrane transporter (e.g., an ATP-binding cassette, or ABC, transporter, an RND pump, multi-drug efflux protein, etc.) to facilitate wax ester secretion. For example, a transporter can be encoded by at least one gene selected from a group including, but not limited to, ABC transporters such as *A. thaliana* Atlg51500 (AY734542), CER5, WBC11, AtMRPS, AmiS2 and AtPGP1 or fatty acid transporter (FATP) genes from *Saccharomyces, Drosophila* (e.g., CG7400-PA, isoform A, at locus NP_524723), *C. elegans*, mycobacterial species, or mammalian species. Additional transporter proteins that can be encoded by a non-native gene in a host microorganism of the invention include, but are not limited to, *Rhodococcus erythopolis* ansP (AAN73268), multi-drug efflux protein *E. coli* acrAB (NP_414996.1, NP_414995.1) or AcrEF (NP_417731.1, NP_417732.1), efflux protein *E. coli* tolC (NP_417507.2), *T. elongatus* BP-I tlll618, (NP_682408.1), *T. elongatus* BP-I tlll619 (NP_682409), *T. elongatus* BP-I tllO139 (NP 680930), and transporters from *Acinetobacter* sp. HOl-N. The polypeptide encoded by the additional gene may be exogenous or endogenous; if endogenous, the recombinant host cell may be engineered to overexpress or overproduce the endogenous polypeptide. If exogenous, the gene encoding the polypeptide may be located on a vector or may be integrated into the host genome, may be is under the control of a promoter (e.g., a regulatable promoter such as an inducible promoter).

Additionally but optionally, the recombinant host cell can be engineered to attenuate or eliminate the expression of one or more beta-oxidation pathway enzymes. For example, the recombinant host cell may be engineered to attenuate or eliminate expression of at least one of glycerol-3-phosphate dehydrogenase, acetaldehyde-CoA dehydrogenase, pyruvate dehydrogenase and acetate kinase. The recombinant host cell may be engineered to attenuate or eliminate any gene that functions to shunt substrates from the wax ester production pathway, to convert produced wax esters or fatty alcohols to a non-wax ester product, or to increase fatty alcohol or wax ester toxicity to the cell.

Mutations to attenuate or eliminate expression of known genes can be introduced either by recombinant or non-recombinant methods. The genes may be targeted specifically by disruption, deletion, replacement, or generation of antisense sequences, e.g., by use of micro RNAs or shRNA constructs, generation of ribozymes and/or other recombinant approaches known to the practitioner. Inactivation of the genes can additionally or alternatively be accomplished by random mutation techniques such as exposure to UV and/or chemical mutagens followed by screening of the cells for successful mutants. Additionally or alternatively, the proteins encoded by the genes can be inhibited by intracellular generation of appropriate antibodies, intracellular generation of peptide inhibitors, or the like, or some combination thereof.

The above-described recombinant host cells may be used in any of the methods or systems of producing a wax ester described herein.

Methods of Producing a Wax Ester

The invention provides methods of producing a wax ester using a recombinant host cell as disclosed herein, such as a recombinant microorganism expressing non-native genes encoding a thioesterase, an acyl-CoA synthetase, an alcohol-forming fatty acyl reductase, and a wax ester synthase, e.g., any of the recombinant host cells described herein. The genes can encode any thioesterase, acyl-CoA synthetase, alcohol-forming fatty acyl reductase, and wax ester synthase as disclosed herein. For example, the thioesterase can be an acyl-ACP thioesterase and/or the alcohol-forming fatty acyl reductase can be an alcohol-forming acyl-CoA reductase.

In a particular illustrative examples, the thioesterase encoded by the non-native nucleic acid sequence of the host microorganism is or comprises the polypeptide of SEQ ID NO: 1, the acyl-CoA synthetase encoded by the non-native nucleic acid sequence of the host microorganism is or comprises the polypeptide of SEQ ID NO: 10, the alcohol-forming fatty acyl reductase encoded by the non-native nucleic acid sequence of the host microorganism is or comprises the polypeptide of SEQ ID NO: 15, and the wax ester synthase encoded by the non-native nucleic acid sequence of the host microorganism is or comprises the polypeptide of SEQ ID NO: 22. The nucleic acid sequences encoding the wax ester synthase and one or more of the thioesterase, the acyl-CoA synthetase, and the alcohol-forming fatty acyl reductase, can be provided in an operon, where the operon can include a promoter heterologous or homologous with respect to the host microorganism, and where a homologous promoter can optionally be a promoter endogenous to the host microorganism and the transcriptional unit that includes the nucleic acid sequences encoding the wax ester synthase and one or more of the thioesterase, the acyl-CoA synthetase, and the alcohol-forming fatty acyl reductase can be intergrated into the host genome downstream of the endogenous promoter.

The method comprises the steps of: (1) culturing a recombinant host cell that comprises a non-native nucleic acid sequence that encodes a polypeptide having wax ester synthase activity and one or more of a non-native nucleic acid sequences that encode a thioesterase, a non-native nucleic acid sequence that encodes an acyl-CoA synthetase, and a non-native nucleic acid sequence that encodes an alcohol-forming acyl-CoA reductase in a suitable culture medium; and (2) allowing expression of the non-native nucleic acid sequences, wherein the expression results in the production of a wax ester. Preferably, one or more fatty acids or alcohols (e.g., one or more fatty alcohols) are not provided in the culture medium. In some examples, the recombinant host cell is a photosynthetic microorganism and the method comprises the steps of: (1) culturing a recombinant host cell in a suitable culture medium, wherein the recombinant host cell is a photosynthetic microorganism that comprises a non-native nucleic acid sequence encoding an acyl-ACP thioesterase, a non-native nucleic acid sequence encoding an acyl-CoA synthetase, a non-native nucleic acid sequence encoding an alcohol-forming acyl-CoA reductase, and a non-native nucleic acid sequence encoding a polypeptide having wax ester synthase activity, and (2) allowing expression of the non-native nucleic acid sequences, wherein the expression results in the production of a wax ester.

In various examples, the recombinant photosynthetic microorganism may be cultured photoautotrophically. The photosynthetic microorganism can be, for example, a *cyanobacterium*. The nucleic acid sequences encoding any of the thioesterase, acyl-CoA synthetase, alcohol-forming fatty acyl reductase, and/or wax ester synthase may optionally be codon-optimized for expression in the recombinant host cell (e.g., a photosynthetic microorganism such as a *cyanobacterium*).

The non-native nucleic acid sequences encoding the thioesterase, acyl-CoA synthetase, alcohol-forming fatty acyl reductase, and/or wax ester synthase can be heterologous with respect to the recombinant photosynthetic microorganism and can be any as described herein. In various aspects, one or more (e.g., all) of the nucleic acid sequence(s) can be integrated into a chromosome of the recombinant photosynthetic microorganism, and the nucleic acid sequence encoding a wax ester synthase and one or more of the nucleic acid sequences encoding a thioesterase, an acyl-CoA synthetase, and an alcohol-forming fatty acyl reductase may be organized in an operon in which the sequences are operably linked to a promoter, which may be e.g., a promoter endogenous to the recombinant photosynthetic microorganism, or can be, for example, a heterologous promoter, and which in some examples may be regulatable. For example, the promoter (whether endogenous to the host or exogenous, whether heterologous or homologous with respect to the host species) can be inducible, and the method may further comprise the step of inducing expression of the non-native genes encoding the thioesterase, acyl-CoA synthetase, alcohol-forming fatty acyl reductase, and/or wax ester synthase. Optionally, all of the nucleic acid sequences encoding the thioesterase, acyl-CoA synthetase, alcohol-forming fatty acyl reductase, and wax ester synthase may be configured in the same operon.

The recombinant photosynthetic microorganism can be grown mixotrophically, using both light and a reduced carbon source, or can be cultured phototrophically. When cultured phototrophically, the photosynthetic microorganism can advantageously use light as an energy source. An "inorganic" or non-reduced carbon source can be used for synthesis of biomolecules by the photosynthetic microorganism. Typically a "non-reduced carbon source" can be in the form of $CO_2$ (carbon dioxide), carbonic acid, bicarbonate salts, carbonate salts, hydrogen carbonate salts, or the like, or combinations thereof, which cannot be further oxidized for sustainable energy nor used as a source of reducing power by host cells. In some examples, inorganic carbon can be substantially the only carbon source present in the culture medium. In these examples, if an organic (reduced) carbon source or compound is present in the culture medium of a host cell grown phototrophically, it generally cannot be taken up and/or metabolized by the cell for energy or as a carbon source for the synthesis of biomolecules, and/or is not present in an amount sufficient to provide sustainable energy for the growth of the cell culture or production or organic molecules.

Microorganisms that can be useful as host cells in accordance with the methods of the present invention can be found in various locations and environments throughout the world. Without being bound by theory, it is observed that, perhaps as a consequence of their isolation from other species and/or their evolutionary divergence, the particular growth medium for optimal growth and generation of lipid and/or hydrocarbon constituents can vary. In some cases, certain strains of microorganisms may be unable to grow in a particular growth medium because of the presence of some inhibitory component or the absence of some essential nutritional requirement required by the particular strain of microorganism.

Solid and liquid growth media are generally available from a wide variety of sources, as are instructions for the preparation of particular media suitable for a wide variety of host cell types. For example, various fresh water and salt water media are well known in the art, e.g., those described in Barsanti (2005) Algae: Anatomy, Biochemistry & Biotechnology, CRC Press for media and methods for culturing algae. The growth medium used in exemplary methods is not supplemented with either of a fatty acid or a fatty alcohol.

The culture methods can include inducing expression of a particular gene described herein for the production of wax esters (e.g., a thioesterase gene, an acyl-CoA synthetase gene, an alcohol-forming fatty acyl reductase gene, and/or a wax ester synthase gene), and/or for regulating metabolic pathways in the microorganism. Inducing expression can include adding a nutrient or compound to the culture, removing one or more components from the culture medium, increasing or decreasing light and/or temperature, and/or other manipulations that promote expression of the gene of interest. Such manipulations can largely depend on the nature of the promoter operably linked to the gene of interest.

In some aspects of the methods, the recombinant host cells can be cultured in a bioreactor. Bioreactors can offer many advantages for use in heterotrophic growth and propagation methods. To produce biomass for use in food, microorganisms are preferably fermented in large quantities in liquid, such as, e.g., in suspension cultures. Bioreactors such as steel fermentors can accommodate very large culture volumes (40,000 liter and greater capacity bioreactors can be used in various aspects of the invention). Bioreactors can also typically allow for the control of one or more culture conditions such as temperature, pH, oxygen tension, carbon dioxide levels, and the like, as well as combinations thereof. Bioreactors can typically be configurable, for example, using ports attached to tubing, to allow gaseous components, such as $CO_2$, $CO_2$-enriched air, oxygen and/or nitrogen, to be contacted with (e.g., bubbled through) a liquid culture. Other culture parameters, such as the pH of the culture media, the identity and/or concentration of trace elements and/or nutrients, the identity and/or concentration of other media constituents, or the like, or combinations thereof, can typically be more readily manipulated using a bioreactor.

In some aspects, the cells (e.g., photosynthetic microorganisms) can be cultured in a bioreactor equipped with a natural or artificial light source (a "photobioreactor"), and/or can have one or more walls that is transparent enough to light, including sunlight, to enable, facilitate and/or maintain acceptable microorganism growth. For production of wax esters, the recombinant host cells can additionally or alternatively be cultured in shake flasks, test tubes, vials, microtiter dishes, petri dishes, or the like, or combinations thereof.

Genetically engineered photosynthetic microorganisms may also be grown in, e.g., ponds, canals, trenches, raceways, channels, or the like, or combinations thereof. As with standard bioreactors, a source of inorganic carbon including, but not limited to, air, $CO_2$-enriched air, flue gas, etc., or combinations thereof, can be supplied to the culture. When supplying flue gas and/or other sources of inorganic carbon that may contain CO in addition to $CO_2$, it may be necessary to pretreat such sources such that the CO level introduced into the (photo)bioreactor does not constitute a dangerous and/or lethal dose vis-à-vis the growth and/or survival of the microorganisms. In some aspects, the carbon source is a non-reduced carbon source, e.g., (such as, but not limited to, $CO_2$, bicarbonate, carbonate salts, and the like). In some aspects, the carbon source does not provide a source of energy in the production of a wax ester.

In some aspects, the wax ester produced by a system of the invention can be secreted into the culture medium by the recombinant host cell. Additionally or alternatively, the wax ester may be extracted from the recombinant host cell. In some aspects, the wax ester may be isolated using a method described herein.

The recombinant host cell can optionally secrete at least a portion of the produced wax ester into the growth media. For example, the ratio of the amount of wax ester produced to the amount of wax ester secreted can be less than about 10:1, 9:1, 8:1, 7:1, 6:1, 5:1, 4:1, 3:1, 2:1 or 1:1. For example, the ratio of the amount of wax ester produced to the amount of wax ester secreted can be less than about 5:1, 4:1, 3:1, 2:1 or 1:1. The recombinant host cell may express an exogenous transmembrane transporter such as, but not limited to, those disclosed herein (e.g., an ATP-binding cassette (ABC) transporter, multidrug efflux protein, or an RND pump) to facilitate wax ester secretion. Expression of a transporter protein may increase the amount of a wax ester released from the recombinant host cell and/or may increase production of a wax ester by the recombinant host cell. Secretion of the wax ester may in some examples be regulatable, and in some examples secretion of the wax ester may be inducible.

The method can further comprise the step of isolating the produced wax ester. For example, wax esters can be recovered from the culture medium by recovery means known to those of ordinary skill in the art, such as by whole culture extraction, e.g., using immiscible (e.g., organic) solvents. Additionally or alternatively, particulate adsorbents can be employed. These may include, e.g., lipophilic particulates and/or ion exchange resins, depending on the design of the recovery method. The particulate absorbents may circulate in the separated medium and then undergo collection, and/or the medium may be passed over a fixed bed column, for example a chromatographic column, containing the particulates. The wax esters can then be eluted from the particulate adsorbents, e.g. by the use of an appropriate solvent. The solvent may then be evaporated, followed by further processing of the isolated lipids to yield chemicals and/or fuels that can be used for a variety of purposes. Isolation of the wax ester may in some examples occur simultaneously with wax ester production. In some examples, isolation of the wax ester may be continuous.

Alternatively or in addition, recovery of wax esters may be enhanced by homogenization of the host cells (via, e.g., heat, treatment with an acid or base, treatment with enzymes, osmotic shock, mechanical disruption, sonication, freeze-thaw, etc.). In some examples, material containing cells or cell fractions can be treated with proteases to degrade contaminating proteins. After digestion, the lipids may be purified from residual proteins, peptide fragments and amino acids, e.g., by centrifugation and/or filtration. The recovery method can be adapted to efficiently recover only the released wax esters, only the wax esters produced and stored within the cells, or both the stored and released wax esters.

The methods of the invention may result in the production of at least 0.1, 0.5, 1, 2, 3, 4, 5, 6, 7, 8, 9, 10, 11, 12, 13, 14, 15, 16, 17, 18, 19, 20, 21, 22, 23, 24, 25, 26, 27, 28, 29 or 30 mg/L of one or more wax esters over a culture period of 1, 2, 3, 4, 5, 6, 7, 8, 9, 10, 11, 12, 13 or 14 days. For example, the recombinant host cell can produce at least 1, 2, 5 or 10 mg/L of wax ester. In some examples, the methods of the invention can produce at least 1-5 mg/L of wax ester over a seven day culture period. Alternatively or in addition, the recombinant host cell comprising nucleic acid sequences encoding a) a thioesterase, b) an acyl-CoA synthetase, c) an alcohol-forming fatty acyl reductase, and d) a wax ester synthase can produce an increased level (e.g., at least 10%, 20%, 30%, 40%, 50%, 60%, 70%, 80%, 90%, 100%, 200%, 300%, 400%, 500%, 600%, 700%, 800%, 900% or 1000% more) of wax ester relative to a control host cell lacking the nucleic acid sequences. For example, the recombinant host cell comprising nucleic acid sequences encoding a) an acyl-ACP thioesterase, b) an acyl-CoA synthetase, c) an alcohol-forming acyl-CoA reductase, and d) a wax ester synthase can produce an increased level (e.g., at least 10%, 20%, 30%, 40%, 50%, 60%, 70%, 80%, 90%, 100%, 200%, 300%, 400%, 500%, 600%, 700%, 800%, 900% or 1000% more) of wax ester relative to a control host cell lacking the nucleic acid sequences.

Alternatively in addition to any of the above, the recombinant host cell comprising nucleic acid sequences encoding a) a thioesterase, b) an acyl-CoA synthetase, c) an alcohol-forming fatty acyl reductase, and d) a wax ester synthase can produce at least 0.5 milligrams per liter of wax esters in a period of seven days, for example, at least 1 mg/L, 2 mg/L, 5 mg/L or 10 mg/L of wax esters in a period of seven days, or an average of at least 0.1 mg/L, 0.2 mg/L, 0.5 mg/L, 1 mg/L or 2 mg/L of wax esters per day for a culture period of from about one day to about thirty days, or between about 0.5 milligrams per liter and about 500 milligrams per liter, or between about 1 mg/L and about 250 mg/L, or between about 1 mg/L and about 100 mg/L, or between about 2 mg/L and about 200 mg/L, or between about 2 mg/L and about 25 mg/L, or between about 5 mg/L and about 100 mg/L, or between about 2 mg/L and about 50 mg/L, or between about 2 mg/L and about 25 mg/L, or between about 5 mg/L and about 25 mg/L, or between about 5 mg/L and about 50 mg/L, or between about 10 mg/L and about 50 mg/L, or between about 10 mg/L and about 100 mg/L of wax esters per day for a culture period of from about one day to about thirty days.

Figure 6:
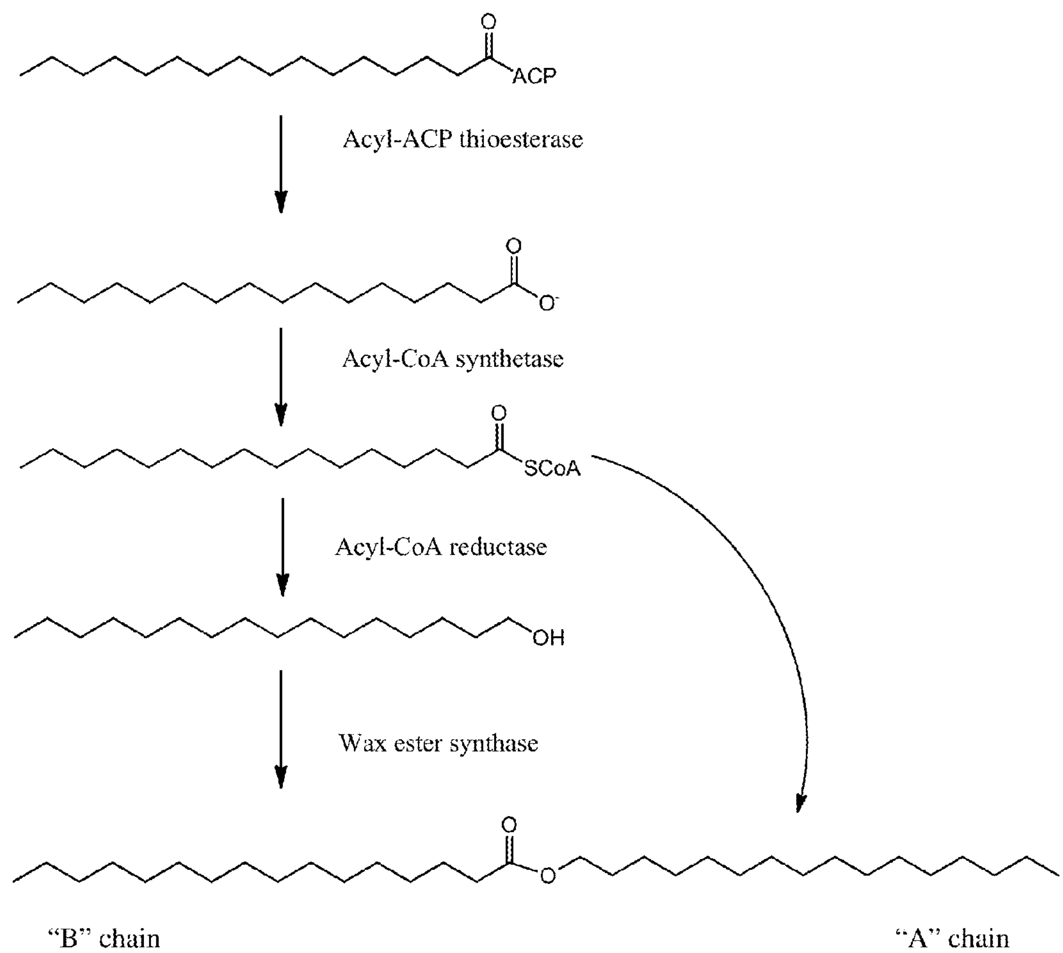
FIG. 6 is a schematic representation of a four-step metabolic pathway for producing wax esters from acyl-ACP.

Wax esters typically comprise an A chain derived from a fatty alcohol and a B chain derived from acyl-CoA (see, e.g., FIG. 6). Using the four-gene wax ester synthesis reagents and methods of the invention, both the A chain and the B chain of a wax ester can be produced without the addition of substrate fatty acids or fatty acid derivatives (e.g., fatty alcohols).

The methods of the invention can produce wax esters comprising at least one wax ester molecule wherein both the A chain and the B chain have chain lengths of C8-C24. For example, both the A chain and the B chain can have chain lengths of C12-C18. The A and/or B chain of a wax ester in the wax ester can comprise, e.g., C6, C8, C10, C12, C14, C16, C18, C20, C22 or C24 fatty alcohol molecules, in any combination. For example, at least 80%, at least 85%, at least 90%, at least 92%, at least 95%, at least 97% or at least 99% by weight of the total produced wax esters are wax esters comprising C8 to C24 A and/or B chains. For example, at least 80%, at least 85%, at least 90%, at least 92%, at least 95%, at least 97% or at least 99% by weight of the total produced wax esters can comprise C12 to C20 A and/or B chains. For example, at least 80%, at least 85%, at least 90%, at least 92%, at least 95%, at least 97% or at least 99% by weight of the total produced wax esters can comprise C12 to C18 A and/or B chains. In preferred examples, both the A and B chains of a wax ester produced by the methods of the invention have chain lengths of C8-C24. In further preferred examples, both the A and B chains of a wax ester produced by the methods of the invention have chain lengths of C12-C18.

The A and B chains of the wax esters produced by the methods of the invention may comprise straight chain, branched chain and/or cyclic chains, and may comprise saturated, monounsaturated and/or polyunsaturated chains. It is understood that a reference to a "Cx fatty acid" includes both saturated and unsaturated fatty acids having "x" carbon atoms, and that a reference to a "Cx fatty alcohol" includes both saturated and unsaturated fatty alcohols having "x" carbon atoms.

The invention also provides a composition comprising a wax ester isolated according to the methods of the invention. Wax esters as described herein can be used as components of fuel compositions. Wax esters are produced by the methods provided herein can include one or more wax esters having both an A chain and a B chain with chain lengths of C8-C24. For example, a wax ester composition can comprise at least one wax ester molecule produced by a method disclosed herein that has both an A chain and a B chain of C12-C18. Compositions of the invention may, according to certain aspects, comprise a mixture of different wax esters where the mixture comprises different wax esters in similar proportions (for example, within +/−1, 2, 3, 4, 5, 6, 7, 8, 9, 10, 11, 12, 13, 14, 15, 16, 17, 18, 19, or 20%) to those produced by a recombinant host cell of the invention. Additionally or alternatively, a wax ester composition of the invention may, according to certain aspects, be identifiable as having been produced according to a method of the invention by detection of a minor impurity in the composition which identifies its source from a recombinant host cell of the invention. For example, the composition may contain one or more nucleic acid molecules as a minor component which my be detected for example, by polymerase chain reaction (PCR) or by an alternative sequence-specific nucleic acid amplification detection method, where the nucleic acid molecules may comprise a sequence encoding a portion of one or more sequences corresponding to any of SEQ ID NOS: 1-30.

Methods of the invention as described herein may be carried out using a variety of nucleic acid molecules, vectors, polypeptides, host cells, and/or systems (e.g., those described herein).

Systems

The invention also provides a system for producing a wax ester, e.g., in a four-gene wax ester synthesis pathway. The system can comprise a recombinant host cell that comprises a nucleic acid sequence encoding a) a thioesterase, b) a nucleic acid sequence encoding an acyl-CoA synthetase, c) a nucleic acid sequence encoding an alcohol-forming fatty acyl reductase, and/or d) a nucleic acid sequence encoding a wax ester synthase, wherein any of the sequences may optionally be non-native. The system can comprise a prokaryotic and/or photosynthetic host microorganism.

The recombinant host cell may be, e.g., any of the recombinant host cells described herein and may comprise any of the nucleic acid sequences described herein. For example, the recombinant host cell can be a recombinant photosynthetic microorganism and can be cultured in a medium that does not include a substantial amount of a reduced carbon source. In such examples, the recombinant photosynthetic microorganism is preferably exposed to light for at least a portion of the production period.

In some aspects, the systems of the invention can produce at least 0.1, 0.5, 1, 2, 3, 4, 5, 6, 7, 8, 9, 10, 11, 12, 13, 14, 15, 16, 17, 18, 19, 20, 21, 22, 23, 24, 25, 26, 27, 28, 29 or 30 mg/L of wax ester over a culture period of up to 1, 2, 3, 4, 5, 6, 7, 8, 9, 10, 11, 12, 13 or 14 days by culturing recombinant host cells described herein. In some aspects, the systems of the invention can produce at least 1-100, 1-50, 1-20, 1-10, or 1-5 mg/L of wax ester over a culture period of up to 1, 2, 3, 4, 5, 6, 7, 8, 9, 10, 11, 12, 13, or 14 days by culturing recombinant host cells as described herein.

Systems of the invention as described herein may use a variety of nucleic acid molecules, vectors, polypeptides and/or host cells. In some aspects, the systems use one or more nucleic acid molecules, vectors, polypeptides and/or host cells described herein. Further, the systems may be used to perform any of the methods for producing a wax ester described herein.

Additionally or alternatively, the present invention can include one or more of the following embodiments.

EMBODIMENTS

Embodiment 1

An isolated or recombinant nucleic acid molecule comprising a nucleic acid sequence encoding a wax ester synthase and at least one of (a) a nucleic acid sequence encoding an acyl-ACP thioesterase, an acyl-CoA thioesterase, or a hydroxybenzoylthioesterase; (b) a nucleic acid sequence encoding an acyl-CoA synthetase; and (c) a nucleic acid sequence encoding an alcohol-forming fatty acyl reductase; wherein the nucleic acid sequence encoding a wax ester synthase and at least one of the nucleic acid sequences encoding a thioesterase, an acyl-CoA synthetase, or an alcohol-forming fatty acyl reductase are configured as a single transcriptional unit; and optionally wherein the nucleic acid molecule further comprises at least one nucleic acid sequence of at least 50, 100, 200, 300, 400, 500, 600, 700, 800, 900, 1000, or 1500 nucleotides derived from the genome of a prokaryotic and/or photosynthetic microorganism.

Embodiment 2

The isolated or recombinant nucleic acid molecule according to embodiment 1, comprising: (a) a nucleic acid sequence encoding an acyl-ACP thioesterase; (b) a nucleic acid sequence encoding an acyl-CoA synthetase; (c) a nucleic acid sequence encoding an alcohol-forming acyl-CoA reductase; and (d) a nucleic acid sequence encoding a wax ester synthase wherein (a), (b), (c), and (d) are configured as a single transcriptional unit.

Embodiment 3

The isolated or recombinant nucleic acid molecule according to embodiment 1 or 2, wherein: (a) is a nucleic acid sequence encoding an acyl-ACP thioesterase derived from a plant species, optionally a *Cuphea* species or an *Elaeis* species, and/or is selected from the group consisting of an acyl-ACP thioesterase of: *Cuphea wrightii* (GenBank Accession AAC49784), *Cuphea lanceolata* (GenBank Accession CAA54060), *Cuphea palustris*, (GenBank Accessions AAC49783; AAC49179); *Cuphea hookeriana* (GenBank Accessions AAC72882; AAC49269; AAC72881; AAC72883), *Cuphea calophylla* (GenBank Accession ABB71580), *Arabidopsis* (GenBank Accessions XP_002885681; NP_172327); *Arachis hypogaea* (GenBank Accession ABO38556); *Brassica* (GenBank Accession CAA52069.1), *Camellia oleifera* (GenBank Accession ACQ57189); *Cinnamonum camphorum* (GenBank Accession AAC49151); *Cocos nucifera* (GenBank Accessions AEM72519; AEM72520; AEM72521); *Glycine max* (GenBank Accession ABD91726); *Garcinia mangostana* (GenBank Accession AAB51525); *Gossypium hirsutum* (GenBank Accession AAD01982); *Helianthus annuus* (GenBank Accession AAQ08226); *Jatropha curcas* (GenBank Accession ABU96744); *Macadamia tetraphylla* (GenBank Accession ADA79524); *Elaeis oleifera* (GenBank Accession AAM09524); *Elaeis guineensis* (GenBank Accession AAD42220); *Oryza sativa* (GenBank Accession BAA83582); *Populus tomentosa* (GenBank Accession ABC47311); *Umbellularia californica* (GenBank Accession AAC49001); *Ulmus Americana* (GenBank Accession AAB71731); *Zea mays* (GenBank Accession ACG41291), *Cuphea carthagenensis* cc1FatB1 (SEQ ID NO:1 or SEQ ID NO:2), *Cuphea decandra* Cd1FatB1 (SEQ ID NO:3 or SEQ ID NO:4), *Cuphea paucipetala* Cp1FatB1 (SEQ ID NO:5 or SEQ ID NO:6), *Elaeis guineensis* thioesterase (SEQ ID NO:7, SEQ ID NO:8, or SEQ ID NO:9) and *Physcomitrella patens* (GenBank Accession XP 001770108); wherein (b) is a nucleic acid sequence encoding an acyl-CoA synthetase selected from the group consisting of: *E. coli* FadD (GenBank Accession NP_416319), *E. coli* FadK (GenBank Accession NP_416216), or the acyl-CoA synthetase of *Vibrio splendidus* (GenBank Accession EGU44230), *Marinobacter adhaerens* HP15 (GenBank Accession ADP96803), *Acinetobacter* sp. ADP1 (fadD, GenBank Accession YP_045024), *Haemophilus influenza* RdKW20 (fadD, GenBank Accession NP_438551), *Bacillus halodurans* C-125 BH3103 (GenBank Accession NP_243969), *Bacillus subtilis* yhF1 (GenBank Accession NP_388908), *Pseudomonas fluorescens* Pfo-1 Pfl-4354 (GenBank Accession YP_350082), *Comamonas testosteroni* KF-1 EAV15023 (GenBank Accession ZP_01520072), *Pseudomonas aeruginosa* fadD1 (GenBank Accession NP_251989), *Pseudomonas aeurginosa* PAO1 fadD2 (GenBank Accession NP_251990), *Rhizobium etli* CFN42 fadD (GenBank Accession YP_468026), *Rhodopseudomo nas palustris* Bis B18 RPC_4074 (GenBank Accession YP_533919), *Rasltonia Solanacearum* GM1 1000 fadD1 (GenBank Accession NP_520978), *Mycobacterium tuberculosis* H37Rv fadDD35 (GenBank Accession NP_217021), *Mycobacterium tuberculosis* H37Rv fadDD22 (GenBank Accession NP_217464), *Stenotrophomon as Maltophilia* R551-3 PRK0059 (GenBank Accession ZP_01644857), *Saccharomyces cerevisiae* (Faa2p, GenBank Accession NP_010931), *Saccharomyces cerevisiae* (SCRG_04483, GenBank Accession EDV08843), *Yarrowia lipolytica* (GenBank Accession CAG77892), *Brassica napus* (GenBank Accession CAC19877), *Arabidopsis thaliana* (GenBank Accession AEE74324), *Glycine max* (GenBank Accession XP_003524920), *Chlamydomonas reinhardtii* (GenBank Accession XP_001693692), *Nannochloropsis oculata* (e.g., GenBank Accession ADP09391), or *Chlorella*

*variabilis* (e.g., GenBank Accession EFN56588). *Apis mellifera*, (GenBank Accession NP_001193902) and *Mus musculus* (GenBank Accession EDL17174); wherein (c) is a nucleic acid sequence encoding an alcohol-forming acyl-CoA reductase selected from the group consisting of: *Marinobacter aquaeolei* VT8 Maqu_2220 (SEQ ID NO: 15, GenBank Accession YP_959486), *Marinobacter algicola* DG893 (GenBank Accession ZP_01892457); *Hahella chejuensis* KCTC 2396 HCH_05075; SEQ ID NO: 20, GenBank Accession YP_436183); *Oceanobacter* sp. RED65 (GenBank Accession ZP_01305629), *Marinobacter aquaeoli* VT8 2220 Maqu_2507 gene (SEQ ID NO:19, GenBank Accession ABM19582), *Bombyx mmori* (GenBank Accession BAC79426), *Simmondsia chinensis* (SEQ ID NO: 21, GenBank Accession AAD38039), *Triticum aestivum* (GenBank Accession CAD30694 or CAD30692), *Mus musculus* (GenBank Accession NP_081655), *Mus musculus* (GenBank Accession NP_848912), *H. sapiens* (GenBank Accession NP_115604), *Ostrinia scapulalis* (SEQ ID NO: 18, GenBank Accession ACJ06520), *Z. mays* (GenBank Accession NP_001151388 or EU970865), *Arabidopsis thaliana* (GenBank Accession NP_187805), *Arabidopsis thaliana* FAR4 (GenBank Accession NP_001030809 or NP_190040), *Arabidopsis thaliana* FAR6 (SEQ ID NO: 16, SEQ ID NO: 17, GenBank Accession 67633703), *Arabidopsis thaliana* CER4 (GenBank Accession NP_567936) or *Arabidopsis thaliana* (GenBank Accession NP567936) *Yponomeuta evonymellus* (GenBank Accession GQ907231-GQ907233), *Yponomeuta rorellus* (GenBank Accession GQ907234), *Yponomeuta padellus* (GenBank Accession GQ907235), *Ostrinia nubilalis* (GenBank Accession FJ807735), and *Homo sapiens* (GenBank Accession AAT42129); and/or wherein (d) is a nucleic acid sequence encoding a wax ester synthase selected from the group consisting of: *Marinobacter hydrocarbonoclasticus* WS1 (GenBank Accession ABO21020), *M. hydrocarbonoclasticus* DSM 8798 WS2 (GenBank Accession ABO21021), M. sp. ELB 17 (GenBank Accession EBA00388), *M. aquaeolei* Maqu_0168 WS (GenBank Accession YP_957462), *M. adhaerens* HP15 WS (ADP99639), *Hahella chejuensis* KCTC 2396 (GenBank Accession YP_432512), *Acinetobacter baumannii* wax ester synthase (GenBank Accession EGJ63408), *A. calcoaceticus* WS/DGAT (GenBank Accession ZP_06058985) *Acinetobacter baylyi* ADP1 wax ester synthase (GenBank Accession AAO17391 or Q8GGG1), *Bradyrhizobium japonicum* USDA 110 (GenBank Accession NP_769520), *Erythrobacter litoralis* HTCC 2594 (GenBank Accession YP_457389), *Rhodococcus opacus* wax ester synthase (GenBank Accession BAH53702), *Mycobacterium tuberculosis* wax ester synthase (GenBank Accession NP_334638), *M. smegmatis* wax ester synthase (GenBank Accession ABK74273), the "WS/DGAT/MGAT" subfamily proteins of *Alcanivorax* species (GenBank Accessions CAL17252; EDX90960; EDX89052; ZP_05043539; ZP_05041631), wsadp1 from *Nocardia farcinica* IFM 10152 (GenBank Accession YP_117375), *Photobacterium profundum* SS9 (GenBank Accession YP_130413), *Rhodoferax ferrireducens* DSM 15236 (GenBank Accession ZP_00691704), and *Salinibacter ruber* DSM 13855 (GenBank Accession YP_446603), JjWS (GenBank Accession AF149919), *Euglena gracilis* wax ester synthase (GenBank Accession ADI60058), *Arabidiopsis thaliana* WSD1 O-acyltransferase (GenBank Accession NP_568547), *Arabidiopsis thaliana* GPAT acyltransferase (GenBank Accession NP_174499), the putative long-chain-alcohol O-fatty-acyltransferase 4 of *Arabidiopsis thaliana* (GenBank Accession NP_200346) *Murraya koenigii* wax ester synthase, acyl-CoA wax alcohol acyltransferase 2 from *H. sapiens* (GenBank Accession NP_001002254), mWS from *Mus musculus* (GenBank Accession Q6E1M8), SAAT from *Fragaria xananas* (GenBank Accession AAG13130), the membrane bound O-acyltransferase (MBOAT) of *Zea mays* (GenBank Accession NP_001131179), and mdAAT2 from *Malus x domestica* (GenBank Accession AAS79797).

Embodiment 4

The nucleic acid molecule according to any of claims 1-3, wherein: (a) the nucleic acid sequence encoding an acyl-ACP thioesterase encodes an acyl-ACP thioesterase having sequence identity of at least 30%, 40%, 45%, 50%, 55%, 60%, 65%, 70%, 75%, 80%, 85%, 86%, 87%, 88%, 89%, 90%, 91%, 92%, 93%, 94%, 95%, 96%, 97%, 98%, or 99%, or sequence identity of 100% to the amino acid sequence of any one of SEQ ID NOS: 1-9, or to a functional fragment thereof; (b) the nucleic acid sequence encoding an acyl-CoA synthetase encodes an acyl-CoA synthetase having a sequence identity of at least 30%, 40%, 45%, 50%, 55%, 60%, 65%, 70%, 75%, 80%, 85%, 86%, 87%, 88%, 89%, 90%, 91%, 92%, 93%, 94%, 95%, 96%, 97%, 98%, or 99%, or sequence identity of 100% to the amino acid sequence of any one of SEQ ID NOS: 10-14, or to a functional fragment thereof; (c) the nucleic acid sequence encoding an alcohol-forming acyl-CoA reductase encodes an alcohol-forming acyl-CoA reductase having sequence identity of at least 30%, 40%, 45%, 50%, 55%, 60%, 65%, 70%, 75%, 80%, 85%, 86%, 87%, 88%, 89%, 90%, 91%, 92%, 93%, 94%, 95%, 96%, 97%, 98%, or 99%, or sequence identity of 100% to the amino acid sequence of any one of 15-21, or to a functional fragment thereof; and (d) the nucleic acid sequence encoding a wax ester synthase encodes a wax ester synthase having sequence identity of at least 30%, 40%, 45%, 50%, 55%, 60%, 65%, 70%, 75%, 80%, 85%, 86%, 87%, 88%, 89%, 90%, 91%, 92%, 93%, 94%, 95%, 96%, 97%, 98%, 99%, or 100% to the nucleotide sequence of any one of SEQ ID NOS: 22-30, or to a functional fragment thereof.

Embodiment 5

The nucleic acid molecule according to any one of embodiments 2-4, wherein the nucleic acid sequences are in an order selected from:

(a) acyl-ACP thioesterase-acyl-CoA synthetase-alcohol-forming acyl-CoA reductase-wax ester synthase;
(b) acyl-ACP thioesterase-acyl-CoA synthetase-wax ester synthase-alcohol-forming acyl-CoA reductase;
(c) acyl-ACP thioesterase-alcohol-forming acyl-CoA reductase-acyl-CoA synthetase-wax ester synthase;
(d) acyl-ACP thioesterase-wax ester synthase-acyl-CoA synthetase-alcohol-forming acyl-CoA reductase;
(e) acyl-ACP thioesterase-alcohol-forming acyl-CoA reductase-wax ester synthase-acyl-CoA synthetase;
(f) acyl-ACP thioesterase-wax ester synthase-alcohol-forming acyl-CoA reductase-acyl-CoA synthetase;
(g) wax ester synthase-acyl-ACP thioesterase-acyl-CoA synthetase-alcohol-forming acyl-CoA reductase;
(h) wax ester synthase-acyl-ACP thioesterase-alcohol-forming acyl-CoA reductase-acyl-CoA synthetase;
(i) wax ester synthase-acyl-CoA synthetase-acyl-ACP thioesterase-alcohol-forming acyl-CoA reductase;
(j) wax ester synthase-alcohol-forming acyl-CoA reductase-acyl-ACP thioesterase-acyl-CoA synthetase;
(k) wax ester synthase-acyl-CoA synthetase-alcohol-forming acyl-CoA reductase-acyl-ACP thioesterase;

(l) wax ester synthase-alcohol-forming acyl-CoA reductase-acyl-CoA synthetase-acyl-ACP thioesterase;

(m) alcohol-forming acyl-CoA reductase-wax ester synthase-acyl-ACP thioesterase-acyl-CoA synthetase;

(n) alcohol-forming acyl-CoA reductase-wax ester synthase-acyl-CoA synthetase-acyl-ACP thioesterase;

(o) alcohol-forming acyl-CoA reductase-acyl-ACP thioesterase-wax ester synthase-acyl-CoA synthetase;

(p) alcohol-forming acyl-CoA reductase-acyl-CoA synthetase-wax ester synthase-acyl-ACP thioesterase;

(q) alcohol-forming acyl-CoA reductase-acyl-ACP thioesterase-acyl-CoA synthetase-wax ester synthase;

(r) alcohol-forming acyl-CoA reductase-acyl-CoA synthetase-acyl-ACP thioesterase-wax ester synthase;

(s) acyl-CoA synthetase-alcohol-forming acyl-CoA reductase-wax ester synthase-acyl-ACP thioesterase;

(t) acyl-CoA synthetase-alcohol-forming acyl-CoA reductase-acyl-ACP thioesterase-wax ester synthase;

(u) acyl-CoA synthetase-wax ester synthase-alcohol-forming acyl-CoA reductase-acyl-ACP thioesterase;

(v) acyl-CoA synthetase-acyl-ACP thioesterase-alcohol-forming acyl-CoA reductase-wax ester synthase;

(w) acyl-CoA synthetase-wax ester synthase-acyl-ACP thioesterase-alcohol-forming acyl-CoA reductase; or (x) acyl-CoA synthetase-acyl-ACP thioesterase-wax ester synthase-alcohol-forming acyl-CoA reductase.

Embodiment 6

The nucleic acid molecule according to any of the previous embodiments, wherein one or more, and optionally all, of the nucleic acid sequences encoding the thioesterase, the nucleic acid sequence encoding the acyl-CoA synthetase, the nucleic acid sequence encoding the alcohol-forming fatty acyl reductase, and the nucleic acid sequence encoding the wax ester synthase comprise an initiation codon, and further optionally wherein one or more, and optionally all, of the nucleic acid sequences encoding the thioesterase, the nucleic acid sequence encoding the acyl-CoA synthetase, the nucleic acid sequence encoding the alcohol-forming fatty acyl reductase, and the nucleic acid sequence encoding the wax ester synthase comprise a heterologous translational regulatory sequence upstream of the initiation codon.

Embodiment 7

The nucleic acid molecule according to any of embodiments 1-6, wherein the nucleic acid sequence encoding the wax ester synthase and one or more of the nucleic acid sequence encoding the thioesterase, the nucleic acid sequence encoding acyl-CoA synthetase, and the nucleic acid sequence encoding the alcohol-forming fatty acyl reductase, are in an operon, optionally wherein the nucleic acid sequences are operably linked to a promoter derived from a prokaryotic and/or photosynthetic microorganism.

Embodiment 8

The nucleic acid molecule according to any of embodiments 1-7, wherein the nucleic acid molecule comprises a nucleic acid sequence derived from the genome of a prokaryotic and/or photosynthetic microorganism comprising a sequence derived from the 5' region of a gene, optionally wherein the sequence derived from the 5' region of a gene comprises at least a portion of a promoter; preferably further wherein the nucleic acid sequence derived from the 5' region of a gene of a prokaryotic and/or photosynthetic microorganism is positioned 5' of the transcriptional unit; and further optionally wherein nucleic acid sequence (d) and one or more of nucleic acid sequences (a), (b), and (c), and preferably all of nucleic acid sequences (a), (b), (c), and (d), are configured as an operon, optionally wherein the 5' region of the gene of a prokaryotic and/or photosynthetic microorganism comprises the promoter of the operon.

Embodiment 9

The nucleic acid molecule according to any of embodiments 1-6, wherein the nucleic acid molecule does not comprise a promoter sequence operably linked to any of the nucleic acid sequences.

Embodiment 10

A vector comprising the nucleic acid molecule of any of the previous embodiments, wherein the vector optionally comprises: (a) one or more of a selectable marker, optionally a selectable marker conferring resistance to an antibiotic or herbicide; and/or (b) an origin of replication for propagation in a cloning strain, optionally wherein the cloning strain, optionally wherein the cloning strain is yeast or *E. coli*.

Embodiment 11

A recombinant host cell comprising any of the nucleic acid molecules or vectors of embodiments 1-10.

Embodiment 12

A recombinant host cell according to embodiment 11, wherein the nucleic acid molecule is integrated into the genome of the recombinant host cell, optionally wherein the nucleic acid molecule is integrated into a genomic site within or adjacent to the 5' region of a gene endogenous to the recombinant host cell, further optionally wherein the 5' region includes a promoter operably linked to one or more, and preferably all, of nucleic acid sequences a)-d) of the nucleic acid molecule, and further optionally wherein the nucleic acid molecule inactivates the endogenous gene, for example, a gene that encodes a oxidoreductase or a polypeptide that participates in carbohydrate, starch, or polyhydroxyalkanoate synthesis.

Embodiment 13

A recombinant host cell according to embodiment 11 or 12, wherein the recombinant host cell is a prokaryote, a photosynthetic microorganism, or a *cyanobacterium*, or an *Agmenellum, Anabaena, Anabaenopsis, Anacystis, Aphanizomenon, Arthrospira, Asterocapsa, Borzia, Calothrix, Chamaesiphon, Chlorogloeopsis, Chroococcidiopsis, Chroococcus, Crinalium, Cyanobacterium, Cyanobium, Cyanocystis, Cyanospira, Cyanothece, Cylindrospermopsis, Cylindrospermum, Dactylococcopsis, Dermocarpella, Fischerella, Fremyella, Geitleria, Geitlerinema, Gloeobacter, Gloeocapsa, Gloeothece, Halospirulina, Iyengariella, Leptolyngbya, Limnothrix, Lyngbya, Microcoleus, Microcystis, Myxosarcina, Nodularia, Nostoc, Nostochopsis, Oscillatoria, Phormidium, Planktothrix, Pleurocapsa, Prochlorococcus, Prochloron, Prochlorothrix, Pseudanabaena, Rivularia, Schizothrix, Scytonema, Spirulina, Stanieria, Starria,*

*Stigonema, Symploca, Synechococcus, Synechocystis, Thermosynechococcus, Tolypothrix, Trichodesmium, Tychonema*, or *Xenococcus* species.

Embodiment 14

A recombinant host cell according to embodiment 13, wherein any of the following are satisfied: the transcriptional unit is operably linked to the 5' region of an oxidoreductase gene, a dehydrogenase gene, a glycogen synthase gene, a glucose-1-phosphate adenylyltransferase gene, a glycogen branching enzyme gene; the transcriptional unit is operably linked to a promoter endogenous to the recombinant host cell; the recombinant host cell is a species of *Synechocystis* or *Synechococcus* (optionally wherein any or any combination of the following are satisfied: the recombinant host cell is *Synechocystis* sp. PCC 6803, the nucleic acid molecule is integrated at the RS1 site; the transcriptional unit is operably linked to the 5' region of the slr0338 (NCBI protein accession number BAA10046; gi:1001423) gene, the transcriptional unit is operably linked to the promoter of the slr0338 gene).

Embodiment 15

A recombinant host cell according to any of embodiments 11-14, wherein any of the following are satisfied: the recombinant host cell produces an increased level of wax ester relative to a control host cell lacking one or more of the nucleic acid sequences a)-d); the recombinant host cell produces an increased level of wax ester relative to a control host cell lacking (d) a nucleic acid sequence encoding a wax ester synthase; the recombinant host cell produces at least 1, 2, 3, 4, 5, 6, 7, 8, 9, or 10 mg/L of wax ester over a period of 1, 2, 3, 4, 5, 6, 7, 8, 9, 10, 11, 12, 13, or 14 days; the one or more wax esters comprise at least one wax ester molecule having an A chain derived from a fatty alcohol and a B chain derived from acyl-CoA, wherein both the A chain and the B chain have chain lengths of C8-C24, or chain lengths of C12-C18; and wherein at least a portion of the produced wax ester is secreted by the host cell.

Embodiment 16

The recombinant host cell according to any of embodiments 11-15, wherein any of the following are satisfied: acyl-ACP production is upregulated in the recombinant host cell; the recombinant host cell expresses or produces at least one exogenous polypeptide; the recombinant host cell overexpresses or overproduces at least one endogenous polypeptide, optionally selected from the group consisting of a beta-ketoacyl synthetase, an acetyl-CoA carboxylase, a malonyl CoA: ACP transacylase, an acyl-ACP synthetase, ribulose 1,5-bisphosphate carboxylase, a phycobiliprotein, acyl carrier protein, and a transmembrane transporter.

Embodiment 17

A method for producing one or more wax esters, comprising the steps of: a) culturing a recombinant host cell according to any of embodiments 13-19 in a suitable culture medium; and b) allowing expression of the nucleic acid sequences encoding the thioesterase (e.g., an acyl-ACP thioesterase), the acyl-CoA synthetase, the alcohol-forming fatty acyl reductase (e.g., an alcohol-forming acyl-CoA reductase), and the wax ester synthase, wherein the expression of the nucleic acid sequences results in the production of one or more wax esters; optionally wherein the suitable culture medium does not comprise a substantial amount of a reduced carbon source and/or does not include an alcohol or a fatty acid.

Embodiment 18

The method according to embodiment 17, wherein one or any combination of the following is satisfied: the recombinant host cell produces an increased level of wax ester relative to a control host cell lacking one or more of the nucleic acid sequences; the recombinant host cell produces an increased level of wax ester relative to a control host cell lacking (d) a nucleic acid sequence encoding a wax ester synthase; the recombinant host cell produces at least 1, 2, 3, 4, 5, 6, 7, 8, 9, or 10 mg/L of wax ester over a period of 1, 2, 3, 4, 5, 6, 7, 8, 9, 10, 11, 12, 13, or 14 days; the recombinant host cell produces at least 1-5 mg/L of wax ester over a period of 7 days; wherein the one or more wax esters comprise at least one wax ester molecule having an A chain derived from a fatty alcohol and a B chain derived from acyl-CoA, wherein both the A chain and the B chain have chain lengths of C8-C24; wherein the one or more wax esters comprise at least one wax ester molecule having an A chain derived from a fatty alcohol and a B chain derived from acyl-CoA, wherein both the A chain and the B chain have chain lengths of C12-C18; wherein at least a portion of the produced wax ester is secreted by the host cell.

Embodiment 19

The method according to embodiment 17 or 18, wherein any of the following are satisfied: acyl-ACP production is upregulated in the recombinant host cell; the recombinant host cell expresses or produces at least one exogenous polypeptide, or overexpresses or overproduces at least one endogenous polypeptide, selected from a beta-ketoacyl synthetase, an acetyl-CoA carboxylase, a malonyl CoA:ACP transacylase, an acyl-ACP synthetase, ribulose 1,5-bisphosphate carboxylase, a phycobiliprotein, acyl carrier protein, and a transmembrane transporter.

Embodiment 20

The method according to any of embodiments 17-19, further comprising the step of isolating the produced wax ester.

Embodiment 21

A composition comprising the wax ester isolated according to the method of embodiment 22, optionally wherein at least 70%, at least 80%, at least 85%, at least 90%, or at least 95% of the wax esters have both A chain and the B chain lengths of C8-C24 or both A chain and the B chain lengths of C12-C18; optionally wherein the composition comprises at least one detectable nucleic acid molecule derived from the recombinant host microorganism; optionally wherein the composition comprises at least a detectable amount of a nucleic acid molecule or vector of any of claims 1-10.

Embodiment 24

A system for producing one or more wax esters, comprising a recombinant host cell according to any of embodiments 11-16 cultured in a medium that does not include a reduced carbon source, and wherein the recombinant host cell is exposed to light for at least a portion of the production period, optionally further comprising a non-reduced carbon source, which is preferably $CO_2$ and/or carbonate.

EXAMPLES

Example 1

Synthesis of Wax Ester Pathway Operons

To engineer *Synechocystis* for the production of wax esters, the following genes were chemically synthesized by DNA 2.0 in cloning vectors: the *Cuphea carthagenensis* Cc1FatB1 thioesterase gene, codon-optimized for expression in *Synechocystis* (SEQ ID NO: 31); the *Saccharomyces cerevisiae* acyl-CoA synthetase Faa2p gene (SEQ ID NO: 40), the *Marinobacter aquaeolei* 0168 WS gene ("Maqu_0168"; SEQ ID NO: 55), the *Marinobacter* sp. ELB17 MELB17 WS gene ("MELB17_04692"; SEQ ID NO: 54), the *Marinobacter* sp. ELB17 MELB17 WS gene codon-optimized for expression in *Synechocystis* (SEQ ID NO: 53), and the petunia wax synthase gene (SEQ ID NO: 59).

The genes were then used to create constructs in which the *Cuphea carthagenensis* Cc1FatB1 thioesterase gene (SEQ ID NO: 31), the *Saccharomyces* Faa2p acyl-CoA synthetase gene (SEQ ID NO: 40), and the Maqu_2220 alcohol forming acyl reductase gene (SEQ ID NO: 45) were arranged in tandem along with a wax synthase gene, which was either the petunia wax synthase (WS) gene (SEQ ID NO: 59), *Marinobacter aquaeolei* Maqu_0168 gene (SEQ ID NO: 55), the *Marinobacter* sp. ELB17 MELB17 WS gene (SEQ ID NO: 54), or the *Marinobacter* sp. ELB17 MELB17 WS gene codon-optimized for expression in *Synechocystis* (SEQ ID NO: 53). As controls, constructs were made with only the Cc1FatB1 acyl-ACP thioesterase gene (SEQ ID NO: 31) (single gene construct); with the Cc1FatB1 acyl-ACP thioesterase gene (SEQ ID NO: 31) and the Faa2p acyl-CoA synthetase gene (SEQ ID NO: 40) (two gene operon construct); and with the Cc1FatB1 acyl-ACP thioesterase gene (SEQ ID NO: 31), the Faa2p acyl-CoA synthetase gene (SEQ ID NO: 40), and the Maqu 2220 alcohol-forming reductase gene (SEQ ID NO: 45) (three gene operon construct). The genes were amplified using high temperature polymerases (PCR) with compatible ends to create the constructs of Table 1.

The four gene operon constructs were engineered such that the "rbs" ribosome binding site derived from the TrcE promoter (SEQ ID NO: 68) preceded each of the genes of the operon.

Figure 9:
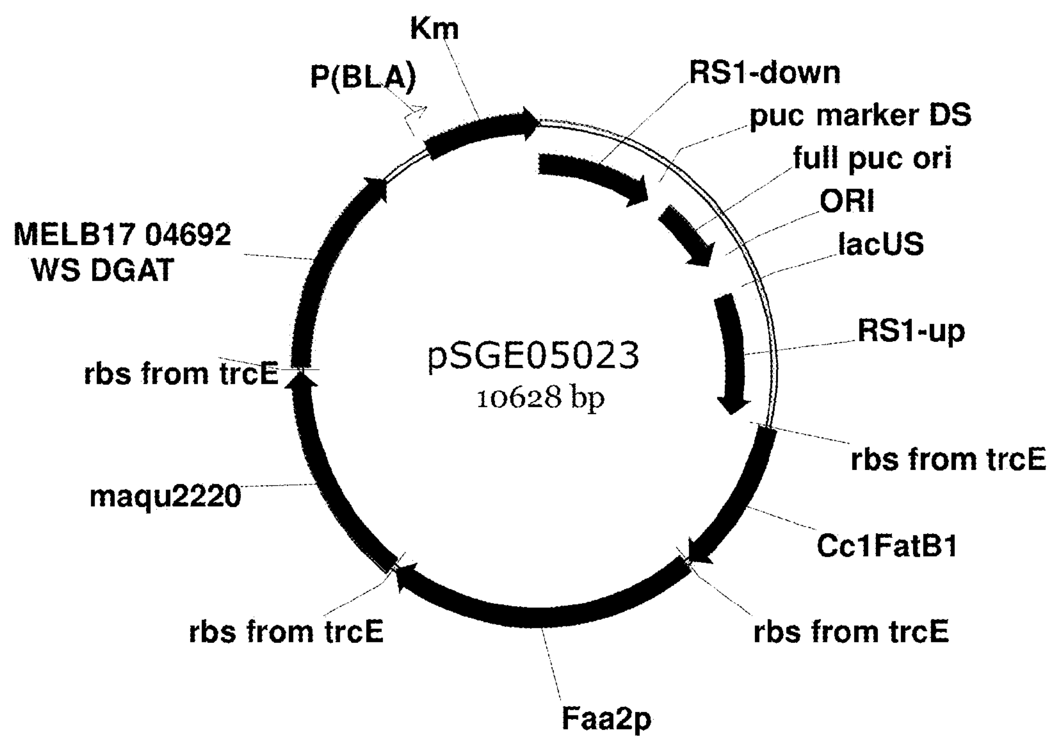
FIG. 9 shows a plasmid map (pSGE05023; SEQ ID NO: 72) of an integration vector that includes four wax ester synthesis pathway genes in the order: cc1FatB1, Faa2p, Maqu_2220, and MELB17 WS. The vector does not contain an isolated promoter sequence cloned 5' of these genes. RS1-down and RS1-up refer to integration sites on the chromosome of *Synechocystis* sp. PCC 6803.
Figure 10:
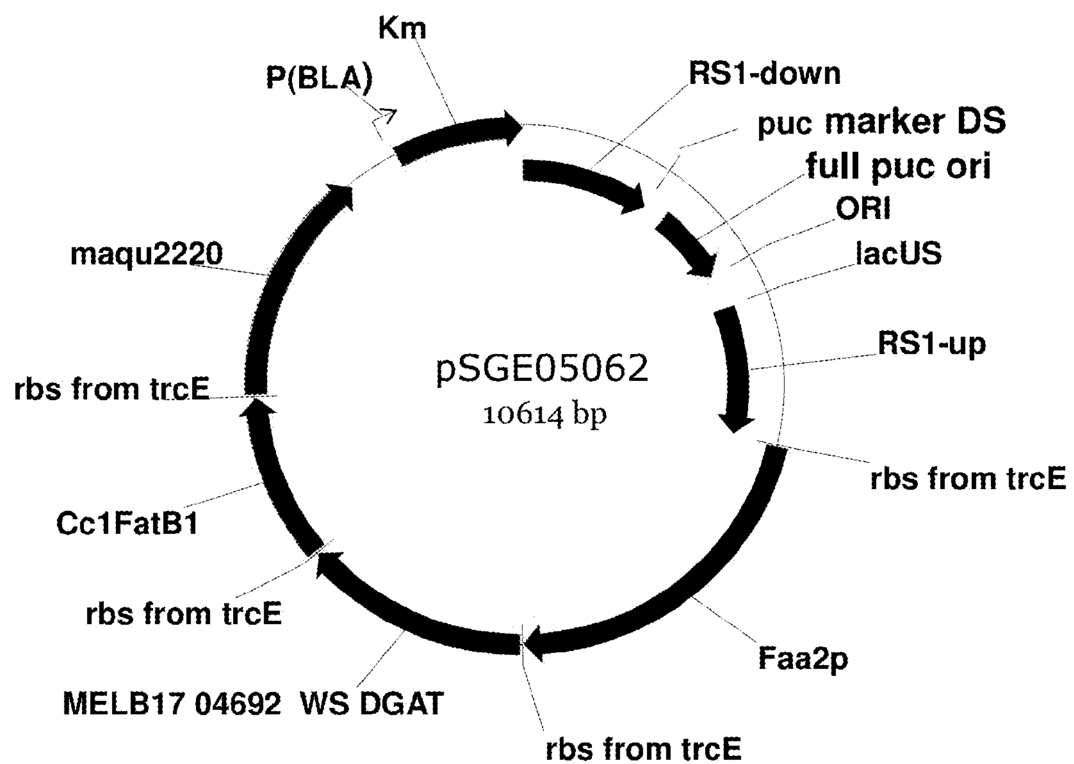
FIG. 10 shows a plasmid map (pSGE05062; SEQ ID NO: 73) of an integration vector that includes four wax ester synthesis pathway genes in the order: Faa2p, MELB17 WS, cc1FatB1, and Maqu_2220. The vector does not contain an isolated promoter sequence cloned 5' to these genes. RS1-down and RS1-up refer to integration sites on the chromosome of *Synechocystis* sp. PCC 6803.

The genes were cloned without the addition of a promoter in a cloning vector that included "RS1" sites for recombination into the *Synechocystis* genome (see FIGS. 7-10) to create constructs 5020, 5021, 5022, 5059, 5060, 5084, 5023, and 5062 (see Table 1). The genes were cloned between the "RS1-up" (SEQ ID NO: 63) and "RS1-down" (SEQ ID NO: 64) *Synechocystis* genomic DNA sequences of the vector. The RS1 landing region of the *Synechocystis* genome, spanning sequences 2298515 to 2300500 (genome sequence Accession number AP012205.1; GI:339272262) and used for homologous recombination, includes the slr0338 gene of the oxidoreductase family (NAD-binding Rossman fold; NCBI protein accession number BAA10046; gi:1001423) and is proximal to slr0168 (hypothetical open reading frame; NCBI protein accession number BAA10047; gi:1001424). The "RS1-up" sequence includes approximately 830 nucleotides of the 5' region of the slr0338, that is, sequence upstream of the coding region of the slr0338 gene, as well as approximately 158 nucleotides of the 5' end of the slr0338 gene. Cloning of a gene downstream of this sequence (as depicted in FIGS. 9 and 10 for constructs 5023 (SEQ ID NO: 72) and 5062 (SEQ ID NO: 73)) may allow gene expression sequences from the "RS1-up" genomic sequence to mediate transcription of the transgenes.

Figure 7:
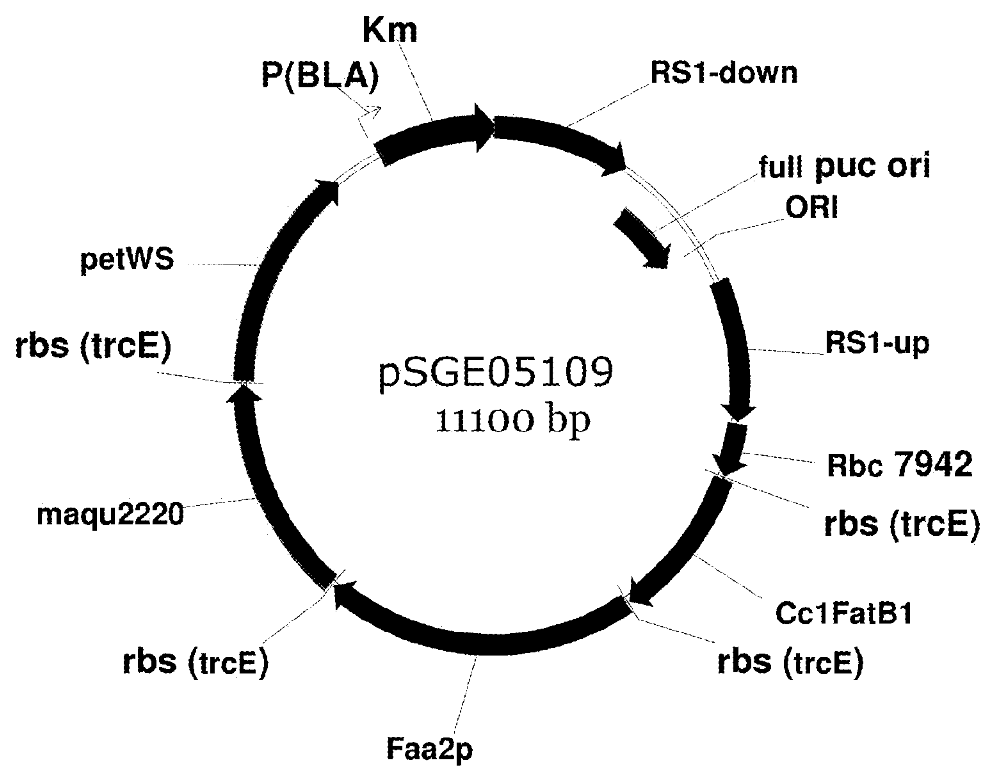
FIG. 7 shows a plasmid map (pSGE05109; SEQ ID NO: 70) of an integration vector that includes four wax ester synthesis pathway genes in the order: cc1FatB1, Faa2p, Maqu_2220, and petunia WS, operably linked to a Prbc promoter. RS1-down and RS1-up refer to integration sites on the chromosome of *Synechocystis* sp. PCC 6803.
Figure 8:
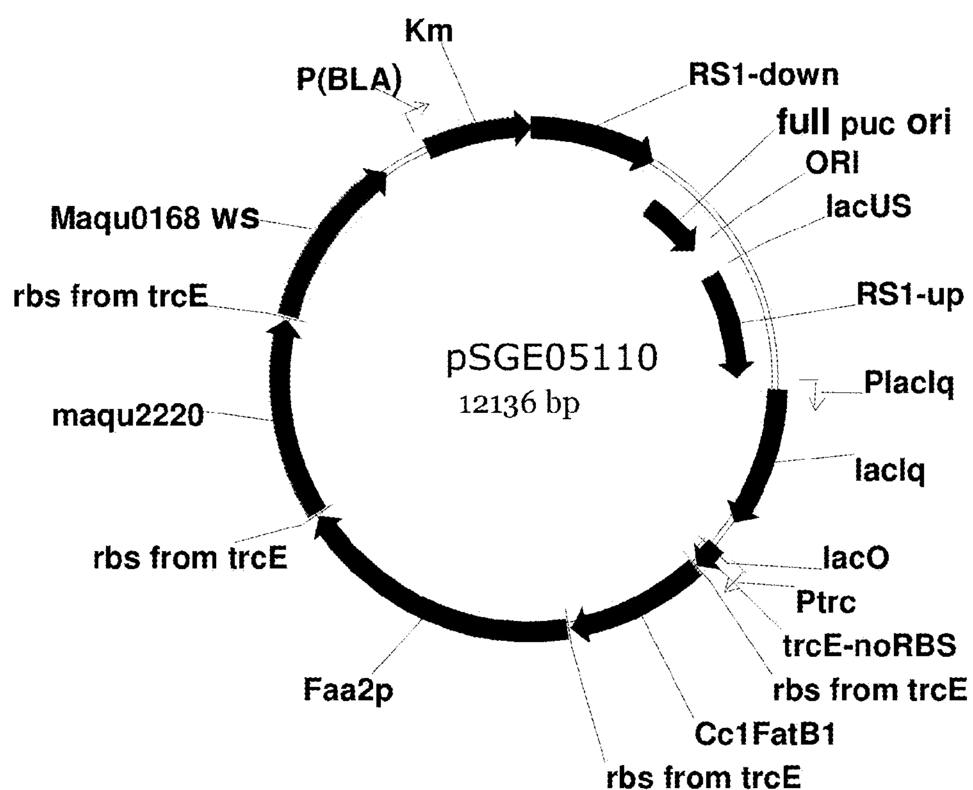
FIG. 8 shows a plasmid map (pSGE05110; SEQ ID NO: 71) of an integration vector that includes four wax ester synthesis pathway genes in the order: cc1FatB1, Faa2p, Maqu_2220, and Maqu0168 WS1, operably linked to a TrcE promoter. RS1-down and RS1-up refer to integration sites on the chromosome of *Synechocystis* sp. PCC 6803.

Additionally, constructs were made in which the TrcE promoter (SEQ ID NO: 67) or the Prbc (large subunit ribulose bisphosphate carboxylase) promoter of *Synechococcus elongatus* (SEQ ID NO: 69) were cloned 5' of the first gene of the operon (see, for example, FIG. 7 depicting the 5109 construct (SEQ ID NO: 70) and FIG. 8 depicting the 5110 construct (SEQ ID NO: 71)).

TABLE 1

Constructs for Wax Ester Synthesis

| Construct | Promoter | Genes, in operon order |
|---|---|---|
| 5020 | (RS1) | cc1FatB1 |
| 5021 | (RS1) | cc1FatB1 - Faa2p |
| 5022 | (RS1) | cc1FatB1 - Faa2p - Maqu2220 |
| 5059 | (RS1) | cc1FatB1 - Faa2p - Maqu2220 - petuniaWS |
| 5108 | trcE/lacIQmut | cc1FatB1 - Faa2p - Maqu2220 - petuniaWS |
| 5109 (SEQ ID NO: 70) | Prbc/sc7942 | cc1FatB1 - Faa2p - Maqu2220 - petuniaWS |
| 5060 | (RS1) | cc1FatB1 - Faa2p - Maqu2220 - Maqu0168WS |
| 5110 (SEQ ID NO: 71) | trcE/lacIQmut | cc1FatB1 - Faa2p - Maqu2220 - Maqu0168WS |
| 5114 | Prbc/sc7942 | cc1FatB1 - Faa2p - Maqu2220 - Maqu0168WS |
| 5084 | (RS1) | cc1FatB1 - Faa2p - Maqu2220 - Melb17WS |
| 5023 (SEQ ID NO: 72) | (RS1) | cc1FatB1 - Faa2p - Maqu2220 - Melb17WSopt |
| 5062 (SEQ ID NO: 73) | (RS1) | Faa2p - Melb17WSopt - cc1FatB1 - Maqu2220 |
| 5064 | Prbc/sc7942 | cc1FatB1 - Faa2p - Maqu2220 - Melb17WSopt |
| 5065 | trcE - no lacIQ | cc1FatB1 - Faa2p - Maqu2220 - Melb17WSopt |
| 5066 | trcE/lacIQ | cc1FatB1 - Faa2p - Maqu2220 - Melb17WSopt |

To introduce the one, two, three, and four gene operon constructs into cyanobacteria, *Synechocystis* sp. PCC 6803 cells were cultured in BG-11 media to an OD (730 nm) of about 0.7-0.9. About 10 mL of the culture was spun down at approximately 2000 g for 15 minutes, then the cell pellet was resuspended in 1 mL fresh BG-11 media. An aliquot of 300 μL of cells was transformed with about 100 ng of integration vector. The cells were incubated under lights (80 μE) for about 6 hours, then spread onto Minipore filters and placed on top of BG-11 agar plates containing no antibiotics. The plates were incubated at about 30° C. under about 80 μE of light for about 24 hours. The filters were then transferred onto fresh BG-11 1.5% agar plates with 20 μg/mL kanamycin and cultured for 7 days. Colonies of *Synechocystis* sp. PCC 6803 were picked and patched onto new agar plates.

TABLE 2

ATCC 616 Medium BG-11 for Cyanobacteria

| | |
|---|---|
| $NaNO_3$ | 1.5 g |
| $K_2HPO_4$ | 0.04 g |
| $MgSO_4 * 7H_2O$ | 0.075 g |
| $CaCl_2 * 2H_2O$ | 0.036 g |
| Citric acid | 6.0 mg |
| Ferric ammonium citrate | 6.0 mg |
| EDTA | 1.0 mg |

TABLE 2-continued

| ATCC 616 Medium BG-11 for Cyanobacteria | | |
|---|---|---|
| $Na_2CO_3$ | | 0.02 g |
| Trace Metal Mix A5# | | 1.0 ml |
| Agar (if needed) | | (up to) 10.0 g |
| Distilled water | | 1.0 L |
| Trace Metal Mix A5 | $H_3BO_3$ | 2.86 g |
| | $MnCl_2 * 4H_2O$ | 1.81 g |
| | $ZnSO_4 * 7H_2O$ | 0.22 g |
| | $Na_2MoO_4 * 2H_2O$ | 0.39 g |
| | $CuSO_4 * 5H_2O$ | 0.080 g |
| | $Co(NO_3)_2 * 6H_2O$ | 49.4 mg |
| | Distilled water | to 1.0 L |

Example 2

Lipid Production by *Synechocystis* sp. PCC 6803 Strains Expressing Wax Synthesis Pathway Genes Cultures of *Synechocystis* sp. PCC 6803 transformed with the constructs of Table 1 were grown for testing free fatty acid, fatty alcohol, and wax ester production. Three different colony patches for each clone were inoculated into 20 mL glass scintillation vials containing 10 mL of BG-11 liquid media with 50 μg/ml kanamycin. BG-11 medium, which does not include a substantial amount of a reduced carbon source, supports photoautotrophic growth of *Synechocystis*. Cultures were covered with filter floss tape. The scintillation vials were incubated at about 30° C. with about 5% ambient $CO_2$ and continuously shaken at about 200 rpm under about 70 μE of light for 7 days. 5 mL of each culture was then spun down at approximately 5000 rpm and resuspended in 0.4 mL of water, then extracted by a hexane/sulfuric acid solvent system to extract neutral lipids.

Approximately 0.5 mL of glass beads were added to the resuspended cells, along with 50 μl of 50% $H_2SO4$ and 100 μl of 5M NaCl. The cells were subjected to bead beating for 5 min at 1000 rpm, after which 2 mL of hexane were added. The vials were then capped, placed in white ACME racks, and bead-beaten again for 5 min at 1000 rpm. The samples were then shaken on a multi-tube vortexer for 30 min at 1000 rpm, followed by 30 sec at 2500 rpm. The samples were then centrifuged for 4 min at 2000 rpm. Approximately 0.5 ml of the upper hexane layer was transferred to an HPLC vial. Fifty microliters of an internal standards stock was then added to the hexane extract to a final concentration of 100 μg per ml. The internal standards were oleoyl oleate, oleic acid, cholesterol, 1,2-diolein, 1-monolein, 1-octadeconal, and n-eicosane. The vials were capped and vortexed prior to analysis.

For analysis of fatty acids and wax esters, an Agilent 1200 series HPLC equipped with a binary pump and an ES Industries Chormegasphere SI-60 150 mm×4.6 mm, 10 μm pore column was used with the following solvent system: [eluent A: hexanes; eluent B: hexanes/isopropanol/ethyl acetate/10% formic acid in isopropanol in a 80:10:10:1 ratio]. A 20 μL injection was used, the flow rate was set to 2 mL/min, the column compartment set to 40° C., and the solvent gradient started at 98% eluent A, 2% eluent B and ramped up to 2% eluent A, 98% eluent B over an 11 minute run. ELSD was set at 30° C., 3.5 bar N2, and a gain of 5 was used. Analytes were quantified via an 8-point calibration curve from 1.5-100 μg/mL.

Example 3

Gas Chromatography of *Synechocystis* sp. PCC 6803 Expressing Wax Synthesis Operons The same samples were analyzed by gas chromatography for fatty alcohols. For this analysis, 0.5 mL of the hexanes (upper) layer of the extract were transferred to a 2.0 mL GC vial and 50 μL of internal standard (1 mg/mL 1-pentadecanol in $CH_2Cl_2$) were added for a final concentration of internal standard of 100 μg/mL. The vials were then vortexed and analyzed by GC/MS-SCAN/SIM. The GC run conditions were as follows: 1.4 mL/min $H_2$ with an oven temperature of 100° C. for 0.5 min, then ramped at 20° C./min to 270° C. and held for 1 min. The solvent delay was set at 4.3 min. A 1 μL injection was made on an inlet set at 280° C. utilizing a 3:1 split and containing a deactivated single gooseneck liner w/glass wool. The GC column was an Agilent HP-5MS, 30 m×0.25 mm×0.25 μm. The mass spectrometer scan range was set for m/z of 35-275, the SIM ions monitored were 55.0 and 41.0, and a 10 ms dwell time was used. Analytes were quantified via a 5-point calibration curve from 2-200 μg/mL.

As shown in Table 3, expression of all the operons with four gene combinations (acyl-ACP thioesterase, acyl-CoA synthetase, alcohol-forming reductase, and wax synthase) resulted in the production of fatty alcohol and wax esters. The wax ester productivity was not noticeably affected by the specific wax synthase gene. Petunia WS (SEQ ID NO: 55), *M. aquaeolei* Maqu_0168 WS (SEQ ID NO: 55), and the M. species ELB17 WS (SEQ ID NO: 54), and codon-optimized M. species ELB 17 WS (SEQ ID NO: 53) all demonstrated comparable productivity when expressed as part of a *Synechocystis* operon. By contrast, expression of the one, two, and three gene operons (all of which lacked a wax synthase gene) did not produce wax esters (rows 1-3 of Table 3). The particular promoter used to direct expression of the four gene operon (RS1 endogenous promoter, TrcE, or Prbc) also did not affect the amount of wax ester produced, although the stronger promoters (e.g., TrcE, Prbc) did result in a higher level of fatty alcohol, a wax ester precursor, possibly indicating that the activity of the wax synthase gene was limiting. Changing the gene order within the operon did not noticeably improve wax ester production (see plasmid, for example Table 3, construct 5062).

TABLE 3

Production of lipids by *Synechocystis* strains containing wax ester synthesis operons

| Construct | Promoter | genes, in operon order | FFA mg/L | FOH mg/L | WE mg/L |
|---|---|---|---|---|---|
| 5020 | RS1 | cc1FatB1 | — | — | — |
| 5021 | RS1 | cc1FatB1-Faa2p | — | — | — |
| 5022 | RS1 | cc1FatB1-Faa2p-Maqu2220 | — | — | — |
| 5059 | RS1 | cc1FatB1-Faa2p-Maqu2220-petuniawtWS | — | 5-10 | 1-5 |
| 5108 | trcE/lacIQmut | cc1FatB1-Faa2p-Maqu2220-petuniawtWS | — | 10-15 | 1-5 |
| 5109 | Prbc/sc7942 | cc1FatB1-Faa2p-Maqu2220-petuniawtWS | 1-5 | 10-15 | 1-5 |
| 5060 | RS1 | cc1FatB1-Faa2p-Maqu2220-Maqu0168WS | — | 5-10 | 1-5 |
| 5110 | trcE/lacIQmut | cc1FatB1-Faa2p-Maqu2220-Maqu0168WS | — | 15-20 | 1-5 |
| 5114 | Prbc/sc7942 | cc1FatB1-Faa2p-Maqu2220-Maqu0168WS | — | 10-15 | 1-5 |
| 5084 | RS1 | cc1FatB1-Faa2p-Maqu2220-Melb17WSwt | — | 5-10 | 1-5 |

TABLE 3-continued

Production of lipids by *Synechocystis* strains containing wax ester synthesis operons

| Construct | Promoter | genes, in operon order | FFA mg/L | FOH mg/L | WE mg/L |
|---|---|---|---|---|---|
| 5023 | RS1 | cc1FatB1-Faa2p-MAqu2220-Melb17WS | — | — | — |
| 5062 | RS1 | Faa2p-Melb17WS-cc1FatB1-Maqu2220 | — | 1-5 | 1-5 |
| 5064 | Prbc/sc7942 | cc1FatB1-Faa2p-MAqu2220-Melb17WS | — | 10-15 | 1-5 |
| 5065 | trcE-nolacIQ | cc1FatB1-Faa2p-MAqu2220-Melb17WS | — | 10-15 | 1-5 |
| 5066 | trcE/lacIQ | cc1FatB1-Faa2p-MAqu2220-Melb17WS | — | 5-10 | 1-5 |

What is claimed is:

1. A nucleic acid molecule comprising:

a) a nucleic acid sequence encoding a thioesterase belonging to Pfam PF01643 or PF02551;

b) a nucleic acid sequence encoding an acyl-CoA synthetase;

c) a nucleic acid sequence encoding an alcohol-forming fatty acyl-CoA reductase selected from the group consisting of amino acid sequences having at least 85% sequence identity to any one of SEQ ID NOs:15-21; and d) a nucleic acid sequence encoding a wax ester synthase belonging to Pfam PF03007 or PF13813 selected from the group consisting of amino acid sequences having at least 85% sequence identity to any one of SEQ ID NOs: 22-30;

wherein the thioesterase belonging to Pfam PF01643 or PF02551 is capable of releasing a free fatty acid from an acyl-ACP substrate; and wherein the nucleic acid sequence encoding a wax ester synthase belonging to Pfam PF03007 or PF13813 and at least one of the nucleic acid sequence encoding a thioesterase belonging to Pfam PF01643 or PF02551, the nucleic acid sequence encoding an acyl-CoA synthetase, and the nucleic acid sequence encoding an alcohol-forming fatty acyl reductase are configured as a transcriptional unit; and further wherein the nucleic acid molecule comprises at least one additional nucleic acid sequence of at least 50 nucleotides for mediating recombination of the transcriptional unit into a host genome, wherein the additional nucleic acid sequence of at least 50 nucleotides is derived from a 5' region of a gene from a photosynthetic microorganism, and further wherein the additional nucleic acid sequence of at least 50 nucleotides comprises a promoter positioned upstream of the transcriptional unit in the nucleic acid molecule, wherein the promoter and the transcriptional unit are configured as an operon.

2. The nucleic acid molecule according to claim 1, wherein the nucleic acid sequence encoding a wax ester synthase belonging to Pfam PF03007 or PF13813, the nucleic acid sequence encoding a thioesterase belonging to Pfam PF01643 or PF02551, the nucleic acid sequence encoding an acyl-CoA synthetase, and the nucleic acid sequence encoding an alcohol-forming fatty acyl-CoA reductase are configured as a transcriptional unit.

3. The nucleic acid molecule according to claim 1, wherein the at least one additional nucleic acid sequence comprises at least 100 nucleotides.

4. The nucleic acid molecule according to claim 1, wherein the nucleic acid sequence of a) encodes an acyl-ACP thioesterase having at least 85% sequence identity to any one of SEQ ID NOs: 1-9; and wherein the nucleic acid sequence of b) encodes an acyl-CoA synthetase having at least 85% sequence identity to any one of SEQ ID NOs:10-14.

5. The nucleic acid molecule according to claim 4, wherein a) encodes SEQ ID NO:1, b) encodes SEQ ID NO:10, c) encodes SEQ ID NO:15, and d) encodes SEQ ID NO:22.

6. The nucleic acid molecule according to claim 2, wherein the nucleic acid sequences a)-d) each comprise an initiation codon.

7. The nucleic acid molecule according to claim 2, wherein the at least one additional nucleic acid sequence of at least 50 nucleotides comprises a genomic sequence that, in the photosynthetic microorganism, is positioned immediately upstream of the coding region of a gene, and wherein the at least one additional nucleic acid sequence of at least 50 nucleotides is positioned immediately upstream of sequences a)-d) of the nucleic acid molecule.

8. A vector comprising the nucleic acid molecule according to claim 2.

9. The vector according to claim 8, wherein the vector includes at least one selectable marker.

10. A recombinant photosynthetic microorganism that comprises a nucleic acid molecule according to claim 1, integrated into a genomic site of the recombinant photosynthetic microorganism, wherein the recombinant photosynthetic microorganism produces a wax ester.

11. The recombinant photosynthetic microorganism according to claim 10, wherein integration of the nucleic acid molecule into the genomic site inactivates an endogenous gene.

12. The recombinant photosynthetic microorganism according to claim 10, wherein the recombinant photosynthetic microorganism is a *cyanobacterium.*

13. The recombinant photosynthetic microorganism according to claim 12, wherein the *cyanobacterium* is of an *Agmenellum, Anabaena, Anabaenopsis, Anacystis, Aphanizomenon, Arthrospira, Asterocapsa, Borzia, Calothrix, Chamaesiphon, Chlorogloeopsis, Chroococcidiopsis, Chroococcus, Crinalium, Cyanobacterium, Cyanobium, Cyanocystis, Cyanospira, Cyanothece, Cylindrospermopsis, Cylindrospermum, Dactylococcopsis, Dermocarpella, Fischerella, Fremyella, Geitleria, Geitlerinema, Gloeobacter, Gloeocapsa, Gloeothece, Halospirulina, Iyengariella, Leptolyngbya, Limnothrix, Lyngbya, Microcoleus, Microcystis, Myxosarcina, Nodularia, Nostoc, Nostochopsis, Oscillatoria, Phormidium, Planktothrix, Pleurocapsa, Prochlorococcus, Prochloron, Prochlorothrix, Pseudanabaena, Rivularia, Schizothrix, Scytonema, Spirulina, Stanieria, Starria, Stigonema, Symploca, Synechococcus, Synechocystis, Thermosynechococcus, Tolypothrix, Trichodesmium, Tychonema*, or *Xenococcus* species.

14. The recombinant photosynthetic microorganism according to claim 11, wherein the endogenous gene encodes an oxidoreductase, a dehydrogenase, a glycogen synthase, or a glucose-1-phosphate adenyltransferase.

15. The recombinant photosynthetic microorganism according to claim 10, wherein the alcohol-forming fatty acyl-CoA reductase is a prokaryotic alcohol-forming fatty acyl-CoA reductase.

16. The recombinant photosynthetic microorganism according to claim 10, wherein the wax ester synthase belonging to Pfam PF03007 or PF13813 is a prokaryotic wax ester synthase.

17. The recombinant photosynthetic microorganism according to claim 10, wherein the thioesterase belonging to Pfam PF01643 or PF02551 is an acyl-ACP thioesterase, an acyl-CoA thioesterase, or a hydroxybenzoyl thioesterase.

18. The recombinant photosynthetic microorganism according to claim 17, wherein the thioesterase belonging to Pfam PF01643 or PF02551 is an acyl-ACP thioesterase.

19. The nucleic acid molecule according to claim 6, wherein one or more of nucleic acid sequences a)-d) comprise a heterologous translational regulatory sequence upstream of the initiation codon.

20. The nucleic acid molecule according to claim 1, wherein the additional nucleic acid sequence of at least 50 nucleotides has at least 200 nucleotides.

21. The nucleic acid molecule according to claim 20, wherein the additional nucleic acid sequence of at least 50 nucleotides has at least 400 nucleotides.

22. The nucleic acid molecule according to claim 5, wherein the nucleic acid sequences respectively comprise the nucleotide sequences of SEQ ID NOs: 31, 40, 45, and 53.

23. The nucleic acid molecule according to claim 1, wherein the nucleic acid sequence of c) has at least 90% sequence identity to any one of SEQ ID NOs:15-21; and wherein the nucleic acid sequence of d) has at least 90% sequence identity to any one of SEQ ID NOs:22-30.

24. The nucleic acid molecule according to claim 4, wherein the nucleic acid sequence of a) has at least 90% sequence identity to any one of SEQ ID NOs:1-9; and wherein the nucleic acid sequence of b) has at least 90% sequence identity to any one of SEQ ID NOs:10-14.

25. A method for producing one or more wax esters, comprising the steps of:

a) culturing a recombinant photosynthetic microorganism according to claim 10 in a suitable culture medium; and b) allowing expression of the non-native nucleic acid sequences a)-d), wherein expression of the non-native nucleic acid sequences results in the production of one or more wax esters.

26. The method according to claim 25, wherein the culture medium does not comprise an alcohol or a fatty acid.

27. The method according to claim 25, wherein the culture medium does not comprise a substantial amount of a reduced carbon source.

28. The method according to claim 25, wherein the recombinant photosynthetic microorganism produces an increased amount of a wax ester relative to a control host cell lacking the non-native nucleic acid sequences.

29. The method according to claim 25, wherein the one or more wax esters comprise at least one wax ester molecule having an A chain derived from a fatty alcohol and a B chain derived from acyl-CoA, wherein both the A chain and the B chain have chain lengths of C12-C18.

30. The method according to claim 25, further comprising the step of isolating a wax ester from the cells, the culture medium, or both.

31. The method according to claim 25, wherein integration of the nucleic acid molecule into the genomic site of the recombinant photosynthetic microorganism inactivates an endogenous gene.

32. The method according to claim 31, wherein the endogenous gene encodes an oxidoreductase, a dehydrogenase, a glycogen synthase, or a glucose-1-phosphate adenyltransferase.

33. The method according to claim 25, wherein the nucleic acid sequence encoding a wax ester synthase belonging to Pfam PF03007 or PF13813, the nucleic acid sequence encoding a thioesterase belonging to Pfam PF01643 or PF02551, the nucleic acid sequence encoding an acyl-CoA synthetase, and the nucleic acid sequence encoding an alcohol-forming fatty acyl reductase are configured as a transcriptional unit.

* * * * *

SEQUENCE LISTING

```
<160> NUMBER OF SEQ ID NOS: 73

<210> SEQ ID NO 1
<211> LENGTH: 361
<212> TYPE: PRT
<213> ORGANISM: Artificial Sequence
<220> FEATURE:
<223> OTHER INFORMATION: Amino acid sequence of Cc1FatB1 construct for
      expression in Synechocystis

<400> SEQUENCE: 1

Met Ala Asn Gly Ser Ala Val Ser Leu Lys Ser Gly Ser Leu Asn Thr
1               5                   10                  15

Gln Glu Asp Thr Ser Ser Ser Pro Pro Pro Arg Ala Phe Ile Asn Gln
            20                  25                  30

Leu Pro Asp Trp Ser Met Leu Leu Thr Ala Ile Thr Thr Val Phe Val
        35                  40                  45

Ala Ala Glu Lys Gln Trp Thr Met Leu Asp Arg Lys Ser Lys Arg Ser
    50                  55                  60

Asp Met Leu Val Asp Ser Phe Gly Met Glu Arg Ile Val Gln Asp Gly
65                  70                  75                  80

Leu Val Phe Arg Gln Ser Phe Ser Ile Arg Ser Tyr Glu Ile Gly Ala
                85                  90                  95

Asp Arg Arg Ala Ser Ile Glu Thr Leu Met Asn His Leu Gln Glu Thr
            100                 105                 110

Ser Leu Asn His Cys Lys Ser Ile Arg Leu Leu Asn Glu Gly Phe Gly
        115                 120                 125

Arg Thr Pro Glu Met Cys Lys Arg Asp Leu Ile Trp Val Val Thr Arg
    130                 135                 140

Met His Ile Met Val Asn Arg Tyr Pro Thr Trp Gly Asp Thr Val Glu
145                 150                 155                 160

Ile Asn Thr Trp Val Ser Gln Ser Gly Lys Asn Gly Met Gly Arg Asp
                165                 170                 175

Trp Leu Ile Ser Asp Cys Asn Thr Gly Glu Ile Leu Ile Arg Ala Thr
            180                 185                 190

Ser Ala Trp Ala Met Met Asn Gln Lys Thr Arg Arg Leu Ser Lys Leu
        195                 200                 205

Pro Tyr Glu Val Ser Gln Glu Ile Ala Pro His Phe Val Asp Ser Pro
    210                 215                 220

Pro Val Ile Glu Asp Gly Asp Arg Lys Leu His Lys Phe Asp Val Lys
225                 230                 235                 240

Thr Gly Asp Ser Ile Arg Lys Gly Leu Thr Pro Arg Trp Asn Asp Leu
                245                 250                 255
```

```
Asp Val Asn Gln His Val Asn Asn Val Lys Tyr Ile Gly Trp Ile Leu
            260                 265                 270

Glu Ser Met Pro Thr Glu Val Leu Glu Thr His Glu Leu Cys Phe Leu
        275                 280                 285

Thr Leu Glu Tyr Arg Arg Glu Cys Gly Arg Asp Ser Val Leu Glu Ser
    290                 295                 300

Val Thr Ala Met Asp Pro Ser Asn Glu Gly Gly Arg Ser His Tyr Gln
305                 310                 315                 320

His Leu Leu Arg Leu Glu Asp Gly Thr Asp Ile Val Lys Gly Arg Thr
                325                 330                 335

Glu Trp Arg Pro Lys Asn Ala Arg Asn Ile Gly Ala Ile Ser Thr Gly
            340                 345                 350

Lys Thr Ser Asn Gly Asn Pro Ala Ser
        355                 360


<210> SEQ ID NO 2
<211> LENGTH: 413
<212> TYPE: PRT
<213> ORGANISM: Cuphea carthagenensis

<400> SEQUENCE: 2

Ala Ala Ser Ser Ala Phe Phe Pro Val Thr Thr Pro Gly Thr Ser Arg
1               5                   10                  15

Lys Pro Gly Lys Phe Gly Asn Trp Leu Ser Ser Leu Ser Pro Pro Phe
            20                  25                  30

Arg Pro Lys Ser Ile Pro Ser Gly Gly Phe Gln Val Lys Ala Asn Ala
        35                  40                  45

Ser Ala His Pro Lys Ala Asn Gly Ser Ala Val Ser Leu Lys Ser Gly
    50                  55                  60

Ser Leu Asn Thr Gln Glu Asp Thr Ser Ser Ser Pro Pro Pro Arg Ala
65                  70                  75                  80

Phe Ile Asn Gln Leu Pro Asp Trp Ser Met Leu Leu Thr Ala Ile Thr
                85                  90                  95

Thr Val Phe Val Ala Ala Glu Lys Gln Trp Thr Met Leu Asp Arg Lys
            100                 105                 110

Ser Lys Arg Ser Asp Met Leu Val Asp Ser Phe Gly Met Glu Arg Ile
        115                 120                 125

Val Gln Asp Gly Leu Val Phe Arg Gln Ser Phe Ser Ile Arg Ser Tyr
    130                 135                 140

Glu Ile Gly Ala Asp Arg Arg Ala Ser Ile Glu Thr Leu Met Asn His
145                 150                 155                 160

Leu Gln Glu Thr Ser Leu Asn His Cys Lys Ser Ile Arg Leu Leu Asn
                165                 170                 175

Glu Gly Phe Gly Arg Thr Pro Glu Met Cys Lys Arg Asp Leu Ile Trp
            180                 185                 190

Val Val Thr Arg Met His Ile Met Val Asn Arg Tyr Pro Thr Trp Gly
        195                 200                 205

Asp Thr Val Glu Ile Asn Thr Trp Val Ser Gln Ser Gly Lys Asn Gly
    210                 215                 220

Met Gly Arg Asp Trp Leu Ile Ser Asp Cys Asn Thr Gly Glu Ile Leu
225                 230                 235                 240

Ile Arg Ala Thr Ser Ala Trp Ala Met Met Asn Gln Lys Thr Arg Arg
                245                 250                 255

Leu Ser Lys Leu Pro Tyr Glu Val Ser Gln Glu Ile Ala Pro His Phe
```

260 265 270

Val Asp Ser Pro Pro Val Ile Glu Asp Gly Asp Arg Lys Leu His Lys
275 280 285

Phe Asp Val Lys Thr Gly Asp Ser Ile Arg Lys Gly Leu Thr Pro Arg
290 295 300

Trp Asn Asp Leu Asp Val Asn Gln His Val Asn Asn Val Lys Tyr Ile
305 310 315 320

Gly Trp Ile Leu Glu Ser Met Pro Thr Glu Val Leu Glu Thr His Glu
325 330 335

Leu Cys Phe Leu Thr Leu Glu Tyr Arg Arg Glu Cys Gly Arg Asp Ser
340 345 350

Val Leu Glu Ser Val Thr Ala Met Asp Pro Ser Asn Glu Gly Gly Arg
355 360 365

Ser His Tyr Gln His Leu Leu Arg Leu Glu Asp Gly Thr Asp Ile Val
370 375 380

Lys Gly Arg Thr Glu Trp Arg Pro Lys Asn Ala Arg Asn Ile Gly Ala
385 390 395 400

Ile Ser Thr Gly Lys Thr Ser Asn Gly Asn Pro Ala Ser
405 410

<210> SEQ ID NO 3
<211> LENGTH: 362
<212> TYPE: PRT
<213> ORGANISM: Artificial Sequence
<220> FEATURE:
<223> OTHER INFORMATION: Amino acid sequence of Cd1FatB1 construct for expression in Synechocystis

<400> SEQUENCE: 3

Met Gly Ile Asn Gly Ser Ser Val Gly Leu Lys Ser Gly Ser Leu Lys
1 5 10 15

Thr Gln Glu Asp Thr Pro Ser Ser Pro Pro Pro Arg Thr Phe Ile Asn
20 25 30

Gln Leu Pro Asp Trp Ser Met Leu Leu Ala Ala Ile Thr Thr Val Phe
35 40 45

Leu Ala Ala Glu Lys Gln Trp Met Met Leu Asp Trp Lys Pro Lys Arg
50 55 60

Pro Asp Met Leu Val Asp Pro Phe Gly Leu Gly Arg Ile Val Gln Asp
65 70 75 80

Gly Leu Val Phe Arg Gln Asn Phe Ser Ile Arg Ser Tyr Glu Ile Gly
85 90 95

Ala Asp Arg Thr Ala Ser Ile Glu Thr Leu Met Asn His Leu Gln Glu
100 105 110

Thr Ala Leu Asn His Val Lys Ser Ala Gly Leu Leu Asn Asp Gly Phe
115 120 125

Gly Arg Thr Pro Glu Met Tyr Lys Arg Asp Leu Ile Trp Val Val Ala
130 135 140

Lys Met Gln Val Met Val Asn Arg Tyr Pro Thr Trp Gly Asp Thr Val
145 150 155 160

Glu Val Asn Thr Trp Val Ala Lys Ser Gly Lys Asn Gly Met Arg Arg
165 170 175

Asp Trp Leu Ile Ser Asp Cys Asn Thr Gly Glu Ile Leu Thr Arg Ala
180 185 190

Ser Ser Val Trp Val Met Met Asn Gln Lys Thr Arg Arg Leu Ser Lys
195 200 205

Ile Pro Asp Glu Val Arg His Glu Ile Glu Pro His Phe Val Asp Ser
210 215 220

Pro Pro Val Ile Glu Asp Asp Asp Arg Lys Leu Pro Lys Leu Asp Glu
225 230 235 240

Lys Thr Ala Asp Ser Ile Arg Lys Gly Leu Thr Pro Arg Trp Asn Asp
245 250 255

Leu Asp Val Asn Gln His Val Asn Asn Val Lys Tyr Ile Gly Trp Ile
260 265 270

Leu Glu Ser Thr Pro Gln Glu Val Leu Glu Thr Gln Glu Leu Cys Ser
275 280 285

Leu Thr Leu Glu Tyr Arg Arg Glu Cys Gly Arg Asp Ser Val Leu Glu
290 295 300

Ser Leu Thr Ala Val Asp His Ser Gly Lys Gly Ser Gly Ser Asn Phe
305 310 315 320

Gln His Leu Leu Arg Leu Glu Asp Gly Gly Glu Ile Val Lys Gly Arg
325 330 335

Thr Glu Trp Arg Pro Lys Asn Ala Val Ile Asn Gly Ala Val Ala Pro
340 345 350

Gly Glu Thr Ser Pro Gly Asn Ser Val Ser
355 360

<210> SEQ ID NO 4
<211> LENGTH: 412
<212> TYPE: PRT
<213> ORGANISM: Cuphea decandra

<400> SEQUENCE: 4

Ala Ala Ser Ser Ala Cys Phe Pro Val Pro Ser Pro Asp Ala Ser Arg
1 5 10 15

Lys Pro Gly Lys His Gly Asn Gly Ala Ser Ser Leu Ser Pro Phe Lys
20 25 30

Pro Lys Ser Ile Pro Ser Gly Gly Leu Gln Val Gln Ala Asn Ala Ser
35 40 45

Ala Pro Pro Lys Ile Asn Gly Ser Ser Val Gly Leu Lys Ser Gly Ser
50 55 60

Leu Lys Thr Gln Glu Asp Thr Pro Ser Ser Pro Pro Pro Arg Thr Phe
65 70 75 80

Ile Asn Gln Leu Pro Asp Trp Ser Met Leu Leu Ala Ala Ile Thr Thr
85 90 95

Val Phe Leu Ala Ala Glu Lys Gln Trp Met Met Leu Asp Trp Lys Pro
100 105 110

Lys Arg Pro Asp Met Leu Val Asp Pro Phe Gly Leu Gly Arg Ile Val
115 120 125

Gln Asp Gly Leu Val Phe Arg Gln Asn Phe Ser Ile Arg Ser Tyr Glu
130 135 140

Ile Gly Ala Asp Arg Thr Ala Ser Ile Glu Thr Leu Met Asn His Leu
145 150 155 160

Gln Glu Thr Ala Leu Asn His Val Lys Ser Ala Gly Leu Leu Asn Asp
165 170 175

Gly Phe Gly Arg Thr Pro Glu Met Tyr Lys Arg Asp Leu Ile Trp Val
180 185 190

Val Ala Lys Met Gln Val Met Val Asn Arg Tyr Pro Thr Trp Gly Asp
195 200 205

Thr Val Glu Val Asn Thr Trp Val Ala Lys Ser Gly Lys Asn Gly Met
210 215 220

```
Arg Arg Asp Trp Leu Ile Ser Asp Cys Asn Thr Gly Glu Ile Leu Thr
225                 230                 235                 240

Arg Ala Ser Ser Val Trp Val Met Met Asn Gln Lys Thr Arg Arg Leu
                245                 250                 255

Ser Lys Ile Pro Asp Glu Val Arg His Glu Ile Glu Pro His Phe Val
            260                 265                 270

Asp Ser Pro Pro Val Ile Glu Asp Asp Asp Arg Lys Leu Pro Lys Leu
        275                 280                 285

Asp Glu Lys Thr Ala Asp Ser Ile Arg Lys Gly Leu Thr Pro Arg Trp
    290                 295                 300

Asn Asp Leu Asp Val Asn Gln His Val Asn Asn Val Lys Tyr Ile Gly
305                 310                 315                 320

Trp Ile Leu Glu Ser Thr Pro Gln Glu Val Leu Glu Thr Gln Glu Leu
                325                 330                 335

Cys Ser Leu Thr Leu Glu Tyr Arg Arg Glu Cys Gly Arg Asp Ser Val
            340                 345                 350

Leu Glu Ser Leu Thr Ala Val Asp His Ser Gly Lys Gly Ser Gly Ser
        355                 360                 365

Asn Phe Gln His Leu Leu Arg Leu Glu Asp Gly Gly Glu Ile Val Lys
    370                 375                 380

Gly Arg Thr Glu Trp Arg Pro Lys Asn Ala Val Ile Asn Gly Ala Val
385                 390                 395                 400

Ala Pro Gly Glu Thr Ser Pro Gly Asn Ser Val Ser
                405                 410


<210> SEQ ID NO 5
<211> LENGTH: 356
<212> TYPE: PRT
<213> ORGANISM: Artificial Sequence
<220> FEATURE:
<223> OTHER INFORMATION: Amino acid sequence of Cp1FatB1 construct for
      expression in Synechocystis

<400> SEQUENCE: 5

Met Ala Asn Gly Ser Ala Val Ser Leu Lys Asp Gly Ser Leu Glu Thr
1               5                   10                  15

Gln Glu Gly Thr Ser Ser Ser Ser His Pro Pro Arg Thr Phe Ile Asn
            20                  25                  30

Gln Leu Pro Asp Trp Ser Met Leu Leu Ser Ala Ile Thr Thr Val Phe
        35                  40                  45

Val Ala Ala Glu Lys Gln Trp Thr Met Leu Asp Arg Lys Ser Lys Arg
    50                  55                  60

Pro Asp Met Leu Val Glu Pro Phe Val Gln Asp Gly Val Ser Phe Arg
65                  70                  75                  80

Gln Ser Phe Ser Ile Arg Ser Tyr Glu Ile Gly Ala Asp Arg Thr Ala
                85                  90                  95

Ser Ile Glu Thr Leu Met Asn Ile Phe Gln Glu Thr Ser Leu Asn His
            100                 105                 110

Cys Lys Ser Leu Gly Leu Leu Asn Asp Gly Phe Gly Arg Thr Pro Glu
        115                 120                 125

Met Cys Lys Arg Asp Leu Ile Trp Val Val Thr Lys Met Gln Ile Glu
    130                 135                 140

Val Asn Arg Tyr Pro Thr Trp Gly Asp Thr Ile Glu Val Thr Thr Trp
145                 150                 155                 160

Val Ser Glu Ser Gly Lys Asn Gly Met Ser Arg Asp Trp Leu Ile Ser
```

```
                165                 170                 175

Asp Cys His Thr Gly Glu Ile Leu Ile Arg Ala Thr Ser Val Trp Ala
            180                 185                 190

Met Met Asn Gln Lys Thr Arg Arg Leu Ser Lys Ile Pro Asp Glu Val
        195                 200                 205

Arg Gln Glu Ile Val Pro Tyr Phe Val Asp Ser Ala Pro Val Ile Glu
    210                 215                 220

Asp Asp Arg Lys Leu His Lys Leu Asp Val Lys Thr Gly Asp Ser Ile
225                 230                 235                 240

Arg Asn Gly Leu Thr Pro Arg Trp Asn Asp Leu Asp Val Asn Gln His
                245                 250                 255

Val Asn Asn Val Lys Tyr Ile Gly Trp Ile Leu Lys Ser Val Pro Thr
            260                 265                 270

Glu Val Phe Val Thr Gln Glu Leu Cys Gly Leu Thr Leu Glu Tyr Arg
        275                 280                 285

Arg Glu Cys Arg Arg Asp Ser Val Leu Glu Ser Val Thr Ala Met Asp
    290                 295                 300

Pro Ser Lys Glu Gly Asp Arg Ser Leu Tyr Gln His Leu Leu Arg Leu
305                 310                 315                 320

Glu Asn Gly Ala Asp Ile Ala Leu Gly Arg Thr Glu Trp Arg Pro Lys
                325                 330                 335

Asn Ala Gly Thr Asn Gly Ala Ile Ser Thr Thr Lys Thr Ser Pro Gly
            340                 345                 350

Asn Ser Val Ser
        355


<210> SEQ ID NO 6
<211> LENGTH: 389
<212> TYPE: PRT
<213> ORGANISM: Cuphea paucipetala

<400> SEQUENCE: 6

Ala Ala Ser Ser Ala Phe Phe Ser Phe Pro Ala Pro Gly Thr Ser Leu
1               5                   10                  15

Lys Pro Gly Lys Phe Gly Asn Trp Pro Ser Asn Leu Ser Val Pro Phe
            20                  25                  30

Asn Pro Lys Ala Asn His Asn Gly Gly Phe His Val Lys Ala Asn Thr
        35                  40                  45

Ser Ala His Pro Lys Ala Asn Gly Ser Ala Val Ser Leu Lys Asp Gly
    50                  55                  60

Ser Leu Glu Thr Gln Glu Gly Thr Ser Ser Ser Ser His Pro Pro Arg
65                  70                  75                  80

Thr Phe Ile Asn Gln Leu Pro Asp Trp Ser Met Leu Leu Ser Ala Ile
                85                  90                  95

Thr Thr Val Phe Val Ala Ala Glu Lys Gln Trp Thr Met Leu Asp Arg
            100                 105                 110

Lys Ser Lys Arg Pro Asp Met Leu Val Glu Pro Phe Val Gln Asp Gly
        115                 120                 125

Val Ser Phe Arg Gln Ser Phe Ser Ile Arg Ser Tyr Glu Ile Gly Ala
    130                 135                 140

Asp Arg Thr Ala Ser Ile Glu Thr Leu Met Asn Ile Phe Gln Glu Thr
145                 150                 155                 160

Ser Leu Asn His Cys Lys Ser Leu Gly Leu Leu Asn Asp Gly Phe Gly
                165                 170                 175
```

```
Arg Thr Pro Glu Met Cys Lys Arg Asp Leu Ile Trp Val Val Thr Lys
            180                 185                 190

Met Gln Ile Glu Val Asn Arg Tyr Pro Thr Trp Gly Asp Thr Ile Glu
        195                 200                 205

Val Thr Thr Trp Val Ser Glu Ser Gly Lys Asn Gly Met Ser Arg Asp
    210                 215                 220

Trp Leu Ile Ser Asp Cys His Thr Gly Glu Ile Leu Ile Arg Ala Thr
225                 230                 235                 240

Ser Val Trp Ala Met Met Asn Gln Lys Thr Arg Arg Leu Ser Lys Ile
                245                 250                 255

Pro Asp Glu Val Arg Gln Glu Ile Val Pro Tyr Phe Val Asp Ser Ala
            260                 265                 270

Pro Val Ile Glu Asp Asp Arg Lys Leu His Lys Leu Asp Val Lys Thr
        275                 280                 285

Gly Asp Ser Ile Arg Asn Gly Leu Thr Pro Arg Trp Asn Asp Leu Asp
    290                 295                 300

Val Asn Gln His Val Asn Asn Val Lys Tyr Ile Gly Trp Ile Leu Lys
305                 310                 315                 320

Ser Val Pro Thr Glu Val Phe Val Thr Gln Glu Leu Cys Gly Leu Thr
                325                 330                 335

Leu Glu Tyr Arg Arg Glu Cys Arg Arg Asp Ser Val Leu Glu Ser Val
            340                 345                 350

Thr Ala Met Asp Pro Ser Lys Glu Gly Asp Arg Ser Leu Tyr Gln His
        355                 360                 365

Leu Leu Arg Leu Glu Asn Gly Ala Asp Ile Ala Leu Gly Arg Thr Glu
    370                 375                 380

Trp Arg Pro Lys Thr
385
```

<210> SEQ ID NO 7
<211> LENGTH: 417
<212> TYPE: PRT
<213> ORGANISM: Elaeis guineensis

<400> SEQUENCE: 7

```
Met Val Ala Ser Ile Val Ala Trp Ala Phe Phe Pro Thr Pro Ser Phe
1               5                   10                  15

Ser Pro Thr Ala Ser Ala Lys Ala Ser Lys Thr Ile Gly Glu Gly Ser
            20                  25                  30

Glu Asn Leu Asn Val Arg Gly Ile Ile Ala Lys Pro Thr Ser Ser Ser
        35                  40                  45

Ala Ala Lys Gln Gly Lys Val Met Ala Gln Ala Val Pro Lys Ile Asn
    50                  55                  60

Gly Ala Lys Val Gly Leu Lys Ala Glu Ser Gln Lys Ala Glu Glu Asp
65                  70                  75                  80

Ala Ala Pro Ser Ser Ala Pro Arg Thr Phe Tyr Asn Gln Leu Pro Asp
                85                  90                  95

Trp Ser Val Leu Leu Ala Ala Val Thr Thr Ile Phe Leu Ala Ala Glu
            100                 105                 110

Lys Gln Trp Thr Leu Leu Asp Trp Lys Pro Arg Arg Pro Asp Met Leu
        115                 120                 125

Thr Gly Ala Phe Ser Leu Gly Lys Ile Val Gln Asp Gly Leu Val Phe
    130                 135                 140

Arg Gln Asn Phe Ser Ile Arg Ser Tyr Glu Ile Gly Ala Asp Arg Thr
145                 150                 155                 160
```

```
Ala Ser Ile Glu Thr Leu Met Asn His Leu Gln Glu Thr Ala Leu Asn
                165                 170                 175

His Val Arg Asn Ala Gly Leu Leu Gly Asp Gly Phe Gly Ala Thr Pro
            180                 185                 190

Glu Met Ser Lys Arg Asn Leu Ile Trp Val Val Thr Lys Met Gln Val
        195                 200                 205

Leu Ile Glu His Tyr Pro Ser Trp Gly Asp Val Val Glu Val Asp Thr
    210                 215                 220

Trp Val Gly Ala Ser Gly Lys Asn Gly Met Arg Arg Asp Trp His Val
225                 230                 235                 240

Arg Asp Tyr Arg Thr Gly Gln Thr Ile Leu Arg Ala Thr Ser Ile Trp
                245                 250                 255

Val Met Met Asp Lys His Thr Arg Lys Leu Ser Lys Met Pro Glu Glu
            260                 265                 270

Val Arg Ala Glu Ile Gly Pro Tyr Phe Met Glu His Ala Ala Ile Val
        275                 280                 285

Asp Glu Asp Ser Arg Lys Leu Pro Lys Leu Asp Asp Asp Thr Ala Asp
    290                 295                 300

Tyr Ile Lys Trp Gly Leu Thr Pro Arg Trp Ser Asp Leu Asp Val Asn
305                 310                 315                 320

Gln His Val Asn Asn Val Lys Tyr Ile Gly Trp Ile Leu Glu Ser Ala
                325                 330                 335

Pro Ile Ser Ile Leu Glu Asn His Glu Leu Ala Ser Met Thr Leu Glu
            340                 345                 350

Tyr Arg Arg Glu Cys Gly Arg Asp Ser Val Leu Gln Ser Leu Thr Ala
        355                 360                 365

Val Ala Asn Asp Cys Thr Gly Gly Leu Pro Glu Ala Ser Ile Glu Cys
    370                 375                 380

Gln His Leu Leu Gln Leu Glu Cys Gly Ala Glu Ile Val Arg Gly Arg
385                 390                 395                 400

Thr Gln Trp Arg Pro Arg Arg Ala Ser Gly Pro Thr Ser Ala Gly Ser
                405                 410                 415

Ala


<210> SEQ ID NO 8
<211> LENGTH: 324
<212> TYPE: PRT
<213> ORGANISM: Elaeis guineensis

<400> SEQUENCE: 8

Leu Pro Asp Trp Ser Val Leu Leu Ala Ala Val Thr Thr Ile Phe Leu
1               5                   10                  15

Ala Ala Glu Lys Gln Trp Thr Leu Leu Asp Trp Lys Pro Arg Arg Pro
            20                  25                  30

Asp Met Leu Thr Gly Ala Phe Ser Leu Gly Lys Ile Val Gln Asp Gly
        35                  40                  45

Leu Val Phe Arg Gln Asn Phe Ser Ile Arg Ser Tyr Glu Ile Gly Ala
    50                  55                  60

Asp Arg Thr Ala Ser Ile Glu Thr Leu Met Asn His Leu Gln Glu Thr
65                  70                  75                  80

Ala Leu Asn His Val Arg Asn Ala Gly Leu Leu Gly Asp Gly Phe Gly
                85                  90                  95

Ala Thr Pro Glu Met Ser Lys Arg Asn Leu Ile Trp Val Val Thr Lys
            100                 105                 110
```

```
Met Gln Val Leu Ile Glu His Tyr Pro Ser Trp Gly Asp Val Val Glu
        115                 120                 125

Val Asp Thr Trp Val Gly Ala Ser Gly Lys Asn Gly Met Arg Arg Asp
    130                 135                 140

Trp His Val Arg Asp Tyr Arg Thr Gly Gln Thr Ile Leu Arg Ala Thr
145                 150                 155                 160

Ser Ile Trp Val Met Met Asp Lys His Thr Arg Lys Leu Ser Lys Met
                165                 170                 175

Pro Glu Glu Val Arg Ala Glu Ile Gly Pro Tyr Phe Met Glu His Ala
            180                 185                 190

Ala Ile Val Asp Glu Asp Ser Arg Lys Leu Pro Lys Leu Asp Asp Asp
        195                 200                 205

Thr Ala Asp Tyr Ile Lys Trp Gly Leu Thr Pro Arg Trp Ser Asp Leu
    210                 215                 220

Asp Val Asn Gln His Val Asn Asn Val Lys Tyr Ile Gly Trp Ile Leu
225                 230                 235                 240

Glu Ser Ala Pro Ile Ser Ile Leu Glu Asn His Glu Leu Ala Ser Met
                245                 250                 255

Thr Leu Glu Tyr Arg Arg Glu Cys Gly Arg Asp Ser Val Leu Gln Ser
            260                 265                 270

Leu Thr Ala Val Ala Asn Asp Cys Thr Gly Gly Leu Pro Glu Ala Ser
        275                 280                 285

Ile Glu Cys Gln His Leu Leu Gln Leu Glu Cys Gly Ala Glu Ile Val
    290                 295                 300

Arg Gly Arg Thr Gln Trp Arg Pro Arg Arg Ala Ser Gly Pro Thr Ser
305                 310                 315                 320

Ala Gly Ser Ala


<210> SEQ ID NO 9
<211> LENGTH: 299
<212> TYPE: PRT
<213> ORGANISM: Elaeis guineensis

<400> SEQUENCE: 9

Asp Trp Lys Pro Arg Arg Pro Asp Met Leu Thr Gly Ala Phe Ser Leu
1               5                   10                  15

Gly Lys Ile Val Gln Asp Gly Leu Val Phe Arg Gln Asn Phe Ser Ile
            20                  25                  30

Arg Ser Tyr Glu Ile Gly Ala Asp Arg Thr Ala Ser Ile Glu Thr Leu
        35                  40                  45

Met Asn His Leu Gln Glu Thr Ala Leu Asn His Val Arg Asn Ala Gly
    50                  55                  60

Leu Leu Gly Asp Gly Phe Gly Ala Thr Pro Glu Met Ser Lys Arg Asn
65                  70                  75                  80

Leu Ile Trp Val Val Thr Lys Met Gln Val Leu Ile Glu His Tyr Pro
                85                  90                  95

Ser Trp Gly Asp Val Val Glu Val Asp Thr Trp Val Gly Ala Ser Gly
            100                 105                 110

Lys Asn Gly Met Arg Arg Asp Trp His Val Arg Asp Tyr Arg Thr Gly
        115                 120                 125

Gln Thr Ile Leu Arg Ala Thr Ser Ile Trp Val Met Met Asp Lys His
    130                 135                 140

Thr Arg Lys Leu Ser Lys Met Pro Glu Glu Val Arg Ala Glu Ile Gly
145                 150                 155                 160
```

```
Pro Tyr Phe Met Glu His Ala Ala Ile Val Asp Glu Asp Ser Arg Lys
                165                 170                 175

Leu Pro Lys Leu Asp Asp Asp Thr Ala Asp Tyr Ile Lys Trp Gly Leu
            180                 185                 190

Thr Pro Arg Trp Ser Asp Leu Asp Val Asn Gln His Val Asn Asn Val
        195                 200                 205

Lys Tyr Ile Gly Trp Ile Leu Glu Ser Ala Pro Ile Ser Ile Leu Glu
    210                 215                 220

Asn His Glu Leu Ala Ser Met Thr Leu Glu Tyr Arg Arg Glu Cys Gly
225                 230                 235                 240

Arg Asp Ser Val Leu Gln Ser Leu Thr Ala Val Ala Asn Asp Cys Thr
                245                 250                 255

Gly Gly Leu Pro Glu Ala Ser Ile Glu Cys Gln His Leu Leu Gln Leu
            260                 265                 270

Glu Cys Gly Ala Glu Ile Val Arg Gly Arg Thr Gln Trp Arg Pro Arg
        275                 280                 285

Arg Ala Ser Gly Pro Thr Ser Ala Gly Ser Ala
    290                 295


<210> SEQ ID NO 10
<211> LENGTH: 744
<212> TYPE: PRT
<213> ORGANISM: Saccharomyces cerevisiae

<400> SEQUENCE: 10

Met Ala Ala Pro Asp Tyr Ala Leu Thr Asp Leu Ile Glu Ser Asp Pro
1               5                   10                  15

Arg Phe Glu Ser Leu Lys Thr Arg Leu Ala Gly Tyr Thr Lys Gly Ser
            20                  25                  30

Asp Glu Tyr Ile Glu Glu Leu Tyr Ser Gln Leu Pro Leu Thr Ser Tyr
        35                  40                  45

Pro Arg Tyr Lys Thr Phe Leu Lys Lys Gln Ala Val Ala Ile Ser Asn
    50                  55                  60

Pro Asp Asn Glu Ala Gly Phe Ser Ser Ile Tyr Arg Ser Ser Leu Ser
65                  70                  75                  80

Ser Glu Asn Leu Val Ser Cys Val Asp Lys Asn Leu Arg Thr Ala Tyr
                85                  90                  95

Asp His Phe Met Phe Ser Ala Arg Arg Trp Pro Gln Arg Asp Cys Leu
            100                 105                 110

Gly Ser Arg Pro Ile Asp Lys Ala Thr Gly Thr Trp Glu Glu Thr Phe
        115                 120                 125

Arg Phe Glu Ser Tyr Ser Thr Val Ser Lys Arg Cys His Asn Ile Gly
    130                 135                 140

Ser Gly Ile Leu Ser Leu Val Asn Thr Lys Arg Lys Arg Pro Leu Glu
145                 150                 155                 160

Ala Asn Asp Phe Val Val Ala Ile Leu Ser His Asn Asn Pro Glu Trp
                165                 170                 175

Ile Leu Thr Asp Leu Ala Cys Gln Ala Tyr Ser Leu Thr Asn Thr Ala
            180                 185                 190

Leu Tyr Glu Thr Leu Gly Pro Asn Thr Ser Glu Tyr Ile Leu Asn Leu
        195                 200                 205

Thr Glu Ala Pro Ile Leu Ile Phe Ala Lys Ser Asn Met Tyr His Val
    210                 215                 220

Leu Lys Met Val Pro Asp Met Lys Phe Val Asn Thr Leu Val Cys Met
```

-continued

```
225                 230                 235                 240

Asp Glu Leu Thr His Asp Glu Leu Arg Met Leu Asn Glu Ser Leu Leu
                245                 250                 255

Pro Val Lys Cys Asn Ser Leu Asn Glu Lys Ile Thr Phe Phe Ser Leu
            260                 265                 270

Glu Gln Val Glu Gln Val Gly Cys Phe Asn Lys Ile Pro Ala Ile Pro
        275                 280                 285

Pro Thr Pro Asp Ser Leu Tyr Thr Ile Ser Phe Thr Ser Gly Thr Thr
    290                 295                 300

Gly Leu Pro Lys Gly Val Glu Met Ser His Arg Asn Ile Ala Ser Gly
305                 310                 315                 320

Ile Ala Phe Ala Phe Ser Thr Phe Arg Ile Pro Pro Asp Lys Arg Asn
                325                 330                 335

Gln Gln Leu Tyr Asp Met Cys Phe Leu Pro Leu Ala His Ile Phe Glu
            340                 345                 350

Arg Met Val Ile Ala Tyr Asp Leu Ala Ile Gly Phe Gly Ile Gly Phe
        355                 360                 365

Leu His Lys Pro Asp Pro Thr Val Leu Val Glu Asp Leu Lys Ile Leu
    370                 375                 380

Lys Pro Tyr Ala Val Ala Leu Val Pro Arg Ile Leu Thr Arg Phe Glu
385                 390                 395                 400

Ala Gly Ile Lys Asn Ala Leu Asp Lys Ser Thr Val Gln Arg Asn Val
                405                 410                 415

Ala Asn Thr Ile Leu Asp Ser Lys Ser Ala Arg Phe Thr Ala Arg Gly
            420                 425                 430

Gly Pro Asp Lys Ser Ile Met Asn Phe Leu Val Tyr His Arg Val Leu
        435                 440                 445

Ile Asp Lys Ile Arg Asp Ser Leu Gly Leu Ser Asn Asn Ser Phe Ile
    450                 455                 460

Ile Thr Gly Ser Ala Pro Ile Ser Lys Asp Thr Leu Leu Phe Leu Arg
465                 470                 475                 480

Ser Ala Leu Asp Ile Gly Ile Arg Gln Gly Tyr Gly Leu Thr Glu Thr
                485                 490                 495

Phe Ala Gly Val Cys Leu Ser Glu Pro Phe Glu Lys Asp Val Gly Ser
            500                 505                 510

Cys Gly Ala Ile Gly Ile Ser Ala Glu Cys Arg Leu Lys Ser Val Pro
        515                 520                 525

Glu Met Gly Tyr His Ala Asp Lys Asp Leu Lys Gly Glu Leu Gln Ile
    530                 535                 540

Arg Gly Pro Gln Val Phe Glu Arg Tyr Phe Lys Asn Pro Asn Glu Thr
545                 550                 555                 560

Ser Lys Ala Val Asp Gln Asp Gly Trp Phe Ser Thr Gly Asp Val Ala
                565                 570                 575

Phe Ile Asp Gly Lys Gly Arg Ile Ser Val Ile Asp Arg Val Lys Asn
            580                 585                 590

Phe Phe Lys Leu Ala His Gly Glu Tyr Ile Ala Pro Glu Lys Ile Glu
        595                 600                 605

Asn Ile Tyr Leu Ser Ser Cys Pro Tyr Ile Thr Gln Ile Phe Val Phe
    610                 615                 620

Gly Asp Pro Leu Lys Thr Phe Leu Val Gly Ile Val Gly Val Asp Val
625                 630                 635                 640

Asp Ala Ala Gln Pro Ile Leu Ala Ala Lys His Pro Glu Val Lys Thr
                645                 650                 655
```

```
Trp Thr Lys Glu Val Leu Val Glu Asn Leu Asn Arg Asn Lys Lys Leu
            660                 665                 670

Arg Lys Glu Phe Leu Asn Lys Ile Asn Lys Cys Thr Asp Gly Leu Gln
        675                 680                 685

Gly Phe Glu Lys Leu His Asn Ile Lys Val Gly Leu Glu Pro Leu Thr
    690                 695                 700

Leu Glu Asp Asp Val Val Thr Pro Thr Phe Lys Ile Lys Arg Ala Lys
705                 710                 715                 720

Ala Ser Lys Phe Phe Lys Asp Thr Leu Asp Gln Leu Tyr Ala Glu Gly
                725                 730                 735

Ser Leu Val Lys Thr Glu Lys Leu
            740


<210> SEQ ID NO 11
<211> LENGTH: 744
<212> TYPE: PRT
<213> ORGANISM: Saccharomyces cerevisiae

<400> SEQUENCE: 11

Met Ala Ala Pro Asp Tyr Ala Leu Thr Asp Leu Ile Glu Ser Asp Pro
1               5                   10                  15

Arg Phe Glu Ser Leu Lys Thr Arg Leu Ala Gly Tyr Thr Lys Gly Ser
            20                  25                  30

Asp Glu Tyr Ile Glu Glu Leu Tyr Ser Gln Leu Pro Leu Thr Ser Tyr
        35                  40                  45

Pro Arg Tyr Lys Thr Phe Leu Lys Lys Gln Ala Val Ala Ile Ser Asn
    50                  55                  60

Pro Asp Asn Glu Ala Gly Phe Ser Ser Ile Tyr Arg Ser Ser Leu Ser
65                  70                  75                  80

Ser Glu Asn Leu Val Ser Cys Val Asp Lys Asn Leu Arg Thr Ala Tyr
                85                  90                  95

Asp His Phe Met Phe Ser Ala Arg Arg Trp Pro Gln Arg Asp Cys Leu
            100                 105                 110

Gly Ser Arg Pro Ile Asp Lys Ala Thr Gly Thr Trp Glu Glu Thr Phe
        115                 120                 125

Arg Phe Glu Ser Tyr Ser Thr Val Ser Lys Arg Cys His Asn Ile Gly
    130                 135                 140

Ser Gly Ile Leu Ser Leu Val Asn Thr Lys Arg Lys Arg Pro Leu Glu
145                 150                 155                 160

Ala Asn Asp Phe Val Val Ala Ile Leu Ser His Asn Asn Pro Glu Trp
                165                 170                 175

Ile Leu Thr Asp Leu Ala Cys Gln Ala Tyr Ser Leu Thr Asn Thr Ala
            180                 185                 190

Leu Tyr Glu Thr Leu Gly Pro Asn Thr Ser Glu Tyr Ile Leu Asn Leu
        195                 200                 205

Thr Glu Ala Pro Ile Leu Ile Phe Ala Lys Ser Asn Met Tyr His Val
    210                 215                 220

Leu Lys Met Val Pro Asp Met Lys Phe Val Asn Thr Leu Val Cys Met
225                 230                 235                 240

Asp Glu Leu Thr His Asp Glu Leu Arg Met Leu Asn Glu Ser Leu Leu
                245                 250                 255

Pro Val Lys Cys Asn Ser Leu Asn Glu Lys Ile Thr Phe Phe Ser Leu
            260                 265                 270

Glu Gln Val Glu Gln Val Gly Cys Phe Asn Lys Ile Pro Ala Ile Pro
```

-continued

```
        275                 280                 285

Pro Thr Pro Asp Ser Leu Tyr Thr Ile Ser Phe Thr Ser Gly Thr Thr
    290                 295                 300

Gly Leu Pro Lys Gly Val Glu Met Ser His Arg Asn Ile Ala Ser Gly
305                 310                 315                 320

Ile Ala Phe Ala Phe Ser Thr Phe Arg Ile Pro Pro Asp Lys Arg Asn
                325                 330                 335

Gln Gln Leu Tyr Asp Met Cys Phe Leu Pro Leu Ala His Ile Phe Glu
            340                 345                 350

Arg Met Val Ile Ala Tyr Asp Leu Ala Ile Gly Phe Gly Ile Gly Phe
        355                 360                 365

Leu His Lys Pro Asp Pro Thr Val Leu Val Glu Asp Leu Lys Ile Leu
    370                 375                 380

Lys Pro Tyr Ala Val Ala Leu Val Pro Arg Ile Leu Thr Arg Phe Glu
385                 390                 395                 400

Ala Gly Ile Lys Asn Ala Leu Asp Lys Ser Thr Val Gln Arg Asn Val
                405                 410                 415

Ala Asn Thr Ile Leu Asp Ser Lys Ser Ala Arg Phe Thr Ala Arg Gly
            420                 425                 430

Gly Pro Asp Lys Ser Ile Met Asn Phe Leu Val Tyr His Arg Val Leu
        435                 440                 445

Ile Asp Lys Ile Arg Asp Ser Leu Gly Leu Ser Asn Asn Ser Phe Ile
    450                 455                 460

Ile Thr Gly Ser Ala Pro Ile Ser Lys Asp Thr Leu Leu Phe Leu Arg
465                 470                 475                 480

Ser Ala Leu Asp Ile Gly Ile Arg Gln Gly Tyr Gly Leu Thr Glu Thr
                485                 490                 495

Phe Ala Gly Val Cys Leu Ser Glu Pro Phe Glu Lys Asp Val Gly Ser
            500                 505                 510

Cys Gly Ala Ile Gly Ile Ser Ala Glu Cys Arg Leu Lys Ser Val Pro
        515                 520                 525

Glu Met Gly Tyr His Ala Asp Lys Tyr Leu Lys Gly Glu Leu Gln Ile
    530                 535                 540

Arg Gly Pro Gln Val Phe Glu Arg Tyr Phe Lys Asn Pro Asn Glu Thr
545                 550                 555                 560

Ser Lys Ala Val Asp Gln Asp Gly Trp Phe Ser Thr Gly Asp Val Ala
                565                 570                 575

Phe Ile Asp Gly Lys Gly Arg Ile Ser Val Ile Asp Arg Val Lys Asn
            580                 585                 590

Phe Phe Lys Leu Ala His Gly Glu Tyr Ile Ala Pro Glu Lys Ile Glu
        595                 600                 605

Asn Ile Tyr Leu Ser Ser Cys Pro Tyr Ile Thr Gln Ile Phe Val Phe
    610                 615                 620

Gly Asp Pro Leu Lys Thr Phe Leu Val Gly Ile Val Gly Val Asp Val
625                 630                 635                 640

Asp Ala Ala Gln Pro Ile Leu Ala Ala Lys His Pro Glu Val Lys Thr
                645                 650                 655

Trp Thr Lys Glu Val Leu Val Glu Asn Leu Asn Arg Asn Lys Lys Leu
            660                 665                 670

Arg Lys Glu Phe Leu Asn Lys Ile Asn Lys Cys Thr Asp Gly Leu Gln
        675                 680                 685

Gly Phe Glu Lys Leu His Asn Ile Lys Val Gly Leu Glu Pro Leu Thr
    690                 695                 700
```

```
Leu Glu Asp Asp Val Val Thr Pro Thr Phe Lys Ile Lys Arg Ala Lys
705                 710                 715                 720

Ala Ser Lys Phe Phe Lys Asp Thr Leu Asp Gln Leu Tyr Ala Glu Gly
                725                 730                 735

Ser Leu Val Lys Thr Glu Lys Leu
            740


<210> SEQ ID NO 12
<211> LENGTH: 561
<212> TYPE: PRT
<213> ORGANISM: Escherichia coli

<400> SEQUENCE: 12

Met Lys Lys Val Trp Leu Asn Arg Tyr Pro Ala Asp Val Pro Thr Glu
1               5                   10                  15

Ile Asn Pro Asp Arg Tyr Gln Ser Leu Val Asp Met Phe Glu Gln Ser
            20                  25                  30

Val Ala Arg Tyr Ala Asp Gln Pro Ala Phe Val Asn Met Gly Glu Val
        35                  40                  45

Met Thr Phe Arg Lys Leu Glu Glu Arg Ser Arg Ala Phe Ala Ala Tyr
    50                  55                  60

Leu Gln Gln Gly Leu Gly Leu Lys Lys Gly Asp Arg Val Ala Leu Met
65                  70                  75                  80

Met Pro Asn Leu Leu Gln Tyr Pro Val Ala Leu Phe Gly Ile Leu Arg
                85                  90                  95

Ala Gly Met Ile Val Val Asn Val Asn Pro Leu Tyr Thr Pro Arg Glu
            100                 105                 110

Leu Glu His Gln Leu Asn Asp Ser Gly Ala Ser Ala Ile Val Ile Val
        115                 120                 125

Ser Asn Phe Ala His Thr Leu Glu Lys Val Val Asp Lys Thr Ala Val
    130                 135                 140

Gln His Val Ile Leu Thr Arg Met Gly Asp Gln Leu Ser Thr Ala Lys
145                 150                 155                 160

Gly Thr Val Val Asn Phe Val Val Lys Tyr Ile Lys Arg Leu Val Pro
                165                 170                 175

Lys Tyr His Leu Pro Asp Ala Ile Ser Phe Arg Ser Ala Leu His Asn
            180                 185                 190

Gly Tyr Arg Met Gln Tyr Val Lys Pro Glu Leu Val Pro Glu Asp Leu
        195                 200                 205

Ala Phe Leu Gln Tyr Thr Gly Gly Thr Thr Gly Val Ala Lys Gly Ala
    210                 215                 220

Met Leu Thr His Arg Asn Met Leu Ala Asn Leu Glu Gln Val Asn Ala
225                 230                 235                 240

Thr Tyr Gly Pro Leu Leu His Pro Gly Lys Glu Leu Val Val Thr Ala
                245                 250                 255

Leu Pro Leu Tyr His Ile Phe Ala Leu Thr Ile Asn Cys Leu Leu Phe
            260                 265                 270

Ile Glu Leu Gly Gly Gln Asn Leu Leu Ile Thr Asn Pro Arg Asp Ile
        275                 280                 285

Pro Gly Leu Val Lys Glu Leu Ala Lys Tyr Pro Phe Thr Ala Ile Thr
    290                 295                 300

Gly Val Asn Thr Leu Phe Asn Ala Leu Leu Asn Asn Lys Glu Phe Gln
305                 310                 315                 320

Gln Leu Asp Phe Ser Ser Leu His Leu Ser Ala Gly Gly Gly Met Pro
```

```
                325                 330                 335

Val Gln Gln Val Val Ala Glu Arg Trp Val Lys Leu Thr Gly Gln Tyr
            340                 345                 350

Leu Leu Glu Gly Tyr Gly Leu Thr Glu Cys Ala Pro Leu Val Ser Val
        355                 360                 365

Asn Pro Tyr Asp Ile Asp Tyr His Ser Gly Ser Ile Gly Leu Pro Val
    370                 375                 380

Pro Ser Thr Glu Ala Lys Leu Val Asp Asp Asp Asp Asn Glu Val Pro
385                 390                 395                 400

Pro Gly Gln Pro Gly Glu Leu Cys Val Lys Gly Pro Gln Val Met Leu
                405                 410                 415

Gly Tyr Trp Gln Arg Pro Asp Ala Thr Asp Glu Ile Ile Lys Asn Gly
            420                 425                 430

Trp Leu His Thr Gly Asp Ile Ala Val Met Asp Glu Glu Gly Phe Leu
        435                 440                 445

Arg Ile Val Asp Arg Lys Lys Asp Met Ile Leu Val Ser Gly Phe Asn
    450                 455                 460

Val Tyr Pro Asn Glu Ile Glu Asp Val Val Met Gln His Pro Gly Val
465                 470                 475                 480

Gln Glu Val Ala Ala Val Gly Val Pro Ser Gly Ser Ser Gly Glu Ala
                485                 490                 495

Val Lys Ile Phe Val Val Lys Lys Asp Pro Ser Leu Thr Glu Glu Ser
            500                 505                 510

Leu Val Thr Phe Cys Arg Arg Gln Leu Thr Gly Tyr Lys Val Pro Lys
        515                 520                 525

Leu Val Glu Phe Arg Asp Glu Leu Pro Lys Ser Asn Val Gly Lys Ile
    530                 535                 540

Leu Arg Arg Glu Leu Arg Asp Glu Ala Arg Gly Lys Val Asp Asn Lys
545                 550                 555                 560

Ala


<210> SEQ ID NO 13
<211> LENGTH: 548
<212> TYPE: PRT
<213> ORGANISM: Escherichia coli

<400> SEQUENCE: 13

Met Lys Val Thr Leu Thr Phe Asn Glu Gln Arg Arg Ala Ala Tyr Arg
1               5                   10                  15

Gln Gln Gly Leu Trp Gly Asp Ala Ser Leu Ala Asp Tyr Trp Gln Gln
            20                  25                  30

Thr Ala Arg Ala Met Pro Asp Lys Ile Ala Val Val Asp Asn His Gly
        35                  40                  45

Ala Ser Tyr Thr Tyr Ser Ala Leu Asp His Ala Ala Ser Cys Leu Ala
    50                  55                  60

Asn Trp Met Leu Ala Lys Gly Ile Glu Ser Gly Asp Arg Ile Ala Phe
65                  70                  75                  80

Gln Leu Pro Gly Trp Cys Glu Phe Thr Val Ile Tyr Leu Ala Cys Leu
                85                  90                  95

Lys Ile Gly Ala Val Ser Val Pro Leu Leu Pro Ser Trp Arg Glu Ala
            100                 105                 110

Glu Leu Val Trp Val Leu Asn Lys Cys Gln Ala Lys Met Phe Phe Ala
        115                 120                 125

Pro Thr Leu Phe Lys Gln Thr Arg Pro Val Asp Leu Ile Leu Pro Leu
```

```
    130                 135                 140

Gln Asn Gln Leu Pro Gln Leu Gln Gln Ile Val Gly Val Asp Lys Leu
145                 150                 155                 160

Ala Pro Ala Thr Ser Ser Leu Ser Leu Ser Gln Ile Ile Ala Asp Asn
                165                 170                 175

Thr Ser Leu Thr Thr Ala Ile Thr Thr His Gly Asp Glu Leu Ala Ala
            180                 185                 190

Val Leu Phe Thr Ser Gly Thr Glu Gly Leu Pro Lys Gly Val Met Leu
        195                 200                 205

Thr His Asn Asn Ile Leu Ala Ser Glu Arg Ala Tyr Cys Ala Arg Leu
    210                 215                 220

Asn Leu Thr Trp Gln Asp Val Phe Met Met Pro Ala Pro Leu Gly His
225                 230                 235                 240

Ala Thr Gly Phe Leu His Gly Val Thr Ala Pro Phe Leu Ile Gly Ala
                245                 250                 255

Arg Ser Val Leu Leu Asp Ile Phe Thr Pro Asp Ala Cys Leu Ala Leu
            260                 265                 270

Leu Glu Gln Gln Arg Cys Thr Cys Met Leu Gly Ala Thr Pro Phe Val
        275                 280                 285

Tyr Asp Leu Leu Asn Val Leu Glu Lys Gln Pro Ala Asp Leu Ser Ala
    290                 295                 300

Leu Arg Phe Phe Leu Cys Gly Gly Thr Thr Ile Pro Lys Lys Val Ala
305                 310                 315                 320

Arg Glu Cys Gln Gln Arg Gly Ile Lys Leu Leu Ser Val Tyr Gly Ser
                325                 330                 335

Thr Glu Ser Ser Pro His Ala Val Val Asn Leu Asp Asp Pro Leu Ser
            340                 345                 350

Arg Phe Met His Thr Asp Gly Tyr Ala Ala Ala Gly Val Glu Ile Lys
        355                 360                 365

Val Val Asp Asp Ala Arg Lys Thr Leu Pro Pro Gly Cys Glu Gly Glu
    370                 375                 380

Glu Ala Ser Arg Gly Pro Asn Val Phe Met Gly Tyr Phe Asp Glu Pro
385                 390                 395                 400

Glu Leu Thr Ala Arg Ala Leu Asp Glu Glu Gly Trp Tyr Tyr Ser Gly
                405                 410                 415

Asp Leu Cys Arg Met Asp Glu Ala Gly Tyr Ile Lys Ile Thr Gly Arg
            420                 425                 430

Lys Lys Asp Ile Ile Val Arg Gly Gly Glu Asn Ile Ser Ser Arg Glu
        435                 440                 445

Val Glu Asp Ile Leu Leu Gln His Pro Lys Ile His Asp Ala Cys Val
    450                 455                 460

Val Ala Met Ser Asp Glu Arg Leu Gly Glu Arg Ser Cys Ala Tyr Val
465                 470                 475                 480

Val Leu Lys Ala Pro His His Ser Leu Ser Leu Glu Glu Val Val Ala
                485                 490                 495

Phe Phe Ser Arg Lys Arg Val Ala Lys Tyr Lys Tyr Pro Glu His Ile
            500                 505                 510

Val Val Ile Glu Lys Leu Pro Arg Thr Thr Ser Gly Lys Ile Gln Lys
        515                 520                 525

Phe Leu Leu Arg Lys Asp Ile Met Arg Arg Leu Thr Gln Asp Val Cys
    530                 535                 540

Glu Glu Ile Glu
545
```

<210> SEQ ID NO 14
<211> LENGTH: 573
<212> TYPE: PRT
<213> ORGANISM: Mus musculus

<400> SEQUENCE: 14

```
Met Gln Trp Leu Lys Ser Phe Gln Ile Cys Lys Val Leu Gln Gly Phe
1               5                   10                  15

Ser Leu Ser Pro Thr Gln Leu His Arg Arg Leu Phe Ser Arg Val Gly
            20                  25                  30

Ala Pro Arg Trp Asn Asp His Asp Ser Pro Glu Glu Phe Asn Phe Ala
        35                  40                  45

Ser Asp Val Leu Asp Tyr Trp Ala Gln Met Glu Glu Glu Gly Lys Arg
    50                  55                  60

Gly Pro Ser Pro Ala Phe Trp Trp Val Asn Gly Gln Gly Asp Glu Ile
65                  70                  75                  80

Lys Trp Ser Phe Arg Lys Leu Arg Asp Leu Thr Cys Arg Thr Ala Asn
                85                  90                  95

Val Phe Glu Gln Ile Cys Gly Leu Gln Gln Gly Asp His Leu Ala Leu
            100                 105                 110

Ile Leu Pro Arg Val Pro Glu Trp Trp Leu Val Thr Val Gly Cys Met
        115                 120                 125

Arg Thr Gly Ile Ile Phe Met Pro Gly Thr Thr Gln Leu Lys Ala Lys
    130                 135                 140

Asp Ile Leu Tyr Arg Ile Gln Ile Ser Arg Ala Lys Ala Ile Val Thr
145                 150                 155                 160

Thr Ala Ser Leu Val Pro Glu Val Glu Ser Val Ala Ser Glu Cys Pro
                165                 170                 175

Asp Leu Lys Thr Lys Leu Val Val Ser Asp His Ser His Glu Gly Trp
            180                 185                 190

Leu Asp Phe Cys Ser Leu Ile Lys Ser Ala Ser Pro Asp His Thr Cys
        195                 200                 205

Ile Lys Ser Lys Met Lys Asp Pro Met Ala Ile Phe Phe Thr Ser Gly
    210                 215                 220

Thr Thr Gly Tyr Pro Lys Met Ala Lys His Asn Gln Gly Leu Ala Phe
225                 230                 235                 240

Arg Ser Tyr Ile Pro Ser Cys Arg Lys Leu Leu Lys Leu Lys Thr Ser
                245                 250                 255

Asp Ile Leu Trp Cys Met Ser Asp Pro Gly Trp Ile Leu Ala Thr Val
            260                 265                 270

Gly Cys Leu Ile Glu Pro Trp Thr Ser Gly Cys Thr Val Phe Ile His
        275                 280                 285

His Leu Pro Gln Phe Asp Pro Lys Val Ile Val Glu Val Leu Phe Lys
    290                 295                 300

Tyr Pro Ile Thr Gln Cys Leu Ala Ala Pro Gly Val Tyr Arg Met Val
305                 310                 315                 320

Leu Gln Gln Lys Thr Ser Asn Leu Arg Phe Pro Thr Leu Glu His Cys
                325                 330                 335

Thr Thr Gly Gly Glu Ser Leu Leu Pro Glu Glu Tyr Glu Gln Trp Lys
            340                 345                 350

Gln Arg Thr Gly Leu Ser Ile His Glu Val Tyr Gly Gln Ser Glu Thr
        355                 360                 365

Gly Ile Ser Ser Ala Thr Leu Arg Glu Met Lys Ile Lys Arg Gly Ser
```

```
    370                 375                 380

Ile Gly Lys Ala Ile Leu Pro Phe Asp Leu Gln Ile Ile Asp Glu Lys
385                 390                 395                 400

Gly Asn Ile Leu Pro Pro Asn Thr Glu Gly Tyr Ile Gly Ile Arg Ile
                405                 410                 415

Lys Pro Thr Arg Pro Leu Gly Leu Phe Met Glu Tyr Glu Asn Ser Pro
            420                 425                 430

Glu Ser Thr Ser Glu Val Glu Cys Gly Asp Phe Tyr Asn Ser Gly Asp
        435                 440                 445

Arg Ala Thr Ile Asp Glu Glu Gly Tyr Ile Trp Phe Leu Gly Arg Gly
    450                 455                 460

Asp Asp Val Ile Asn Ala Ser Gly Tyr Arg Ile Gly Pro Ala Glu Val
465                 470                 475                 480

Glu Asn Ala Leu Ala Glu His Pro Ala Val Ala Glu Ser Ala Val Val
                485                 490                 495

Ser Ser Pro Asp Lys Asp Arg Gly Glu Val Val Lys Ala Phe Ile Val
            500                 505                 510

Leu Asn Pro Glu Phe Leu Ser His Asp Gln Glu Gln Leu Ile Lys Glu
        515                 520                 525

Leu Gln His His Val Lys Ser Val Thr Ala Pro Tyr Lys Tyr Pro Arg
    530                 535                 540

Lys Val Glu Phe Val Ser Glu Leu Pro Lys Thr Val Thr Gly Lys Ile
545                 550                 555                 560

Lys Arg Lys Glu Leu Arg Asn Lys Glu Phe Gly Gln Leu
                565                 570
```

<210> SEQ ID NO 15
<211> LENGTH: 513
<212> TYPE: PRT
<213> ORGANISM: Marinobacter aquaeoli

<400> SEQUENCE: 15

```
Met Ala Ile Gln Gln Val His His Ala Asp Thr Ser Ser Ser Lys Val
1               5                   10                  15

Leu Gly Gln Leu Arg Gly Lys Arg Val Leu Ile Thr Gly Thr Thr Gly
            20                  25                  30

Phe Leu Gly Lys Val Val Leu Glu Arg Leu Ile Arg Ala Val Pro Asp
        35                  40                  45

Ile Gly Ala Ile Tyr Leu Leu Ile Arg Gly Asn Lys Arg His Pro Asp
    50                  55                  60

Ala Arg Ser Arg Phe Leu Glu Glu Ile Ala Thr Ser Ser Val Phe Asp
65                  70                  75                  80

Arg Leu Arg Glu Ala Asp Ser Glu Gly Phe Asp Ala Phe Leu Glu Glu
                85                  90                  95

Arg Ile His Cys Val Thr Gly Glu Val Thr Glu Ala Gly Phe Gly Ile
            100                 105                 110

Gly Gln Glu Asp Tyr Arg Lys Leu Ala Thr Glu Leu Asp Ala Val Ile
        115                 120                 125

Asn Ser Ala Ala Ser Val Asn Phe Arg Glu Glu Leu Asp Lys Ala Leu
    130                 135                 140

Ala Ile Asn Thr Leu Cys Leu Arg Asn Ile Ala Gly Met Val Asp Leu
145                 150                 155                 160

Asn Pro Lys Leu Ala Val Leu Gln Val Ser Thr Cys Tyr Val Asn Gly
                165                 170                 175
```

```
Met Asn Ser Gly Gln Val Thr Glu Ser Val Ile Lys Pro Ala Gly Glu
            180                 185                 190

Ala Val Pro Arg Ser Pro Asp Gly Phe Tyr Glu Ile Glu Glu Leu Val
        195                 200                 205

Arg Leu Leu Gln Asp Lys Ile Glu Asp Val Gln Ala Arg Tyr Ser Gly
    210                 215                 220

Lys Val Leu Glu Arg Lys Leu Val Asp Leu Gly Ile Arg Glu Ala Asn
225                 230                 235                 240

Arg Tyr Gly Trp Ser Asp Thr Tyr Thr Phe Thr Lys Trp Leu Gly Glu
                245                 250                 255

Gln Leu Leu Met Lys Ala Leu Asn Gly Arg Thr Leu Thr Ile Leu Arg
            260                 265                 270

Pro Ser Ile Ile Glu Ser Ala Leu Glu Glu Pro Ala Pro Gly Trp Ile
        275                 280                 285

Glu Gly Val Lys Val Ala Asp Ala Ile Ile Leu Ala Tyr Ala Arg Glu
    290                 295                 300

Lys Val Thr Leu Phe Pro Gly Lys Arg Ser Gly Ile Ile Asp Val Ile
305                 310                 315                 320

Pro Val Asp Leu Val Ala Asn Ser Ile Ile Leu Ser Leu Ala Glu Ala
                325                 330                 335

Leu Gly Glu Pro Gly Arg Arg Arg Ile Tyr Gln Cys Cys Ser Gly Gly
            340                 345                 350

Gly Asn Pro Ile Ser Leu Gly Glu Phe Ile Asp His Leu Met Ala Glu
        355                 360                 365

Ser Lys Ala Asn Tyr Ala Ala Tyr Asp His Leu Phe Tyr Arg Gln Pro
    370                 375                 380

Ser Lys Pro Phe Leu Ala Val Asn Arg Ala Leu Phe Asp Leu Val Ile
385                 390                 395                 400

Ser Gly Val Arg Leu Pro Leu Ser Leu Thr Asp Arg Val Leu Lys Leu
                405                 410                 415

Leu Gly Asn Ser Arg Asp Leu Lys Met Leu Arg Asn Leu Asp Thr Thr
            420                 425                 430

Gln Ser Leu Ala Thr Ile Phe Gly Phe Tyr Thr Ala Pro Asp Tyr Ile
        435                 440                 445

Phe Arg Asn Asp Glu Leu Met Ala Leu Ala Asn Arg Met Gly Glu Val
    450                 455                 460

Asp Lys Gly Leu Phe Pro Val Asp Ala Arg Leu Ile Asp Trp Glu Leu
465                 470                 475                 480

Tyr Leu Arg Lys Ile His Leu Ala Gly Leu Asn Arg Tyr Ala Leu Lys
                485                 490                 495

Glu Arg Lys Val Tyr Ser Leu Lys Thr Ala Arg Gln Arg Lys Lys Ala
            500                 505                 510

Ala


<210> SEQ ID NO 16
<211> LENGTH: 527
<212> TYPE: PRT
<213> ORGANISM: Arabidopsis thaliana

<400> SEQUENCE: 16

Met Ala Thr Thr Asn Val Leu Ala Thr Ser His Ala Phe Lys Leu Asn
1               5                   10                  15

Gly Val Ser Tyr Phe Ser Ser Phe Pro Arg Lys Pro Asn His Tyr Met
            20                  25                  30
```

```
Pro Arg Arg Arg Leu Ser His Thr Thr Arg Arg Val Gln Thr Ser Cys
        35                  40                  45

Phe Tyr Gly Glu Thr Ser Phe Glu Ala Val Thr Ser Leu Val Thr Pro
    50                  55                  60

Lys Thr Glu Thr Ser Arg Asn Ser Asp Gly Ile Gly Ile Val Arg Phe
65                  70                  75                  80

Leu Glu Gly Lys Ser Tyr Leu Val Thr Gly Ala Thr Gly Phe Leu Ala
                85                  90                  95

Lys Val Leu Ile Glu Lys Leu Leu Arg Glu Ser Leu Glu Ile Gly Lys
            100                 105                 110

Ile Phe Leu Leu Met Arg Ser Lys Asp Gln Glu Ser Ala Asn Lys Arg
        115                 120                 125

Leu Tyr Asp Glu Ile Ile Ser Ser Asp Leu Phe Lys Leu Leu Lys Gln
    130                 135                 140

Met His Gly Ser Ser Tyr Glu Ala Phe Met Lys Arg Lys Leu Ile Pro
145                 150                 155                 160

Val Ile Gly Asp Ile Glu Glu Asp Asn Leu Gly Ile Lys Ser Glu Ile
                165                 170                 175

Ala Asn Met Ile Ser Glu Glu Ile Asp Val Ile Ile Ser Cys Gly Gly
            180                 185                 190

Arg Thr Thr Phe Asp Asp Arg Tyr Asp Ser Ala Leu Ser Val Asn Ala
        195                 200                 205

Leu Gly Pro Ala Tyr Val Thr Gly Lys Arg Glu Gly Thr Val Leu Glu
    210                 215                 220

Thr Pro Leu Cys Ile Gly Glu Asn Ile Thr Ser Asp Leu Asn Ile Lys
225                 230                 235                 240

Ser Glu Leu Lys Leu Ala Ser Glu Ala Val Arg Lys Phe Arg Gly Arg
                245                 250                 255

Glu Glu Ile Lys Lys Leu Lys Glu Leu Gly Phe Glu Arg Ala Gln His
            260                 265                 270

Tyr Gly Trp Glu Asn Ser Tyr Thr Phe Thr Lys Ala Ile Gly Glu Ala
        275                 280                 285

Val Ile His Ser Lys Arg Gly Asn Leu Pro Val Val Ile Ile Arg Pro
    290                 295                 300

Ser Ile Ile Glu Ser Ser Tyr Asn Glu Pro Phe Pro Gly Trp Ile Gln
305                 310                 315                 320

Gly Thr Arg Met Ala Asp Pro Ile Ile Leu Ala Tyr Ala Lys Gly Gln
                325                 330                 335

Ile Ser Asp Phe Trp Ala Asp Pro Gln Ser Leu Met Asp Ile Ile Pro
            340                 345                 350

Val Asp Met Val Ala Asn Ala Ala Ile Ala Ala Met Ala Lys His Gly
        355                 360                 365

Cys Gly Val Pro Glu Phe Lys Val Tyr Asn Leu Thr Ser Ser Ser His
    370                 375                 380

Val Asn Pro Met Arg Ala Gly Lys Leu Ile Asp Leu Ser His Gln His
385                 390                 395                 400

Leu Cys Asp Phe Pro Leu Glu Glu Thr Val Ile Asp Leu Glu His Met
                405                 410                 415

Lys Ile His Ser Ser Leu Glu Gly Phe Thr Ser Ala Leu Ser Asn Thr
            420                 425                 430

Ile Ile Lys Gln Glu Arg Val Ile Asp Asn Glu Gly Gly Gly Leu Ser
        435                 440                 445

Thr Lys Gly Lys Arg Lys Leu Asn Tyr Phe Val Ser Leu Ala Lys Thr
```

```
    450                 455                 460

Tyr Glu Pro Tyr Thr Phe Phe Gln Ala Arg Phe Asp Asn Thr Asn Thr
465                 470                 475                 480

Thr Ser Leu Ile Gln Glu Met Ser Met Glu Glu Lys Lys Thr Phe Gly
                485                 490                 495

Phe Asp Ile Lys Gly Ile Asp Trp Glu His Tyr Ile Val Asn Val His
            500                 505                 510

Leu Pro Gly Leu Lys Lys Glu Phe Leu Ser Lys Lys Lys Thr Glu
        515                 520                 525


<210> SEQ ID NO 17
<211> LENGTH: 480
<212> TYPE: PRT
<213> ORGANISM: Arabidopsis thaliana

<400> SEQUENCE: 17

Cys Phe Tyr Gly Glu Thr Ser Phe Glu Ala Val Thr Ser Leu Val Thr
1               5                   10                  15

Pro Lys Thr Glu Thr Ser Arg Asn Ser Asp Gly Ile Gly Ile Val Arg
            20                  25                  30

Phe Leu Glu Gly Lys Ser Tyr Leu Val Thr Gly Ala Thr Gly Phe Leu
        35                  40                  45

Ala Lys Val Leu Ile Glu Lys Leu Leu Arg Glu Ser Leu Glu Ile Gly
    50                  55                  60

Lys Ile Phe Leu Leu Met Arg Ser Lys Asp Gln Glu Ser Ala Asn Lys
65                  70                  75                  80

Arg Leu Tyr Asp Glu Ile Ile Ser Ser Asp Leu Phe Lys Leu Leu Lys
                85                  90                  95

Gln Met His Gly Ser Ser Tyr Glu Ala Phe Met Lys Arg Lys Leu Ile
            100                 105                 110

Pro Val Ile Gly Asp Ile Glu Glu Asp Asn Leu Gly Ile Lys Ser Glu
        115                 120                 125

Ile Ala Asn Met Ile Ser Glu Glu Ile Asp Val Ile Ile Ser Cys Gly
    130                 135                 140

Gly Arg Thr Thr Phe Asp Asp Arg Tyr Asp Ser Ala Leu Ser Val Asn
145                 150                 155                 160

Ala Leu Gly Pro Ala Tyr Val Thr Gly Lys Arg Glu Gly Thr Val Leu
                165                 170                 175

Glu Thr Pro Leu Cys Ile Gly Glu Asn Ile Thr Ser Asp Leu Asn Ile
            180                 185                 190

Lys Ser Glu Leu Lys Leu Ala Ser Glu Ala Val Arg Lys Phe Arg Gly
        195                 200                 205

Arg Glu Glu Ile Lys Lys Leu Lys Glu Leu Gly Phe Glu Arg Ala Gln
    210                 215                 220

His Tyr Gly Trp Glu Asn Ser Tyr Thr Phe Thr Lys Ala Ile Gly Glu
225                 230                 235                 240

Ala Val Ile His Ser Lys Arg Gly Asn Leu Pro Val Val Ile Ile Arg
                245                 250                 255

Pro Ser Ile Ile Glu Ser Ser Tyr Asn Glu Pro Phe Pro Gly Trp Ile
            260                 265                 270

Gln Gly Thr Arg Met Ala Asp Pro Ile Ile Leu Ala Tyr Ala Lys Gly
        275                 280                 285

Gln Ile Ser Asp Phe Trp Ala Asp Pro Gln Ser Leu Met Asp Ile Ile
    290                 295                 300
```

```
Pro Val Asp Met Val Ala Asn Ala Ala Ile Ala Ala Met Ala Lys His
305                 310                 315                 320

Gly Cys Gly Val Pro Glu Phe Lys Val Tyr Asn Leu Thr Ser Ser Ser
                325                 330                 335

His Val Asn Pro Met Arg Ala Gly Lys Leu Ile Asp Leu Ser His Gln
            340                 345                 350

His Leu Cys Asp Phe Pro Leu Glu Glu Thr Val Ile Asp Leu Glu His
        355                 360                 365

Met Lys Ile His Ser Ser Leu Glu Gly Phe Thr Ser Ala Leu Ser Asn
    370                 375                 380

Thr Ile Ile Lys Gln Glu Arg Val Ile Asp Asn Glu Gly Gly Gly Leu
385                 390                 395                 400

Ser Thr Lys Gly Lys Arg Lys Leu Asn Tyr Phe Val Ser Leu Ala Lys
                405                 410                 415

Thr Tyr Glu Pro Tyr Thr Phe Phe Gln Ala Arg Phe Asp Asn Thr Asn
            420                 425                 430

Thr Thr Ser Leu Ile Gln Glu Met Ser Met Glu Glu Lys Lys Thr Phe
        435                 440                 445

Gly Phe Asp Ile Lys Gly Ile Asp Trp Glu His Tyr Ile Val Asn Val
    450                 455                 460

His Leu Pro Gly Leu Lys Lys Glu Phe Leu Ser Lys Lys Lys Thr Glu
465                 470                 475                 480


<210> SEQ ID NO 18
<211> LENGTH: 462
<212> TYPE: PRT
<213> ORGANISM: Ostrinia scapulalis

<400> SEQUENCE: 18

Met Ser Ala Asn Thr Met Glu Thr Asp Glu Gln Phe Thr Asp Asn Ser
1               5                   10                  15

Pro Ile Val Asn Phe Tyr Ser Gly Lys Ser Val Phe Val Thr Gly Ala
            20                  25                  30

Thr Gly Phe Leu Gly Thr Val Leu Val Glu Lys Leu Leu Phe Ser Cys
        35                  40                  45

Lys Gly Ile Asn Asn Ile Tyr Ile Leu Ile Lys Gln Thr Glu Asp Leu
    50                  55                  60

Thr Ile Glu Ala Arg Ile Leu Asn Tyr Leu Asn Ser Lys Ala Phe His
65                  70                  75                  80

Arg Val Lys Asn Thr Asn Pro Glu Leu Met Lys Lys Ile Ile Pro Ile
                85                  90                  95

Cys Gly Asn Leu Glu Asp Lys Asn Leu Gly Ile Ser Asp Ser Asp Met
            100                 105                 110

Lys Thr Leu Leu Glu Glu Val Ser Ile Val Phe His Val Ala Ala Lys
        115                 120                 125

Leu Leu Phe Lys Met Ser Leu Thr Ala Ala Val Asn Ile Asn Thr Lys
    130                 135                 140

Pro Thr Glu Gln Leu Ile Ala Ile Cys Lys Lys Met Arg Arg Asn Pro
145                 150                 155                 160

Ile Phe Ile Tyr Val Ser Ser Ala Tyr Ser Asn Val Asn Glu Gln Ile
                165                 170                 175

Ile Asp Glu Lys Val Tyr Asn Thr Gly Val Pro Leu Glu Thr Ile Tyr
            180                 185                 190

Asp Thr Leu Asp Thr Glu Asn Thr Arg Ile Thr Asp Ile Phe Leu Asp
        195                 200                 205
```

```
Lys Arg Pro Asn Thr Tyr Thr Tyr Ser Lys Ala Leu Ala Glu Val Val
    210                 215                 220

Val Glu Lys Glu Phe Asp Glu Ser Ala Ala Ile Val Arg Pro Ser Ile
225                 230                 235                 240

Ile Val Ser Ser Ile Arg Glu Pro Ile Pro Gly Trp Leu Ser Gly Ser
                245                 250                 255

His Gly Phe Pro Arg Val Val Gly Ala Ala Cys Lys Gly Leu Leu Leu
            260                 265                 270

Arg Trp His Gly Asp Gly Thr Val Val Cys Asp Leu Ile Pro Val Asp
        275                 280                 285

His Val Ala Asn Leu Ile Ile Ala Ala Ala Trp Glu Ser Asn Glu Arg
    290                 295                 300

Arg Leu Met Gly Asn Lys Gly Val Lys Val Tyr Asn Cys Cys Ser Ser
305                 310                 315                 320

Leu Arg Asn Pro Ile Asp Val Ile Thr Val Val Lys Thr Cys Ile Lys
                325                 330                 335

Tyr Arg Lys Tyr Phe Gly Thr Arg Thr Met Ser Ile Phe Thr Pro Arg
            340                 345                 350

Phe Ile Met Lys Lys Asn Tyr Phe Ile Tyr Lys Leu Leu Tyr Phe Thr
        355                 360                 365

Cys His Thr Ile Pro Ala Ala Ile Ile Asp Gly Phe Phe Trp Leu Thr
    370                 375                 380

Gly Arg Thr Pro Ile Met Leu Lys Thr Leu Asp Lys Leu Ser Lys Ile
385                 390                 395                 400

Ser Ser Val Leu Glu Tyr Phe Thr His His Gln Phe Ile Phe Leu Asp
                405                 410                 415

Ser Asn Val Arg Gly Leu Leu Arg Arg Met Glu Gly Thr Asp Arg Gln
            420                 425                 430

Thr Phe Asn Phe Asp Val Thr Glu Ile Glu Trp Glu Pro Tyr Leu Gln
        435                 440                 445

Asn Phe Val Arg Gly Ile Ala Asn Asn Tyr Asp Tyr Ser Met
    450                 455                 460


<210> SEQ ID NO 19
<211> LENGTH: 661
<212> TYPE: PRT
<213> ORGANISM: Marinobacter aquaeoli

<400> SEQUENCE: 19

Met Asn Tyr Phe Leu Thr Gly Gly Thr Gly Phe Ile Gly Arg Phe Leu
1               5                   10                  15

Val Glu Lys Leu Leu Ala Arg Gly Gly Thr Val Tyr Val Leu Val Arg
            20                  25                  30

Glu Gln Ser Gln Asp Lys Leu Glu Arg Leu Arg Glu Arg Trp Gly Ala
        35                  40                  45

Asp Asp Lys Gln Val Lys Ala Val Ile Gly Asp Leu Thr Ser Lys Asn
    50                  55                  60

Leu Gly Ile Asp Ala Lys Thr Leu Lys Ser Leu Lys Gly Asn Ile Asp
65                  70                  75                  80

His Val Phe His Leu Ala Ala Val Tyr Asp Met Gly Ala Asp Glu Glu
                85                  90                  95

Ala Gln Ala Ala Thr Asn Ile Glu Gly Thr Arg Ala Ala Val Gln Ala
            100                 105                 110

Ala Glu Ala Met Gly Ala Lys His Phe His His Val Ser Ser Ile Ala
```

```
        115                 120                 125

Ala Ala Gly Leu Phe Lys Gly Ile Phe Arg Glu Asp Met Phe Glu Glu
    130                 135                 140

Ala Glu Lys Leu Asp His Pro Tyr Leu Arg Thr Lys His Glu Ser Glu
145                 150                 155                 160

Lys Val Val Arg Glu Glu Cys Lys Val Pro Phe Arg Ile Tyr Arg Pro
                165                 170                 175

Gly Met Val Ile Gly His Ser Glu Thr Gly Glu Met Asp Lys Val Asp
            180                 185                 190

Gly Pro Tyr Tyr Phe Phe Lys Met Ile Gln Lys Ile Arg His Ala Leu
        195                 200                 205

Pro Gln Trp Val Pro Thr Ile Gly Ile Glu Gly Gly Arg Leu Asn Ile
    210                 215                 220

Val Pro Val Asp Phe Val Val Asp Ala Leu Asp His Ile Ala His Leu
225                 230                 235                 240

Glu Gly Glu Asp Gly Asn Cys Phe His Leu Val Asp Ser Asp Pro Tyr
                245                 250                 255

Lys Val Gly Glu Ile Leu Asn Ile Phe Cys Glu Ala Gly His Ala Pro
            260                 265                 270

Arg Met Gly Met Arg Ile Asp Ser Arg Met Phe Gly Phe Ile Pro Pro
        275                 280                 285

Phe Ile Arg Gln Ser Ile Lys Asn Leu Pro Pro Val Lys Arg Ile Thr
    290                 295                 300

Gly Ala Leu Leu Asp Asp Met Gly Ile Pro Pro Ser Val Met Ser Phe
305                 310                 315                 320

Ile Asn Tyr Pro Thr Arg Phe Asp Thr Arg Glu Leu Glu Arg Val Leu
                325                 330                 335

Lys Gly Thr Asp Ile Glu Val Pro Arg Leu Pro Ser Tyr Ala Pro Val
            340                 345                 350

Ile Trp Asp Tyr Trp Glu Arg Asn Leu Asp Pro Asp Leu Phe Lys Asp
        355                 360                 365

Arg Thr Leu Lys Gly Thr Val Glu Gly Lys Val Cys Val Val Thr Gly
    370                 375                 380

Ala Thr Ser Gly Ile Gly Leu Ala Thr Ala Glu Lys Leu Ala Glu Ala
385                 390                 395                 400

Gly Ala Ile Leu Val Ile Gly Ala Arg Thr Lys Glu Thr Leu Asp Glu
                405                 410                 415

Val Ala Ala Ser Leu Glu Ala Lys Gly Gly Asn Val His Ala Tyr Gln
            420                 425                 430

Cys Asp Phe Ser Asp Met Asp Asp Cys Asp Arg Phe Val Lys Thr Val
        435                 440                 445

Leu Asp Asn His Gly His Val Asp Val Leu Val Asn Asn Ala Gly Arg
    450                 455                 460

Ser Ile Arg Arg Ser Leu Ala Leu Ser Phe Asp Arg Phe His Asp Phe
465                 470                 475                 480

Glu Arg Thr Met Gln Leu Asn Tyr Phe Gly Ser Val Arg Leu Ile Met
                485                 490                 495

Gly Phe Ala Pro Ala Met Leu Glu Arg Arg Arg Gly His Val Val Asn
            500                 505                 510

Ile Ser Ser Ile Gly Val Leu Thr Asn Ala Pro Arg Phe Ser Ala Tyr
        515                 520                 525

Val Ser Ser Lys Ser Ala Leu Asp Ala Phe Ser Arg Cys Ala Ala Ala
    530                 535                 540
```

Glu Trp Ser Asp Arg Asn Val Thr Phe Thr Thr Ile Asn Met Pro Leu
545 550 555 560

Val Lys Thr Pro Met Ile Ala Pro Thr Lys Ile Tyr Asp Ser Val Pro
565 570 575

Thr Leu Thr Pro Asp Glu Ala Ala Gln Met Val Ala Asp Ala Ile Val
580 585 590

Tyr Arg Pro Lys Arg Ile Ala Thr Arg Leu Gly Val Phe Ala Gln Val
595 600 605

Leu His Ala Leu Ala Pro Lys Met Gly Glu Ile Ile Met Asn Thr Gly
610 615 620

Tyr Arg Met Phe Pro Asp Ser Pro Ala Ala Ala Gly Ser Lys Ser Gly
625 630 635 640

Glu Lys Pro Lys Val Ser Thr Glu Gln Val Ala Phe Ala Ala Ile Met
645 650 655

Arg Gly Ile Tyr Trp
660

<210> SEQ ID NO 20
<211> LENGTH: 505
<212> TYPE: PRT
<213> ORGANISM: Hahella chejuensis

<400> SEQUENCE: 20

Met Lys Gln Ser Leu Thr Leu Thr Ala Phe Ala Asn Lys Asn Val Leu
1 5 10 15

Ile Thr Gly Thr Thr Gly Phe Val Gly Lys Val Val Leu Glu Lys Leu
20 25 30

Leu Arg Ser Val Pro Thr Ile Gly Lys Ile Tyr Leu Leu Ile Arg Gly
35 40 45

Asn Ser Lys Asn Pro Thr Ala Arg Lys Arg Phe Gln Asn Glu Ile Ala
50 55 60

Thr Ser Ser Ile Phe Asp Thr Leu Lys Ala Ser Gln Gly Ser Arg Phe
65 70 75 80

Glu Glu Leu Cys Glu Thr Arg Ile His Cys Val Thr Gly Glu Val Thr
85 90 95

Glu Pro Leu Phe Gly Leu Ser Glu Lys Asp Phe Thr Asp Leu Ala Ala
100 105 110

Asp Ile Asp Val Ile Ile Asn Ser Ala Ala Ser Val Asn Phe Arg Glu
115 120 125

Ala Leu Asp Gln Ala Leu Thr Ile Asn Thr Leu Cys Leu Lys Asn Ile
130 135 140

Ile Glu Leu Ser Arg Arg Ala Ala Asp Cys Pro Val Val Gln Val Ser
145 150 155 160

Thr Cys Tyr Val Asn Gly Phe Asn Gln Gly Val Met Glu Glu Glu Ile
165 170 175

Val Ser Pro Ala Gly Glu Arg Ile Glu Arg Ser Glu Arg Gly Tyr Tyr
180 185 190

Glu Val Glu Pro Leu Ile Ala Arg Leu Leu Gln Asp Val Glu Gln Val
195 200 205

Ser Ala Ala Ala Ala Asp Asp His Ser Arg Glu Lys Asp Leu Ile Asp
210 215 220

Leu Gly Ile Lys Glu Ala Asn Lys Tyr Gly Trp Asn Asp Thr Tyr Thr
225 230 235 240

Phe Thr Lys Trp Met Gly Glu Gln Leu Leu Met Lys Glu Leu Tyr Gly

```
                245                 250                 255

Lys Thr Leu Thr Ile Leu Arg Pro Ser Ile Val Glu Ser Thr Leu Leu
            260                 265                 270

Gly Pro Ala Pro Gly Trp Ile Glu Gly Val Lys Val Ala Asp Ala Ile
        275                 280                 285

Ile Leu Ala Tyr Ala Arg Glu Lys Val Ser Leu Phe Pro Gly Lys Lys
    290                 295                 300

Asn Ala Val Ile Asp Ile Ile Pro Ala Asp Leu Val Ala Asn Ser Ile
305                 310                 315                 320

Ile Leu Ser Ala Thr Glu Ala Leu Leu Asp Ser Gly Ala His Arg Ile
                325                 330                 335

Tyr Gln Cys Cys Ser Ser Glu Val Asn Pro Ile Arg Ile Arg Glu Val
            340                 345                 350

Ile Gly His Val Gln Gln Glu Ala Glu His Asn Tyr Gln Thr His Asp
        355                 360                 365

Lys Leu Phe Tyr Arg Lys Pro Lys Lys Pro Phe Val Met Ile Pro Gly
    370                 375                 380

Ala Val Phe His Ala Leu Met Ala Ile Ser Phe His Met Leu Lys Trp
385                 390                 395                 400

Ser Ser Arg Leu Gln Ser Leu Phe Gly Arg Lys Ala Ser Gly Arg Lys
                405                 410                 415

Leu Ser Asn Met Glu Thr Thr Met Lys Leu Ser Lys Val Phe Ser Phe
            420                 425                 430

Tyr Thr Ser Pro Ser Tyr Thr Phe Ser Asn Arg Arg Leu Gln Glu Leu
        435                 440                 445

Ser Thr Arg Leu Gly Glu Tyr Asp Gln Ser Glu Phe Pro Val Asn Ala
    450                 455                 460

Gly Met Tyr Asp Trp Ala His Tyr Leu Arg Glu Val His Val Ala Gly
465                 470                 475                 480

Leu Asn Lys Tyr Ala Leu Arg Pro Lys Val Val Lys Met Asn Pro Pro
                485                 490                 495

Ala Ala Lys Pro Arg Ser Arg Ala Ala
            500                 505


<210> SEQ ID NO 21
<211> LENGTH: 493
<212> TYPE: PRT
<213> ORGANISM: Simmondsia chinensis

<400> SEQUENCE: 21

Met Glu Glu Met Gly Ser Ile Leu Glu Phe Leu Asp Asn Lys Ala Ile
1               5                   10                  15

Leu Val Thr Gly Ala Thr Gly Ser Leu Ala Lys Ile Phe Val Glu Lys
            20                  25                  30

Val Leu Arg Ser Gln Pro Asn Val Lys Lys Leu Tyr Leu Leu Leu Arg
        35                  40                  45

Ala Thr Asp Asp Glu Thr Ala Ala Leu Arg Leu Gln Asn Glu Val Phe
    50                  55                  60

Gly Lys Glu Leu Phe Lys Val Leu Lys Gln Asn Leu Gly Ala Asn Phe
65                  70                  75                  80

Tyr Ser Phe Val Ser Glu Lys Val Thr Val Val Pro Gly Asp Ile Thr
                85                  90                  95

Gly Glu Asp Leu Cys Leu Lys Asp Val Asn Leu Lys Glu Glu Met Trp
            100                 105                 110
```

```
Arg Glu Ile Asp Val Val Val Asn Leu Ala Ala Thr Ile Asn Phe Ile
        115                 120                 125

Glu Arg Tyr Asp Val Ser Leu Leu Ile Asn Thr Tyr Gly Ala Lys Tyr
    130                 135                 140

Val Leu Asp Phe Ala Lys Lys Cys Asn Lys Leu Lys Ile Phe Val His
145                 150                 155                 160

Val Ser Thr Ala Tyr Val Ser Gly Glu Lys Asn Gly Leu Ile Leu Glu
                165                 170                 175

Lys Pro Tyr Tyr Met Gly Glu Ser Leu Asn Gly Arg Leu Gly Leu Asp
            180                 185                 190

Ile Asn Val Glu Lys Lys Leu Val Glu Ala Lys Ile Asn Glu Leu Gln
        195                 200                 205

Ala Ala Gly Ala Thr Glu Lys Ser Ile Lys Ser Thr Met Lys Asp Met
    210                 215                 220

Gly Ile Glu Arg Ala Arg His Trp Gly Trp Pro Asn Val Tyr Val Phe
225                 230                 235                 240

Thr Lys Ala Leu Gly Glu Met Leu Leu Met Gln Tyr Lys Gly Asp Ile
                245                 250                 255

Pro Leu Thr Ile Ile Arg Pro Thr Ile Ile Thr Ser Thr Phe Lys Glu
            260                 265                 270

Pro Phe Pro Gly Trp Val Glu Gly Val Arg Thr Ile Asp Asn Val Pro
        275                 280                 285

Val Tyr Tyr Gly Lys Gly Arg Leu Arg Cys Met Leu Cys Gly Pro Ser
    290                 295                 300

Thr Ile Ile Asp Leu Ile Pro Ala Asp Met Val Val Asn Ala Thr Ile
305                 310                 315                 320

Val Ala Met Val Ala His Ala Asn Gln Arg Tyr Val Glu Pro Val Thr
                325                 330                 335

Tyr His Val Gly Ser Ser Ala Ala Asn Pro Met Lys Leu Ser Ala Leu
            340                 345                 350

Pro Glu Met Ala His Arg Tyr Phe Thr Lys Asn Pro Trp Ile Asn Pro
        355                 360                 365

Asp Arg Asn Pro Val His Val Gly Arg Ala Met Val Phe Ser Ser Phe
    370                 375                 380

Ser Thr Phe His Leu Tyr Leu Thr Leu Asn Phe Leu Leu Pro Leu Lys
385                 390                 395                 400

Val Leu Glu Ile Ala Asn Thr Ile Phe Cys Gln Trp Phe Lys Gly Lys
                405                 410                 415

Tyr Met Asp Leu Lys Arg Lys Thr Arg Leu Leu Leu Arg Leu Val Asp
            420                 425                 430

Ile Tyr Lys Pro Tyr Leu Phe Phe Gln Gly Ile Phe Asp Asp Met Asn
        435                 440                 445

Thr Glu Lys Leu Arg Ile Ala Ala Lys Glu Ser Ile Val Glu Ala Asp
    450                 455                 460

Met Phe Tyr Phe Asp Pro Arg Ala Ile Asn Trp Glu Asp Tyr Phe Leu
465                 470                 475                 480

Lys Thr His Phe Pro Gly Val Val Glu His Val Leu Asn
                485                 490
```

<210> SEQ ID NO 22
<211> LENGTH: 489
<212> TYPE: PRT
<213> ORGANISM: Marinobacter sp. ELB17

<400> SEQUENCE: 22

```
Met Lys Arg Leu Ala Thr Leu Asp Ala Ser Trp Leu Ala Val Glu Ser
1               5                   10                  15

Asp Asp Thr Pro Met His Val Gly Asn Leu Gln Ile Phe Ser Leu Pro
            20                  25                  30

Asp Asn Ala Pro Ser Thr Phe Ala Gly Asp Leu Val Lys Ser Met Lys
        35                  40                  45

Gln Ala Gly Asn Val Glu Leu Pro Trp Gly Cys Lys Leu Val Trp Pro
    50                  55                  60

Gly Phe Leu Gly Arg Val Leu Ala Pro Thr Trp Lys His Asp Lys His
65                  70                  75                  80

Ile Asp Leu Asp Tyr His Val Arg His Ser Ala Leu Pro Lys Pro Gly
                85                  90                  95

Gly Glu Arg Glu Leu Gly Glu Leu Val Ser Arg Leu His Ser Asn Pro
            100                 105                 110

Leu Asp Leu Ser Arg Pro Leu Trp Glu Cys His Met Ile Glu Gly Leu
        115                 120                 125

Glu His Asn Arg Phe Ala Leu Tyr Thr Lys Met His His Cys Met Ile
    130                 135                 140

Asp Gly Ile Ser Gly Val Arg Leu Met Gln Arg Val Leu Ser Lys Ser
145                 150                 155                 160

Pro Asp Glu Arg Asp Met Leu Pro Pro Trp Ser Val Arg Pro Glu Ser
                165                 170                 175

Thr Arg Gly Lys Lys Thr Asp Ser Glu Ala Ser Val Pro Gly Ala Ile
            180                 185                 190

Ser Gln Ala Met Glu Ala Leu Lys Leu Gln Leu Gly Leu Ala Pro Arg
        195                 200                 205

Leu Trp Gln Ala Ser Asn Arg Leu Ile His Ser Val Arg His Pro Glu
    210                 215                 220

Asp Gly Leu Thr Ala Pro Phe Thr Gly Pro Val Ser Lys Ile Asn His
225                 230                 235                 240

Arg Val Thr Gly Gln Arg Arg Phe Ala Thr Gln Gln Tyr Gln Leu Glu
                245                 250                 255

Asp Met Lys Ala Met Ala Arg Ala Ser Gly Ser Ser Met Asn Asp Ile
            260                 265                 270

Val Leu Tyr Leu Cys Gly Thr Ala Leu Arg Arg Phe Leu Leu Glu Gln
        275                 280                 285

Asp Asp Leu Pro Glu Ile Ser Leu Thr Ala Gly Ile Pro Val Asn Ile
    290                 295                 300

Arg Pro Ala Asp Asp Glu Gly Thr Gly Thr Gln Ile Ser Phe Met Ile
305                 310                 315                 320

Ala Ala Leu Ala Thr Asn Gln Pro Asp Pro Leu Thr Arg Leu Lys Cys
                325                 330                 335

Ile Lys Glu Ser Ser Cys Lys Ala Lys Glu His Leu Gln Lys Leu Pro
            340                 345                 350

Lys Lys Ala Leu Thr Gln Tyr Thr Met Met Leu Met Ser Pro Tyr Ile
        355                 360                 365

Leu Gln Leu Met Ser Gly Leu Gly Gly Arg Met Arg Pro Val Phe Asn
    370                 375                 380

Val Thr Ile Ser Asn Val Pro Gly Pro Thr Glu Asp Leu Tyr Tyr Glu
385                 390                 395                 400

Gly Ala Lys Leu Glu Ala Met Tyr Pro Val Ser Leu Ile Thr His Gly
                405                 410                 415
```

```
Gly Ala Leu Asn Ile Thr Cys Leu Ser Tyr Ala Gly Ser Leu Asn Phe
            420                 425                 430

Gly Phe Thr Gly Cys Arg Asp Thr Leu Pro Ser Met Gln Lys Leu Ala
        435                 440                 445

Val Tyr Thr Gly Glu Ala Leu Glu Glu Leu Arg Thr Leu Leu Leu Pro
    450                 455                 460

Pro Lys Lys Lys Pro Ser Pro Arg Lys Pro Arg Thr Ala Ala Lys Lys
465                 470                 475                 480

Lys Pro Ala Val Asn Ser Asn Ala Ser
                485


<210> SEQ ID NO 23
<211> LENGTH: 455
<212> TYPE: PRT
<213> ORGANISM: Marinobacter aquaeoli

<400> SEQUENCE: 23

Met Thr Pro Leu Asn Pro Thr Asp Gln Leu Phe Leu Trp Leu Glu Lys
1               5                   10                  15

Arg Gln Gln Pro Met His Val Gly Gly Leu Gln Leu Phe Ser Phe Pro
            20                  25                  30

Glu Gly Ala Pro Asp Asp Tyr Val Ala Gln Leu Ala Asp Gln Leu Arg
        35                  40                  45

Gln Lys Thr Glu Val Thr Ala Pro Phe Asn Gln Arg Leu Ser Tyr Arg
    50                  55                  60

Leu Gly Gln Pro Val Trp Val Glu Asp Glu His Leu Asp Leu Glu His
65                  70                  75                  80

His Phe Arg Phe Glu Ala Leu Pro Thr Pro Gly Arg Ile Arg Glu Leu
                85                  90                  95

Leu Ser Phe Val Ser Ala Glu His Ser His Leu Met Asp Arg Glu Arg
            100                 105                 110

Pro Met Trp Glu Val His Leu Ile Glu Gly Leu Lys Asp Arg Gln Phe
        115                 120                 125

Ala Leu Tyr Thr Lys Val His His Ser Leu Val Asp Gly Val Ser Ala
    130                 135                 140

Met Arg Met Ala Thr Arg Met Leu Ser Glu Asn Pro Asp Glu His Gly
145                 150                 155                 160

Met Pro Pro Ile Trp Asp Leu Pro Cys Leu Ser Arg Asp Arg Gly Glu
                165                 170                 175

Ser Asp Gly His Ser Leu Trp Arg Ser Val Thr His Leu Leu Gly Leu
            180                 185                 190

Ser Gly Arg Gln Leu Gly Thr Ile Pro Thr Val Ala Lys Glu Leu Leu
        195                 200                 205

Lys Thr Ile Asn Gln Ala Arg Lys Asp Pro Ala Tyr Asp Ser Ile Phe
    210                 215                 220

His Ala Pro Arg Cys Met Leu Asn Gln Lys Ile Thr Gly Ser Arg Arg
225                 230                 235                 240

Phe Ala Ala Gln Ser Trp Cys Leu Lys Arg Ile Arg Ala Val Cys Glu
                245                 250                 255

Ala Tyr Gly Thr Thr Val Asn Asp Val Val Thr Ala Met Cys Ala Ala
            260                 265                 270

Ala Leu Arg Thr Tyr Leu Met Asn Gln Asp Ala Leu Pro Glu Lys Pro
        275                 280                 285

Leu Val Ala Phe Val Pro Val Ser Leu Arg Arg Asp Asp Ser Ser Gly
    290                 295                 300
```

```
Gly Asn Gln Val Gly Val Ile Leu Ala Ser Leu His Thr Asp Val Gln
305                 310                 315                 320

Glu Ala Gly Glu Arg Leu Leu Lys Ile His His Gly Met Glu Glu Ala
                325                 330                 335

Lys Gln Arg Tyr Arg His Met Ser Pro Glu Glu Ile Val Asn Tyr Thr
            340                 345                 350

Ala Leu Thr Leu Ala Pro Ala Ala Phe His Leu Leu Thr Gly Leu Ala
        355                 360                 365

Pro Lys Trp Gln Thr Phe Asn Val Val Ile Ser Asn Val Pro Gly Pro
    370                 375                 380

Ser Arg Pro Leu Tyr Trp Asn Gly Ala Lys Leu Glu Gly Met Tyr Pro
385                 390                 395                 400

Val Ser Ile Asp Met Asp Arg Leu Ala Leu Asn Met Thr Leu Thr Ser
                405                 410                 415

Tyr Asn Asp Gln Val Glu Phe Gly Leu Ile Gly Cys Arg Arg Thr Leu
            420                 425                 430

Pro Ser Leu Gln Arg Met Leu Asp Tyr Leu Glu Gln Gly Leu Ala Glu
        435                 440                 445

Leu Glu Leu Asn Ala Gly Leu
    450                 455


<210> SEQ ID NO 24
<211> LENGTH: 455
<212> TYPE: PRT
<213> ORGANISM: Marinobacter adhaerens

<400> SEQUENCE: 24

Met Lys Pro Leu Ser Pro Thr Asp Gln Leu Phe Leu Trp Leu Glu Lys
1               5                   10                  15

Arg Gln Gln Pro Met His Val Gly Gly Leu Gln Leu Phe Ser Phe Pro
            20                  25                  30

Glu Gly Ala Pro Asp Asp Tyr Val Ala Gln Leu Ala Asp Arg Leu Arg
        35                  40                  45

Gln His Thr Lys Val Thr Pro Pro Phe Asn Gln Arg Leu Asp Tyr Arg
    50                  55                  60

Phe Gly Gln Pro Val Trp Val Glu Asp Glu His Leu Asp Leu Glu His
65                  70                  75                  80

His Phe Arg Phe Glu Ala Leu Pro Thr Pro Gly Arg Val Arg Glu Leu
                85                  90                  95

Leu Ser Phe Val Ser Ala Glu His Ser His Leu Met Asp Arg Glu Arg
            100                 105                 110

Pro Leu Trp Glu Phe His Leu Ile Glu Gly Leu Gly Glu Arg Gln Phe
        115                 120                 125

Ala Val Tyr Ile Lys Val His His Ala Leu Val Asp Gly Val Ser Ala
    130                 135                 140

Met Arg Met Val Thr Arg Met Leu Cys Gln Asp Thr Gly Glu Arg Asp
145                 150                 155                 160

Met Pro Pro Ile Trp Ala Met Pro Pro Arg Pro Glu Arg Glu Lys Asp
                165                 170                 175

Asp Gly Gly Pro Ser Leu Trp Arg Ser Ile Gly His Leu Leu Gly Glu
            180                 185                 190

Ser Gly Lys Gln Leu Gly Thr Val Pro Thr Val Ala Arg Glu Leu Leu
        195                 200                 205

Arg Thr Ile Asn Asn Ala Arg Lys Asp Pro Ala Tyr Ser Ser Ile Phe
```

```
    210                 215                 220

His Ala Pro Arg Ser Ile Leu Asn Gln Lys Ile Thr Gly Ser Arg Arg
225                 230                 235                 240

Phe Ala Ala Gln Ser Tyr Asp Leu Ser Arg Ile Lys Ala Val Cys Lys
                245                 250                 255

Ile Tyr Gly Thr Thr Val Asn Asp Val Val Met Ala Met Cys Ala Thr
            260                 265                 270

Ala Leu Arg Ser Tyr Leu Met Asn Gln Asp Ala Leu Pro Glu Lys Pro
        275                 280                 285

Leu Ile Ala Met Val Pro Val Ser Leu Arg Lys Asp Asp Ser Ser Gly
    290                 295                 300

Gly Asn Gln Val Gly Val Ile Leu Ala Ser Leu His Thr Asp Val Thr
305                 310                 315                 320

Ser Pro Val Thr Arg Leu Met Gln Ile His Glu Asp Val Lys Ala Ala
                325                 330                 335

Lys Asp Arg Tyr Ala His Met Ser Ala Glu Glu Ile Ile Asn Tyr Thr
            340                 345                 350

Ala Leu Thr Leu Ala Pro Ala Ala Phe His Leu Leu Thr Gly Met Ala
        355                 360                 365

Pro Lys Trp Gln Thr Phe Asn Val Val Ile Ser Asn Val Pro Gly Pro
    370                 375                 380

Arg Glu Thr Cys Tyr Trp Asn Gly Ala Met Met Asp Gly Met Tyr Pro
385                 390                 395                 400

Val Ser Ile Ala Met Asp Arg Leu Ala Leu Asn Met Thr Leu Thr Ser
                405                 410                 415

Tyr Gly Asp Gln Val Glu Phe Gly Leu Ile Gly Cys Arg Arg Thr Leu
            420                 425                 430

Pro Ser Leu Gln Arg Met Leu Asp Tyr Leu Glu Glu Ala Leu Val Glu
        435                 440                 445

Leu Glu Thr Ala Ala Gly Leu
    450                 455


<210> SEQ ID NO 25
<211> LENGTH: 455
<212> TYPE: PRT
<213> ORGANISM: Marinobacter hydrocarbonoclasticus

<400> SEQUENCE: 25

Met Thr Pro Leu Asn Pro Thr Asp Gln Leu Phe Leu Trp Leu Glu Lys
1               5                   10                  15

Arg Gln Gln Pro Met His Val Gly Gly Leu Gln Leu Phe Ser Phe Pro
            20                  25                  30

Glu Gly Ala Pro Asp Asp Tyr Val Ala Gln Leu Ala Asp Gln Leu Arg
        35                  40                  45

Gln Lys Thr Glu Val Thr Ala Pro Phe Asn Gln Arg Leu Ser Tyr Arg
    50                  55                  60

Leu Gly Gln Pro Val Trp Val Glu Asp Glu His Leu Asp Leu Glu His
65                  70                  75                  80

His Phe Arg Phe Glu Ala Leu Pro Thr Pro Gly Arg Ile Arg Glu Leu
                85                  90                  95

Leu Ser Phe Val Ser Ala Glu His Ser His Leu Met Asp Arg Glu Arg
            100                 105                 110

Pro Met Trp Glu Val His Leu Ile Glu Gly Leu Lys Asp Arg Gln Phe
        115                 120                 125
```

```
Ala Leu Tyr Thr Lys Val His His Ser Leu Val Asp Gly Val Ser Ala
    130                 135                 140

Met Arg Met Ala Thr Arg Met Leu Ser Glu Asn Pro Asp Glu His Gly
145                 150                 155                 160

Met Pro Pro Ile Trp Asp Leu Pro Cys Leu Ser Arg Asp Arg Gly Glu
                165                 170                 175

Ser Asp Gly His Ser Leu Trp Arg Ser Val Thr His Leu Leu Gly Leu
            180                 185                 190

Ser Gly Arg Gln Leu Gly Thr Ile Pro Thr Val Ala Lys Glu Leu Leu
        195                 200                 205

Lys Thr Ile Asn Gln Ala Arg Lys Asp Pro Ala Tyr Asp Ser Ile Phe
    210                 215                 220

His Ala Pro Arg Cys Met Leu Asn Gln Lys Ile Thr Gly Ser Arg Arg
225                 230                 235                 240

Phe Ala Ala Gln Ser Trp Cys Leu Lys Arg Ile Arg Ala Val Cys Glu
                245                 250                 255

Ala Tyr Gly Thr Thr Val Asn Asp Val Val Thr Ala Met Cys Ala Ala
            260                 265                 270

Ala Leu Arg Thr Tyr Leu Met Asn Gln Asp Ala Leu Pro Glu Lys Pro
        275                 280                 285

Leu Val Ala Phe Val Pro Val Ser Leu Arg Arg Asp Asp Ser Ser Gly
    290                 295                 300

Gly Asn Gln Val Gly Val Ile Leu Ala Ser Leu His Thr Asp Val Gln
305                 310                 315                 320

Glu Ala Gly Glu Arg Leu Leu Lys Ile His His Gly Met Glu Glu Ala
                325                 330                 335

Lys Gln Arg Tyr Arg His Met Ser Pro Glu Glu Ile Val Asn Tyr Thr
            340                 345                 350

Ala Leu Thr Leu Ala Pro Ala Ala Phe His Leu Leu Thr Gly Leu Ala
        355                 360                 365

Pro Lys Trp Gln Thr Phe Asn Val Val Ile Ser Asn Val Pro Gly Pro
    370                 375                 380

Ser Arg Pro Leu Tyr Trp Asn Gly Ala Lys Leu Glu Gly Met Tyr Pro
385                 390                 395                 400

Val Ser Ile Asp Met Asp Arg Leu Ala Leu Asn Met Thr Leu Thr Ser
                405                 410                 415

Tyr Asn Asp Gln Val Glu Phe Gly Leu Ile Gly Cys Arg Arg Thr Leu
            420                 425                 430

Pro Ser Leu Gln Arg Met Leu Asp Tyr Leu Glu Gln Gly Leu Ala Glu
        435                 440                 445

Leu Glu Leu Asn Ala Gly Leu
    450                 455
```

<210> SEQ ID NO 26
<211> LENGTH: 473
<212> TYPE: PRT
<213> ORGANISM: Marinobacter hydrocarbonoclasticus

<400> SEQUENCE: 26

```
Met Lys Arg Leu Gly Thr Leu Asp Ala Ser Trp Leu Ala Val Glu Ser
1               5                   10                  15

Glu Asp Thr Pro Met His Val Gly Thr Leu Gln Ile Phe Ser Leu Pro
            20                  25                  30

Glu Gly Ala Pro Glu Thr Phe Leu Arg Asp Met Val Thr Arg Met Lys
        35                  40                  45
```

```
Glu Ala Gly Asp Val Ala Pro Pro Trp Gly Tyr Lys Leu Ala Trp Ser
    50                  55                  60

Gly Phe Leu Gly Arg Val Ile Ala Pro Ala Trp Lys Val Asp Lys Asp
65                  70                  75                  80

Ile Asp Leu Asp Tyr His Val Arg His Ser Ala Leu Pro Arg Pro Gly
                85                  90                  95

Gly Glu Arg Glu Leu Gly Ile Leu Val Ser Arg Leu His Ser Asn Pro
            100                 105                 110

Leu Asp Phe Ser Arg Pro Leu Trp Glu Cys His Val Ile Glu Gly Leu
        115                 120                 125

Glu Asn Asn Arg Phe Ala Leu Tyr Thr Lys Met His His Ser Met Ile
    130                 135                 140

Asp Gly Ile Ser Gly Val Arg Leu Met Gln Arg Val Leu Thr Thr Asp
145                 150                 155                 160

Pro Glu Arg Cys Asn Met Pro Pro Pro Trp Thr Val Arg Pro His Gln
                165                 170                 175

Arg Arg Gly Ala Lys Thr Asp Lys Glu Ala Ser Val Pro Ala Ala Val
            180                 185                 190

Ser Gln Ala Met Asp Ala Leu Lys Leu Gln Ala Asp Met Ala Pro Arg
        195                 200                 205

Leu Trp Gln Ala Gly Asn Arg Leu Val His Ser Val Arg His Pro Glu
    210                 215                 220

Asp Gly Leu Thr Ala Pro Phe Thr Gly Pro Val Ser Val Leu Asn His
225                 230                 235                 240

Arg Val Thr Ala Gln Arg Arg Phe Ala Thr Gln His Tyr Gln Leu Asp
                245                 250                 255

Arg Leu Lys Asn Leu Ala His Ala Ser Gly Gly Ser Leu Asn Asp Ile
            260                 265                 270

Val Leu Tyr Leu Cys Gly Thr Ala Leu Arg Arg Phe Leu Ala Glu Gln
        275                 280                 285

Asn Asn Leu Pro Asp Thr Pro Leu Thr Ala Gly Ile Pro Val Asn Ile
    290                 295                 300

Arg Pro Ala Asp Asp Glu Gly Thr Gly Thr Gln Ile Ser Phe Met Ile
305                 310                 315                 320

Ala Ser Leu Ala Thr Asp Glu Ala Asp Pro Leu Asn Arg Leu Gln Gln
                325                 330                 335

Ile Lys Thr Ser Thr Arg Arg Ala Lys Glu His Leu Gln Lys Leu Pro
            340                 345                 350

Lys Ser Ala Leu Thr Gln Tyr Thr Met Leu Leu Met Ser Pro Tyr Ile
        355                 360                 365

Leu Gln Leu Met Ser Gly Leu Gly Gly Arg Met Arg Pro Val Phe Asn
    370                 375                 380

Val Thr Ile Ser Asn Val Pro Gly Pro Glu Gly Thr Leu Tyr Tyr Glu
385                 390                 395                 400

Gly Ala Arg Leu Glu Ala Met Tyr Pro Val Ser Leu Ile Ala His Gly
                405                 410                 415

Gly Ala Leu Asn Ile Thr Cys Leu Ser Tyr Ala Gly Ser Leu Asn Phe
            420                 425                 430

Gly Phe Thr Gly Cys Arg Asp Thr Leu Pro Ser Met Gln Lys Leu Ala
        435                 440                 445

Val Tyr Thr Gly Glu Ala Leu Asp Glu Leu Glu Ser Leu Ile Leu Pro
    450                 455                 460
```

```
Pro Lys Lys Arg Ala Arg Thr Arg Lys
465                 470


<210> SEQ ID NO 27
<211> LENGTH: 521
<212> TYPE: PRT
<213> ORGANISM: Petunia x hybrida

<400> SEQUENCE: 27

Met Lys Ser Leu Ala Thr Glu Leu Arg Asn Arg Ser Ser Glu Pro Cys
1               5                   10                  15

Leu Lys Pro Ile Glu Thr Lys Arg Lys Thr Ile Glu Glu Tyr Glu Thr
            20                  25                  30

Val Ala Val Glu Glu Glu Pro Leu Ser Pro Thr Ala Arg Leu Phe His
        35                  40                  45

Asp Ala Asn Phe Asn Val His Val Val Val Ile Ile Ala Leu Asp Thr
    50                  55                  60

Arg Ile Ser Pro Gln Pro Ile Lys Asp Lys Leu Val His Thr Leu Leu
65                  70                  75                  80

Lys His Pro Arg Phe Thr Ser Leu Met Val Val Asp Glu Glu Asn Leu
                85                  90                  95

Ala Asp Met Lys Trp Val Gln Thr Lys Ile Asp Leu Asp Gln His Ile
            100                 105                 110

Ile Val Pro Glu Val Asp Glu Thr Gln Leu Glu Ser Pro Asp Lys Phe
        115                 120                 125

Val Glu Asp Tyr Ile Tyr Asn Leu Thr Lys Thr Ser Leu Asp Arg Thr
    130                 135                 140

Lys Pro Leu Trp Asp Leu His Leu Val Asn Val Lys Thr Arg Asp Ala
145                 150                 155                 160

Glu Ala Val Ala Leu Leu Arg Val His His Ser Leu Gly Asp Gly Thr
                165                 170                 175

Ser Leu Ile Ser Leu Leu Leu Ala Cys Thr Arg Gln Thr Ala Asp Glu
            180                 185                 190

Leu Lys Leu Pro Thr Ile Pro Thr Lys Lys Arg Arg Pro Thr Pro Ser
        195                 200                 205

Gly Tyr Ser Thr Lys Glu Glu Ser Phe Lys Leu Trp His Tyr Leu Ala
    210                 215                 220

Val Ile Trp Leu Phe Ile Arg Met Ile Gly Asn Thr Leu Val Asp Val
225                 230                 235                 240

Leu Met Phe Ile Ile Thr Val Ile Phe Leu Lys Asp Thr Lys Thr Pro
                245                 250                 255

Ile Asn Thr Val Pro Asp Ser Glu Ser Arg Val Arg Arg Ile Val His
            260                 265                 270

Arg Ile Ile Asp Leu Asp Asp Leu Lys Leu Val Lys Asn Ala Met Asn
        275                 280                 285

Met Thr Ile Asn Asp Val Ala Leu Gly Ile Thr Gln Ala Gly Leu Ser
    290                 295                 300

Lys Tyr Leu Asn Arg Arg Tyr Ala Val Asp Glu Glu Asp Lys Gly Asp
305                 310                 315                 320

Thr Glu Arg Asn Asn Asn Leu Pro Lys Asn Ile Arg Leu Arg Ser Cys
                325                 330                 335

Leu Val Ile Asn Leu Arg Pro Ser Ala Gly Ile Glu Asp Leu Ala Asp
            340                 345                 350

Met Met Glu Lys Gly Pro Lys Glu Lys Arg Gly Trp Gly Asn Trp Phe
        355                 360                 365
```

```
Gly Tyr Val Leu Leu Pro Phe Lys Ile Ala Leu Arg Asp Asp Pro Leu
    370                 375                 380

Asp Tyr Val Lys Glu Ala Lys Ala Thr Val Asp Arg Lys Lys Arg Ser
385                 390                 395                 400

Phe Glu Ala Leu Tyr Thr Leu Ile Met Ala Glu Val Leu Ile Lys Ile
                405                 410                 415

Phe Gly Ile Lys Val Ala Thr Ala Val Thr Val Arg Val Phe Ser Asn
            420                 425                 430

Ala Thr Val Cys Phe Ser Asn Val Val Gly Pro Gln Glu Glu Ile Gly
        435                 440                 445

Phe Cys Gly His Pro Ile Ser Tyr Leu Ala Pro Ser Ile Tyr Gly Gln
    450                 455                 460

Pro Ser Ala Leu Met Ile Asn Phe Gln Ser Tyr Ile Asp Lys Met Ile
465                 470                 475                 480

Ile Val Val Ala Val Asp Glu Gly Ala Ile Pro Asp Pro Gln Gln Leu
                485                 490                 495

Leu Asp Asp Phe Glu Asn Ser Leu His Leu Ile Lys Glu Ala Val Leu
            500                 505                 510

Glu Arg Gly Leu Val Lys Asn Leu Lys
        515                 520


<210> SEQ ID NO 28
<211> LENGTH: 333
<212> TYPE: PRT
<213> ORGANISM: Mus musculus

<400> SEQUENCE: 28

Met Phe Trp Pro Thr Lys Lys Asp Leu Lys Thr Ala Met Glu Val Phe
1               5                   10                  15

Ala Leu Phe Gln Trp Ala Leu Ser Ala Leu Val Ile Val Thr Thr Val
            20                  25                  30

Ile Ile Val Asn Leu Tyr Leu Val Val Phe Thr Ser Tyr Trp Pro Val
        35                  40                  45

Thr Val Leu Met Leu Thr Trp Leu Ala Phe Asp Trp Lys Thr Pro Glu
    50                  55                  60

Arg Gly Gly Arg Arg Phe Thr Cys Val Arg Lys Trp Arg Leu Trp Lys
65                  70                  75                  80

His Tyr Ser Asp Tyr Phe Pro Leu Lys Met Val Lys Thr Lys Asp Ile
                85                  90                  95

Ser Pro Asp Arg Asn Tyr Ile Leu Val Cys His Pro His Gly Leu Met
            100                 105                 110

Ala His Ser Cys Phe Gly His Phe Ala Thr Asp Thr Thr Gly Phe Ser
        115                 120                 125

Lys Thr Phe Pro Gly Ile Thr Pro Tyr Met Leu Thr Leu Gly Ala Phe
    130                 135                 140

Phe Trp Val Pro Phe Leu Arg Asp Tyr Val Met Ser Thr Gly Ser Cys
145                 150                 155                 160

Ser Val Ser Arg Ser Ser Met Asp Phe Leu Leu Thr Gln Lys Gly Thr
                165                 170                 175

Gly Asn Met Leu Val Val Val Val Gly Gly Leu Ala Glu Cys Arg Tyr
            180                 185                 190

Ser Thr Pro Gly Ser Thr Thr Leu Phe Leu Lys Lys Arg Gln Gly Phe
        195                 200                 205

Val Arg Thr Ala Leu Lys His Gly Val Ser Leu Ile Pro Ala Tyr Ala
```

```
    210                 215                 220

Phe Gly Glu Thr Asp Leu Tyr Asp Gln His Ile Phe Thr Pro Gly Gly
225                 230                 235                 240

Phe Val Asn Arg Phe Gln Lys Trp Phe Gln Lys Met Val His Ile Tyr
                245                 250                 255

Pro Cys Ala Phe Tyr Gly Arg Gly Leu Thr Lys Asn Ser Trp Gly Leu
            260                 265                 270

Leu Pro Tyr Ser Gln Pro Val Thr Thr Val Val Gly Glu Pro Leu Pro
        275                 280                 285

Leu Pro Lys Ile Glu Asn Pro Ser Glu Glu Ile Val Ala Lys Tyr His
    290                 295                 300

Thr Leu Tyr Ile Asp Ala Leu Arg Lys Leu Phe Asp Gln His Lys Thr
305                 310                 315                 320

Lys Phe Gly Ile Ser Glu Thr Gln Glu Leu Val Ile Val
                325                 330


<210> SEQ ID NO 29
<211> LENGTH: 352
<212> TYPE: PRT
<213> ORGANISM: Simmondsia chinensis

<400> SEQUENCE: 29

Met Glu Val Glu Lys Glu Leu Lys Thr Phe Ser Glu Val Trp Ile Ser
1               5                   10                  15

Ala Ile Ala Ala Ala Cys Tyr Cys Arg Phe Val Pro Ala Val Ala Pro
            20                  25                  30

His Gly Gly Ala Leu Arg Leu Leu Leu Leu Leu Pro Val Val Leu Leu
        35                  40                  45

Phe Ile Phe Leu Pro Leu Arg Leu Ser Ser Phe His Leu Gly Gly Pro
    50                  55                  60

Thr Ala Leu Tyr Leu Val Trp Leu Ala Asn Phe Lys Leu Leu Leu Phe
65                  70                  75                  80

Ala Phe His Leu Gly Pro Leu Ser Asn Pro Ser Leu Ser Leu Leu His
                85                  90                  95

Phe Ile Ser Thr Thr Leu Leu Pro Ile Lys Phe Arg Asp Asp Pro Ser
            100                 105                 110

Asn Asp His Glu Lys Asn Lys Arg Thr Leu Ser Phe Glu Trp Arg Lys
        115                 120                 125

Val Val Leu Phe Val Ala Lys Leu Val Phe Phe Ala Gly Ile Leu Lys
    130                 135                 140

Ile Tyr Glu Phe Arg Lys Asp Leu Pro His Phe Val Ile Ser Val Leu
145                 150                 155                 160

Tyr Cys Phe His Phe Tyr Leu Gly Thr Glu Ile Thr Leu Ala Ala Ser
                165                 170                 175

Ala Val Ile Ala Arg Ala Thr Leu Gly Leu Asp Leu Tyr Pro Gln Phe
            180                 185                 190

Asn Glu Pro Tyr Leu Ala Thr Ser Leu Gln Asp Phe Trp Gly Arg Arg
        195                 200                 205

Trp Asn Leu Met Val Ser Asp Ile Leu Gly Leu Thr Thr Tyr Gln Pro
    210                 215                 220

Val Arg Arg Val Leu Ser Arg Trp Val Arg Leu Arg Trp Glu Val Ala
225                 230                 235                 240

Gly Ala Met Leu Val Ala Phe Thr Val Ser Gly Leu Met His Glu Val
                245                 250                 255
```

```
Phe Phe Phe Tyr Leu Thr Arg Ala Arg Pro Ser Trp Glu Val Thr Gly
            260                 265                 270

Phe Phe Val Leu His Gly Val Cys Thr Ala Val Glu Met Val Val Lys
        275                 280                 285

Lys Ala Val Ser Gly Lys Val Arg Leu Arg Arg Glu Val Ser Gly Ala
    290                 295                 300

Leu Thr Val Gly Phe Val Met Val Thr Gly Gly Trp Leu Phe Leu Pro
305                 310                 315                 320

Gln Leu Val Arg His Gly Val Asp Leu Lys Thr Ile Asp Glu Tyr Pro
                325                 330                 335

Val Met Phe Asn Tyr Thr Gln Lys Lys Leu Met Gly Leu Leu Gly Trp
            340                 345                 350


<210> SEQ ID NO 30
<211> LENGTH: 458
<212> TYPE: PRT
<213> ORGANISM: Acinetobacter sp. ADP1

<400> SEQUENCE: 30

Met Arg Pro Leu His Pro Ile Asp Phe Ile Phe Leu Ser Leu Glu Lys
1               5                   10                  15

Arg Gln Gln Pro Met His Val Gly Gly Leu Phe Leu Phe Gln Ile Pro
            20                  25                  30

Asp Asn Ala Pro Asp Thr Phe Ile Gln Asp Leu Val Asn Asp Ile Arg
        35                  40                  45

Ile Ser Lys Ser Ile Pro Val Pro Pro Phe Asn Asn Lys Leu Asn Gly
    50                  55                  60

Leu Phe Trp Asp Glu Asp Glu Glu Phe Asp Leu Asp His His Phe Arg
65                  70                  75                  80

His Ile Ala Leu Pro His Pro Gly Arg Ile Arg Glu Leu Leu Ile Tyr
                85                  90                  95

Ile Ser Gln Glu His Ser Thr Leu Leu Asp Arg Ala Lys Pro Leu Trp
            100                 105                 110

Thr Cys Asn Ile Ile Glu Gly Ile Glu Gly Asn Arg Phe Ala Met Tyr
        115                 120                 125

Phe Lys Ile His His Ala Met Val Asp Gly Val Ala Gly Met Arg Leu
    130                 135                 140

Ile Glu Lys Ser Leu Ser His Asp Val Thr Glu Lys Ser Ile Val Pro
145                 150                 155                 160

Pro Trp Cys Val Glu Gly Lys Arg Ala Lys Arg Leu Arg Glu Pro Lys
                165                 170                 175

Thr Gly Lys Ile Lys Lys Ile Met Ser Gly Ile Lys Ser Gln Leu Gln
            180                 185                 190

Ala Thr Pro Thr Val Ile Gln Glu Leu Ser Gln Thr Val Phe Lys Asp
        195                 200                 205

Ile Gly Arg Asn Pro Asp His Val Ser Ser Phe Gln Ala Pro Cys Ser
    210                 215                 220

Ile Leu Asn Gln Arg Val Ser Ser Ser Arg Arg Phe Ala Ala Gln Ser
225                 230                 235                 240

Phe Asp Leu Asp Arg Phe Arg Asn Ile Ala Lys Ser Leu Asn Val Thr
                245                 250                 255

Ile Asn Asp Val Val Leu Ala Val Cys Ser Gly Ala Leu Arg Ala Tyr
            260                 265                 270

Leu Met Ser His Asn Ser Leu Pro Ser Lys Pro Leu Ile Ala Met Val
        275                 280                 285
```

```
Pro Ala Ser Ile Arg Asn Asp Asp Ser Asp Val Ser Asn Arg Ile Thr
    290                 295                 300

Met Ile Leu Ala Asn Leu Ala Thr His Lys Asp Asp Pro Leu Gln Arg
305                 310                 315                 320

Leu Glu Ile Ile Arg Arg Ser Val Gln Asn Ser Lys Gln Arg Phe Lys
                325                 330                 335

Arg Met Thr Ser Asp Gln Ile Leu Asn Tyr Ser Ala Val Val Tyr Gly
            340                 345                 350

Pro Ala Gly Leu Asn Ile Ile Ser Gly Met Met Pro Lys Arg Gln Ala
        355                 360                 365

Phe Asn Leu Val Ile Ser Asn Val Pro Gly Pro Arg Glu Pro Leu Tyr
    370                 375                 380

Trp Asn Gly Ala Lys Leu Asp Ala Leu Tyr Pro Ala Ser Ile Val Leu
385                 390                 395                 400

Asp Gly Gln Ala Leu Asn Ile Thr Met Thr Ser Tyr Leu Asp Lys Leu
                405                 410                 415

Glu Val Gly Leu Ile Ala Cys Arg Asn Ala Leu Pro Arg Met Gln Asn
            420                 425                 430

Leu Leu Thr His Leu Glu Glu Glu Ile Gln Leu Phe Glu Gly Val Ile
        435                 440                 445

Ala Lys Gln Glu Asp Ile Lys Thr Ala Asn
    450                 455
```

<210> SEQ ID NO 31
<211> LENGTH: 1086
<212> TYPE: DNA
<213> ORGANISM: Artificial Sequence
<220> FEATURE:
<223> OTHER INFORMATION: DNA sequence of Cc1FatB1 construct for expression, codon-optimized for Synechocystis

<400> SEQUENCE: 31

```
atggcgaacg gtagcgctgt ctctctgaag agcggctcct tgaatacgca agaggacact     60

tcttcttccc caccgccacg cgcgttcatc aaccaattac ccgactggtc catgttattg    120

acggcgatta ccactgtctt tgttgccgca gagaaacagt ggactatgtt agaccgcaag    180

agcaagcgct ccgatatgtt agtggattct tttggcatgg aacgcattgt gcaggatggc    240

ttagtgtttc gtcaatcttt tagcattcgt tcttatgaaa tcggtgcaga tcgtcgtgca    300

tccattgaaa ccttaatgaa ccatctgcag gaaactagct tgaatcattg caaatccatt    360

cgcttgttga atgagggttt tggtcgcacc cccgagatgt gcaaacgtga cttgatctgg    420

gtggttaccc gcatgcacat catggtcaac cgctacccta cctggggtga taccgttgag    480

attaacactt gggtttccca aagcggcaag aatggtatgg gtcgtgattg gctgatttcc    540

gactgtaata ccggcgaaat cctgatccgc gcgacgtctg catgggcgat gatgaaccaa    600

aagacccgtc gtctgtctaa actgccttac gaagtcagcc aagagattgc tccgcacttc    660

gtcgacagcc ctcccgtgat cgaggacggc gaccgtaagt tacacaagtt cgatgtgaaa    720

accggcgaca gcatccgtaa aggtttgact ccgcgttgga atgacttaga tgttaatcag    780

cacgttaaca acgttaagta tatcggctgg atcttagaga gcatgccgac cgaggtcttg    840

gaaactcatg aactgtgttt cttaactctg gagtatcgtc gcgagtgcgg tcgcgatagc    900

gtgctggaat ctgtgaccgc gatggatcct tctaatgaag gtggtcgctc ccactaccag    960

catttactgc gcttggagga cggtactgac atcgttaagg gccgcactga gtggcgtcca   1020
```

aagaatgccc ggaatattgg tgccattagt accggtaaaa ccagtaatgg taatcccgcc 1080
agttaa 1086

<210> SEQ ID NO 32
<211> LENGTH: 2320
<212> TYPE: DNA
<213> ORGANISM: Cuphea carthagenensis

<400> SEQUENCE: 32
gcagcaagtt ccgcattctt ccccgttaca accccgggaa cctcccgtaa acccgggaag 60
tttggcaact ggctatcgag cttgagccct cccttcaggc ccaagtcaat ccccagtggc 120
ggatttcagg ttaaggcaaa cgccagtgcc catcctaagg ctaacggttc tgcagtaagt 180
ctaaagtctg gcagcctcaa cactcaggag gacacttcgt cgtcccctcc tcctcgggct 240
ttcattaacc agttgcccga ttggagtatg cttttaaccg cgatcacgac ggtcttcgtg 300
gcggcagaga agcagtggac tatgcttgat cggaaatcta agaggtctga catgcttgtg 360
gactcgtttg ggatggagag gatagttcag gatgggcttg tgttcagaca gagtttttcg 420
attaggtctt atgaaatagg tgctgatcga agagcctcta tagagacgct gatgaaccac 480
ttgcaggtac tgctttgaaa ctatacattc atcgaatatg ctagtgatca gtaaatgagc 540
cacaacttga cgatgacata gataacaccg aattgccggt ataacaagct aattctgtcc 600
actttgattc aatgaaggaa ccatcagctg taaattttcg attacgttta agtatggtga 660
aagttaaaac gcattctgat aagtagttcg tccaaaaatg cttgcattag tttgcttata 720
tttcctcgtt aactgcattg tctttgtttg tgattttttt ttaatctaaa caggaaacat 780
ctctcaatca ttgtaagagt atccgtcttc taaatgaagg ctttggccgt actcctgaga 840
tgtgtaaaag ggacctcatt tgggtggtta cgagaatgca tatcatggtg aatcgctatc 900
caacttggta agtttgtcac tggcttgtct gtcttttggt ccgtgagtgc ctcttaagat 960
aacagttgta aatatagttg aatgtaatag cctgtatgtg atctgtatgg taggggcgat 1020
actgtcgaga tcaatacctg ggtctcccag tcgggaaaaa acggtatggg tcgcgattgg 1080
ctaataagtg attgcaatac aggagaaatt cttataagag caacgaggta ggattttctg 1140
gttctgagtt tacattctca aaccttctga tgctcgatcc atgagtagac atttggcatg 1200
tttaatatgt aaagttgagt catgccaatc tcatattatc gcagtgcatg ggctatgatg 1260
aatcaaaaga cgagaagact gtcaaaactg ccttatgagg tttcacagga gatagcgcct 1320
cattttgtgg actctcctcc tgtcattgaa gacggtgata ggaaattgca caagtttgat 1380
gtgaagacgg gtgattccat tcgcaagggt ctaactgtaa gtccctatct ttcactatga 1440
tattagccgt ttttatgaag tatcatgtct ctgagacgat cttcctcttc acggtttgta 1500
gccaaggtgg aatgacttgg atgtcaatca gcacgttaat aacgtgaagt acattgggtg 1560
gattctcgag gtacccttt catcatacga acaactgata tagttttggg ttgatgataa 1620
taaaatcaat aaactgtgat attgcttatt taaatatcat agactagtat ttccccgagt 1680
ttgtcaaagc ttggattccg gttccgctta acaaatctgc aatctatacg aatgcttgtt 1740
gcagagtatg ccaacagaag ttttggagac ccatgagcta tgcttcctga cccttgaata 1800
taggcgggaa tgcggaaggg acagtgtgct ggagtccgtg accgctatgg atccctcaaa 1860
tgagggaggc cggtctcact accaacacct tctgcggctt gaggatggga ctgatatcgt 1920
gaagggaaga actgagtggc ggccgaagaa tgcaagaaat attggggcaa tatcaacagg 1980
aaagacttca aatggaaacc cggcctctta gaaggggctc aggatccttc tgagatatgc 2040

```
atttcttttt cattttctgg tgagctgaaa gaagagcatg tatttgcaat cagtaaattg   2100

tgtggttcgt ttgcagtttc tcgcttcgct cctttgtata ataacatggc cagtcgtctt   2160

tgtatcatct catgttttcc gtttgattta cgccatattc tttgcaatct attcgtttca   2220

agacgaacag cgcatcgcta aatctcgaaa caagtacttg tccaaaatgc atatatgtgc   2280

ctttgaagat cacaatgcag tccgccaaat agacattcaa                         2320
```

<210> SEQ ID NO 33
<211> LENGTH: 1092
<212> TYPE: DNA
<213> ORGANISM: Artificial Sequence
<220> FEATURE:
<223> OTHER INFORMATION: DNA sequence of Cd1FatB1 construct for expression, codon-optimized for Synechocystis

<400> SEQUENCE: 33

```
atgggcatta acggttccag cgtcggcctg aagtccggct ccttgaagac ccaggaagat     60

accccctcca gccctcctcc ccggactttt atcaatcagt tgcccgattg gtccatgctt    120

ctggctgcta tcaccaccgt gttcctggct gccgagaaac agtggatgat gttggactgg    180

aagcccaagc gtcccgacat gctggtggac cccttcggtt tgggccggat cgtccaggat    240

ggtttggtat ttcgccaaaa cttttccatt cgttcctatg agattggtgc cgatcggacc    300

gcttccatcg aaaccctcat gaatcacctc caagagactg ctctgaatca cgttaaaagc    360

gccggcttgt tgaatgacgg ttttggccgc actcctgaaa tgtacaaacg cgatctgatt    420

tgggttgtgg ccaagatgca ggtcatggtg aaccggtacc ctacctgggg cgacaccgtg    480

gaggtgaaca cctgggttgc caagtccggt aaaaacggca tgcgccggga ctggctgatt    540

tccgattgca ataccggtga aattctcacc cgtgcttcca gcgtttgggt tatgatgaac    600

cagaagaccc gccgtttgag caagattccc gatgaggtgc gccatgagat tgaaccccat    660

ttcgtggact cccccccgt tattgaggat gacgatcgca aactccccaa gttggacgaa    720

aagaccgctg actccatccg taagggcctg acccccggt ggaacgatct ggatgtgaac     780

caacacgtca acaatgtgaa atatattggc tggattttgg aatccacccc ccaagaagtg    840

ttggaaaccc aagagttgtg tagcttgacc ttggagtacc gccgcgaatg cggccgggat    900

tccgtgctgg aatccttgac tgccgttgat cactccggta aaggttccgg ttccaacttt    960

cagcatctgt tgcgcttgga ggatggtggc gagattgtga aaggtcggac cgaatggcgc   1020

cccaaaaatg ccgtgattaa tggcgccgtg gcccccggcg aaacttcccc tggcaattcc   1080

gtgtcctaat aa                                                       1092
```

<210> SEQ ID NO 34
<211> LENGTH: 2246
<212> TYPE: DNA
<213> ORGANISM: Cuphea decandra

<400> SEQUENCE: 34

```
gcagcaagtt ctgcatgctt ccccgtacca tcgccggacg cctcccggaa acccggaaag     60

cacggcaatg gggcatcgag cttgagcccc ttcaagccca aatcgatccc cagtggaggt    120

ttgcaggttc aggcaaacgc cagtgcccct cctaagatta atggttcctc ggtcggtcta    180

aagtccggca gcctcaagac tcaggaagac actccttcat cccctcctcc tcggactttt    240

atcaaccagt tgcccgattg gagtatgctt ctggctgcaa tcactaccgt cttcttagcg    300

gctgagaagc agtggatgat gcttgattgg aaacctaaga ggcctgacat gcttgtggac    360
```

```
ccgttcggtt tgggaaggat tgttcaggat gggcttgtgt tcaggcagaa tttttcgatt    420
aggtcatatg aaattggcgc tgatcgcact gcatctatag agacactgat gaaccacttg    480
caggtactga tgcatgttgc atttaagcta ttcgattctt gaaatgcttg attccatcaa    540
ctgagaatac ttgactatgg catacataat ataaccgtga atttgacaaa gaaaaggggt    600
gcatcgcatt cctctttcta tttgcacgag gtaatataat acagggttac ctatttcgtg    660
atgattttct cattctcagg gtgagatttg tcatgccgag tctctgaagg aatcatcagc    720
catacttttt ttaatttaat ttacgtgatg aaagtttata tggggctctc tcagacctta    780
atctttggaa aagaaatctc attttaaata acttgtttag ttttagatga tatatacttg    840
atttcttata ttcttgcatt agtttgctta taattttagt tcaattgatt atcattgttc    900
tggtgctctt tttttttttc cttcttttca caggaaacag ctctcaatca cgtgaagagc    960
gctgggcttc tcaatgacgg ctttggtcgt actcccgaga tgtataaaag ggaccttatt   1020
tgggttgtgg caaaaatgca ggtcatggtt aatcgctatc ctacttggtg agtttgccac   1080
cagcctgtct gtctatggtc cccagaagct tcatacggtt ttatctgtca acacagctgt   1140
agtgatggtt ctgttttcat tactttatgc tatatcacgt tgtaacgggt gctcaccttt   1200
acagacctaa cgagatggtg tttctattca ctgtgacacc gataatgcaa atctccttta   1260
tcttgtgcaa cctaaatgct tgtgatctat attcaggggt gacacagttg aagtcaatac   1320
ttgggttgcc aagtcgggga aaaatggcat gcgtcgtgat tggctcataa gtgattgcaa   1380
tactggagaa attcttacta gagcatcgag gtatgatgtt ctgtctagta tttgatcttc   1440
ctgaactttc tagttgtcaa tttgtgagca ttcaagctct agatattaca gtgaaagttg   1500
agttctgtta ccctgacatt atcgcagcgt gtgggtcatg atgaatcaaa agacaagaag   1560
attgtcaaaa attccagatg aggttcgaca tgagatagag cctcattttg tggactctcc   1620
tcctgtcatt gaagatgatg atcgaaaact tcccaagctg gatgagaaaa cagctgactc   1680
catccgcaag ggtctaactg taaggcctta aactttcatt gtgatggtag gtagcatgca   1740
tttgttaatt tcatgtccct tagacgatct ttctcttcac gctttttagc cgaggtggaa   1800
cgacttggat gtcaatcagc acgttaacaa cgtgaagtac attggatgga ttcttgaggt   1860
aattatttaa cttcttagtc gattatttac tttttataat tagatctata aacatagata   1920
ttgacccgtg taaatgctag caatcaagaa ttaattatat ttccccgagt tttctgcaga   1980
gtactccaca agaagttctg gagacccagg agttatgttc cctcaccctc gaatacagga   2040
gggagtgcgg gagggacagc gtgctggagt ccctcaccgc tgtagaccac tctggaaagg   2100
gctcagggtc aaatttccag caccttctgc ggcttgagga tggaggtgag atcgtgaagg   2160
ggagaactga gtggcgacct aagaacgcag taatcaatgg ggcagtggca cccggggaga   2220
cttcacctgg aaactctgtc tcttag                                        2246
```

<210> SEQ ID NO 35
<211> LENGTH: 1097
<212> TYPE: DNA
<213> ORGANISM: Artificial Sequence
<220> FEATURE:
<223> OTHER INFORMATION: DNA sequence of Cp1FatB1 construct for expression, codon-optimized for Synechocystis

<400> SEQUENCE: 35

```
atggctaatg gttctgccgt gagcttgaaa gatggtagct tagaaactca agagggtact     60
tcttcttcct cccatccacc acgcaccttt atcaatcagc tgcctgattg gtccatgctg    120
```

```
ctgtccgcga tcacgaccgt ctttgtcgct gcggagaaac agtggaccat gttagaccgc    180

aagagcaaac gtcccgatat gctggtggag ccctttgtgc aagatggtgt ctctttccgc    240

cagtctttca gcatccgttc ctatgagatt ggcgccgatc gtaccgcaag cattgaaacc    300

ttaatgaata tcttccaaga aacctctttg aaccactgca agtctttagg cttattgaat    360

gacggtttcg gtcgcactcc ggagatgtgt aagcgtgatt tgatttgggt tgtcaccaag    420

atgcagattg aggttaaccg ttacccgact tggggcgaca ccatcgaggt taccacttgg    480

gtgtctgaat ccggtaagaa cggcatgtcc cgcgattggt tgatttccga ctgtcacacc    540

ggcgagatct taatccgcgc aacttccgtt tgggcgatga tgaatcagaa aactcgccgc    600

ttatctaaga tccctgacga agtgcgtcaa gaaatcgtgc cctatttcgt tgactctgcg    660

cctgttatcg aggacgaccg caaactgcat aagttggatg tgaaaactgg tgactccatt    720

cgtaatggct tgacgccacg ttggaacgac ctggacgtca accaacacgt caacaacgtc    780

aagtacatcg gttggattct gaaaagcgtg cctaccgaag tgtttgttac ccaggagttg    840

tgcggcttaa ctttggaata ccgtcgcgag tgtcgtcgtg attccgtctt ggaaagcgtt    900

accgcgatgg atcctagcaa agaaggtgat cgtagcttgt accaacactt actgcgcctg    960

gagaacggtg cggacattgc attaggtcgc accgaatggc gtccgaagaa tgcaggcacc   1020

aacggtgcca tctctaccac caagacgtcc ccaggtaata gcgtgagcta ataatgatca   1080

gatccggagt ttgtaga                                                  1097


<210> SEQ ID NO 36
<211> LENGTH: 1967
<212> TYPE: DNA
<213> ORGANISM: Cuphea paucipetala

<400> SEQUENCE: 36

gcagcaagtt cagcattctt ctcctttcca gccccgggaa cctcccttaa acccgggaag     60

ttcggcaatt ggccatcgaa cttgagcgtc cccttcaatc ccaaagcaaa ccacaatggt    120

ggctttcatg ttaaggcaaa caccagtgcc catcctaagg ctaacggttc tgcagtaagt    180

ctaaaggatg gcagccttga gactcaggag ggcacttcat cgtcgtccca tcctcctcgg    240

actttcatta accagttgcc cgactggagt atgcttctgt ccgcaatcac aactgtcttt    300

gttgcagctg agaagcagtg gacgatgctt gatcggaaat ctaagaggcc cgacatgctc    360

gtggaaccgt ttgttcagga tggtgtttcg ttcagacaga gtttttcgat aaggtcttat    420

gaaataggcg ctgatcgaac agcctcaata gagacgttga tgaacatctt ccaggtattg    480

cattgaaact attcaaccat agcattgcta gtgatctgta aacgatccac tactcgacga    540

tgacatagat aacaccgaaa gttgtggcca ttttaattta gaggtgctgt tttttgctca    600

tgatgagatt tgtttctcag ggtgagattt gtcaggttga ttcaagggag taaccataag    660

ctgtaaattt tcgactacgt ttaggtgtga tgaaagttaa atactcttat tcgaataaga    720

aaaaaaggct atgcattctt atgataagta tttcttctta gatgcgtgca tctgtttgct    780

tatatttccc cgttaactcc attgtctttg ttctaagttt tttgtttctc taaacaggaa    840

acatctctga atcattgtaa gagtctcggt cttctcaatg acggctttgg tcgtactcct    900

gagatgtgta agagggacct catttgggtg gttacgaaaa tgcagattga ggttaatcgc    960

tatcctactt ggtaagtttg tctctggctt gtttgtcttt cggtccacaa atgcctctta   1020

cggtaatagc tgtaaacata gtggaatgta atggcctgtg tgatctatat ggtaggggcg   1080
```

```
atactatcga ggtcactact tgggtctccg agtcggggaa aaacggtatg agtcgagatt   1140

ggctgataag tgattgccat acaggagaaa ttcttataag agcaacgagg tagacttttt   1200

ctggttctca ttttacattc tcagaccttc tgatgttcga tctgagagca gacatttggt   1260

atgttttata ttgaaagttg agtcaagtca ctctaatatt atcgcagcgt gtgggctatg   1320

atgaatcaaa agacgagaag attgtcaaaa attccagatg aggttcgaca ggagatagtg   1380

ccttattttg tggactctgc tcctgtcatt gaagacgatc gaaaattgca caagcttgat   1440

gtgaagacgg gtgattccat tcgcaatggt ctaactgtaa gtccctatat ttcagtatga   1500

tatttggcat gtttatgaaa catcaagtct ctgaggcgat ctttctcttc acggtttgta   1560

gccaaggtgg aatgacttgg atgtcaatca gcacgttaac aatgtgaagt acattgggtg   1620

gattctcaag gtaccctttt catcatacaa acaactgata ataagatcaa taaacttaga   1680

tcttgccccg agtttgtgaa tgcttgattt acacagttcg gctaaacaaa tcagtaatct   1740

atacgaatgc ttgttgcaga gtgttccaac agaagttttc gtgacccagg agctatgtgg   1800

cctcaccctt gagtataggc gggaatgcag aagggacagt gtgctggagt ccgtgaccgc   1860

tatggatcct tcaaaagagg gagaccggtc tctgtaccag caccttcttc ggcttgagaa   1920

tggggctgat atcgccttag gcagaactga gtggagaccg aagactg                 1967
```

```
<210> SEQ ID NO 37
<211> LENGTH: 1254
<212> TYPE: DNA
<213> ORGANISM: Elaeis guineensis

<400> SEQUENCE: 37

atggttgctt cgattgtcgc ttgggccttt ttccccacac catctttctc ccccacggca     60

tcagcaaaag cttcgaagac cattggtgaa ggctccgaga atttgaatgt tcggggtatc    120

atagccaaac ccacttcttc ttcggcggct aagcagggta aggtgatggc ccaagccgtc    180

cccaagatca atggcgcgaa ggttggcctg aaagctgaat cccaaaaggc cgaggaagat    240

gctgcccctt cctcagcccc gaggacattc tataatcaac tacctgactg gagcgtgctc    300

cttgccgccg taacaacgat ctttttggct gccgagaagc agtggaccct tcttgattgg    360

aagccacggc gtcccgacat gcttactggt gcatttagcc ttgggaagat tgtgcaggat    420

ggactagttt tcaggcagaa cttttccatc aggtcatatg agattggggc tgatcggacg    480

gcttctatag aaacgttaat gaaccattta caggaaacag cacttaatca tgtgaggaat    540

gctgggcttc tgggcgatgg ttttggtgcc acaccagaga tgagtaaaag aaatttgatt    600

tgggttgtca ctaaaatgca ggtcctgatt gagcactatc cttcctgggg ggatgttgtt    660

gaagtagata catgggttgg tgcatctggt aaaaatggga tgcgtcgtga ttggcatgtt    720

cgtgactacc gaacaggcca aactatattg agagccacca gtatctgggt gatgatggat    780

aaacacacta ggaagttgtc taaaatgccc gaagaagtca gagcagagat agggccttac    840

tttatggaac atgctgctat tgtggacgag gacagcagaa agcttccaaa gcttgatgat    900

gatactgcag attatattaa atggggcctg actcctcgat ggagtgattt agatgtgaat    960

cagcatgtga acaatgtcaa atatataggc tggattcttg agagcgctcc aatatcaatc   1020

ctggagaatc acgagctggc gagtatgact ctggaatata ggagggagtg tgggagggac   1080

agcgttctgc aatccctcac cgcagtcgct aatgactgca ctggtggcct tccagaagct   1140

agcatcgagt gccagcatct gctgcagctg gaatgcgggg ccgagattgt taggggacgg   1200

acacagtgga ggcccaggcg tgcctccggt cccacttcag ctggaagtgc ttaa         1254
```

<210> SEQ ID NO 38
<211> LENGTH: 975
<212> TYPE: DNA
<213> ORGANISM: Elaeis guineensis

<400> SEQUENCE: 38

```
ctacctgact ggagcgtgct ccttgccgcc gtaacaacga tctttttggc tgccgagaag     60
cagtggaccc ttcttgattg gaagccacgg cgtcccgaca tgcttactgg tgcatttagc    120
cttgggaaga ttgtgcagga tggactagtt ttcaggcaga acttttccat caggtcatat    180
gagattgggg ctgatcggac ggcttctata gaaacgttaa tgaaccattt acaggaaaca    240
gcacttaatc atgtgaggaa tgctgggctt ctgggcgatg gttttggtgc cacaccagag    300
atgagtaaaa gaaatttgat ttgggttgtc actaaaatgc aggtcctgat tgagcactat    360
ccttcctggg gggatgttgt tgaagtagat acatgggttg gtgcatctgg taaaaatggg    420
atgcgtcgtg attggcatgt tcgtgactac cgaacaggcc aaactatatt gagagccacc    480
agtatctggg tgatgatgga taaacacact aggaagttgt ctaaaatgcc cgaagaagtc    540
agagcagaga tagggcctta ctttatggaa catgctgcta ttgtggacga ggacagcaga    600
aagcttccaa agcttgatga tgatactgca gattatatta aatggggcct gactcctcga    660
tggagtgatt tagatgtgaa tcagcatgtg aacaatgtca aatatatagg ctggattctt    720
gagagcgctc caatatcaat cctggagaat cacgagctgg cgagtatgac tctggaatat    780
aggagggagt gtgggaggga cagcgttctg caatccctca ccgcagtcgc taatgactgc    840
actggtggcc ttccagaagc tagcatcgag tgccagcatc tgctgcagct ggaatgcggg    900
gccgagattg ttaggggacg gacacagtgg aggcccaggc gtgcctccgg tcccacttca    960
gctggaagtg cttaa                                                     975
```

<210> SEQ ID NO 39
<211> LENGTH: 900
<212> TYPE: DNA
<213> ORGANISM: Elaeis guineensis

<400> SEQUENCE: 39

```
gattggaagc cacggcgtcc cgacatgctt actggtgcat ttagccttgg gaagattgtg     60
caggatggac tagttttcag gcagaacttt tccatcaggt catatgagat tggggctgat    120
cggacggctt ctatagaaac gttaatgaac catttacagg aaacagcact taatcatgtg    180
aggaatgctg ggcttctggg cgatggtttt ggtgccacac cagagatgag taaaagaaat    240
ttgatttggg ttgtcactaa aatgcaggtc ctgattgagc actatccttc ctggggggat    300
gttgttgaag tagatacatg ggttggtgca tctggtaaaa atgggatgcg tcgtgattgg    360
catgttcgtg actaccgaac aggccaaact atattgagag ccaccagtat ctgggtgatg    420
atggataaac acactaggaa gttgtctaaa atgcccgaag aagtcagagc agagataggg    480
ccttacttta tggaacatgc tgctattgtg gacgaggaca gcagaaagct tccaaagctt    540
gatgatgata ctgcagatta tattaaatgg ggcctgactc ctcgatggag tgatttagat    600
gtgaatcagc atgtgaacaa tgtcaaatat ataggctgga ttcttgagag cgctccaata    660
tcaatcctgg agaatcacga gctggcgagt atgactctgg aatataggag ggagtgtggg    720
agggacagcg ttctgcaatc cctcaccgca gtcgctaatg actgcactgg tggccttcca    780
gaagctagca tcgagtgcca gcatctgctg cagctggaat gcggggccga gattgttagg    840
```

```
ggacggacac agtggaggcc caggcgtgcc tccggtccca cttcagctgg aagtgcttaa    900
```

<210> SEQ ID NO 40
<211> LENGTH: 2235
<212> TYPE: DNA
<213> ORGANISM: Saccharomyces cerevisiae

<400> SEQUENCE: 40

```
atggccgctc cagattatgc acttaccgat ttaattgaat cggatcctcg tttcgaaagt     60
ttgaagacaa gattagccgg ttacaccaaa ggctctgatg aatatattga agagctatac    120
tctcaattac cactgaccag ctatcccagg tacaaaacat ttttaaagaa acaggcggtt    180
gccatttcga atccggataa tgaagctggt tttagctcga tttataggag ttctctttct    240
tctgaaaatc tagtgagctg tgtggataaa aacttaagaa ctgcatacga tcacttcatg    300
ttttctgcaa ggagatggcc tcaacgtgac tgtttaggtt caaggccaat tgataaagcc    360
acaggcacct gggaggaaac attccgtttc gagtcgtact ccacggtatc taaaagatgt    420
cataatatcg gaagtggtat attgtctttg gtaaacacga aaaggaaacg tcctttggaa    480
gccaatgatt ttgttgttgc tatcttatca cacaacaacc ctgaatggat cctaacagat    540
ttggcctgtc aggcctattc tctaactaac acggctttgt acgaaacatt aggtccaaac    600
acctccgagt acatattgaa tttaaccgag gcccccattc tgatttttgc aaaatcaaat    660
atgtatcatg tattgaagat ggtgcctgat atgaaatttg ttaatacttt ggtttgtatg    720
gatgaattaa ctcatgacga gctccgtatg ctaaatgaat cgttgctacc cgttaagtgc    780
aactctctca atgaaaaaat cacatttttt tcattggagc aggtagaaca agttggttgc    840
tttaacaaaa ttcctgcaat tccacctacc ccagattcct tgtatactat ttcgtttact    900
tctggtacta caggtttacc taaaggtgtg gaaatgtctc acagaaacat tgcgtctggg    960
atagcatttg ctttttctac cttcagaata ccgccagata aaagaaacca acagttatat   1020
gatatgtgtt ttttgccatt ggctcatatt tttgaaagaa tggttattgc gtatgatcta   1080
gccatcgggt ttggaatagg cttcttacat aaaccagacc caactgtatt ggtagaggat   1140
ttgaagattt tgaaacctta cgcggttgcc ctggttccta gaatattaac acggtttgaa   1200
gccggtataa aaaacgcttt ggataaatcg actgtccaga ggaacgtagc aaatactata   1260
ttggattcta aatcggccag atttaccgca agaggtggtc cagataaatc gattatgaat   1320
tttctagttt atcatcgcgt attgattgat aaaatcagag actctttagg tttgtccaat   1380
aactcgttta taattaccgg atcagctccc atatctaaag ataccttact atttttaaga   1440
agtgccttgg atattggtat aagacagggc tacggcttaa ctgaaacttt tgctggtgtc   1500
tgtttaagcg aaccgtttga aaaagatgtc ggatcttgtg gtgccatagg tatttctgca   1560
gaatgtagat tgaagtctgt tccagaaatg ggttaccatg ccgacaagga tttaaaaggt   1620
gaactgcaaa ttcgtggccc acaggttttt gaaagatatt ttaaaaatcc gaatgaaact   1680
tcaaaagccg ttgaccaaga tggttggttt tccacgggag atgttgcatt tatcgatgga   1740
aaaggtcgca tcagcgtcat tgatcgagtc aagaactttt tcaagctagc acatggtgaa   1800
tatattgctc cagagaaaat cgaaaatatt tatttatcat catgccccta tatcacgcaa   1860
atatttgtct ttggagatcc tttaaagaca tttttagttg gcatcgttgg tgttgatgtt   1920
gatgcagcgc aaccgatttt agctgcaaag cacccagagg tgaaaacgtg gactaaggaa   1980
gtgctagtag aaaacttaaa tcgtaataaa aagctaagga aggaattttt aaacaaaatt   2040
aataaatgca ccgatgggct acaaggattc gaaaaattgc ataacatcaa agtcggactt   2100
```

gagcctttaa ctctcgagga tgatgttgtg acgccaactt ttaaaataaa gcgtgccaaa 2160
gcatcaaaat tcttcaaaga tacattagac caactatacg ccgaaggttc actagtcaag 2220
acagaaaagc tttag 2235

<210> SEQ ID NO 41
<211> LENGTH: 2235
<212> TYPE: DNA
<213> ORGANISM: Saccharomyces cerevisiae

<400> SEQUENCE: 41
atggccgctc cagattatgc acttaccgat ttaattgaat cggatcctcg tttcgaaagt 60
ttgaagacaa gattagccgg ttacaccaaa ggctctgatg aatatattga agagctatac 120
tctcaattac cactgaccag ctatcccagg tacaaaacat ttttaaagaa acaggcggtt 180
gccatttcga atccggataa tgaagctggt tttagctcga tttataggag ttctctttct 240
tctgaaaatc tagtgagctg tgtggataaa aacttaagaa ctgcatacga tcacttcatg 300
ttttctgcaa ggagatggcc tcaacgtgac tgtttaggtt caaggccaat tgataaagcc 360
acaggcacct gggaggaaac attccgtttc gagtcgtact ccacggtatc taaaagatgt 420
cataatatcg gaagtggtat attgtctttg gtaaacacga aaaggaaacg tcctttggaa 480
gccaatgatt ttgttgttgc tatcttatca cacaacaacc ctgaatggat cctaacagat 540
ttggcctgtc aggcctattc tctaactaac acggctttgt acgaaacatt aggtccaaac 600
acctccgagt acatattgaa tttaaccgag gcccccattc tgatttttgc aaaatcaaat 660
atgtatcatg tattgaagat ggtgcctgat atgaaatttg ttaatacttt ggtttgtatg 720
gatgaattaa ctcatgacga gctccgtatg ctaaatgaat cgttgctacc cgttaagtgc 780
aactctctca atgaaaaaat cacatttttt tcattggagc aggtagaaca agttggttgc 840
tttaacaaaa ttcctgcaat tccacctacc ccagattcct tgtatactat ttcgtttact 900
tctggtacta caggtttacc taaaggtgtg gaaatgtctc acagaaacat tgcgtctggg 960
atagcatttg ctttttctac cttcagaata ccgccagata aaagaaacca acagttatat 1020
gatatgtgtt ttttgccatt ggctcatatt tttgaaagaa tggttattgc gtatgatcta 1080
gccatcgggt ttggaatagg cttcttacat aaaccagacc caactgtatt ggtagaggat 1140
ttgaagattt tgaaacctta cgcggttgcc ctggttccta gaatattaac acggtttgaa 1200
gccggtataa aaaacgcttt ggataaatcg actgtccaga ggaacgtagc aaatactata 1260
ttggattcta aatcggccag atttaccgca agaggtggtc cagataaatc gattatgaat 1320
tttctagttt atcatcgcgt attgattgat aaaatcagag actctttagg tttgtccaat 1380
aactcgttta taattaccgg atcagctccc atatctaaag ataccttact atttttaaga 1440
agtgccttgg atattggtat aagacagggc tacggcttaa ctgaaacttt tgctggtgtc 1500
tgtttaagcg aaccgtttga aaaagatgtc ggatcttgtg gtgccatagg tatttctgca 1560
gaatgtagat tgaagtctgt tccagaaatg ggttaccatg ccgacaagta tttaaaaggt 1620
gaactgcaaa ttcgtggccc acaggttttt gaaagatatt ttaaaaatcc gaatgaaact 1680
tcaaaagccg ttgaccaaga tggttggttt tccacgggag atgttgcatt tatcgatgga 1740
aaaggtcgca tcagcgtcat tgatcgagtc aagaactttt tcaagctagc acatggtgaa 1800
tatattgctc cagagaaaat cgaaaatatt tatttatcat catgccccta tatcacgcaa 1860
atatttgtct ttggagatcc tttaaagaca tttttagttg gcatcgttgg tgttgatgtt 1920

```
gatgcagcgc aaccgatttt agctgcaaag cacccagagg tgaaaacgtg gactaaggaa   1980

gtgctagtag aaaacttaaa tcgtaataaa aagctaagga aggaattttt aaacaaaatt   2040

aataaatgca ccgatgggct acaaggattc gaaaaattgc ataacatcaa agtcggactt   2100

gagcctttaa ctctcgagga tgatgttgtg acgccaactt ttaaaataaa gcgtgccaaa   2160

gcatcaaaat tcttcaaaga tacattagac caactatacg ccgaaggttc actagtcaag   2220

acagaaaagc tttag                                                    2235
```

<210> SEQ ID NO 42
<211> LENGTH: 1686
<212> TYPE: DNA
<213> ORGANISM: Escherichia coli

<400> SEQUENCE: 42

```
ttgaagaagg tttggcttaa ccgttatccc gcggacgttc cgacggagat caaccctgac     60

cgttatcaat ctctggtaga tatgtttgag cagtcggtcg cgcgctacgc cgatcaacct    120

gcgtttgtga atatgggggga ggtaatgacc ttccgcaagc tggaagaacg cagtcgcgcg    180

tttgccgctt atttgcaaca agggttgggg ctgaagaaag gcgatcgcgt tgcgttgatg    240

atgcctaatt tattgcaata tccggtggcg ctgtttggca ttttgcgtgc cgggatgatc    300

gtcgtaaacg ttaacccgtt gtataccccg cgtgagcttg agcatcagct taacgatagc    360

ggcgcatcgg cgattgttat cgtgtctaac tttgctcaca cactggaaaa agtggttgat    420

aaaaccgccg ttcagcacgt aattctgacc cgtatgggcg atcagctatc tacggcaaaa    480

ggcacggtag tcaatttcgt tgttaaatac atcaagcgtt tggtgccgaa ataccatctg    540

ccagatgcca tttcatttcg tagcgcactg cataacggct accggatgca gtacgtcaaa    600

cccgaactgg tgccggaaga tttagctttt ctgcaataca ccggcggcac cactggtgtg    660

gcgaaaggcg cgatgctgac tcaccgcaat atgctggcga acctggaaca ggttaacgcg    720

acctatggtc cgctgttgca tccgggcaaa gagctggtgg tgacggcgct gccgctgtat    780

cacatttttg ccctgaccat taactgcctg ctgtttatcg aactgggtgg gcagaacctg    840

cttatcacta acccgcgcga tattccaggg ttggtaaaag agttagcgaa atatccgttt    900

accgctatca cgggcgttaa caccttgttc aatgcgttgc tgaacaataa agagttccag    960

cagctggatt tctccagtct gcatctttcc gcaggcggtg ggatgccagt gcagcaagtg   1020

gtggcagagc gttgggtgaa actgaccgga cagtatctgc tggaaggcta tggccttacc   1080

gagtgtgcgc cgctggtcag cgttaaccca tatgatattg attatcatag tggtagcatc   1140

ggtttgccgg tgccgtcgac ggaagccaaa ctggtggatg atgatgataa tgaagtacca   1200

ccaggtcaac cgggtgagct ttgtgtcaaa ggaccgcagg tgatgctggg ttactggcag   1260

cgtcccgatg ctaccgatga aatcatcaaa aatggctggt tacacaccgg cgacatcgcg   1320

gtaatggatg aagaaggatt cctgcgcatt gtcgatcgta aaaaagacat gattctggtt   1380

tccggtttta acgtctatcc caacgagatt gaagatgtcg tcatgcagca tcctggcgta   1440

caggaagtcg cggctgttgg cgtaccttcc ggctccagtg gtgaagcggt gaaaatcttc   1500

gtagtgaaaa aagatccatc gcttaccgaa gagtcactgg tgactttttg ccgccgtcag   1560

ctcacgggat acaaagtacc gaagctggtg gagtttcgtg atgagttacc gaaatctaac   1620

gtcggaaaaa ttttgcgacg agaattacgt gacgaagcgc gcggcaaagt ggacaataaa   1680

gcctga                                                              1686
```

<210> SEQ ID NO 43
<211> LENGTH: 1647
<212> TYPE: DNA
<213> ORGANISM: Escherichia coli

<400> SEQUENCE: 43

```
atgaaagtga cattaacgtt taacgaacaa cgtcgtgcgg cgtatcgtca gcaagggtta      60
tggggcgatg cttcgctggc cgattactgg cagcagaccg ctcgtgcgat gccagacaaa     120
attgccgtgg tcgataatca tggtgcatcg tacacctata gcgcgctcga tcacgccgcg     180
agctgtctgg caaactggat gttagcgaag ggtattgaat caggcgatcg catcgcattt     240
caactgcctg gctggtgtga atttaccgtt atctatcttg cctgcctgaa aatcggtgca     300
gtttccgtgc cgctgttgcc ttcctggcgg gaagcagaac tggtgtgggt gctcaataag     360
tgtcaggcaa aaatgttctt tgcaccgacg ttgtttaaac aaacgcgtcc ggtagattta     420
atcctgccgc tgcaaaatca gcttccacaa ctacaacaaa ttgtcggcgt ggacaaactg     480
gctcccgcca cctcttccct ctcattaagt cagattatcg ccgacaatac ctcactgacc     540
acggcgataa cgacccacgg cgatgaatta gctgcggtgc tgtttacctc cggaaccgag     600
ggtctgccaa agggcgtgat gctaacgcat aacaatattc tcgccagtga gcgggcttat     660
tgcgcgcgac tgaatctgac ctggcaggat gtctttatga tgcctgcgcc acttggtcac     720
gcaacgggct ttctgcatgg cgtaacggca ccattcttaa ttggcgctcg cagcgtgttg     780
ttagatattt tcactcctga tgcgtgtctc gcgctgcttg agcagcagcg ttgcacctgt     840
atgctcggcg caacgccgtt tgtctatgat cttttgaatg tactagagaa acaacccgcg     900
gacctttcag cgctgcgttt ctttctttgc ggcggaacca caatccccaa aaaagtggcg     960
cgtgaatgcc agcagcgcgg cattaaatta ttaagtgttt atggttccac agaaagttcg    1020
ccgcatgcgg tggtgaatct cgatgatcct ttgtcgcgct ttatgcacac cgatggttac    1080
gctgccgcag gtgtagagat taaagtggtc gatgacgcac gcaagacctt accgccaggt    1140
tgcgaaggtg aagaagcctc gcgtggcccc aatgtgttta tggggtattt tgatgaacct    1200
gaattaaccg cccgtgccct ggatgaagaa ggctggtatt acagcggcga tctctgccgt    1260
atggatgagg ctggctatat aaaaattacc ggacgcaaaa aagatattat tgtccgcggc    1320
ggcgaaaata ttagcagccg tgaagtggaa gatattttat tgcagcatcc taaaattcac    1380
gatgcctgtg tggttgcaat gtccgatgaa cgtttaggtg aacgatcatg cgcttatgtc    1440
gtgctgaaag cgccgcatca ttcattatcg ctggaagagg tagtggcttt ttttagccgt    1500
aaacgggtcg caaaatataa atatcctgaa catatcgtgg taatcgaaaa actaccgcga    1560
actacctcag gtaaaataca aaagtttttg ttaagaaaag atattatgcg gcgtttaacg    1620
caggatgtct gtgaagagat tgaataa                                        1647
```

<210> SEQ ID NO 44
<211> LENGTH: 1722
<212> TYPE: DNA
<213> ORGANISM: Mus musculus

<400> SEQUENCE: 44

```
atgcagtggc tgaagagttt ccagatctgc aaagtcttac agggcttctc cctaagcccc      60
acccagctgc acagacggtt gttttcaaga gttggagctc caagatggaa tgaccatgat     120
tcacctgagg agtttaactt tgcaagtgat gtcctggact actgggctca aatggaggag     180
gagggcaaga gaggaccaag tccagccttt tggtgggtga atggccaagg agatgaaata     240
```

```
aagtggagct tcaggaagct gagggacctc acctgtcgca ctgccaacgt ctttgagcag    300
atttgtggcc tgcagcaagg agatcacctg gccttgattc tgccccgagt gcccgagtgg    360
tggttggtga cagtgggctg catgcgaaca gggatcatct tcatgcctgg gactacccaa    420
ctgaaagcca aggacattct ctaccgaata caaatatctc gagccaaagc cattgtgacc    480
acagctagcc ttgtcccaga ggtggaatct gtggcttctg agtgtcctga tctgaaaacc    540
aagctggtgg tgtctgatca cagccatgaa gggtggcttg atttctgttc actgattaaa    600
tcagcatccc cagaccatac ttgtattaag tcaaagatga aggatcccat ggccatcttc    660
ttcaccagtg ggaccacagg ctaccccaag atggcaaagc acaaccaggg acttgccttc    720
cggtcatata tcccttcatg cagaaaatta ttgaagctga agacatctga catcttgtgg    780
tgcatgtcag acccaggatg gattctggct accgtggggt gcctgatcga gccatggaca    840
tcaggatgta cagtcttcat ccaccacctc cctcaattcg accccaaagt cattgtagag    900
gtactgttca aataccccat cactcagtgc cttgctgccc caggcgtgta tcgaatggtt    960
cttcagcaga aaacctccaa cctcaggttc ccccaccctg agcattgcac tactggtggg   1020
gagagcctgc tgcctgagga gtatgagcag tggaagcaaa ggacaggtct ttccatccac   1080
gaggtctatg gacagtcaga aacggggatc agcagtgcca ccctccggga aatgaagatc   1140
aagcgaggct ccatagggaa ggccatctta ccctttgact tgcagatcat cgatgaaaag   1200
ggcaacatcc tcccacccaa cactgaagga tacattggca tcaggatcaa gcccaccagg   1260
cctctaggcc tcttcatgga atatgagaat agcccagaga gcacatctga agtggagtgt   1320
ggggactttt acaatagtgg ggatagagcg accattgatg aagagggcta catctggttc   1380
ttgggaaggg gcgatgatgt catcaatgct tccgggtatc gcatcgggcc tgtagaggtg   1440
gagaacgcct tggcggagca cccagcagtg gcagagtctg cggtggtgag cagcccggac   1500
aaggatcgag gagaggtggt gaaggcgttt attgtcctca acccagagtt cctgtcacac   1560
gatcaggaac agcttatcaa agagctacag catcatgtga agtcagtgac ggcaccatac   1620
aagtacccca ggaaggtgga gtttgtttca gaattgccca aaactgtcac aggcaaaatc   1680
aaaaggaagg aacttcgaaa caaggagttt ggtcagctat ga                      1722
```

```
<210> SEQ ID NO 45
<211> LENGTH: 1542
<212> TYPE: DNA
<213> ORGANISM: Marinobacter aquaeoli

<400> SEQUENCE: 45
```

```
tcaggcagct tttttgcgct ggcgcgcggt tttcagactg tacacctttc gttctttcag     60
ggcatagcga ttgagcccgg ccaggtgaat cttgcgcagg tagagctccc agtcaatcag    120
gcgggcatcc accgggaaca gccctttatc gacctcaccc atccggttcg ccagcgccat    180
cagctcatcg ttccggaaga tataatccgg cgcggtgtag aaaccaaaaa tggttgccag    240
cgactgggtg gtatccagat tcctgagcat tttcaggtcc cgggaatttc ccagtaattt    300
gagcacacgg tccgtcaggg agagcggtaa gcgaacacca ctgatcacca aatcaaacag    360
cgcccggtta accgccagaa acggcttgct gggctgccgg tagaacaggt gatcgtaggc    420
agcgtaattg gcttttgatt ccgccatgag atgatcgatg aactcaccca gggagattgg    480
attgccgccc ccgctgcaac attgatagat gcgacgtcga ccgggttctc caagagcttc    540
cgccagggaa aggatgatgg agttggccac caggtccact ggaatcacat cgatgatacc    600
ggagcgtttg cccgggaaga gggtgacttt ttcccgtgcg taagccagga tgatggcatc    660
```

```
tgccaccttc accccctcaa tccagccggg cgctggttcc tccagggcac tttcgataat    720

cgaaggacgc agaatggtca gcgtgcgccc gtttaacgcc ttcatcagca actgttcgcc    780

cagccacttg gtaaaggtgt aggtatcgct ccagccatag cggttggctt cccgaatccc    840

caggtccacc agcttcctct ccagcacttt gccggaataa cgggcctgaa cgtcttcaat    900

tttatcctga agcaggcgaa caagctcttc tatctcatag aagccgtccg gggaacgcgg    960

cacggcctcg cctgccggct tgatcaccga ttcggttacc tgccccgagt tcatgccatt   1020

gacatagcag gtggagacct gcaggaccgc aagcttcgga ttcaaatcca ccatgccggc   1080

aatattccga aggcacaggg tgttgatggc cagcgccttg tcgagctctt cacggaaatt   1140

cacgcttgca gcggagttga tcaccgcatc cagttcggtg gcgagtttgc gatagtcttc   1200

ctgccctatc ccgaaacccg cttcggtcac ctcaccggtc acgcagtgaa tgcgctcttc   1260

cagaaaggcg tcaaatccct ctgaatcggc ctcgcgaaga cggtcaaaca ccgaggaggt   1320

ggcaatttct tccaggaaac gggaacgagc atccggatgc cgtttattgc cccggatcag   1380

caggtaaatt gcgccgatat caggcaccgc ccgaatcagc ctttcgagga ccaccttgcc   1440

cagaaagcca gtggtaccgg tgatcagaac ccgcttgcca cggagctgtc cgagcacctt   1500

tgatgatgaa gtgtcagcgt gatgtacctg ctgtattgcc at                      1542
```

```
<210> SEQ ID NO 46
<211> LENGTH: 1542
<212> TYPE: DNA
<213> ORGANISM: Artificial Sequence
<220> FEATURE:
<223> OTHER INFORMATION: Maqu_2220 reductase (ABM19299.1) DNA sequence,
      codon-optimized for Synechocystis

<400> SEQUENCE: 46
```

```
atggcaatac agcaggtaca tcacgctgac acttcatcat caaaggtgct cggacagctc     60

cgtggcaagc gggttctgat caccggtacc actggctttc tgggcaaggt ggtcctcgaa    120

aggctgattc gggcggtgcc tgatatcggc gcaatttacc tgctgatccg gggcaataaa    180

cggcatccgg atgctcgttc ccgtttcctg gaagaaattg ccacctcctc ggtgtttgac    240

cgtcttcgcg aggccgattc agagggattt gacgcctttc tggaagagcg cattcactgc    300

gtgaccggtg aggtgaccga agcgggtttc gggatagggc aggaagacta tcgcaaactc    360

gccaccgaac tggatgcggt gatcaactcc gctgcaagcg tgaatttccg tgaagagctc    420

gacaaggcgc tggccatcaa caccctgtgc cttcggaata ttgccggcat ggtggatttg    480

aatccgaagc ttgcggtcct gcaggtctcc acctgctatg tcaatggcat gaactcgggg    540

caggtaaccg aatcggtgat caagccggca ggcgaggccg tgccgcgttc cccggacggc    600

ttctatgaga tagaagagct tgttcgcctg cttcaggata aaattgaaga cgttcaggcc    660

cgttattccg gcaaagtgct ggagaggaag ctggtggacc tggggattcg ggaagccaac    720

cgctatggct ggagcgatac ctacaccttt accaagtggc tgggcgaaca gttgctgatg    780

aaggcgttaa acgggcgcac gctgaccatt ctgcgtcctt cgattatcga aagtgccctg    840

gaggaaccag cgcccggctg gattgagggg gtgaaggtgg cagatgccat catcctggct    900

tacgcacggg aaaaagtcac cctcttcccg ggcaaacgct ccggtatcat cgatgtgatt    960

ccagtggacc tggtggccaa ctccatcatc ctttccctgg cggaagctct tggagaaccc   1020

ggtcgacgtc gcatctatca atgttgcagc gggggcggca atccaatctc cctgggtgag   1080

ttcatcgatc atctcatggc ggaatcaaaa gccaattacg ctgcctacga tcacctgttc   1140
```

```
taccggcagc ccagcaagcc gtttctggcg gttaaccggg cgctgtttga tttggtgatc   1200

agtggtgttc gcttaccgct ctccctgacg gaccgtgtgc tcaaattact gggaaattcc   1260

cgggacctga aaatgctcag gaatctggat accacccagt cgctggcaac cattttttggt  1320

ttctacaccg cgccggatta tatcttccgg aacgatgagc tgatggcgct ggcgaaccgg   1380

atgggtgagg tcgataaagg gctgttcccg gtggatgccc gcctgattga ctgggagctc   1440

tacctgcgca agattcacct ggccgggctc aatcgctatg ccctgaaaga acgaaaggtg   1500

tacagtctga aaaccgcgcg ccagcgcaaa aaagctgcct aa                      1542
```

<210> SEQ ID NO 47
<211> LENGTH: 1584
<212> TYPE: DNA
<213> ORGANISM: Arabidopsis thaliana

<400> SEQUENCE: 47

```
atggctacca caaatgtcct cgccacgagc cacgccttca aattgaatgg tgtcagctac     60

ttctcctctt ttccccgcaa acctaaccac tacatgcctc gtcgtcgttt atcacatact    120

actcgtagag tccaaacttc gtgtttttat ggtgagacgt cttttgaagc tgtaacgtcg    180

ttagttacgc ctaagacaga aacaagtcgt aacagtgacg gaattggaat cgtccgtttc    240

ttagaaggga aaagctatct tgttactggt gcaacagggt ttcttgccaa agtgttgatt    300

gagaaactgt tgagggaaag tcttgaaatt gggaagatct tccttctgat gagatccaag    360

gatcaagaat cagcaaacaa gagactctac gatgagatca taagctcgga tctgttcaag    420

cttctgaagc aaatgcatgg gagctcttac gaagctttca tgaagagaaa gttgattcca    480

gtaattggag acattgagga agacaatcta gggatcaaat ctgaaatagc aaacatgatc    540

agtgaggaga ttgatgttat tatcagttgt ggtggtcgta caacattcga cgacagatac    600

gattctgccc taagtgtcaa tgctcttgga ccggcttacg tgactggtaa gagagagggg    660

acagtactag aaactcctct ctgcattgga gaaaacataa cttctgactt gaacatcaaa    720

tccgagctga aactagcttc agaagctgta agaaagttcc gtggcagaga agaaatcaag    780

aaactcaaag aactcggttt tgaaagagct caacactatg ggtgggaaaa tagttacaca    840

ttcacaaaag ccataggtga ggctgtaatt cacagcaagc gaggaaactt gcctgtagtg    900

atcataaggc ctagtattat cgaaagctct tacaatgagc ctttccctgg ctggatccaa    960

gggacaagaa tggctgatcc aatcatcttg gcttatgcca aaggccagat ttctgacttc   1020

tgggcagatc ctcaatcttt gatggacatt atacctgttg acatggttgc aaacgcagca   1080

atagcagcca tggcaaagca tggttgtggt gtcccagagt tcaaagttta caatttaact   1140

tcttcatctc atgtgaaccc catgcgtgct ggcaaattga tagacctctc tcatcaacat   1200

ctgtgtgact ttccattgga agaaacagtg atagacttag agcatatgaa aatccacagt   1260

tccttagagg gtttcacttc tgctttatcg aacacaataa taaaacagga aagagtgatt   1320

gataatgaag gaggaggatt gagcacgaag ggaaagagga agctaaacta ttttgtgtcc   1380

ttggcaaaaa catatgagcc ttacacattc tttcaagctc ggtttgacaa caccaataca   1440

acaagtctga tacaggagat gtcaatggaa gagaaaaaaa cgtttgggtt cgatatcaaa   1500

ggcattgact gggagcatta cattgtcaac gttcatcttc caggtctcaa aaaggaattt   1560

ctttctaaga agaagactga gtaa                                          1584
```

<210> SEQ ID NO 48

<211> LENGTH: 1443
<212> TYPE: DNA
<213> ORGANISM: Arabidopsis thaliana

<400> SEQUENCE: 48

```
tgtttttatg gtgagacgtc ttttgaagct gtaacgtcgt tagttacgcc taagacagaa     60
acaagtcgta acagtgacgg aattggaatc gtccgtttct tagaagggaa aagctatctt    120
gttactggtg caacagggtt tcttgccaaa gtgttgattg agaaactgtt gagggaaagt    180
cttgaaattg ggaagatctt ccttctgatg agatccaagg atcaagaatc agcaaacaag    240
agactctacg atgagatcat aagctcggat ctgttcaagc ttctgaagca aatgcatggg    300
agctcttacg aagctttcat gaagagaaag ttgattccag taattggaga cattgaggaa    360
gacaatctag ggatcaaatc tgaaatagca aacatgatca gtgaggagat tgatgttatt    420
atcagttgtg gtggtcgtac aacattcgac gacagatacg attctgccct aagtgtcaat    480
gctcttggac cggcttacgt gactggtaag agagagggga cagtactaga aactcctctc    540
tgcattggag aaaacataac ttctgacttg aacatcaaat ccgagctgaa actagcttca    600
gaagctgtaa gaaagttccg tggcagagaa gaaatcaaga aactcaaaga actcggtttt    660
gaaagagctc aacactatgg gtgggaaaat agttacacat tcacaaaagc cataggtgag    720
gctgtaattc acagcaagcg aggaaacttg cctgtagtga tcataaggcc tagtattatc    780
gaaagctctt acaatgagcc tttccctggc tggatccaag ggacaagaat ggctgatcca    840
atcatcttgg cttatgccaa aggccagatt tctgacttct gggcagatcc tcaatctttg    900
atggacatta tacctgttga catggttgca aacgcagcaa tagcagccat ggcaaagcat    960
ggttgtggtg tcccagagtt caaagtttac aatttaactt cttcatctca tgtgaacccc   1020
atgcgtgctg gcaaattgat agacctctct catcaacatc tgtgtgactt tccattggaa   1080
gaaacagtga tagacttaga gcatatgaaa atccacagtt ccttagaggg tttcacttct   1140
gctttatcga acacaataat aaaacaggaa agagtgattg ataatgaagg aggaggattg   1200
agcacgaagg gaaagaggaa gctaaactat tttgtgtcct tggcaaaaac atatgagcct   1260
tacacattct ttcaagctcg gtttgacaac accaatacaa caagtctgat acaggagatg   1320
tcaatggaag agaaaaaaac gtttgggttc gatatcaaag gcattgactg ggagcattac   1380
attgtcaacg ttcatcttcc aggtctcaaa aaggaatttc tttctaagaa gaagactgag   1440
taa                                                                 1443
```

<210> SEQ ID NO 49
<211> LENGTH: 1628
<212> TYPE: DNA
<213> ORGANISM: Ostrinia scapulalis

<400> SEQUENCE: 49

```
gaaaacagtc tagaaaaatg tcagcaaata ccatggaaac tgatgaacaa tttactgata     60
attcaccaat tgtgaatttt tactctggaa aatctgtttt tgttactgga gctacaggat    120
ttctggggac ggttttagtc gagaaactgc tgttctcttg caaaggaata aataatattt    180
acattttgat aaagcagaca gaagacctga ccattgaagc gaggatttta aattatttga    240
attcgaaggc ttttcataga gtgaaaaata caaacccaga gttgatgaaa aaaattatac    300
cgatatgtgg gaatttggaa gataaaaatc ttggtatcag cgacagcgac atgaaaacgc    360
ttctagagga ggtatccatc gtttttcatg tagctgcaaa attgttattt aaaatgagct    420
tgactgcagc agtcaatata aataccaaac ccactgaaca gctcatagcg atttgcaaaa    480
```

```
aaatgcggcg taatcccatt ttcatctatg tctctagcgc atacagtaat gtaaatgaac    540

aaataatcga tgaaaaagtg tacaacactg gagtaccttt ggaaactatt tatgatacgc    600

tggatacaga aaatacacga ataacggata ttttttaga taaaagacca aatacgtata    660

cctattcaaa agctcttgca gaagtagtag ttgaaaaaga atttgatgaa tcagcagcca    720

ttgttcggcc ttcgataatt gtgtcttcga ttcgggaacc cataccggga tggttgagcg    780

gttcgcacgg attccctagg gtagtaggag cagcatgcaa ggggctcctc ttgcggtggc    840

atggggacgg tacagttgtc tgcgacctta tacctgtaga ccacgttgcg aacctcatca    900

ttgcagcagc atgggaatcc aatgaaagac ggttaatggg caacaaagga gtcaaggtat    960

ataactgttg ttcaagccta cggaacccaa tagacgtgat caccgtagtt aaaacttgca   1020

taaaatacag gaaatatttt ggaactcgca ccatgtccat atttacccca cgatttatta   1080

tgaaaaagaa ttactttatc tacaaattgt tgtacttcac ctgccacaca ataccggcag   1140

ctataataga cggcttcttc tggctcactg gacggactcc aataatgctg aagaccctgg   1200

acaaactcag caaaatctct tctgtcctgg agtacttcac gcaccaccaa tttatattcc   1260

tggacagcaa cgtcagagga cttctcagaa ggatggaggg cacagacaga caaacgttta   1320

attttgatgt cactgaaatt gagtgggagc cgtatctaca aaactttgtg cgcggcatcg   1380

caaataatta cgactatagt atgtaatata gtattgaggt ttgatattga ttgaggagag   1440

gtgaaattta gcctatgtta ctcgtgaata atgtagcttt cgaatggtga aagaattatt   1500

aaaaacggtc cagtagtttt tgagcctata aattacaacc aaacaaacct aatattagtg   1560

tagatttgaa tttgaaaagt gaggtataaa atcttgtcat tactgtcaaa aaaaaaaaaa   1620

aaaaaaaa                                                            1628
```

<210> SEQ ID NO 50
<211> LENGTH: 1986
<212> TYPE: DNA
<213> ORGANISM: Marinobacter aquaeoli

<400> SEQUENCE: 50

```
atgaattatt tcctgacagg cggcaccggt tttatcggtc gttttctggt tgagaaactc     60

ttggcgcgcg gcggcaccgt gtatgttctg gttcgcgagc agtcccagga caagctggag    120

cggctccggg agcgctgggg tgcagacgac aagcaagtga aggctgtgat cggcgacctc    180

accagcaaaa accttggtat tgacgcgaaa acgctgaaat cactgaaagg aaatatcgac    240

cacgtattcc atcttgccgc ggtctacgac atgggcgcag acgaagaagc ccaggccgcc    300

accaatatcg aaggcaccag ggcggctgtt caggccgccg aagccatggg cgccaagcat    360

ttccatcatg tgtcatccat cgcggcagcg ggtctgttca agggtatctt ccgggaggat    420

atgttcgaag aagccgagaa gcttgatcat ccttacctgc gcaccaagca cgaatccgaa    480

aaagttgtgc gtgaagaatg caaggttccg ttccgcatct accgccctgg tatggtcatt    540

ggccattcgg aaaccggcga aatggacaag gttgacgggc cctattactt cttcaagatg    600

attcagaaga tccgtcatgc gttgccccag tgggtaccca ccatcggtat tgaaggtggc    660

cggctgaaca ttgtgccggt ggatttcgtg gtcgatgcac tggatcacat tgcccatctg    720

gaaggcgaag atggcaactg tttccatctg gtggactccg atccgtataa ggtgggtgag    780

atcctcaata ttttctgcga ggccggccat gccccccgca tgggtatgcg catcgattcc    840

cggatgttcg gttttattcc gccgtttatt cgccagagca tcaagaatct gcctccggtc    900
```

```
aagcgcatta ctggtgcgct tctggatgac atgggcattc cgccctcggt gatgtccttc    960

attaattacc cgacccgttt tgatacccgg gagctggagc gggttctgaa gggcacagac   1020

attgaggtgc cgcgtctgcc gtcctatgcc ccggttatct gggactactg ggagcgcaat   1080

ctggacccgg acctgttcaa ggaccgcacc ctcaagggca cggttgaagg taaggtttgc   1140

gtggtcaccg gcgcgacctc gggtattggc ctggcaacgg cagagaagct ggcagaggcc   1200

ggtgccattc tggtcattgg tgcgcgcacc aaggaaactc tggatgaagt ggcggccagt   1260

ctggaggcca agggtggcaa cgtgcatgcg taccagtgcg acttttcgga catggacgac   1320

tgcgaccgct ttgtgaagac ggtgctggat aatcacggcc acgtggatgt actggtgaat   1380

aacgcgggtc gctccatccg ccgctcgctg gcgttgtctt ttgaccggtt ccacgatttt   1440

gagcggacca tgcagctgaa ctactttggc tccgttcggc tgatcatggg ctttgcgcca   1500

gccatgctgg agcgtcgccg cgggcacgtg gtgaatattt cttccatcgg ggtacttacc   1560

aacgctccgc gtttctcggc ctatgtctcc tcgaaatccg cactggacgc gttcagccgc   1620

tgtgccgctg cagaatggtc ggatcgcaac gtgaccttca ccaccatcaa catgccgttg   1680

gtgaaaacgc cgatgatcgc gcccaccaag atctacgatt ccgtgccgac gctgacgccg   1740

gatgaagccg cccagatggt ggcggatgcg attgtgtacc ggcccaagcg cattgccacc   1800

cgtcttggcg tgttcgcgca ggttctgcat gcgctggcac cgaagatggg tgagatcatt   1860

atgaacactg gctaccggat gttcccggat tctccagcag ccgctggcag caagtccggc   1920

gaaaagccga aagtctctac cgagcaggtg gcctttgcgg cgattatgcg gggatatac   1980

tggtaa                                                              1986
```

```
<210> SEQ ID NO 51
<211> LENGTH: 1518
<212> TYPE: DNA
<213> ORGANISM: Hahella chejuensis

<400> SEQUENCE: 51

ttacgcagcg cggctgcgag gttttgctgc aggcgggttc atcttcacca ctttcggccg     60

cagcgcgtac ttgttcagac ccgccacgtg aacttcccgc aagtagtgcg cccagtcata    120

catacccgca ttcacgggga attcgctctg gtcatattcc ccaagacggg tggatagctc    180

ctgcagacgg cggttgctga aggtatagct gggagaggta tagaaggaaa acaccttgga    240

cagtttcatc gtagtttcca tgttgctcag cttgcgcccg gaagccttac ggccaaacaa    300

gctctgcaga cgggaactcc atttcagcat gtggaaactg atcgccatca acgcgtgaaa    360

cacggcgccg ggaatcatta caaagggctt cttcggcttg cggtagaaca gtttgtcgtg    420

cgtctgataa ttgtgctccg cctcttgctg cacatgccca atgacttccc gaatcctgat    480

tggattaacc tcgctgctgc aacactggta gatgcgatgg gcgccggaat ccagcagcgc    540

ttccgtggcg ctcaggatga tgctgttggc caccaggtcc gccggaatga tatcaatgac    600

cgcattcttc ttgccgggaa acaaagacac cttttctctg gcgtaagcga ggatgatcgc    660

atccgccact ttcacccccct caatccagcc cggcgccggt cccagcagcg tactttcaac    720

aatggaaggt cgcaggatgg tcagggtttt gccatacagc tccttcatca gcaactgctc    780

gcccatccat ttagtgaagg tataggtatc gttccaacca tacttattgg cttctttgat    840

acccaggtcg ataagatcct ttccctgct atgatcatcc gccgcagcgg cggacacttg    900

ctctacatcc tgcagcaaac gcgcaatcag cggctcaact tcatagtagc cgcgttctga    960

acgctcaatg cgttctcccg ccgggctgac gatttcctct tccatcactc cctgattgaa   1020
```

```
gccgttgacg tagcaggtgg atacctgcac gacagggcag tccgccgcgc gccgcgacag   1080

ttcaatgata tttttaaggc acagggtatt gatggtgaga gcctgatcca gcgcttcgcg   1140

gaaattgacg ctggcggctg aattgataat aacgtcgata tctgcggcca ggtcggtaaa   1200

gtccttctcc gacaggccaa acagaggctc cgtcacctct ccggtcacgc agtggatgcg   1260

ggtttcgcac aactcctcga aacgacttcc ctgcgatgcc ttgagagtat cgaaaataga   1320

tgaggtcgcg atctcattct ggaaccgctt tcgcgctgta gggttctttg aattaccccg   1380

tatcagcaaa taaatcttcc caattgtcgg cacgctgcgc agcagcttct ccagtaccac   1440

cttgccgacg aatcccgtcg tccccgtaat cagtacattc ttattagcaa aagcagttaa   1500

cgtaagtgat tgcttcat                                                 1518
```

<210> SEQ ID NO 52
<211> LENGTH: 1768
<212> TYPE: DNA
<213> ORGANISM: Simmondsia chinensis

<400> SEQUENCE: 52

```
aaatcctcca ctcatacact ccacttctct ctctctctct ctctctctga aacaatttga     60

gtagcaaact taaaagaaaa tggaggaaat gggaagcatt ttagagtttc ttgataacaa    120

agccattttg gtcactggtg ctactggctc cttagcaaaa atttttgtgg agaaggtact    180

gaggagtcaa ccgaatgtga agaaactcta tcttcttttg agagcaaccg atgacgagac    240

agctgctcta cgcttgcaaa atgaggtttt tggaaaagag ttgttcaaag ttctgaaaca    300

aaatttaggt gcaaatttct attcctttgt atcagaaaaa gtgactgtag tacccggtga    360

tattactggt gaagacttgt gtctcaaaga cgtcaatttg aaggaagaaa tgtggaggga    420

aatcgatgtt gttgtcaatc tagctgctac aatcaacttc attgaaaggt acgacgtgtc    480

tctgcttatc aacacatatg gagccaagta tgttttggac ttcgcgaaga agtgcaacaa    540

attaaagata tttgttcatg tatctactgc ttatgtatct ggagagaaaa atgggttaat    600

actggagaag ccttattata tgggcgagtc acttaatgga agattaggtc tggacattaa    660

tgtagagaag aaacttgtgg aggcaaaaat caatgaactt caagcagcgg gggcaacgga    720

aaagtccatt aaatcgacaa tgaaggacat gggcatcgag agggcaagac actggggatg    780

gccaaatgtg tatgtattca ccaaggcatt aggggagatg cttttgatgc aatacaaagg    840

ggacattccg cttactatta ttcgtcccac catcatcacc agcactttta aagagccctt    900

tcctggttgg gttgaaggtg tcaggaccat cgataatgta cctgtatatt atggtaaagg    960

gagattgagg tgtatgcttt gcggacccag cacaataatt gacctgatac cggcagatat   1020

ggtcgtgaat gcaacgatag tagccatggt ggcgcacgca aaccaaagat acgtagagcc   1080

ggtgacatac catgtgggat cttcagcggc gaatccaatg aaactgagtg cattaccaga   1140

gatggcacac cgttacttca ccaagaatcc atggatcaac ccggatcgca acccagtaca   1200

tgtgggtcgg gctatggtct tctcctcctt ctccaccttc cacctttatc tcacccttaa   1260

tttcctcctt cctttgaagg tactggagat agcaaataca atattctgcc aatggttcaa   1320

gggtaagtac atggatctta aaggaagacg gaggttgttg ttgcgtttag tagacattta   1380

taaaccctac ctcttcttcc aaggcatctt tgatgacatg aacactgaga agttgcggat   1440

tgctgcaaaa gaaagcatag ttgaagctga tatgttttac tttgatccca gggcaattaa   1500

ctgggaagat tacttcttga aaactcattt cccaggtgtc gtagagcacg ttcttaacta   1560
```

aaagttacgg tacgaaaatg agaagattgg aatgcatgca ccgaaagtac aacataaaag 1620
acgtggttaa agtcatggtc aaaaaagaaa taaaatgcag ttaggtttgt gttgcagttt 1680
tgattccttg tattgttact tgtacttttg atctttttct tttttaatga aatttctctc 1740
tttgttttgt gaacttttaa aaaaaaaa 1768

<210> SEQ ID NO 53
<211> LENGTH: 1470
<212> TYPE: DNA
<213> ORGANISM: Artificial Sequence
<220> FEATURE:
<223> OTHER INFORMATION: MELB17_04692 wax ester synthase (EBA00388.1)
DNA sequence, codon optimized for Synechocystis

<400> SEQUENCE: 53
atgaaacgct tggccacgtt ggatgcgtct tggctcgctg tcgaatctga cgatacgccc 60
atgcatgttg gtaacttgca gatcttctcg ctcccggaca atgcaccttc gacgttcgcc 120
ggtgatctgg tgaagtccat gaagcaagcc ggcaatgtcg aattgccctg gggctgtaaa 180
ctggtttggc ctgggtttct gggccgagtg ttggctccca cctggaaaca cgataagcat 240
attgacctgg attatcacgt ccgccactct gctctcccta aacccggagg cgagcgcgag 300
ttgggcgagc tggtttctcg actccatagt aacccccctcg acctgagtcg cccgctgtgg 360
gaatgccata tgattgaagg cttggaacat aatcggtttg cactgtatac gaaaatgcac 420
cattgcatga ttgacggcat ttccggtgtg cgcttgatgc agcgcgtgtt gtccaagtcg 480
cccgatgagc gcgacatgct gccgccttgg agtgtccgtc ccgagagcac gcggggtaag 540
aaaacggata gcgaagcatc cgtgccagga gctatctcgc aagccatgga ggccctgaag 600
ctgcaactgg gcttggcacc ccgcctctgg caggctagca atcggctgat ccattccgtc 660
cgtcacccgg aggatggatt gactgctcca ttcacgggac cagttagtaa gatcaatcac 720
cgcgttacag gtcaacgacg atttgctact cagcagtacc agctggaaga tatgaaagcg 780
atggcacgcg cgagtgggag ctcgatgaac gatattgtgc tctacctctg tggtacagcg 840
ctgcgacgct ttctgctgga acaggacgat ctccctgaga ttagcctgac cgctgggatt 900
cctgtcaaca ttcgtcccgc agatgacgag ggcaccggta cccagattag cttcatgatc 960
gcggctctgg ccaccaatca acccgatccg ctgacccggc tgaaatgtat caaagaaagt 1020
agctgcaagg cgaaagagca cctccagaaa ttgccgaaga aagcactcac acaatacacc 1080
atgatgctca tgtcgccata catcctgcaa ctcatgtctg gtttgggtgg ccgcatgcgt 1140
ccagtcttta acgttaccat tagcaacgtt cctggcccaa ctgaagatct gtactacgaa 1200
ggcgcgaagc tggaggcgat gtatcccgtt tcgttgatta cccacggcgg agccttgaat 1260
atcacctgcc tgagctatgc cggcagtttg aactttggct tcactgggtg tcgcgatact 1320
ctccccagta tgcaaaaact ggccgtctac acgggggaag ccctcgaaga actccgcaca 1380
ttgctgttgc cgccaaagaa aaagcctagc ccgcgtaaac cgcggacggc tgccaagaag 1440
aaaccggcag tgaattcgaa cgccagttaa 1470

<210> SEQ ID NO 54
<211> LENGTH: 1470
<212> TYPE: DNA
<213> ORGANISM: Marinobacter sp. ELB17

<400> SEQUENCE: 54
atgaaacgcc tggcaacatt ggacgcgtct tggctagcgg tcgagtctga cgatacaccc 60

```
atgcacgtgg gcaacttgca gattttcagc ctgcccgaca acgccccatc tacattcgcg    120

ggcgacttgg tcaaaagcat gaagcaagcc ggtaatgttg agcttccctg gggctgcaag    180

ctggtatggc caggctttct gggccgcgtt ctggcgccca cctggaagca cgacaagcat    240

attgatctgg attatcacgt gcgccactcg gccctaccaa aacccggtgg tgaacgcgaa    300

ctgggggaac tggtatcgcg cctgcactcc aacccgctgg atctgtcgcg gccgctgtgg    360

gagtgccaca tgatcgaagg gctggaacac aaccgttttg ccctgtacac gaagatgcat    420

cactgcatga ttgatggcat cagtggtgta cgcctgatgc aaagggtgct gagcaaatcc    480

cccgacgagc gcgacatgct gccaccctgg tcagtacgcc cggaaagcac gcgcggcaaa    540

aagaccgaca gcgaggccag cgtgccgggt gctatatccc aagctatgga agctctcaaa    600

ctgcagttgg gcttggcacc acggctgtgg caagccagca atcgcctgat tcactcggta    660

cgccatccgg aagacggtct gaccgcgccc ttcaccggcc cggtttccaa gatcaatcat    720

cgggttactg gccagcgccg cttcgccacc cagcagtatc agttagaaga tatgaaagcc    780

atggcccgcg cctcgggcag ctcgatgaac gacattgtgc tgtatttgtg cggtactgcg    840

ttgcggcgtt ttctgctgga acaggacgat ttgcctgaaa tatcattaac agcaggcata    900

ccggtcaaca ttcgcccggc ggatgacgaa ggcacaggaa cccagatcag cttcatgatt    960

gccgccctgg ccaccaacca acctgatccg ctaacgcgcc tgaaatgcat caaggaatct   1020

tcgtgcaaag ccaaagagca cttgcaaaaa ttgcccaaga aagcgttgac ccaatacacc   1080

atgatgctga tgtcgcccta catattgcag ctgatgtctg gcttgggcgg gcgcatgcga   1140

ccggtattta acgtaaccat ctccaacgtt ccggggccca ccgaagatct ttattacgaa   1200

ggcgccaaac tcgaagccat gtatccggtg tcgctgatca cccacggcgg agcgttgaac   1260

attacttgcc tgagctatgc cggatcattg aactttggtt tcactggttg ccgcgacacc   1320

ttacccagca tgcagaagct ggccgtgtat accggggaag cattggaaga actcagaacc   1380

ctgctgttac cgccaaagaa aaaacccagc ccacgcaaac ctagaacggc cgcgaaaaag   1440

aagcccgcgg tgaacagcaa cgctagctaa                                    1470
```

```
<210> SEQ ID NO 55
<211> LENGTH: 1368
<212> TYPE: DNA
<213> ORGANISM: Marinobacter aquaeoli

<400> SEQUENCE: 55
```

```
atgacgcccc tgaatcccac tgaccagctc tttctctggc tggaaaaacg ccagcagccc     60

atgcatgtgg gcggcctcca gctgttttcc ttccccgaag gcgcgccgga cgactatgtc    120

gcgcagctgg cagaccagct tcggcagaag acggaggtga ccgccccctt taaccagcgc    180

ctgagctatc gcctgggcca gccggtatgg gtggaggatg agcacctgga ccttgagcat    240

catttccgct tcgaggcgct gcccacaccc gggcgtattc gggagctgct gtcgttcgta    300

tcggcggagc attcgcacct gatggaccgg gagcgcccca tgtgggaggt gcacctgatc    360

gagggcctga aagaccggca gtttgcgctc tacaccaagg ttcaccattc cctggtggac    420

ggtgtctcgg ccatgcgcat ggccacccgg atgctgagtg aaaacccgga cgaacacggc    480

atgccgccaa tctgggatct gccttgcctg tcacgggata ggggtgagtc ggacggacac    540

tccctctggc gcagtgtcac ccatttgctg ggcgtttcgg gccgccagct cggcaccatt    600

cccactgtgg caaaggagct actgaaaacc atcaatcagg cccggaagga tccggcctac    660

gactccattt tccatgcccc gcgctgcatg ctgaaccaga aaatcaccgg ttcccgtcgt    720
```

```
ttcgccgccc agtcctggtg cctgaaacgg attcgcgccg tgtgcgaggc ctatggcacc    780
acggtcaacg atgtcgtaac tgccatgtgc gcagcggctc tgcgtaccta tctgatgaat    840
caggatgcct tgccggagaa accactggtg gcctttgtgc cggtgtcact acgccgggac    900
gacagctccg gggcaaccaa ggtaggcgtc atcctggcga gccttcacac cgatgtgcag    960
gaggccggcg aacgactgtt aaaaatccac catggcatgg aagaggccaa gcagcgctac   1020
cgtcatatga gcccggagga aatcgtcaac tacacggccc tgaccctggc gccggccgcc   1080
ttccacctgc tgaccgggct ggcgcccaag tggcagacct tcaatgtggt gatttccaat   1140
gtccccgggc catccaggcc cctgtactgg aacggggcga aactggaagg catgtatccg   1200
gtgtctatcg atatggacag actggccctg aacatgacac tgaccagcta taacgaccag   1260
gtggagttcg gcctgattgg ctgtcgccgg accctgccca gcctgcaacg gatgctggac   1320
tacctggaac agggtctggc agagctggag ctcaacgccg gtctgtaa                1368
```

<210> SEQ ID NO 56
<211> LENGTH: 1368
<212> TYPE: DNA
<213> ORGANISM: Marinobacter adhaerens

<400> SEQUENCE: 56

```
gtgaaacctc tcagccccac ggatcagctt tttctctggc tggaaaaacg gcagcagccc     60
atgcacgtgg gcggccttca actgttctct tttcccgaag gcgctccgga tgattacgtc    120
gcccagctgg cggaccggtt aaggcaacac acgaaggtga cgccaccttt caaccagcga    180
ctggactacc gtttcggtca gccggtatgg gtagaggatg agcacctgga tctggagcat    240
cacttccggt tcgaagcgct accgaccccg ggacgggtaa gagagctgtt gtcgtttgtc    300
tcggcggaac actcccacct gatggatcgg gaacgaccgc tgtgggaatt tcatttgatc    360
gaagggctgg gagagcggca gtttgcggtg tacatcaagg tacaccatgc tctggtagac    420
ggtgtatcgg ccatgcggat ggttacccgg atgctgtgtc aggataccgg agagcgggat    480
atgccgccga tctgggccat gccaccacgc ccggagcgtg agaaggatga tggcggcccc    540
tcgctgtggc gaagcattgg ccacctgctg ggtgaatccg gcaaacaact gggcaccgtg    600
cccaccgtcg cccgggaact gctgcgaacc atcaataacg cccgaaaaga ccccgcgtac    660
tcctccatat tccacgcgcc ccgcagcatt cttaaccaga agatcaccgg ctcccgacgc    720
ttcgccgcac agtcctatga cctcagccgt ataaaggcag tgtgtaaaat ctacggaacc    780
acggtgaatg atgtggtgat ggccatgtgc gccaccgcgc tgcgcagcta cctgatgaac    840
caggacgccc tgccggaaaa gccgctgatc gccatggtgc cggtgtccct gcgcaaggat    900
gacagctccg gcggaaacca ggtgggcgtt atcctcgcct cgctacacac cgacgtcacc    960
agcccggtta cccggctgat gcagatccac gaggatgtta aggccgccaa agaccgctac   1020
gcccatatgt ctgcggaaga aattatcaac tacaccgccc tgaccctggc gccggcggcg   1080
ttccatctgc ttaccggcat ggcaccgaaa tggcagacct tcaacgtggt catttcgaac   1140
gtccccgggc cccgggagac ctgctactgg aacggcgcca tgatggatgg catgtacccg   1200
gtctccatcg ccatggaccg cctcgccctg aacatgaccc tgaccagcta cggcgaccag   1260
gtggagttcg gcctcatcgg ctgccgccgc acgctaccca gcctgcagcg gatgctcgac   1320
tacctggaag aggccctggt cgaactggag accgcggccg gcctgtga                1368
```

<210> SEQ ID NO 57

<211> LENGTH: 1368
<212> TYPE: DNA
<213> ORGANISM: Marinobacter hydrocarbonoclasticus

<400> SEQUENCE: 57

```
atgacgcccc tgaatcccac tgaccagctc tttctctggc tggaaaaacg ccagcagccc      60
atgcatgtgg gcggcctcca gctgttttcc ttccccgaag gcgcgccgga cgactatgtc     120
gcgcagctgg cagaccagct tcggcagaag acggaggtga ccgccccctt taaccagcgc     180
ctgagctatc gcctgggcca gccggtatgg gtggaggatg agcacctgga ccttgagcat     240
catttccgct tcgaggcgct gcccacaccc gggcgtattc gggagctgct gtcgttcgta     300
tcggcggagc attcgcacct gatggaccgg gagcgcccca tgtgggaggt gcacctgatc     360
gagggcctga aagaccggca gtttgcgctc tacaccaagg ttcaccattc cctggtggac     420
ggtgtctcgg ccatgcgcat ggccacccgg atgctgagtg aaaacccgga cgaacacggc     480
atgccgccaa tctgggatct gccttgcctg tcacgggata ggggtgagtc ggacggacac     540
tccctctggc gcagtgtcac ccatttgctg ggctttcgg gccgccagct cggcaccatt     600
cccactgtgg caaaggagct actgaaaacc atcaatcagg cccggaagga tccggcctac     660
gactccattt tccatgcccc gcgctgcatg ctgaaccaga aaatcaccgg ttcccgtcgt     720
ttcgccgccc agtcctggtg cctgaaacgg attcgcgccg tgtgcgaggc ctatggcacc     780
acggtcaacg atgtcgtaac tgccatgtgc gcagcggctc tgcgtaccta tctgatgaat     840
caggatgcct tgccggagaa accactggtg gcctttgtgc cggtgtcact acgccgggac     900
gacagctccg gggcaacca ggtaggcgtc atcctggcga gccttcacac cgatgtgcag     960
gaggccggcg aacgactgtt aaaaatccac catggcatgg aagaggccaa gcagcgctac    1020
cgtcatatga gcccggagga aatcgtcaac tacacggccc tgaccctggc gccggccgcc    1080
ttccacctgc tgaccgggct ggcgcccaag tggcagacct tcaatgtggt gatttccaat    1140
gtccccgggc catccaggcc cctgtactgg aacggggcga aactggaagg catgtatccg    1200
gtgtctatcg atatggacag actggccctg aacatgacac tgaccagcta taacgaccag    1260
gtggagttcg gcctgattgg ctgtcgccgg accctgccca gcctgcaacg gatgctggac    1320
tacctggaac agggtctggc agagctggag ctcaacgccg gtctgtaa                1368
```

<210> SEQ ID NO 58
<211> LENGTH: 1425
<212> TYPE: DNA
<213> ORGANISM: Marinobacter hydrocarbonoclasticus

<400> SEQUENCE: 58

```
atgaaacgtc tcggaaccct ggatgcctcc tggctggcgg ttgaatctga agacaccccg      60
atgcatgtgg gtacacttca gattttctca ctgcctgaag gcgcaccaga aaccttcctg     120
cgtgacatgg tcactcgaat gaaagaagcc ggcgatgtgg caccgccctg ggatacaaa      180
ctggcctggt ccggtttcct cgggcgtgta atcgccccgg cctggaaagt cgataaggat     240
atcgatctgg attatcacgt ccggcactcg gccctgcccc gccccggcgg tgagcgcgaa     300
ctgggtattc tggtatcccg gctgcactct aatcccctgg atttttcccg gccgctgtgg     360
gaatgccacg ttattgaagg cctggaaaac aaccggttcg ccctttacac caaaatgcac     420
cactcgatga ttgacggcat cagtggcgta cggctgatgc aaagggtact caccaccgat     480
ccggaacgct gcaatatgcc accgccctgg acggtacgcc cgcatcaacg tcgtggcgca     540
aaaaccgaca aagaggccag tgtgcccgcc gcggtttccc aggccatgga cgccctgaaa     600
```

```
ctgcaggcag acatggcacc caggctatgg caggccggca atcgcctggt gcattcggtt    660
cgacacccgg aagacggact gaccgccccc ttcaccggcc cggtttccgt gctcaaccac    720
cgggttacgg cgcagcggcg attcgccacc cagcactacc agctggaccg gctaaagaac    780
ctcgcccatg cttccggcgg ctccctgaac gacatcgtgc tttacctttg tggcacagca    840
ttgcggcgct ttctggcaga gcagaacaat ctgcccgaca ccccgctgac ggccggtata    900
ccggtaaata tccgaccggc agacgacgag ggtacgggca cccagatcag tttcatgatt    960
gcctcgctgg ccaccgacga agccgacccg ttgaaccgcc tgcaacagat caaaacctcg   1020
acccgacggg ccaaggagca cctgcagaaa cttcccaaaa gcgcactgac ccagtacacc   1080
atgctgctga tgtcacccta cattctgcag ttgatgtcag gtctcggagg gaggatgcgg   1140
ccggttttca acgtgaccat ttccaacgtg cccggcccgg aagacacgct gtattatgag   1200
ggtgcccggc ttgaggccat gtatccggta tcgctgatcg ctcatggcgg cgctctgaat   1260
atcacctgcc tgagctatgc cggatcgctg aatttcggtt ttaccggctg ccgggatacg   1320
ctgccgagca tgcagaaact ggcggtttat accggtgagg ctctggatga gctggaatcg   1380
ctgattctgc cgccgaagaa gaagcgcgcc cgaacccgca agtaa                   1425
```

<210> SEQ ID NO 59
<211> LENGTH: 1566
<212> TYPE: DNA
<213> ORGANISM: Petunia x hybrida

<400> SEQUENCE: 59

```
atgaaatctc tggcgaccga actgcgtaac cgctcttctg agccgtgtct caagccgatc     60
gaaaccaagc gcaaaaccat cgaggagtac gaaacggttg cggtcgaaga agaacctctg    120
tctccgactg cgcgtctgtt ccacgacgcg aatttcaacg ttcacgtggt cgtaattatc    180
gccctggaca ctcgcatttc cccgcagccg attaaggaca agctggtcca caccctcctc    240
aagcacccgc gtttcacttc tctcatggtg gtcgatgaag aaaacctcgc cgacatgaaa    300
tgggtccaga cgaagatcga cctcgaccag cacatcattg ttccggaggt tgacgagacc    360
cagctcgaga gcccggacaa gtttgtagag gactacatct acaacctcac caagaccagc    420
ctggaccgta ctaaaccgct gtgggacctc cacctggtaa acgttaaaac ccgtgacgcg    480
gaagcagtcg ctctgctccg tgtccatcac tctctgggtg acggtacctc tctgatctct    540
ctgctgctcg cctgcacgcg tcagaccgcg gacgagctga aactgccgac catcccgacc    600
aaaaaacgcc gtccgacccc gtccggttac agcaccaaag aggaaagctt caagctgtgg    660
cattacctgg ccgtgatctg gctgttcatt cgcatgatcg gtaacacgct ggtggacgtg    720
ctgatgttca tcatcactgt gatcttcctc aaagacacga agaccccgat caacaccgta    780
ccggactctg agtctcgcgt tcgtcgtatc gttcaccgta ttatcgacct ggacgacctg    840
aagctcgtga agaacgccat gaacatgacg atcaacgacg tggcgctcgg tattacccag    900
gcaggtctgt ctaaatacct gaaccgtcgc tacgcggtag acgaggagga caaaggtgac    960
accgaacgta acaacaatct gccgaagaac atccgtctcc gtagctgcct cgttatcaac   1020
ctgcgtccgt ctgcgggtat tgaagacctc gcggacatga tggagaaagg tccgaaagag   1080
aaacgtggct ggggcaactg gttcggctac gttctcctgc cgttcaaaat cgcgctgcgt   1140
gatgaccctc tcgactacgt aaaagaggcc aaggccaccg ttgaccgtaa gaaacgctct   1200
tttgaggcgc tgtacacgct cattatggcc gaggtgctca tcaagatttt cggcatcaag   1260
```

```
gttgcgacgg cggtgaccgt tcgcgtattc tctaacgcga ccgtttgctt ttctaacgtt   1320

gttggtccgc aggaggagat cggtttctgt ggtcacccga ttagctatct ggcgccgtct   1380

atctatggcc agccatctgc gctcatgatc aacttccaga gctacatcga caaaatgatc   1440

atcgtggttg ccgtggatga gggcgccatt ccggacccgc aacagctgct ggatgacttc   1500

gaaaattccc tgcacctgat caaggaggcc gtgctggaac gcggtctggt taagaatctg   1560

aagtaa                                                              1566
```

<210> SEQ ID NO 60
<211> LENGTH: 1378
<212> TYPE: DNA
<213> ORGANISM: Mus musculus

<400> SEQUENCE: 60

```
gggctccaga gccaaacagc gtctacctgg aactcctgag attctgggca ccatgttctg     60

gcccaccaag aaggacctca agaccgccat ggaggtcttt gctcttttcc agtgggccct    120

cagtgccttg gttatagtca ccactgtgat cattgtcaac ctctacttgg tggtgttcac    180

atcttactgg cctgtcaccg tgttgatgct cacctggctg gcttttgact ggaagacccc    240

tgagcgaggt ggccgcaggt tcacctgtgt gaggaagtgg cgtctgtgga aacactatag    300

cgactacttc ccactcaaga tggtgaagac gaaagatatt tcacctgacc gcaactacat    360

ccttgtctgc catcctcatg ggctcatggc ccattcatgt tttggtcact ttgccactga    420

cacaacaggc ttttccaaga cctttcctgg tatcactcct tatatgctca cactaggagc    480

ctttttctgg gtacctttcc tcagagatta tgtaatgtct acagggtcgt gctctgtgag    540

tagatcctcc atggactttt tgcttaccca gaagggcaca ggcaacatgc ttgtggtggt    600

ggttggtggc ctggctgagt gcagatacag cacgccaggc tctaccaccc tgttcttgaa    660

gaagcggcaa ggctttgtgc gcacagccct taaacatggg gtgtctctaa tcccagctta    720

tgcctttgga gagacagacc tctatgacca gcacattttc actcctgggg gctttgtcaa    780

tcgcttccag aagtggttcc agaagatggt acacatctac cctgtgcttt tctatgggcg    840

tggcctcacc aagaactcct ggggccttct gccctattct cagccagtaa ccactgttgt    900

tggagaacct ctaccattgc ccaagattga gaatccgagc gaggagattg tggccaaata    960

ccacacactc tatattgatg ccctacgaaa attgtttgat cagcataaga ccaagtttgg   1020

catctcagag acccaggagc tggtgatagt ttgaaagaca ttcccttgac tggatggtgt   1080

ggaactgatg acaacagggc aaggttacct gtggagcttc acttctgact tgactggtcc   1140

tcactggagg gaggtggggg tgtgcatcca tgtggttgtt ttctgtgccc atcctttccc   1200

acctccctct ctttctctta gtttttgtct tttcccctg agacagagaa gactctaggc    1260

aaaagtccac tgaagtcatt ggactttcat gaaagcatta gcagcaagga aacctgtagg   1320

tggaataaac agcccatctc tggtaaaaaa aaaaaaaaaa aaaaaaaaaa aaaaaaaa     1378
```

<210> SEQ ID NO 61
<211> LENGTH: 1335
<212> TYPE: DNA
<213> ORGANISM: Simmondsia chinensis

<400> SEQUENCE: 61

```
gtctccatta caatggaggt ggagaaggag ctaaagacct tctcagaggt atggatctcc     60

gccatagccg ccgcctgcta ctgccgcttc gtccccgccg ttgcccctca cggcggcgct    120

ctccgcctcc tcctcctcct ccccgtcgtc ctcctcttca ttttcctccc cctccgcctc    180
```

```
tcctccttcc acctcggcgg gcccaccgcc ttgtatctcg tctggcttgc caacttcaag    240
ctccttctct tcgcctttca tcttggccct ttatctaacc cctctctctc tctccttcac    300
ttcatctcca ccaccctcct ccccatcaag ttcagagatg acccatctaa tgatcatgag    360
aaaaacaaga gaactctgag ttttgagtgg cgtaaagttg ttctttttgt tgctaagttg    420
gtgtttttttg cgggtatttt aaagatttat gagtttagaa aagatttgcc tcattttgtg    480
atctcggtgc tttactgttt tcacttctat ctcgggacgg agatcacctt agcagcaagc    540
gcagtcatag ctcgagccac gctagggtta gacctatacc cccagttcaa cgagccatac    600
ttagccacct cgctgcaaga cttctggggg cgcaggtgga acctcatggt gtcagacatc    660
ttggggttga caacatacca gcctgtccgg cgtgtcctct cgaggtgggt caggctgcgg    720
tgggaggtcg ccggcgcaat gttggtggcg ttcacggtgt cggggctaat gcatgaagtg    780
tttttcttct acttaactcg cgcgaggccc tcgtgggagg tgacggggtt ctttgtgttg    840
catggggttt gcacagccgt ggagatggtg gtgaagaagg cggtttcagg caaggtgcgg    900
ctgcgccggg aggtgtcagg ggcgctgacg gtggggttcg tgatggtgac tggagggtgg    960
ttgtttttgc cgcagctggt gaggcatggg gtagatttga agaccattga tgagtatcct   1020
gtcatgttta attatactca gaagaaattg atgggtttgt tggggtggtg atgaatgatg   1080
agatgatgat catgcatctt ctttttcgga gatcggttgt acgtcacgag gagaacccat   1140
gaaaaatgca gatcaracgg caagacaggt cgggaaaaaa aaatgatcaa tttttcctta   1200
agtagccggc ctgccaccct gtccgattgt ggcatttttg tggtcacttt ttcatatcgt   1260
gtagtatttt tggtttttttg tttttaatgt tttctatgaa ttttgaataa tttgtgcttc   1320
atgaaaattt ttttt                                                     1335
```

<210> SEQ ID NO 62
<211> LENGTH: 1890
<212> TYPE: DNA
<213> ORGANISM: Acinetobacter sp. ADP1

<400> SEQUENCE: 62

```
tggcctacat gcaggcaact taaataaata atttaaaaaa aaccactgtt attgcagtgg     60
ttttttttat gtactcgcta ttcagtataa ttcgttagat ttatgttgat taataacgat    120
atactcaata ctcggttcta taattctaaa aacatagctc ataaagggtt attaatatct    180
ttgcagtgag gcaatccacg ctatgcgccc attacatccg attgatttta tattcctgtc    240
actagaaaaa agacaacagc ctatgcatgt aggtggttta tttttgtttc agattcctga    300
taacgcccca gacaccttta ttcaagatct ggtgaatgat atccggatat caaaatcaat    360
ccctgttcca ccattcaaca ataaactgaa tgggcttttt tgggatgaag atgaagagtt    420
tgatttagat catcattttc gtcatattgc actgcctcat cctggtcgta ttcgtgaatt    480
gcttatttat atttcacaag agcacagtac gctgctagat cgggcaaagc ccttgtggac    540
ctgcaatatt attgaaggaa ttgaaggcaa tcgttttgcc atgtacttca aaattcacca    600
tgcgatggtc gatggcgttg ctggtatgcg gttaattgaa aaatcactct cccatgatgt    660
aacagaaaaa agtatcgtgc caccttggtg tgttgaggga aaacgtgcaa agcgcttaag    720
agaacctaaa acaggtaaaa ttaagaaaat catgtctggt attaagagtc agcttcaggc    780
gacacccaca gtcattcaag agctttctca gacagtattt aaagatattg gacgtaatcc    840
tgatcatgtt tcaagctttc aggcgccttg ttctattttg aatcagcgtg tgagctcatc    900
```

```
gcgacgtttt gcagcacagt cttttgacct agatcgtttt cgtaatattg ccaaatcgtt     960

gaatgtgacc attaatgatg ttgtactagc ggtatgttct ggtgcattac gtgcgtattt    1020

gatgagtcat aatagtttgc cttcaaaacc attaattgcc atggttccag cctctattcg    1080

caatgacgat tcagatgtca gcaaccgtat tacgatgatt ctggcaaatt tggcaaccca    1140

caaagatgat cctttacaac gtcttgaaat tatccgccgt agtgttcaaa actcaaagca    1200

acgcttcaaa cgtatgacca gcgatcagat tctaaattat agtgctgtcg tatatggccc    1260

tgcaggactc aacataattt ctggcatgat gccaaaacgc caagccttca atctggttat    1320

ttccaatgtg cctggcccaa gagagccact ttactggaat ggtgccaaac ttgatgcact    1380

ctacccagct tcaattgtat tagacggtca agcattgaat attacaatga ccagttattt    1440

agataaactt gaagttggtt tgattgcatg ccgtaatgca ttgccaagaa tgcagaattt    1500

actgacacat ttagaagaag aaattcaact atttgaaggc gtaattgcaa agcaggaaga    1560

tattaaaaca gccaattaaa aacaataaac ttgatttttt aatttatcag ataaaactaa    1620

agggctaaat tagcccttta gtttttaaca gtacgacact gtttaagtaa ttgatgacac    1680

acatgatgaa ccattgcagt cgtgatctgg atttctttac cttgatcatt gaccatataa    1740

caagaattgg cagttttgtt atcaaccata tgcgttgaac cttgagctag tattctttca    1800

cttacattca tgcgagatac cccgttattt gctaagacta atatgggaga aaagtctttg    1860

gctatgttgt gtacctagta ttgaaaattc                                     1890
```

<210> SEQ ID NO 63
<211> LENGTH: 989
<212> TYPE: DNA
<213> ORGANISM: Synechocystis PCC6803

<400> SEQUENCE: 63

```
attgctgaag cggaatccct ggttaatgcc gccgccgatg ccaattgcat tctccaagtg      60

gggcacattg aacgcttcaa cccggcattt ttagagctaa ccaaaattct caaaacggaa     120

gagttattgg cgatcgaagc ccatcgcatg agtccctatt cccagcgggc caatgatgtc     180

tccgtggtat tggatttgat gatccatgac attgacctgt tgctggaatt ggtgggttcg     240

gaagtggtta aactgtccgc cagtggcagt cgggcttctg ggtcaggata tttggattat     300

gtcaccgcta cgttaggctt ctcctccggc attgtggcca ccctcaccgc cagtaaggtc     360

acccatcgta aaattcgttc catcgccgcc cactgcaaaa attccctcac cgaagcggat     420

tttctcaata acgaaatttt gatccatcgc caaaccaccg ctgattggag cgcggactat     480

ggccaggtat tgtatcgcca ggatggtcta atcgaaaagg tttacaccag taatattgaa     540

cctctccacg ctgaattaga acattttatt cattgtgtta ggggaggtga tcaaccctca     600

gtgggggga g aacaggccct caaggccctg aagttagcca gtttaattga agaaatggcc     660

ctggacagtc aggaatggca tgggggggaa gttgtgacag aatatcaaga tgccaccctg     720

gccctcagtg cgagtgttta aatcaactta attaatgcaa ttattgcgag ttcaaactcg     780

ataactttgt gaaatattac tgttgaatta atctatgact attcaataca ccccccctagc     840

cgatcgcctg ttggcctacc tcgccgccga tcgcctaaat ctcagcgcca agagtagttc     900

cctcaacacc agtattctgc tcagcagtga cctattcaat caggaagggg gaattgtaac     960

agccaactat ggctttgatg gttatatgg                                       989
```

<210> SEQ ID NO 64
<211> LENGTH: 989

<212> TYPE: DNA
<213> ORGANISM: Synechocystis PCC6803

<400> SEQUENCE: 64

```
ccggtatgga tggcaccgat gcggaatccc aacagattgc ctttgacaac aatgtggcct     60

ggaataacct gggggatttg tccaccacca cccaacgggc ctacacttcg gctattagca    120

cagacacagt gcagagtgtt tatggcgtta atctggaaaa aaacgataac attcccattg    180

tttttgcgtg gcccattttt cccaccaccc ttaatcccac agattttcag gtaatgctta    240

acacggggga aattgtcacc ccggtgatcg cctctttgat tcccaacagt gaatacaacg    300

aacggcaaac ggtagtaatt acgggcaatt ttggtaatcg tttaacccca ggcacggagg    360

gagcgattta tcccgtttcc gtaggcacag tgttggacag tactcctttg gaaatggtgg    420

gacccaacgg cccggtcagt gcggtgggta ttaccattga tagtctcaac cctacgtgg    480

ccggcaatgg tcccaaaatt gtcgccgcta agttagaccg cttcagtgac ctgggggaag    540

gggctcccct ctggttagcc accaatcaaa ataacagtgg cggggattta tatggagacc    600

aagcccaatt tcgtttgcga atttacacca gcgccggttt ttcccccgat ggcattgcca    660

gtttactacc cacagaattt gaacggtatt ttcaactcca agcggaagat attacgggac    720

ggacagttat cctaacccaa actggtgttg attatgaaat tcccggcttt ggtctggtgc    780

aggtgttggg gctggcggat ttggccgggg ttcaggacag ctatgacctg acttacatcg    840

aagatcatga caactattac gacattatcc tcaaagggga cgaagccgca gttcgccaaa    900

ttaagagggt tgctttgccc tccgaagggg attattcggc ggtttataat cccggtggcc    960

ccggcaatga tccagagaat ggtcccccca                                      989
```

<210> SEQ ID NO 65
<211> LENGTH: 1032
<212> TYPE: DNA
<213> ORGANISM: Synechocystis PCC6803

<400> SEQUENCE: 65

```
tatttgcccg tattctgccc tatccccaag ccctagccca ggcgatcgcc gctgggttta     60

cttccgaccg tatcattgct ttgcgccccc ccgtagccga accattggaa aaagccctgt    120

ggcaacaatg gcaaattcaa ggggtggtaa ctaaagcctc cggtgcccag gggggagaat    180

tggttaagca aaaagtggcg gaagcgttgg gggtaaatct gatcagaatt gcccgtcccc    240

agactattcc agggcaaata actgacgatt taagccagat caaccaattt tgccaaagac    300

atttgccaag ctaaaaacga aaatttgtta agtattgcaa cggtggtttc ccaggggcag    360

agcgtccccg taagatgaga tttttaaaga cccccattag cgtggggcta tccctttaaa    420

aaccgtcttt attctggaga atctcaatgc atagcttttt gttggccacc gccgttcccg    480

ccaccctgtc ctggagccct aaagttgctg ggtgatgat tgcttgcaac attttggcga     540

tcgcctttgg taaattgacc atcaaacaac aaaatgtggg cacccccatg ccttcctcta    600

acttctttgg cggctttggt ttagggctg tgctgggcac cgctagcttt ggccacatcc     660

tcggcgctgg agtaattctg ggctagcca atatgggagt actttaaggc tcgattctga     720

atggactagc ttttatcctt tgggaaaata tcaaaggcga tcgggcaatt gaaagaaaag    780

cctggtcgct tttttgttag ggattaggga aaatgccaaa acgcaccaag gtggtaatta    840

tggctccgat gacggcaaga atcaacgccc aaatttgagc attagcccgc cctttgacat    900

ctttaacatc atccttgact gtacctatct ccatcctgac cgcagataac tcggttttca    960
```

```
ccgttgccat atcgatctta agagaagtta catctttttg gaggtcatcg agtttggtct   1020

taatttcccc ca                                                       1032


<210> SEQ ID NO 66
<211> LENGTH: 824
<212> TYPE: DNA
<213> ORGANISM: Synechocystis PCC6803

<400> SEQUENCE: 66

cctttaaatc ggtttctata gttacactca ttggcttttg cctgcaaagc aatatttcct     60

gataccccta gggtaaatca tgggaaatgg cgatcgccgg agtttctcct gtttgctgga    120

gggctgtctg caacatcttg gtgctgacca cggaatcggt ggcgaggtta aagaggggat    180

tagccagaat acctgccagc gaggtagcaa ccaaagtagc gacaatgccc acctgtaggg    240

gacgcatgcc gggtaaattc catttgatgg ccgggtaatt tttgattact tcggacattt    300

cctggggctc cttcaccacc atcattttca ccacccggat gtagtagtag atggaaacta    360

cactggtaac cagaccaagt aggactaggc catacaatcc cgattgccaa ccggcccaga    420

agatgtaaat tttgccgaaa aagcccgcca gaggaggaat gcccccccaag gataataaac    480

aaatgctcaa gcccaaggtt aacaaggggt ctttgtggta cagaccagcg taatcactaa    540

tttggtcact gccagtgcgg agggtgaaga gaataatgca actaaacgcc cccaggttca    600

taaacagata gatgagcatg tagaaaacca tgctggcgta accatcttca ctgccggcca    660

ctaggccaat catcacaaag cctgcttgac cgatggaaga gtaggccaac atccgtttca    720

tgctggtttg ggctaaagcc accacgttgc ccagcaccat gctcaacacg gccagagcgg    780

tgaaaataac gtgccactca tcggtaatac caccaaaggc agtc                     824


<210> SEQ ID NO 67
<211> LENGTH: 208
<212> TYPE: DNA
<213> ORGANISM: Artificial Sequence
<220> FEATURE:
<223> OTHER INFORMATION: TrcE promoter

<400> SEQUENCE: 67

tgttgacaat taatcatccg gctcgtataa tgtgtggaat tgtgagcgga taacaatttc     60

acacaggaaa cagcgccgct gagaaaaagc gaagcggcac tgctctttaa caatttatca    120

gacaatctgt gtgggcactc gaccggaatt atcgattaac tttattatta aaaattaaag    180

aggtatatat taatgtatcg attaaata                                       208


<210> SEQ ID NO 68
<211> LENGTH: 14
<212> TYPE: DNA
<213> ORGANISM: Artificial Sequence
<220> FEATURE:
<223> OTHER INFORMATION: rbs from trcE promoter

<400> SEQUENCE: 68

aggaggaata aacc                                                       14


<210> SEQ ID NO 69
<211> LENGTH: 367
<212> TYPE: DNA
<213> ORGANISM: Synechococcus elongatus

<400> SEQUENCE: 69

actagtcctg aggctgaaag tttcggactc agtagaccta agtacagagt gatgtcaacg     60
```

```
ccttcaagct agacgggagg cggcttttga catgttcagc gatcgctcct catcttcaat    120

aagcagggca tgagccagcg ttaagcaaat caaatcaaat ctcgcttctg ggcttcaata    180

aatggttccg attgatgata ggttgattca tgaggaatct aaggcttaat tctccacaaa    240

agaattaagc gtccgtcgca acggaatgct ccgctggact tgcgctgtgg gactgcagct    300

ttacaggctc cccctgccag aaatcctgaa tcgtcgagca tatctgacat atctctaggg    360

agagacg                                                              367
```

<210> SEQ ID NO 70
<211> LENGTH: 11100
<212> TYPE: DNA
<213> ORGANISM: Artificial Sequence
<220> FEATURE:
<223> OTHER INFORMATION: Wax Ester Synthase Operon construct 5109

<400> SEQUENCE: 70

```
ccggtatgga tggcaccgat gcggaatccc aacagattgc ctttgacaac aatgtggcct     60

ggaataacct gggggatttg tccaccacca cccaacgggc ctacacttcg gctattagca    120

cagacacagt gcagagtgtt tatggcgtta atctggaaaa aaacgataac attcccattg    180

tttttgcgtg gcccattttt cccaccaccc ttaatcccac agattttcag gtaatgctta    240

acacggggga aattgtcacc ccggtgatcg cctctttgat tcccaacagt gaatacaacg    300

aacggcaaac ggtagtaatt acgggcaatt ttggtaatcg tttaacccca ggcacggagg    360

gagcgattta tcccgtttcc gtaggcacag tgttggacag tactcctttg gaaatggtgg    420

gacccaacgg cccggtcagt gcggtgggta ttaccattga tagtctcaac ccctacgtgg    480

ccggcaatgg tcccaaaatt gtcgccgcta agttagaccg cttcagtgac ctgggggaag    540

ggctcccct ctggttagcc accaatcaaa ataacagtgg cggggattta tatggagacc    600

aagcccaatt tcgtttgcga atttacacca gcgccggttt ttcccccgat ggcattgcca    660

gtttactacc cacagaattt gaacggtatt ttcaactcca agcggaagat attacgggac    720

ggacagttat cctaacccaa actggtgttg attatgaaat tcccggcttt ggtctggtgc    780

aggtgttggg gctggcggat ttggccgggg ttcaggacag ctatgacctg acttacatcg    840

aagatcatga caactattac gacattatcc tcaaagggga cgaagccgca gttcgccaaa    900

ttaagagggt tgctttgccc tccgaagggg attattcggc ggtttataat cccggtggcc    960

ccggcaatga tccagagaat ggtcccccac tgtcagacca agtttactca tatatacttt   1020

agattgattt aaaacttcat ttttaattta aaaggatcta ggtgaagatc ctttttgata   1080

atctcatgac caaaatccct taacgtgagt tttcgttcca ctgagcgtca gaccccgtag   1140

aaaagatcaa aggatcttct tgagatcctt tttttctgcg cgtaatctgc tgcttgcaaa   1200

caaaaaaacc accgctacca gcggtggttt gtttgccgga tcaagagcta ccaactcttt   1260

ttccgaaggt aactggcttc agcagagcgc agataccaaa tactgtcctt ctagtgtagc   1320

cgtagttagg ccaccacttc aagaactctg tagcaccgcc tacatacctc gctctgctaa   1380

tcctgttacc agtggctgct gccagtggcg ataagtcgtg tcttaccggg ttggactcaa   1440

gacgatagtt accggataag gcgcagcggt cgggctgaac ggggggttcg tgcacacagc   1500

ccagcttgga gcgaacgacc tacaccgaac tgagatacct acagcgtgag ctatgagaaa   1560

gcgccacgct tcccgaaggg agaaaggcgg acaggtatcc ggtaagcggc agggtcggaa   1620

caggagagcg cacgagggag cttccagggg gaaacgcctg gtatctttat agtcctgtcg   1680
```

```
ggtttcgcca cctctgactt gagcgtcgat ttttgtgatg ctcgtcaggg gggcggagcc   1740
tatggaaaaa cgccagcaac gcggcctttt tacggttcct ggccttttgc tggccttttg   1800
ctcacatgtt ctttcctgcg ttatcccctg attctgtgga taaccgtatt accgcctttg   1860
agtgagctga taccgctcgc cgcagccgaa cgaccgagcg cagcgagtca gtgagcgagg   1920
aagcggaaga gcgcccaata cgcaaaccgc ctctccccgc gcgttggccg attcattaat   1980
gcagctggca cgacaggttt cccgactgga aagcgggcag tgaattgctg aagcggaatc   2040
cctggttaat gccgccgccg atgccaattg cattctccaa gtggggcaca ttgaacgctt   2100
caacccggca tttttagagc taaccaaaat tctcaaaacg gaagagttat tggcgatcga   2160
agcccatcgc atgagtccct attcccagcg ggccaatgat gtctccgtgg tattggattt   2220
gatgatccat gacattgacc tgttgctgga attggtgggt tcggaagtgg ttaaactgtc   2280
cgccagtggc agtcgggctt ctgggtcagg atatttggat tatgtcaccg ctacgttagg   2340
cttctcctcc ggcattgtgg ccaccctcac cgccagtaag gtcacccatc gtaaaattcg   2400
ttccatcgcc gcccactgca aaaattccct caccgaagcg gattttctca ataacgaaat   2460
tttgatccat cgccaaacca ccgctgattg gagcgcggac tatggccagg tattgtatcg   2520
ccaggatggt ctaatcgaaa aggtttacac cagtaatatt gaacctctcc acgctgaatt   2580
agaacatttt attcattgtg ttaggggagg tgatcaaccc tcagtggggg gagaacaggc   2640
cctcaaggcc ctgaagttag ccagtttaat tgaagaaatg gccctggaca gtcaggaatg   2700
gcatgggggg gaagttgtga cagaatatca agatgccacc ctggccctca gtgcgagtgt   2760
ttaaatcaac ttaattaatg caattattgc gagttcaaac tcgataactt tgtgaaatat   2820
tactgttgaa ttaatctatg actattcaat acacccccct agccgatcgc ctgttggcct   2880
acctcgccgc cgatcgccta aatctcagcg ccaagagtag ttccctcaac accagtattc   2940
tgctcagcag tgacctattc aatcaggaag gggaattgt aacagccaac tatggctttg    3000
atggttatat ggggccggcc actagtcctg aggctgaaag tttcggactc agtagaccta   3060
agtacagagt gatgtcaacg ccttcaagct agacgggagg cggcttttga catgttcagc   3120
gatcgctcct catcttcaat aagcagggca tgagccagcg ttaagcaaat caaatcaaat   3180
ctcgcttctg ggcttcaata aatggttccg attgatgata ggttgattca tgaggaatct   3240
aaggcttaat tctccacaaa agaattaagc gtccgtcgca acggaatgct ccgctggact   3300
tgcgctgtgg gactgcagct ttacaggctc cccctgccag aaatcctgaa tcgtcgagca   3360
tatctgacat atctctaggg agagacgacc atttaaatag gaggaataaa ccatggcgaa   3420
cggtagcgct gtctctctga agagcggctc cttgaatacg caagaggaca cttcttcttc   3480
cccaccgcca cgcgcgttca tcaaccaatt acccgactgg tccatgttat tgacggcgat   3540
taccactgtc tttgttgccg cagagaaaca gtggactatg ttagaccgca agagcaagcg   3600
ctccgatatg ttagtggatt cttttggcat ggaacgcatt gtgcaggatg gcttagtgtt   3660
tcgtcaatct tttagcattc gttcttatga aatcggtgca gatcgtcgtg catccattga   3720
aaccttaatg aaccatctgc aggaaactag cttgaatcat tgcaaatcca ttcgcttgtt   3780
gaatgagggt tttggtcgca cccccgagat gtgcaaacgt gacttgatct gggtggttac   3840
ccgcatgcac atcatggtca accgctaccc tacctggggt gataccgttg agattaacac   3900
ttgggtttcc caaagcggca agaatggtat gggtcgtgat tggctgattt ccgactgtaa   3960
taccggcgaa atcctgatcc gcgcgacgtc tgcatgggcg atgatgaacc aaaagacccg   4020
tcgtctgtct aaactgcctt acgaagtcag ccaagagatt gctccgcact tcgtcgacag   4080
```

```
ccctcccgtg atcgaggacg gcgaccgtaa gttacacaag ttcgatgtga aaaccggcga   4140
cagcatccgt aaaggtttga ctccgcgttg gaatgactta gatgttaatc agcacgttaa   4200
caacgttaag tatatcggct ggatcttaga gagcatgccg accgaggtct tggaaactca   4260
tgaactgtgt ttcttaactc tggagtatcg tcgcgagtgc ggtcgcgata gcgtgctgga   4320
atctgtgacc gcgatggatc cttctaatga aggtggtcgc tcccactacc agcatttact   4380
gcgcttggag gacggtactg acatcgttaa gggccgcact gagtggcgtc caaagaatgc   4440
ccggaatatt ggtgccatta gtaccggtaa aaccagtaat ggtaatcccg ccagttaata   4500
aaaatgcggc cgcaggagga ataaaccatg gccgctccag attatgcact taccgattta   4560
attgaatcgg atcctcgttt cgaaagtttg aagacaagat tagccggtta caccaaaggc   4620
tctgatgaat atattgaaga gctatactct caattaccac tgaccagcta tcccaggtac   4680
aaaacatttt taaagaaaca ggcggttgcc atttcgaatc cggataatga agctggtttt   4740
agctcgattt ataggagttc tctttcttct gaaaatctag tgagctgtgt ggataaaaac   4800
ttaagaactg catacgatca cttcatgttt tctgcaagga gatggcctca acgtgactgt   4860
ttaggttcaa ggccaattga taaagccaca ggcacctggg aggaaacatt ccgtttcgag   4920
tcgtactcca cggtatctaa aagatgtcat aatatcggaa gtggtatatt gtctttggta   4980
aacacgaaaa ggaaacgtcc tttggaagcc aatgattttg ttgttgctat cttatcacac   5040
aacaaccctg aatggatcct aacagatttg gcctgtcagg cctattctct aactaacacg   5100
gctttgtacg aaacattagg tccaaacacc tccgagtaca tattgaattt aaccgaggcc   5160
cccattctga tttttgcaaa atcaaatatg tatcatgtat tgaagatggt gcctgatatg   5220
aaatttgtta atactttggt ttgtatggat gaattaactc atgacgagct ccgtatgcta   5280
aatgaatcgt tgctacccgt taagtgcaac tctctcaatg aaaaaatcac attttttttca   5340
ttggagcagg tagaacaagt tggttgcttt aacaaaattc ctgcaattcc acctacccca   5400
gattccttgt atactatttc gtttacttct ggtactacag gtttacctaa aggtgtggaa   5460
atgtctcaca gaaacattgc gtctgggata gcatttgctt tttctacctt cagaataccg   5520
ccagataaaa gaaaccaaca gttatatgat atgtgttttt tgccattggc tcatattttt   5580
gaaagaatgg ttattgcgta tgatctagcc atcgggtttg gaataggctt cttacataaa   5640
ccagacccaa ctgtattggt agaggatttg aagattttga aaccttacgc ggttgccctg   5700
gttcctagaa tattaacacg gtttgaagcc ggtataaaaa acgctttgga taaatcgact   5760
gtccagagga acgtagcaaa tactatattg gattctaaat cggccagatt taccgcaaga   5820
ggtggtccag ataaatcgat tatgaatttt ctagtttatc atcgcgtatt gattgataaa   5880
atcagagact ctttaggttt gtccaataac tcgtttataa ttaccggatc agctcccata   5940
tctaaagata ccttactatt tttaagaagt gccttggata ttggtataag acagggctac   6000
ggcttaactg aaacttttgc tggtgtctgt ttaagcgaac cgtttgaaaa agatgtcgga   6060
tcttgtggtg ccataggtat ttctgcagaa tgtagattga agtctgttcc agaaatgggt   6120
taccatgccg acaaggattt aaaaggtgaa ctgcaaattc gtggcccaca ggtttttgaa   6180
agatatttta aaaatccgaa tgaaacttca aaagccgttg accaagatgg ttggttttcc   6240
acgggagatg ttgcatttat cgatggaaaa ggtcgcatca gcgtcattga tcgagtcaag   6300
aactttttca agctagcaca tggtgaatat attgctccag agaaaatcga aaatatttat   6360
ttatcatcat gcccctatat cacgcaaata tttgtctttg gagatccttt aaagacattt   6420
```

-continued

```
ttagttggca tcgttggtgt tgatgttgat gcagcgcaac cgattttagc tgcaaagcac   6480
ccagaggtga aaacgtggac taaggaagtg ctagtagaaa acttaaatcg taataaaaag   6540
ctaaggaagg aatttttaaa caaaattaat aaatgcaccg atgggctaca aggattcgaa   6600
aaattgcata acatcaaagt cggacttgag cctttaactc tcgaggatga tgttgtgacg   6660
ccaactttta aaataaagcg tgccaaagca tcaaaattct tcaaagatac attagaccaa   6720
ctatacgccg aaggttcact agtcaagaca gaaaagcttt aaggccgcgt ttaaacagga   6780
ggaataaacc atggcaatac agcaggtaca tcacgctgac acttcatcat caaaggtgct   6840
cggacagctc cgtggcaagc gggttctgat caccggtacc actggctttc tgggcaaggt   6900
ggtcctcgaa aggctgattc gggcggtgcc tgatatcggc gcaatttacc tgctgatccg   6960
gggcaataaa cggcatccgg atgctcgttc ccgtttcctg gaagaaattg ccacctcctc   7020
ggtgtttgac cgtcttcgcg aggccgattc agagggattt gacgcctttc tggaagagcg   7080
cattcactgc gtgaccggtg aggtgaccga agcgggtttc gggataggc aggaagacta   7140
tcgcaaactc gccaccgaac tggatgcggt gatcaactcc gctgcaagcg tgaatttccg   7200
tgaagagctc gacaaggcgc tggccatcaa caccctgtgc cttcggaata ttgccggcat   7260
ggtggatttg aatccgaagc ttgcggtcct gcaggtctcc acctgctatg tcaatggcat   7320
gaactcgggg caggtaaccg aatcggtgat caagccggca ggcgaggccg tgccgcgttc   7380
cccggacggc ttctatgaga tagaagagct tgttcgcctg cttcaggata aaattgaaga   7440
cgttcaggcc cgttattccg gcaaagtgct ggagaggaag ctggtggacc tggggattcg   7500
ggaagccaac cgctatggct ggagcgatac ctacaccttt accaagtggc tgggcgaaca   7560
gttgctgatg aaggcgttaa acgggcgcac gctgaccatt ctgcgtcctt cgattatcga   7620
aagtgccctg gaggaaccag cgcccggctg gattgagggg gtgaaggtgg cagatgccat   7680
catcctggct tacgcacggg aaaaagtcac cctcttcccg ggcaaacgct ccggtatcat   7740
cgatgtgatt ccagtggacc tggtggccaa ctccatcatc ctttccctgg cggaagctct   7800
tggagaaccc ggtcgacgtc gcatctatca atgttgcagc gggggcggca atccaatctc   7860
cctgggtgag ttcatcgatc atctcatggc ggaatcaaaa gccaattacg ctgcctacga   7920
tcacctgttc taccggcagc ccagcaagcc gtttctggcg gttaaccggg cgctgtttga   7980
tttggtgatc agtggtgttc gcttaccgct ctccctgacg gaccgtgtgc tcaaattact   8040
gggaaattcc cgggacctga aaatgctcag gaatctggat accacccagt cgctggcaac   8100
catttttggt ttctacaccg cgccggatta tatcttccgg aacgatgagc tgatggcgct   8160
ggcgaaccgg atgggtgagg tcgataaagg gctgttcccg gtggatgccc gcctgattga   8220
ctgggagctc tacctgcgca agattcacct ggccgggctc aatcgctatg ccctgaaaga   8280
acgaaaggtg tacagtctga aaaccgcgcg ccagcgcaaa aaagctgcct aaaaacggcg   8340
cgccaggagg aataaaccat gaaatctctg gcgaccgaac tgcgtaaccg ctcttctgag   8400
ccgtgtctca agccgatcga aaccaagcgc aaaaccatcg aggagtacga aacggttgcg   8460
gtcgaagaag aacctctgtc tccgactgcg cgtctgttcc acgacgcgaa tttcaacgtt   8520
cacgtggtcg taattatcgc cctggacact cgcatttccc cgcagccgat taaggacaag   8580
ctggtccaca ccctcctcaa gcacccgcgt ttcacttctc tcatggtggt cgatgaagaa   8640
aacctcgccg acatgaaatg ggtccagacg aagatcgacc tcgaccagca catcattgtt   8700
ccggaggttg acgagaccca gctcgagagc ccggacaagt ttgtagagga ctacatctac   8760
aacctcacca agaccagcct ggaccgtact aaaccgctgt gggacctcca cctggtaaac   8820
```

```
gttaaaaccc gtgacgcgga agcagtcgct ctgctccgtg tccatcactc tctgggtgac   8880
ggtacctctc tgatctctct gctgctcgcc tgcacgcgtc agaccgcgga cgagctgaaa   8940
ctgccgacca tcccgaccaa aaaacgccgt ccgaccccgt ccggttacag caccaaagag   9000
gaaagcttca agctgtggca ttacctggcc gtgatctggc tgttcattcg catgatcggt   9060
aacacgctgg tggacgtgct gatgttcatc atcactgtga tcttcctcaa agacacgaag   9120
accccgatca acaccgtacc ggactctgag tctcgcgttc gtcgtatcgt tcaccgtatt   9180
atcgacctgg acgacctgaa gctcgtgaag aacgccatga acatgacgat caacgacgtg   9240
gcgctcggta ttacccaggc aggtctgtct aaatacctga accgtcgcta cgcggtagac   9300
gaggaggaca aaggtgacac cgaacgtaac aacaatctgc cgaagaacat ccgtctccgt   9360
agctgcctcg ttatcaacct gcgtccgtct gcgggtattg aagacctcgc ggacatgatg   9420
gagaaaggtc cgaaagagaa acgtggctgg ggcaactggt tcggctacgt tctcctgccg   9480
ttcaaaatcg cgctgcgtga tgaccctctc gactacgtaa aagaggccaa ggccaccgtt   9540
gaccgtaaga aacgctcttt tgaggcgctg tacacgctca ttatggccga ggtgctcatc   9600
aagattttcg gcatcaaggt tgcgacggcg gtgaccgttc gcgtattctc taacgcgacc   9660
gtttgctttt ctaacgttgt tggtccgcag gaggagatcg gtttctgtgg tcacccgatt   9720
agctatctgg cgccgtctat ctatggccag ccatctgcgc tcatgatcaa cttccagagc   9780
tacatcgaca aaatgatcat cgtggttgcc gtggatgagg gcgccattcc ggacccgcaa   9840
cagctgctgg atgacttcga aaattccctg cacctgatca aggaggccgt gctggaacgc   9900
ggtctggtta agaatctgaa gtaatctaga cgcgcctagt taagccagcc ccgacacccg   9960
ccaacacccg ctgacgcgcc ctgacgggct tgtctgctcc cggcatccgc ttacagacaa  10020
gctgtgaccg tctccgggag ctgcatgtgt cagaggtttt caccgtcatc accgaaacgc  10080
gcgagacgaa agggcctcgt gatacgccta tttttatagg ttaatgtcat gataataatg  10140
gtttcttaga cgtcaggtgg cacttttcgg ggaaatgtgc gcggaacccc tatttgttta  10200
tttttctaaa tacattcaaa tatgtatccg ctcatgagac aataaccctg ataaatgctt  10260
caataatatt gaaaaaggaa gagtatgagc catattcaac gggaaacgtc ttgctcgagg  10320
ccgcgattaa attccaacat ggatgctgat ttatatgggt ataaatgggc tcgcgataat  10380
gtcgggcaat caggtgcgac aatctatcga ttgtatggga agcccgatgc gccagagttg  10440
tttctgaaac atggcaaagg tagcgttgcc aatgatgtta cagatgagat ggtcagacta  10500
aactggctga cggaatttat gcctcttccg accatcaagc attttatccg tactcctgat  10560
gatgcatggt tactcaccac tgcgatcccc gggaaaacag cattccaggt attagaagaa  10620
tatcctgatt caggtgaaaa tattgttgat gcgctggcag tgttcctgcg ccggttgcat  10680
tcgattcctg tttgtaattg tccttttaac agcgatcgcg tatttcgtct cgctcaggcg  10740
caatcacgaa tgaataacgg tttggttgat gcgagtgatt ttgatgacga gcgtaatggc  10800
tggcctgttg aacaagtctg gaaagaaatg cataagcttt tgccattctc accggattca  10860
gtcgtcactc atggtgattt ctcacttgat aaccttattt ttgacgaggg gaaattaata  10920
ggttgtattg atgttggacg agtcggaatc gcagaccgat accaggatct tgccatccta  10980
tggaactgcc tcggtgagtt ttctccttca ttacagaaac ggctttttca aaaatatggt  11040
attgataatc ctgatatgaa taaattgcag tttcatttga tgctcgatga gtttttctaa  11100
```

<210> SEQ ID NO 71

<211> LENGTH: 12136
<212> TYPE: DNA
<213> ORGANISM: Artificial Sequence
<220> FEATURE:
<223> OTHER INFORMATION: Wax Ester Synthase Operon construct 5110

<400> SEQUENCE: 71
ccggtatgga tggcaccgat gcggaatccc aacagattgc ctttgacaac aatgtggcct 60
ggaataacct gggggatttg tccaccacca cccaacgggc ctacacttcg gctattagca 120
cagacacagt gcagagtgtt tatggcgtta atctggaaaa aaacgataac attcccattg 180
tttttgcgtg gcccattttt cccaccaccc ttaatcccac agattttcag gtaatgctta 240 acacgggggga aattgtcacc ccggtgatcg cctctttgat tcccaacagt gaatacaacg 300
aacggcaaac ggtagtaatt acgggcaatt ttggtaatcg tttaaccccca ggcacggagg 360 gagcgattta tcccgtttcc gtaggcacag tgttggacag tactcctttg gaaatggtgg 420
gacccaacgg cccggtcagt gcggtgggta ttaccattga tagtctcaac ccctacgtgg 480
ccggcaatgg tcccaaaatt gtcgccgcta agttagaccg cttcagtgac ctgggggaag 540
gggctcccct ctggttagcc accaatcaaa ataacagtgg cggggattta tatggagacc 600
aagcccaatt tcgtttgcga atttacacca gcgccggttt ttcccccgat ggcattgcca 660
gtttactacc cacagaattt gaacggtatt ttcaactcca agcggaagat attacgggac 720
ggacagttat cctaacccaa actggtgttg attatgaaat tcccggcttt ggtctggtgc 780
aggtgttggg gctggcggat ttggccgggg ttcaggacag ctatgacctg acttacatcg 840
aagatcatga caactattac gacattatcc tcaaagggga cgaagccgca gttcgccaaa 900
ttaagagggt tgctttgccc tccgaagggg attattcggc ggtttataat cccggtggcc 960
ccggcaatga tccagagaat ggtcccccac tgtcagacca agtttactca tatatacttt 1020
agattgattt aaaacttcat ttttaattta aaaggatcta ggtgaagatc ctttttgata 1080
atctcatgac caaaatccct taacgtgagt tttcgttcca ctgagcgtca gaccccgtag 1140
aaaagatcaa aggatcttct tgagatcctt tttttctgcg cgtaatctgc tgcttgcaaa 1200
caaaaaaacc accgctacca gcggtggttt gtttgccgga tcaagagcta ccaactcttt 1260
ttccgaaggt aactggcttc agcagagcgc agataccaaa tactgtcctt ctagtgtagc 1320
cgtagttagg ccaccacttc aagaactctg tagcaccgcc tacatacctc gctctgctaa 1380
tcctgttacc agtggctgct gccagtggcg ataagtcgtg tcttaccggg ttggactcaa 1440
gacgatagtt accggataag gcgcagcggt cgggctgaac ggggggttcg tgcacacagc 1500
ccagcttgga gcgaacgacc tacaccgaac tgagatacct acagcgtgag ctatgagaaa 1560
gcgccacgct tcccgaaggg agaaaggcgg acaggtatcc ggtaagcggc agggtcggaa 1620
caggagagcg cacgagggag cttccagggg gaaacgcctg gtatctttat agtcctgtcg 1680
ggtttcgcca cctctgactt gagcgtcgat ttttgtgatg ctcgtcaggg gggcggagcc 1740
tatggaaaaa cgccagcaac gcggcctttt tacggttcct ggccttttgc tggccttttg 1800
ctcacatgtt ctttcctgcg ttatcccctg attctgtgga taaccgtatt accgcctttg 1860
agtgagctga taccgctcgc cgcagccgaa cgaccgagcg cagcgagtca gtgagcgagg 1920
aagcggaaga gcgcccaata cgcaaaccgc ctctccccgc gcgttggccg attcattaat 1980
gcagctggca cgacaggttt cccgactgga aagcgggcag tgaattgctg aagcggaatc 2040
cctggttaat gccgccgccg atgccaattg cattctccaa gtggggcaca ttgaacgctt 2100
caacccggca tttttagagc taaccaaaat tctcaaaacg gaagagttat tggcgatcga 2160

```
agcccatcgc atgagtccct attcccagcg ggccaatgat gtctccgtgg tattggattt   2220
gatgatccat gacattgacc tgttgctgga attggtgggt tcggaagtgg ttaaactgtc   2280
cgccagtggc agtcgggctt ctgggtcagg atatttggat tatgtcaccg ctacgttagg   2340
cttctcctcc ggcattgtgg ccaccctcac cgccagtaag gtcacccatc gtaaaattcg   2400
ttccatcgcc gcccactgca aaaattccct caccgaagcg gattttctca ataacgaaat   2460
tttgatccat cgccaaacca ccgctgattg gagcgcggac tatggccagg tattgtatcg   2520
ccaggatggt ctaatcgaaa aggtttacac cagtaatatt gaacctctcc acgctgaatt   2580
agaacatttt attcattgtg ttaggggagg tgatcaaccc tcagtggggg gagaacaggc   2640
cctcaaggcc ctgaagttag ccagtttaat tgaagaaatg gccctggaca gtcaggaatg   2700
gcatgggggg gaagttgtga cagaatatca agatgccacc ctggccctca gtgcgagtgt   2760
ttaaatcaac ttaattaatg caattattgc gagttcaaac tcgataactt tgtgaaatat   2820
tactgttgaa ttaatctatg actattcaat acaccccccct agccgatcgc ctgttggcct   2880
acctcgccgc cgatcgccta aatctcagcg ccaagagtag ttccctcaac accagtattc   2940
tgctcagcag tgacctattc aatcaggaag gggaattgt aacagccaac tatggctttg   3000
atggttatat ggggccggcc cgttgacacc atcgaatggt gcaaaacctt tcgcggtatg   3060
gcatgatagc gcccggaaga gagtcaattc agggtggtga atgtgaaacc agtaacgtta   3120
tacgatgtcg cagagtatgc cggtgtctct tatcagaccg tttcccgcgt ggtgaaccag   3180
gccagccacg tttctgcgaa aacgcgggaa aaagtggaag cggcgatggc ggagctgaat   3240
tacattccca accgcgtggc acaacaactg gcgggcaaac agtcgttgct gattggcgtt   3300
gccacctcca gtctggccct gcacgcgccg tcgcaaattg tcgcggcgat taaatctcgc   3360
gccgatcaac tgggtgccag cgtggtggtg tcgatggtag aacgaagcgg cgtcgaagcc   3420
tgtaaagcgg cggtgcacaa tcttctcgcg caacgcgtca gtgggctgat cattaactat   3480
ccgctggatg accaggatgc cattgctgtg gaagctgcct gcactaatgt tccggcgtta   3540
tttcttgatg tctctgacca gacacccatc aacagtatta ttttctccca tgaagacggt   3600
acgcgactgg gcgtggagca tctggtcgca ttgggtcacc agcaaatcgc gctgttagcg   3660
ggcccattaa gttctgtctc ggcgcgtctg cgtctggctg gctggcataa atatctcact   3720
cgcaatcaaa ttcagccgat agcggaacgg gaaggcgact ggagtgccat gtccggtttt   3780
caacaaacca tgcaaatgct gaatgagggc atcgttccca ctgcgatgct ggttgccaac   3840
gatcagatgg cgctgggcgc aatgcgcgcc attaccgagt ccgggctgcg cgttggtgcg   3900
gatatctcgg tagtgggata cgacgatacc gaagacagct catgttatat cccgccgtta   3960
accaccatca aacaggattt tcgcctgctg gggcaaacca gcgtggaccg cttgctgcaa   4020
ctctctcagg gccaggcggt gaagggcaat cagctgttgc ccgtctcact ggtgaaaaga   4080
aaaaccaccc tggcgcccaa tacgcaaacc gcctctcccc gcgcgttggc cgattcatta   4140
atgcagctgg cacgacaggt ttcccgactg gaaagcgggc agtgagcgca acgcaattaa   4200
tgtaagttag cgcgaattga tctggtttga cagcttatca tcgactgcac ggtgcaccaa   4260
tgcttctggc gtcaggcagc catcggaagc tgtggtatgg ctgtgcaggt cgtaaatcac   4320
tgcataattc gtgtcgctca aggcgcactc ccgttctgga taatgttttt tgcgccgaca   4380
tcataacggt tctggcaaat attctgaaat gagctgttga caattaatca tccggctcgt   4440
ataatgtgtg gaattgtgag cggataacaa tttcacacag gaaacagcgc cgctgagaaa   4500
```

-continued

```
aagcgaagcg gcactgctct ttaacaattt atcagacaat ctgtgtgggc actcgaccgg   4560
aattatcgat taactttatt attaaaaatt aaagaggtat atattaatgt atcgattaaa   4620
taccatttaa ataggaggaa taaaccatgg cgaacggtag cgctgtctct ctgaagagcg   4680
gctccttgaa tacgcaagag gacacttctt cttccccacc gccacgcgcg ttcatcaacc   4740
aattacccga ctggtccatg ttattgacgg cgattaccac tgtctttgtt gccgcagaga   4800
aacagtggac tatgttagac cgcaagagca agcgctccga tatgttagtg gattcttttg   4860
gcatggaacg cattgtgcag gatggcttag tgtttcgtca atcttttagc attcgttctt   4920
atgaaatcgg tgcagatcgt cgtgcatcca ttgaaacctt aatgaaccat ctgcaggaaa   4980
ctagcttgaa tcattgcaaa tccattcgct tgttgaatga gggttttggt cgcacccccg   5040
agatgtgcaa acgtgacttg atctgggtgg ttacccgcat gcacatcatg gtcaaccgct   5100
accctacctg gggtgatacc gttgagatta acacttgggt ttcccaaagc ggcaagaatg   5160
gtatgggtcg tgattggctg atttccgact gtaataccgg cgaaatcctg atccgcgcga   5220
cgtctgcatg ggcgatgatg aaccaaaaga cccgtcgtct gtctaaactg ccttacgaag   5280
tcagccaaga gattgctccg cacttcgtcg acagccctcc cgtgatcgag gacggcgacc   5340
gtaagttaca caagttcgat gtgaaaaccg gcgacagcat ccgtaaaggt ttgactccgc   5400
gttggaatga cttagatgtt aatcagcacg ttaacaacgt taagtatatc ggctggatct   5460
tagagagcat gccgaccgag gtcttggaaa ctcatgaact gtgtttctta actctggagt   5520
atcgtcgcga gtgcggtcgc gatagcgtgc tggaatctgt gaccgcgatg gatccttcta   5580
atgaaggtgg tcgctcccac taccagcatt tactgcgctt ggaggacggt actgacatcg   5640
ttaagggccg cactgagtgg cgtccaaaga atgcccggaa tattggtgcc attagtaccg   5700
gtaaaaccag taatggtaat cccgccagtt aataaaaatg cggccgcagg aggaataaac   5760
catggccgct ccagattatg cacttaccga tttaattgaa tcggatcctc gtttcgaaag   5820
tttgaagaca agattagccg gttacaccaa aggctctgat gaatatattg aagagctata   5880
ctctcaatta ccactgacca gctatcccag gtacaaaaca tttttaaaga aacaggcggt   5940
tgccatttcg aatccggata atgaagctgg ttttagctcg atttatagga gttctctttc   6000
ttctgaaaat ctagtgagct gtgtggataa aaacttaaga actgcatacg atcacttcat   6060
gttttctgca aggagatggc ctcaacgtga ctgtttaggt tcaaggccaa ttgataaagc   6120
cacaggcacc tgggaggaaa cattccgttt cgagtcgtac tccacggtat ctaaaagatg   6180
tcataatatc ggaagtggta tattgtcttt ggtaaacacg aaaaggaaac gtcctttgga   6240
agccaatgat tttgttgttg ctatcttatc acacaacaac cctgaatgga tcctaacaga   6300
tttggcctgt caggcctatt ctctaactaa cacggctttg tacgaaacat taggtccaaa   6360
cacctccgag tacatattga atttaaccga ggcccccatt ctgatttttg caaaatcaaa   6420
tatgtatcat gtattgaaga tggtgcctga tatgaaattt gttaatactt tggtttgtat   6480
ggatgaatta actcatgacg agctccgtat gctaaatgaa tcgttgctac ccgttaagtg   6540
caactctctc aatgaaaaaa tcacattttt ttcattggag caggtagaac aagttggttg   6600
ctttaacaaa attcctgcaa ttccacctac cccagattcc ttgtatacta tttcgtttac   6660
ttctggtact acaggtttac ctaaaggtgt ggaaatgtct cacagaaaca ttgcgtctgg   6720
gatagcattt gctttttcta ccttcagaat accgccagat aaaagaaacc aacagttata   6780
tgatatgtgt tttttgccat tggctcatat ttttgaaaga atggttattg cgtatgatct   6840
agccatcggg tttggaatag gcttcttaca taaaccagac ccaactgtat tggtagagga   6900
```

```
tttgaagatt ttgaaacctt acgcggttgc cctggttcct agaatattaa cacggtttga   6960

agccggtata aaaaacgctt tggataaatc gactgtccag aggaacgtag caaatactat   7020

attggattct aaatcggcca gatttaccgc aagaggtggt ccagataaat cgattatgaa   7080

ttttctagtt tatcatcgcg tattgattga taaaatcaga gactctttag gtttgtccaa   7140

taactcgttt ataattaccg gatcagctcc catatctaaa gataccttac tatttttaag   7200

aagtgccttg gatattggta taagacaggg ctacggctta actgaaactt ttgctggtgt   7260

ctgtttaagc gaaccgtttg aaaaagatgt cggatcttgt ggtgccatag gtatttctgc   7320

agaatgtaga ttgaagtctg ttccagaaat gggttaccat gccgacaagg atttaaaagg   7380

tgaactgcaa attcgtggcc cacaggtttt tgaaagatat tttaaaaatc cgaatgaaac   7440

ttcaaaagcc gttgaccaag atggttggtt ttccacggga gatgttgcat ttatcgatgg   7500

aaaaggtcgc atcagcgtca ttgatcgagt caagaacttt ttcaagctag cacatggtga   7560

atatattgct ccagagaaaa tcgaaaatat ttatttatca tcatgcccct atatcacgca   7620

aatatttgtc tttggagatc ctttaaagac atttttagtt ggcatcgttg gtgttgatgt   7680

tgatgcagcg caaccgattt tagctgcaaa gcacccagag gtgaaaacgt ggactaagga   7740

agtgctagta gaaaacttaa atcgtaataa aaagctaagg aaggaatttt taaacaaaat   7800

taataaatgc accgatgggc tacaaggatt cgaaaaattg cataacatca aagtcggact   7860

tgagccttta actctcgagg atgatgttgt gacgccaact tttaaaataa agcgtgccaa   7920

agcatcaaaa ttcttcaaag atacattaga ccaactatac gccgaaggtt cactagtcaa   7980

gacagaaaag ctttaaggcc gcgtttaaac aggaggaata aaccatggca atacagcagg   8040

tacatcacgc tgacacttca tcatcaaagg tgctcggaca gctccgtggc aagcgggttc   8100

tgatcaccgg taccactggc tttctgggca aggtggtcct cgaaaggctg attcgggcgg   8160

tgcctgatat cggcgcaatt tacctgctga tccggggcaa taaacggcat ccggatgctc   8220

gttcccgttt cctggaagaa attgccacct cctcggtgtt tgaccgtctt cgcgaggccg   8280

attcagaggg atttgacgcc tttctggaag agcgcattca ctgcgtgacc ggtgaggtga   8340

ccgaagcggg tttcgggata gggcaggaag actatcgcaa actcgccacc gaactggatg   8400

cggtgatcaa ctccgctgca agcgtgaatt tccgtgaaga gctcgacaag gcgctggcca   8460

tcaacaccct gtgccttcgg aatattgccg gcatggtgga tttgaatccg aagcttgcgg   8520

tcctgcaggt ctccacctgc tatgtcaatg gcatgaactc ggggcaggta accgaatcgg   8580

tgatcaagcc ggcaggcgag gccgtgccgc gttccccgga cggcttctat gagatagaag   8640

agcttgttcg cctgcttcag gataaaattg aagacgttca ggcccgttat tccggcaaag   8700

tgctggagag gaagctggtg gacctgggga ttcgggaagc caaccgctat ggctggagcg   8760

atacctacac ctttaccaag tggctgggcg aacagttgct gatgaaggcg ttaaacgggc   8820

gcacgctgac cattctgcgt ccttcgatta tcgaaagtgc cctggaggaa ccagcgcccg   8880

gctggattga gggggtgaag gtggcagatg ccatcatcct ggcttacgca cgggaaaaag   8940

tcaccctctt cccgggcaaa cgctccggta tcatcgatgt gattccagtg gacctggtgg   9000

ccaactccat catcctttcc ctggcggaag ctcttggaga acccggtcga cgtcgcatct   9060

atcaatgttg cagcgggggc ggcaatccaa tctccctggg tgagttcatc gatcatctca   9120

tggcggaatc aaaagccaat tacgctgcct acgatcacct gttctaccgg cagcccagca   9180

agccgtttct ggcggttaac cgggcgctgt ttgatttggt gatcagtggt gttcgcttac   9240
```

```
cgctctccct gacggaccgt gtgctcaaat tactgggaaa ttcccgggac ctgaaaatgc   9300
tcaggaatct ggataccacc cagtcgctgg caaccatttt tggtttctac accgcgccgg   9360
attatatctt ccggaacgat gagctgatgg cgctggcgaa ccggatgggt gaggtcgata   9420
aagggctgtt cccggtggat gcccgcctga ttgactggga gctctacctg cgcaagattc   9480
acctggccgg gctcaatcgc tatgccctga aagaacgaaa ggtgtacagt ctgaaaaccg   9540
cgcgccagcg caaaaaagct gcctaaaaac ggcgcgccag gaggaataaa ccatgacgcc   9600
cctgaatccc actgaccagc tctttctctg gctggaaaaa cgccagcagc ccatgcatgt   9660
gggcggcctc cagctgtttt ccttccccga aggcgcgccg gacgactatg tcgcgcagct   9720
ggcagaccag cttcggcaga agacggaggt gaccgccccc tttaaccagc gcctgagcta   9780
tcgcctgggc cagccggtat gggtggagga tgagcacctg gaccttgagc atcatttccg   9840
cttcgaggcg ctgcccacac ccgggcgtat tcgggagctg ctgtcgttcg tatcggcgga   9900
gcattcgcac ctgatggacc gggagcgccc catgtgggag gtgcacctga tcgagggcct   9960
gaaagaccgg cagtttgcgc tctacaccaa ggttcaccat tccctggtgg acggtgtctc  10020
ggccatgcgc atggccaccc ggatgctgag tgaaaacccg gacgaacacg gcatgccgcc  10080
aatctgggat ctgccttgcc tgtcacggga taggggtgag tcggacggac actccctctg  10140
gcgcagtgtc acccatttgc tggggctttc gggccgccag ctcggcacca ttcccactgt  10200
ggcaaaggag ctactgaaaa ccatcaatca ggcccggaag gatccggcct acgactccat  10260
tttccatgcc ccgcgctgca tgctgaacca gaaaatcacc ggttcccgtc gtttcgccgc  10320
ccagtcctgg tgcctgaaac ggattcgcgc cgtgtgcgag gcctatggca ccacggtcaa  10380
cgatgtcgta actgccatgt gcgcagcggc tctgcgtacc tatctgatga atcaggatgc  10440
cttgccggag aaaccactgg tggcctttgt gccggtgtca ctacgccggg acgacagctc  10500
cgggggcaac caggtaggcg tcatcctggc gagccttcac accgatgtgc aggaggccgg  10560
cgaacgactg ttaaaaatcc accatggcat ggaagaggcc aagcagcgct accgtcatat  10620
gagcccggag gaaatcgtca actacacggc cctgaccctg gcgccggccg ccttccacct  10680
gctgaccggg ctggcgccca agtggcagac cttcaatgtg gtgatttcca atgtccccgg  10740
gccatccagg cccctgtact ggaacggggc gaaactggaa ggcatgtatc cggtgtctat  10800
cgatatggac agactggccc tgaacatgac actgaccagc tataacgacc aggtggagtt  10860
cggcctgatt ggctgtcgcc ggaccctgcc cagcctgcaa cggatgctgg actacctgga  10920
acagggtctg gcagagctgg agctcaacgc cggtctgtaa tctagacgcg cctagttaag  10980
ccagccccga cacccgccaa cacccgctga cgcgccctga cgggcttgtc tgctcccggc  11040
atccgcttac agacaagctg tgaccgtctc cgggagctgc atgtgtcaga ggttttcacc  11100
gtcatcaccg aaacgcgcga gacgaaaggg cctcgtgata cgcctatttt tataggttaa  11160
tgtcatgata ataatggttt cttagacgtc aggtggcact tttcggggaa atgtgcgcgg  11220
aacccctatt tgtttatttt tctaaataca ttcaaatatg tatccgctca tgagacaata  11280
accctgataa atgcttcaat aatattgaaa aaggaagagt atgagccata ttcaacggga  11340
aacgtcttgc tcgaggccgc gattaaattc caacatggat gctgatttat atgggtataa  11400
atgggctcgc gataatgtcg ggcaatcagg tgcgacaatc tatcgattgt atgggaagcc  11460
cgatgcgcca gagttgtttc tgaaacatgg caaaggtagc gttgccaatg atgttacaga  11520
tgagatggtc agactaaact ggctgacgga atttatgcct cttccgacca tcaagcattt  11580
tatccgtact cctgatgatg catggttact caccactgcg atccccggga aaacagcatt  11640
```

```
ccaggtatta gaagaatatc ctgattcagg tgaaaatatt gttgatgcgc tggcagtgtt  11700
cctgcgccgg ttgcattcga ttcctgtttg taattgtcct tttaacagcg atcgcgtatt  11760
tcgtctcgct caggcgcaat cacgaatgaa taacggtttg gttgatgcga gtgattttga  11820
tgacgagcgt aatggctggc ctgttgaaca agtctggaaa gaaatgcata agcttttgcc  11880
attctcaccg gattcagtcg tcactcatgg tgatttctca cttgataacc ttatttttga  11940
cgaggggaaa ttaataggtt gtattgatgt tggacgagtc ggaatcgcag accgatacca  12000
ggatcttgcc atcctatgga actgcctcgg tgagttttct ccttcattac agaaacggct  12060
ttttcaaaaa tatggtattg ataatcctga tatgaataaa ttgcagtttc atttgatgct  12120
cgatgagttt ttctaa                                                  12136
```

<210> SEQ ID NO 72
<211> LENGTH: 10628
<212> TYPE: DNA
<213> ORGANISM: Artificial Sequence
<220> FEATURE:
<223> OTHER INFORMATION: Wax Ester Synthase Operon construct 5023

<400> SEQUENCE: 72

```
ccggtatgga tggcaccgat gcggaatccc aacagattgc ctttgacaac aatgtggcct     60
ggaataacct gggggatttg tccaccacca cccaacgggc ctacacttcg gctattagca    120
cagacacagt gcagagtgtt tatggcgtta atctggaaaa aaacgataac attcccattg    180
tttttgcgtg gcccattttt cccaccaccc ttaatcccac agattttcag gtaatgctta    240
acacggggga aattgtcacc ccggtgatcg cctctttgat tcccaacagt gaatacaacg    300
aacggcaaac ggtagtaatt acgggcaatt ttggtaatcg tttaacccca ggcacggagg    360
gagcgattta tcccgtttcc gtaggcacag tgttggacag tactcctttg gaaatggtgg    420
gacccaacgg cccggtcagt gcggtgggta ttaccattga tagtctcaac ccctacgtgg    480
ccggcaatgg tcccaaaatt gtcgccgcta agttagaccg cttcagtgac ctgggggaag    540
gggctcccct ctggttagcc accaatcaaa ataacagtgg cggggattta tatggagacc    600
aagcccaatt tcgtttgcga atttacacca gcgccggttt ttcccccgat ggcattgcca    660
gtttactacc cacagaattt gaacggtatt ttcaactcca agcggaagat attacgggac    720
ggacagttat cctaacccaa actggtgttg attatgaaat tcccggcttt ggtctggtgc    780
aggtgttggg gctggcggat ttggccgggg ttcaggacag ctatgacctg acttacatcg    840
aagatcatga caactattac gacattatcc tcaaagggga cgaagccgca gttcgccaaa    900
ttaagagggt tgctttgccc tccgaagggg attattcggc ggtttataat cccggtggcc    960
ccggcaatga tccagagaat ggtcccccac tgtcagacca agtttactca tatatacttt   1020
agattgattt aaaacttcat ttttaattta aaaggatcta ggtgaagatc ctttttgata   1080
atctcatgac caaaatccct taacgtgagt tttcgttcca ctgagcgtca gaccccgtag   1140
aaaagatcaa aggatcttct tgagatcctt tttttctgcg cgtaatctgc tgcttgcaaa   1200
caaaaaaacc accgctacca gcggtggttt gtttgccgga tcaagagcta ccaactcttt   1260
ttccgaaggt aactggcttc agcagagcgc agataccaaa tactgtcctt ctagtgtagc   1320
cgtagttagg ccaccacttc aagaactctg tagcaccgcc tacatacctc gctctgctaa   1380
tcctgttacc agtggctgct gccagtggcg ataagtcgtg tcttaccggg ttggactcaa   1440
gacgatagtt accggataag gcgcagcggt cgggctgaac ggggggttcg tgcacacagc   1500
```

```
ccagcttgga gcgaacgacc tacaccgaac tgagatacct acagcgtgag ctatgagaaa   1560
gcgccacgct tcccgaaggg agaaaggcgg acaggtatcc ggtaagcggc agggtcggaa   1620
caggagagcg cacgagggag cttccagggg gaaacgcctg gtatctttat agtcctgtcg   1680
ggtttcgcca cctctgactt gagcgtcgat ttttgtgatg ctcgtcaggg gggcggagcc   1740
tatggaaaaa cgccagcaac gcggcctttt tacggttcct ggccttttgc tggccttttg   1800
ctcacatgtt ctttcctgcg ttatcccctg attctgtgga taaccgtatt accgcctttg   1860
agtgagctga taccgctcgc cgcagccgaa cgaccgagcg cagcgagtca gtgagcgagg   1920
aagcggaaga gcgcccaata cgcaaaccgc ctctccccgc gcgttggccg attcattaat   1980
gcagctggca cgacaggttt cccgactgga aagcgggcag tgaattgctg aagcggaatc   2040
cctggttaat gccgccgccg atgccaattg cattctccaa gtggggcaca ttgaacgctt   2100
caacccggca tttttagagc taaccaaaat tctcaaaacg gaagagttat tggcgatcga   2160
agcccatcgc atgagtccct attcccagcg ggccaatgat gtctccgtgg tattggattt   2220
gatgatccat gacattgacc tgttgctgga attggtgggt tcggaagtgg ttaaactgtc   2280
cgccagtggc agtcgggctt ctgggtcagg atatttggat tatgtcaccg ctacgttagg   2340
cttctcctcc ggcattgtgg ccaccctcac cgccagtaag gtcacccatc gtaaaattcg   2400
ttccatcgcc gcccactgca aaaattccct caccgaagcg gattttctca ataacgaaat   2460
tttgatccat cgccaaacca ccgctgattg gagcgcggac tatggccagg tattgtatcg   2520
ccaggatggt ctaatcgaaa aggtttacac cagtaatatt gaacctctcc acgctgaatt   2580
agaacatttt attcattgtg ttaggggagg tgatcaaccc tcagtggggg gagaacaggc   2640
cctcaaggcc ctgaagttag ccagtttaat tgaagaaatg gccctggaca gtcaggaatg   2700
gcatgggggg gaagttgtga cagaatatca agatgccacc ctggccctca gtgcgagtgt   2760
ttaaatcaac ttaattaatg caattattgc gagttcaaac tcgataactt tgtgaaatat   2820
tactgttgaa ttaatctatg actattcaat acaccccct agccgatcgc ctgttggcct   2880
acctcgccgc cgatcgccta aatctcagcg ccaagagtag ttccctcaac accagtattc   2940
tgctcagcag tgacctattc aatcaggaag gggaattgt aacagccaac tatggctttg   3000
atggttatat ggggccggcc atttaaatag gaggaataaa ccatggcgaa cggtagcgct   3060
gtctctctga agagcggctc cttgaatacg caagaggaca cttcttcttc cccaccgcca   3120
cgcgcgttca tcaaccaatt acccgactgg tccatgttat tgacggcgat taccactgtc   3180
tttgttgccg cagagaaaca gtggactatg ttagaccgca agagcaagcg ctccgatatg   3240
ttagtggatt cttttggcat ggaacgcatt gtgcaggatg gcttagtgtt tcgtcaatct   3300
tttagcattc gttcttatga aatcggtgca gatcgtcgtg catccattga aaccttaatg   3360
aaccatctgc aggaaactag cttgaatcat tgcaaatcca ttcgcttgtt gaatgagggt   3420
tttggtcgca cccccgagat gtgcaaacgt gacttgatct gggtggttac ccgcatgcac   3480
atcatggtca accgctaccc tacctggggt gataccgttg agattaacac ttgggtttcc   3540
caaagcggca agaatggtat gggtcgtgat tggctgattt ccgactgtaa taccggcgaa   3600
atcctgatcc gcgcgacgtc tgcatgggcg atgatgaacc aaaagacccg tcgtctgtct   3660
aaactgcctt acgaagtcag ccaagagatt gctccgcact tcgtcgacag ccctcccgtg   3720
atcgaggacg gcgaccgtaa gttacacaag ttcgatgtga aaaccggcga cagcatccgt   3780
aaaggtttga ctccgcgttg gaatgactta gatgttaatc agcacgttaa caacgttaag   3840
tatatcggct ggatcttaga gagcatgccg accgaggtct tggaaactca tgaactgtgt   3900
```

```
ttcttaactc tggagtatcg tcgcgagtgc ggtcgcgata gcgtgctgga atctgtgacc   3960
gcgatggatc cttctaatga aggtggtcgc tcccactacc agcatttact gcgcttggag   4020
gacggtactg acatcgttaa gggccgcact gagtggcgtc caaagaatgc ccggaatatt   4080
ggtgccatta gtaccggtaa aaccagtaat ggtaatcccg ccagttaata aaaatgcggc   4140
cgcaggagga ataaaccatg gccgctccag attatgcact taccgattta attgaatcgg   4200
atcctcgttt cgaaagtttg aagacaagat tagccggtta caccaaaggc tctgatgaat   4260
atattgaaga gctatactct caattaccac tgaccagcta tcccaggtac aaaacatttt   4320
taaagaaaca ggcggttgcc atttcgaatc cggataatga agctggtttt agctcgattt   4380
ataggagttc tctttcttct gaaaatctag tgagctgtgt ggataaaaac ttaagaactg   4440
catacgatca cttcatgttt tctgcaagga gatggcctca acgtgactgt ttaggttcaa   4500
ggccaattga taaagccaca ggcacctggg aggaaacatt ccgtttcgag tcgtactcca   4560
cggtatctaa aagatgtcat aatatcggaa gtggtatatt gtctttggta aacacgaaaa   4620
ggaaacgtcc tttggaagcc aatgattttg ttgttgctat cttatcacac aacaaccctg   4680
aatggatcct aacagatttg gcctgtcagg cctattctct aactaacacg gctttgtacg   4740
aaacattagg tccaaacacc tccgagtaca tattgaattt aaccgaggcc cccattctga   4800
tttttgcaaa atcaaatatg tatcatgtat tgaagatggt gcctgatatg aaatttgtta   4860
atactttggt ttgtatggat gaattaactc atgacgagct ccgtatgcta aatgaatcgt   4920
tgctacccgt taagtgcaac tctctcaatg aaaaaatcac atttttttca ttggagcagg   4980
tagaacaagt tggttgcttt aacaaaaatc ctgcaattcc acctacccca gattccttgt   5040
atactatttc gtttacttct ggtactacag gtttacctaa aggtgtggaa atgtctcaca   5100
gaaacattgc gtctgggata gcatttgctt tttctacctt cagaataccg ccagataaaa   5160
gaaaccaaca gttatatgat atgtgttttt tgccattggc tcatattttt gaaagaatgg   5220
ttattgcgta tgatctagcc atcgggtttg gaataggctt cttacataaa ccagacccaa   5280
ctgtattggt agaggatttg aagattttga aaccttacgc ggttgccctg gttcctagaa   5340
tattaacacg gtttgaagcc ggtataaaaa acgctttgga taaatcgact gtccagagga   5400
acgtagcaaa tactatattg gattctaaat cggccagatt taccgcaaga ggtggtccag   5460
ataaatcgat tatgaatttt ctagtttatc atcgcgtatt gattgataaa atcagagact   5520
ctttaggttt gtccaataac tcgtttataa ttaccggatc agctcccata tctaaagata   5580
ccttactatt tttaagaagt gccttggata ttggtataag acagggctac ggcttaactg   5640
aaacttttgc tggtgtctgt ttaagcgaac cgtttgaaaa agatgtcgga tcttgtggtg   5700
ccataggtat ttctgcagaa tgtagattga agtctgttcc agaaatgggt taccatgccg   5760
acaaggattt aaaaggtgaa ctgcaaattc gtggcccaca ggtttttgaa agatatttta   5820
aaaatccgaa tgaaacttca aaagccgttg accaagatgg ttggttttcc acgggagatg   5880
ttgcatttat cgatggaaaa ggtcgcatca gcgtcattga tcgagtcaag aactttttca   5940
agctagcaca tggtgaatat attgctccag agaaaatcga aaatatttat ttatcatcat   6000
gcccctatat cacgcaaata tttgtctttg gagatccttt aaagacattt ttagttggca   6060
tcgttggtgt tgatgttgat gcagcgcaac cgattttagc tgcaaagcac ccagaggtga   6120
aaacgtggac taaggaagtg ctagtagaaa acttaaatcg taataaaaag ctaaggaagg   6180
aatttttaaa caaaattaat aaatgcaccg atgggctaca aggattcgaa aaattgcata   6240
```

-continued

```
acatcaaagt cggacttgag cctttaactc tcgaggatga tgttgtgacg ccaactttta   6300
aaataaagcg tgccaaagca tcaaaattct tcaaagatac attagaccaa ctatacgccg   6360
aaggttcact agtcaagaca gaaaagcttt aaggccgcgt ttaaacagga ggaataaacc   6420
atggcaatac agcaggtaca tcacgctgac acttcatcat caaaggtgct cggacagctc   6480
cgtggcaagc gggttctgat caccggtacc actggctttc tgggcaaggt ggtcctcgaa   6540
aggctgattc gggcggtgcc tgatatcggc gcaatttacc tgctgatccg gggcaataaa   6600
cggcatccgg atgctcgttc ccgtttcctg gaagaaattg ccacctcctc ggtgtttgac   6660
cgtcttcgcg aggccgattc agagggattt gacgcctttc tggaagagcg cattcactgc   6720
gtgaccggtg aggtgaccga agcgggtttc gggatagggc aggaagacta tcgcaaactc   6780
gccaccgaac tggatgcggt gatcaactcc gctgcaagcg tgaatttccg tgaagagctc   6840
gacaaggcgc tggccatcaa caccctgtgc cttcggaata ttgccggcat ggtggatttg   6900
aatccgaagc ttgcggtcct gcaggtctcc acctgctatg tcaatggcat gaactcgggg   6960
caggtaaccg aatcggtgat caagccggca ggcgaggccg tgccgcgttc cccggacggc   7020
ttctatgaga tagaagagct tgttcgcctg cttcaggata aaattgaaga cgttcaggcc   7080
cgttattccg gcaaagtgct ggagaggaag ctggtggacc tggggattcg ggaagccaac   7140
cgctatggct ggagcgatac ctacaccttt accaagtggc tgggcgaaca gttgctgatg   7200
aaggcgttaa acgggcgcac gctgaccatt ctgcgtcctt cgattatcga aagtgccctg   7260
gaggaaccag cgcccggctg gattgagggg gtgaaggtgg cagatgccat catcctggct   7320
tacgcacggg aaaaagtcac cctcttcccg ggcaaacgct ccggtatcat cgatgtgatt   7380
ccagtggacc tggtggccaa ctccatcatc ctttccctgg cggaagctct tggagaaccc   7440
ggtcgacgtc gcatctatca atgttgcagc gggggcggca atccaatctc cctgggtgag   7500
ttcatcgatc atctcatggc ggaatcaaaa gccaattacg ctgcctacga tcacctgttc   7560
taccggcagc ccagcaagcc gtttctggcg gttaaccggg cgctgtttga tttggtgatc   7620
agtggtgttc gcttaccgct ctccctgacg gaccgtgtgc tcaaattact gggaaattcc   7680
cgggacctga aaatgctcag gaatctggat accacccagt cgctggcaac catttttggt   7740
ttctacaccg cgccggatta tatcttccgg aacgatgagc tgatggcgct ggcgaaccgg   7800
atgggtgagg tcgataaagg gctgttcccg gtggatgccc gcctgattga ctgggagctc   7860
tacctgcgca agattcacct ggccgggctc aatcgctatg ccctgaaaga acgaaaggtg   7920
tacagtctga aaaccgcgcg ccagcgcaaa aaagctgcct aaaaacggcg cgccaggagg   7980
aataaaccat gaaacgcttg gccacgttgg atgcgtcttg gctcgctgtc gaatctgacg   8040
atacgcccat gcatgttggt aacttgcaga tcttctcgct cccggacaat gcaccttcga   8100
cgttcgccgg tgatctggtg aagtccatga agcaagccgg caatgtcgaa ttgccctggg   8160
gctgtaaact ggtttggcct gggtttctgg gccgagtgtt ggctcccacc tggaaacacg   8220
ataagcatat tgacctggat tatcacgtcc gccactctgc tctccctaaa cccggaggcg   8280
agcgcgagtt gggcgagctg gtttctcgac tccatagtaa cccccctcgac ctgagtcgcc   8340
cgctgtggga atgccatatg attgaaggct tggaacataa tcggtttgca ctgtatacga   8400
aaatgcacca ttgcatgatt gacggcattt ccggtgtgcg cttgatgcag cgcgtgttgt   8460
ccaagtcgcc cgatgagcgc gacatgctgc cgccttggag tgtccgtccc gagagcacgc   8520
ggggtaagaa aacggatagc gaagcatccg tgccaggagc tatctcgcaa gccatggagg   8580
ccctgaagct gcaactgggc ttggcacccc gcctctggca ggctagcaat cggctgatcc   8640
```

```
attccgtccg tcacccggag gatggattga ctgctccatt cacgggacca gttagtaaga   8700
tcaatcaccg cgttacaggt caacgacgat ttgctactca gcagtaccag ctggaagata   8760
tgaaagcgat ggcacgcgcg agtgggagct cgatgaacga tattgtgctc tacctctgtg   8820
gtacagcgct gcgacgcttt ctgctggaac aggacgatct ccctgagatt agcctgaccg   8880
ctgggattcc tgtcaacatt cgtcccgcag atgacgaggg caccggtacc cagattagct   8940
tcatgatcgc ggctctggcc accaatcaac ccgatccgct gacccggctg aaatgtatca   9000
aagaaagtag ctgcaaggcg aaagagcacc tccagaaatt gccgaagaaa gcactcacac   9060
aatacaccat gatgctcatg tcgccataca tcctgcaact catgtctggt ttgggtggcc   9120
gcatgcgtcc agtctttaac gttaccatta gcaacgttcc tggcccaact gaagatctgt   9180
actacgaagg cgcgaagctg gaggcgatgt atcccgtttc gttgattacc cacggcggag   9240
ccttgaatat cacctgcctg agctatgccg gcagtttgaa ctttggcttc actgggtgtc   9300
gcgatactct ccccagtatg caaaaactgg ccgtctacac gggggaagcc ctcgaagaac   9360
tccgcacatt gctgttgccg ccaaagaaaa agcctagccc gcgtaaaccg cggacggctg   9420
ccaagaagaa accggcagtg aattcgaacg ccagttaacg cgcctagtta agccagcccc   9480
gacacccgcc aacacccgct gacgcgccct gacgggcttg tctgctcccg gcatccgctt   9540
acagacaagc tgtgaccgtc tccgggagct gcatgtgtca gaggttttca ccgtcatcac   9600
cgaaacgcgc gagacgaaag ggcctcgtga tacgcctatt tttataggtt aatgtcatga   9660
taataatggt ttcttagacg tcaggtggca cttttcgggg aaatgtgcgc ggaaccccta   9720
tttgtttatt tttctaaata cattcaaata tgtatccgct catgagacaa taaccctgat   9780
aaatgcttca ataatattga aaaaggaaga gtatgagcca tattcaacgg gaaacgtctt   9840
gctcgaggcc gcgattaaat tccaacatgg atgctgattt atatgggtat aaatgggctc   9900
gcgataatgt cgggcaatca ggtgcgacaa tctatcgatt gtatgggaag cccgatgcgc   9960
cagagttgtt tctgaaacat ggcaaaggta gcgttgccaa tgatgttaca gatgagatgg  10020
tcagactaaa ctggctgacg gaatttatgc ctcttccgac catcaagcat tttatccgta  10080
ctcctgatga tgcatggtta ctcaccactg cgatccccgg gaaaacagca ttccaggtat  10140
tagaagaata tcctgattca ggtgaaaata ttgttgatgc gctggcagtg ttcctgcgcc  10200
ggttgcattc gattcctgtt tgtaattgtc cttttaacag cgatcgcgta tttcgtctcg  10260
ctcaggcgca atcacgaatg aataacggtt tggttgatgc gagtgatttt gatgacgagc  10320
gtaatggctg gcctgttgaa caagtctgga aagaaatgca taagcttttg ccattctcac  10380
cggattcagt cgtcactcat ggtgatttct cacttgataa ccttattttt gacgagggga  10440
aattaatagg ttgtattgat gttggacgag tcggaatcgc agaccgatac caggatcttg  10500
ccatcctatg gaactgcctc ggtgagtttt ctccttcatt acagaaacgg ctttttcaaa  10560
aatatggtat tgataatcct gatatgaata aattgcagtt tcatttgatg ctcgatgagt  10620
ttttctaa                                                           10628
```

<210> SEQ ID NO 73
<211> LENGTH: 10614
<212> TYPE: DNA
<213> ORGANISM: Artificial Sequence
<220> FEATURE:
<223> OTHER INFORMATION: Wax Ester Synthase Operon construct 5062

<400> SEQUENCE: 73

```
ccggtatgga tggcaccgat gcggaatccc aacagattgc ctttgacaac aatgtggcct     60
ggaataacct gggggatttg tccaccacca cccaacgggc ctacacttcg gctattagca    120
cagacacagt gcagagtgtt tatggcgtta atctggaaaa aaacgataac attcccattg    180
tttttgcgtg gcccattttt cccaccaccc ttaatcccac agattttcag gtaatgctta    240
acacggggga aattgtcacc ccggtgatcg cctctttgat tcccaacagt gaatacaacg    300
aacggcaaac ggtagtaatt acgggcaatt ttggtaatcg tttaacccca ggcacggagg    360
gagcgattta tcccgtttcc gtaggcacag tgttggacag tactcctttg gaaatggtgg    420
gacccaacgg cccggtcagt gcggtgggta ttaccattga tagtctcaac ccctacgtgg    480
ccggcaatgg tcccaaaatt gtcgccgcta agttagaccg cttcagtgac ctgggggaag    540
gggctcccct ctggttagcc accaatcaaa ataacagtgg cggggattta tatggagacc    600
aagcccaatt tcgtttgcga atttacacca gcgccggttt ttcccccgat ggcattgcca    660
gtttactacc cacagaattt gaacggtatt ttcaactcca agcggaagat attacgggac    720
ggacagttat cctaacccaa actggtgttg attatgaaat tcccggcttt ggtctggtgc    780
aggtgttggg gctggcggat ttggccgggg ttcaggacag ctatgacctg acttacatcg    840
aagatcatga caactattac gacattatcc tcaaagggga cgaagccgca gttcgccaaa    900
ttaagagggt tgctttgccc tccgaagggg attattcggc ggtttataat cccggtggcc    960
ccggcaatga tccagagaat ggtcccccac tgtcagacca agtttactca tatatacttt   1020
agattgattt aaaacttcat ttttaattta aaaggatcta ggtgaagatc ctttttgata   1080
atctcatgac caaaatccct taacgtgagt tttcgttcca ctgagcgtca gaccccgtag   1140
aaaagatcaa aggatcttct tgagatcctt tttttctgcg cgtaatctgc tgcttgcaaa   1200
caaaaaaacc accgctacca gcggtggttt gtttgccgga tcaagagcta ccaactcttt   1260
ttccgaaggt aactggcttc agcagagcgc agataccaaa tactgtcctt ctagtgtagc   1320
cgtagttagg ccaccacttc aagaactctg tagcaccgcc tacatacctc gctctgctaa   1380
tcctgttacc agtggctgct gccagtggcg ataagtcgtg tcttaccggg ttggactcaa   1440
gacgatagtt accggataag gcgcagcggt cgggctgaac ggggggttcg tgcacacagc   1500
ccagcttgga gcgaacgacc tacaccgaac tgagatacct acagcgtgag ctatgagaaa   1560
gcgccacgct tcccgaaggg agaaaggcgg acaggtatcc ggtaagcggc agggtcggaa   1620
caggagagcg cacgagggag cttccagggg gaaacgcctg gtatctttat agtcctgtcg   1680
ggtttcgcca cctctgactt gagcgtcgat ttttgtgatg ctcgtcaggg gggcggagcc   1740
tatggaaaaa cgccagcaac gcggcctttt tacggttcct ggccttttgc tggccttttg   1800
ctcacatgtt ctttcctgcg ttatcccctg attctgtgga taaccgtatt accgcctttg   1860
agtgagctga taccgctcgc cgcagccgaa cgaccgagcg cagcgagtca gtgagcgagg   1920
aagcggaaga gcgcccaata cgcaaaccgc ctctccccgc gcgttggccg attcattaat   1980
gcagctggca cgacaggttt cccgactgga aagcgggcag tgaattgctg aagcggaatc   2040
cctggttaat gccgccgccg atgccaattg cattctccaa gtggggcaca ttgaacgctt   2100
caacccggca tttttagagc taaccaaaat tctcaaaacg gaagagttat tggcgatcga   2160
agcccatcgc atgagtccct attcccagcg ggccaatgat gtctccgtgg tattggattt   2220
gatgatccat gacattgacc tgttgctgga attggtgggt tcggaagtgg ttaaactgtc   2280
cgccagtggc agtcgggctt ctgggtcagg atatttggat tatgtcaccg ctacgttagg   2340
cttctcctcc ggcattgtgg ccaccctcac cgccagtaag gtcacccatc gtaaaattcg   2400
```

```
ttccatcgcc gcccactgca aaaattccct caccgaagcg gattttctca ataacgaaat   2460
tttgatccat cgccaaacca ccgctgattg gagcgcggac tatggccagg tattgtatcg   2520
ccaggatggt ctaatcgaaa aggtttacac cagtaatatt gaacctctcc acgctgaatt   2580
agaacatttt attcattgtg ttaggggagg tgatcaaccc tcagtggggg gagaacaggc   2640
cctcaaggcc ctgaagttag ccagtttaat tgaagaaatg gccctggaca gtcaggaatg   2700
gcatgggggg gaagttgtga cagaatatca agatgccacc ctggccctca gtgcgagtgt   2760
ttaaatcaac ttaattaatg caattattgc gagttcaaac tcgataactt tgtgaaatat   2820
tactgttgaa ttaatctatg actattcaat acacccccct agccgatcgc ctgttggcct   2880
acctcgccgc cgatcgccta aatctcagcg ccaagagtag ttccctcaac accagtattc   2940
tgctcagcag tgacctattc aatcaggaag ggggaattgt aacagccaac tatggctttg   3000
atggttatat ggggccggcc atttaaatag gaggaataaa ccatggccgc tccagattat   3060
gcacttaccg atttaattga atcggatcct cgtttcgaaa gtttgaagac aagattagcc   3120
ggttacacca aaggctctga tgaatatatt gaagagctat actctcaatt accactgacc   3180
agctatccca ggtacaaaac atttttaaag aaacaggcgg ttgccatttc gaatccggat   3240
aatgaagctg gttttagctc gatttatagg agttctcttt cttctgaaaa tctagtgagc   3300
tgtgtggata aaaacttaag aactgcatac gatcacttca tgttttctgc aaggagatgg   3360
cctcaacgtg actgtttagg ttcaaggcca attgataaag ccacaggcac ctgggaggaa   3420
acattccgtt tcgagtcgta ctccacggta tctaaaagat gtcataatat cggaagtggt   3480
atattgtctt tggtaaacac gaaaaggaaa cgtcctttgg aagccaatga ttttgttgtt   3540
gctatcttat cacacaacaa ccctgaatgg atcctaacag atttggcctg tcaggcctat   3600
tctctaacta acacggcttt gtacgaaaca ttaggtccaa acacctccga gtacatattg   3660
aatttaaccg aggcccccat tctgattttt gcaaaatcaa atatgtatca tgtattgaag   3720
atggtgcctg atatgaaatt tgttaatact ttggtttgta tggatgaatt aactcatgac   3780
gagctccgta tgctaaatga atcgttgcta cccgttaagt gcaactctct caatgaaaaa   3840
atcacatttt tttcattgga gcaggtagaa caagttggtt gctttaacaa aattcctgca   3900
attccaccta ccccagattc cttgtatact atttcgttta cttctggtac tacaggttta   3960
cctaaaggtg tggaaatgtc tcacagaaac attgcgtctg ggatagcatt tgctttttct   4020
accttcagaa taccgccaga taaaagaaac caacagttat atgatatgtg tttttttgcca   4080
ttggctcata tttttgaaag aatggttatt gcgtatgatc tagccatcgg gtttggaata   4140
ggcttcttac ataaaccaga cccaactgta ttggtagagg atttgaagat tttgaaacct   4200
tacgcggttg ccctggttcc tagaatatta acacggtttg aagccggtat aaaaaacgct   4260
ttggataaat cgactgtcca gaggaacgta gcaaatacta tattggattc taaatcggcc   4320
agatttaccg caagaggtgg tccagataaa tcgattatga attttctagt ttatcatcgc   4380
gtattgattg ataaaatcag agactcttta ggtttgtcca ataactcgtt tataattacc   4440
ggatcagctc ccatatctaa agatacctta ctatttttaa gaagtgcctt ggatattggt   4500
ataagacagg gctacggctt aactgaaact tttgctggtg tctgtttaag cgaaccgttt   4560
gaaaaagatg tcggatcttg tggtgccata ggtatttctg cagaatgtag attgaagtct   4620
gttccagaaa tgggttacca tgccgacaag gatttaaaag gtgaactgca aattcgtggc   4680
ccacaggttt ttgaaagata ttttaaaaat ccgaatgaaa cttcaaaagc cgttgaccaa   4740
```

```
gatggttggt tttccacggg agatgttgca tttatcgatg gaaaaggtcg catcagcgtc   4800
attgatcgag tcaagaactt tttcaagcta gcacatggtg aatatattgc tccagagaaa   4860
atcgaaaata tttatttatc atcatgcccc tatatcacgc aaatatttgt ctttggagat   4920
cctttaaaga catttttagt tggcatcgtt ggtgttgatg ttgatgcagc gcaaccgatt   4980
ttagctgcaa agcacccaga ggtgaaaacg tggactaagg aagtgctagt agaaaactta   5040
aatcgtaata aaaagctaag gaaggaattt ttaaacaaaa ttaataaatg caccgatggg   5100
ctacaaggat tcgaaaaatt gcataacatc aaagtcggac ttgagccttt aactctcgag   5160
gatgatgttg tgacgccaac ttttaaaata aagcgtgcca aagcatcaaa attcttcaaa   5220
gatacattag accaactata cgccgaaggt tcactagtca agacagaaaa gctttaagcg   5280
gccgcaggag gaataaacca tgaaacgctt ggccacgttg gatgcgtctt ggctcgctgt   5340
cgaatctgac gatacgccca tgcatgttgg taacttgcag atcttctcgc tcccggacaa   5400
tgcaccttcg acgttcgccg gtgatctggt gaagtccatg aagcaagccg gcaatgtcga   5460
attgccctgg ggctgtaaac tggtttggcc tgggtttctg ggccgagtgt tggctcccac   5520
ctggaaacac gataagcata ttgacctgga ttatcacgtc cgccactctg ctctccctaa   5580
acccggaggc gagcgcgagt tgggcgagct ggtttctcga ctccatagta accccctcga   5640
cctgagtcgc ccgctgtggg aatgccatat gattgaaggc ttggaacata atcggtttgc   5700
actgtatacg aaaatgcacc attgcatgat tgacggcatt tccggtgtgc gcttgatgca   5760
gcgcgtgttg tccaagtcgc ccgatgagcg cgacatgctg ccgccttgga gtgtccgtcc   5820
cgagagcacg cggggtaaga aaacggatag cgaagcatcc gtgccaggag ctatctcgca   5880
agccatggag gccctgaagc tgcaactggg cttggcaccc cgcctctggc aggctagcaa   5940
tcggctgatc cattccgtcc gtcacccgga ggatggattg actgctccat tcacgggacc   6000
agttagtaag atcaatcacc gcgttacagg tcaacgacga tttgctactc agcagtacca   6060
gctggaagat atgaaagcga tggcacgcgc gagtgggagc tcgatgaacg atattgtgct   6120
ctacctctgt ggtacagcgc tgcgacgctt tctgctggaa caggacgatc tccctgagat   6180
tagcctgacc gctgggattc ctgtcaacat tcgtcccgca gatgacgagg gcaccggtac   6240
ccagattagc ttcatgatcg cggctctggc caccaatcaa cccgatccgc tgacccggct   6300
gaaatgtatc aaagaaagta gctgcaaggc gaaagagcac ctccagaaat tgccgaagaa   6360
agcactcaca caatacacca tgatgctcat gtcgccatac atcctgcaac tcatgtctgg   6420
tttgggtggc cgcatgcgtc cagtctttaa cgttaccatt agcaacgttc ctggcccaac   6480
tgaagatctg tactacgaag gcgcgaagct ggaggcgatg tatcccgttt cgttgattac   6540
ccacggcgga gccttgaata tcacctgcct gagctatgcc ggcagtttga actttggctt   6600
cactgggtgt cgcgatactc tccccagtat gcaaaaactg gccgtctaca cgggggaagc   6660
cctcgaagaa ctccgcacat tgctgttgcc gccaaagaaa aagcctagcc cgcgtaaacc   6720
gcggacggct gccaagaaga aaccggcagt gaattcgaac gccagttaag tttaaacagg   6780
aggaataaac catggcgaac ggtagcgctg tctctctgaa gagcggctcc ttgaatacgc   6840
aagaggacac ttcttcttcc ccaccgccac gcgcgttcat caaccaatta cccgactggt   6900
ccatgttatt gacggcgatt accactgtct ttgttgccgc agagaaacag tggactatgt   6960
tagaccgcaa gagcaagcgc tccgatatgt tagtggattc ttttggcatg gaacgcattg   7020
tgcaggatgg cttagtgttt cgtcaatctt ttagcattcg ttcttatgaa atcggtgcag   7080
atcgtcgtgc atccattgaa accttaatga accatctgca ggaaactagc ttgaatcatt   7140
```

```
gcaaatccat tcgcttgttg aatgagggtt ttggtcgcac ccccgagatg tgcaaacgtg   7200
acttgatctg ggtggttacc cgcatgcaca tcatggtcaa ccgctaccct acctggggtg   7260
ataccgttga gattaacact tgggtttccc aaagcggcaa gaatggtatg ggtcgtgatt   7320
ggctgatttc cgactgtaat accggcgaaa tcctgatccg cgcgacgtct gcatgggcga   7380
tgatgaacca aaagacccgt cgtctgtcta aactgcctta cgaagtcagc caagagattg   7440
ctccgcactt cgtcgacagc cctcccgtga tcgaggacgg cgaccgtaag ttacacaagt   7500
tcgatgtgaa aaccggcgac agcatccgta aaggtttgac tccgcgttgg aatgacttag   7560
atgttaatca gcacgttaac aacgttaagt atatcggctg gatcttagag agcatgccga   7620
ccgaggtctt ggaaactcat gaactgtgtt tcttaactct ggagtatcgt cgcgagtgcg   7680
gtcgcgatag cgtgctggaa tctgtgaccg cgatggatcc ttctaatgaa ggtggtcgct   7740
cccactacca gcatttactg cgcttggagg acggtactga catcgttaag ggccgcactg   7800
agtggcgtcc aaagaatgcc cggaatattg gtgccattag taccggtaaa accagtaatg   7860
gtaatcccgc cagttaataa ggcgcgccag gaggaataaa ccatggcaat acagcaggta   7920
catcacgctg acacttcatc atcaaaggtg ctcggacagc tccgtggcaa gcgggttctg   7980
atcaccggta ccactggctt tctgggcaag gtggtcctcg aaaggctgat tcgggcggtg   8040
cctgatatcg gcgcaattta cctgctgatc cggggcaata aacggcatcc ggatgctcgt   8100
tcccgtttcc tggaagaaat tgccacctcc tcggtgtttg accgtcttcg cgaggccgat   8160
tcagagggat ttgacgcctt tctggaagag cgcattcact gcgtgaccgg tgaggtgacc   8220
gaagcgggtt tcgggatagg gcaggaagac tatcgcaaac tcgccaccga actggatgcg   8280
gtgatcaact ccgctgcaag cgtgaatttc cgtgaagagc tcgacaaggc gctggccatc   8340
aacaccctgt gccttcggaa tattgccggc atggtggatt tgaatccgaa gcttgcggtc   8400
ctgcaggtct ccacctgcta tgtcaatggc atgaactcgg ggcaggtaac cgaatcggtg   8460
atcaagccgg caggcgaggc cgtgccgcgt tccccggacg gcttctatga gatagaagag   8520
cttgttcgcc tgcttcagga taaaattgaa gacgttcagg cccgttattc cggcaaagtg   8580
ctggagagga agctggtgga cctggggatt cgggaagcca accgctatgg ctggagcgat   8640
acctacacct ttaccaagtg gctgggcgaa cagttgctga tgaaggcgtt aaacgggcgc   8700
acgctgacca ttctgcgtcc ttcgattatc gaaagtgccc tggaggaacc agcgcccggc   8760
tggattgagg gggtgaaggt ggcagatgcc atcatcctgg cttacgcacg ggaaaaagtc   8820
accctcttcc cgggcaaacg ctccggtatc atcgatgtga ttccagtgga cctggtggcc   8880
aactccatca tcctttccct ggcggaagct cttggagaac ccggtcgacg tcgcatctat   8940
caatgttgca gcgggggcgg caatccaatc tccctgggtg agttcatcga tcatctcatg   9000
gcggaatcaa aagccaatta cgctgcctac gatcacctgt tctaccggca gcccagcaag   9060
ccgtttctgg cggttaaccg ggcgctgttt gatttggtga tcagtggtgt tcgcttaccg   9120
ctctccctga cggaccgtgt gctcaaatta ctgggaaatt cccgggacct gaaaatgctc   9180
aggaatctgg ataccaccca gtcgctggca accatttttg gtttctacac cgcgccggat   9240
tatatcttcc ggaacgatga gctgatggcg ctggcgaacc ggatgggtga ggtcgataaa   9300
gggctgttcc cggtggatgc ccgcctgatt gactgggagc tctacctgcg caagattcac   9360
ctggccgggc tcaatcgcta tgccctgaaa gaacgaaagg tgtacagtct gaaaaccgcg   9420
cgccagcgca aaaaagctgc ctaatctaga tagttaagcc agccccgaca cccgccaaca   9480
```

-continued

```
cccgctgacg cgccctgacg ggcttgtctg ctcccggcat ccgcttacag acaagctgtg   9540

accgtctccg ggagctgcat gtgtcagagg ttttcaccgt catcaccgaa acgcgcgaga   9600

cgaaagggcc tcgtgatacg cctattttta taggttaatg tcatgataat aatggtttct   9660

tagacgtcag gtggcacttt tcggggaaat gtgcgcggaa cccctatttg tttatttttc   9720

taaatacatt caaatatgta tccgctcatg agacaataac cctgataaat gcttcaataa   9780

tattgaaaaa ggaagagtat gagccatatt caacgggaaa cgtcttgctc gaggccgcga   9840

ttaaattcca acatggatgc tgatttatat gggtataaat gggctcgcga taatgtcggg   9900

caatcaggtg cgacaatcta tcgattgtat gggaagcccg atgcgccaga gttgtttctg   9960

aaacatggca aaggtagcgt tgccaatgat gttacagatg agatggtcag actaaactgg  10020

ctgacggaat ttatgcctct tccgaccatc aagcatttta tccgtactcc tgatgatgca  10080

tggttactca ccactgcgat ccccgggaaa acagcattcc aggtattaga agaatatcct  10140

gattcaggtg aaaatattgt tgatgcgctg gcagtgttcc tgcgccggtt gcattcgatt  10200

cctgtttgta attgtccttt taacagcgat cgcgtatttc gtctcgctca ggcgcaatca  10260

cgaatgaata acggtttggt tgatgcgagt gattttgatg acgagcgtaa tggctggcct  10320

gttgaacaag tctggaaaga aatgcataag cttttgccat tctcaccgga ttcagtcgtc  10380

actcatggtg atttctcact tgataacctt atttttgacg aggggaaatt aataggttgt  10440

attgatgttg gacgagtcgg aatcgcagac cgataccagg atcttgccat cctatggaac  10500

tgcctcggtg agttttctcc ttcattacag aaacggcttt ttcaaaaata tggtattgat  10560

aatcctgata tgaataaatt gcagtttcat ttgatgctcg atgagttttt ctaa        10614
```